(12) United States Patent
Serber et al.

(10) Patent No.: US 9,701,971 B2
(45) Date of Patent: Jul. 11, 2017

(54) METHODS FOR GENOMIC MODIFICATION

(71) Applicant: Amyris, Inc., Emeryville, CA (US)

(72) Inventors: Zach Serber, Emeryville, CA (US); Andrew Horwitz, Emeryville, CA (US)

(73) Assignee: AMYRIS, INC., Emeryville, CA (US)

( * ) Notice: Subject to any disclaimer, the term of this patent is extended or adjusted under 35 U.S.C. 154(b) by 0 days.

(21) Appl. No.: 14/178,203

(22) Filed: Feb. 11, 2014

(65) Prior Publication Data

US 2014/0186942 A1    Jul. 3, 2014

Related U.S. Application Data

(62) Division of application No. 13/459,034, filed on Apr. 27, 2012, now Pat. No. 8,685,737.

(60) Provisional application No. 61/539,389, filed on Sep. 26, 2011, provisional application No. 61/500,741, filed on Jun. 24, 2011, provisional application No. 61/479,821, filed on Apr. 27, 2011.

(51) Int. Cl.
*C12N 15/90* (2006.01)
*C12N 15/81* (2006.01)

(52) U.S. Cl.
CPC ........... *C12N 15/81* (2013.01); *C12N 15/905* (2013.01)

(58) Field of Classification Search
None
See application file for complete search history.

(56) References Cited

U.S. PATENT DOCUMENTS

| | | | |
|---|---|---|---|
| 5,888,732 | A | 3/1999 | Hartley et al. |
| 6,140,466 | A | 10/2000 | Barbas, III et al. |
| 6,453,242 | B1 | 9/2002 | Eisenberg et al. |
| 6,503,712 | B1 | 1/2003 | Thukral |
| 6,511,808 | B2 | 1/2003 | Wolffe et al. |
| 7,314,712 | B2 | 1/2008 | Storici et al. |
| 7,919,605 | B1 | 4/2011 | Benjamin |
| 2003/0059767 | A1 | 3/2003 | Barbas, III et al. |
| 2003/0108880 | A1 | 6/2003 | Rebar et al. |
| 2008/0274523 | A1 | 11/2008 | Renninger et al. |
| 2009/0205083 | A1 | 8/2009 | Gupta et al. |

(Continued)

FOREIGN PATENT DOCUMENTS

| | | |
|---|---|---|
| EP | 2 180 058 | 4/2010 |
| WO | WO 99/25821 | 5/1999 |

(Continued)

OTHER PUBLICATIONS

Gibson et al. (2008) "One-step assembly in yeast of 25 overlapping DNA fragments to form a complete synthetic Mycoplasma genitalium genome." Proc. Natl. Acad. Sci. 105(51):20404-9.*

(Continued)

*Primary Examiner* — Karen S Weiler
(74) *Attorney, Agent, or Firm* — Squire Patton Boggs (US) LLP

(57) ABSTRACT

Provided herein are methods of integrating one or more exogenous nucleic acids into one or more selected target sites of a host cell genome. In certain embodiments, the methods comprise contacting the host cell genome with one or more integration polynucleotides comprising an exogenous nucleic acid to be integrated into a genomic target site, and a nuclease capable of causing a double-strand break near or within the genomic target site.

44 Claims, 8 Drawing Sheets

(56) References Cited

U.S. PATENT DOCUMENTS

Figure 1:
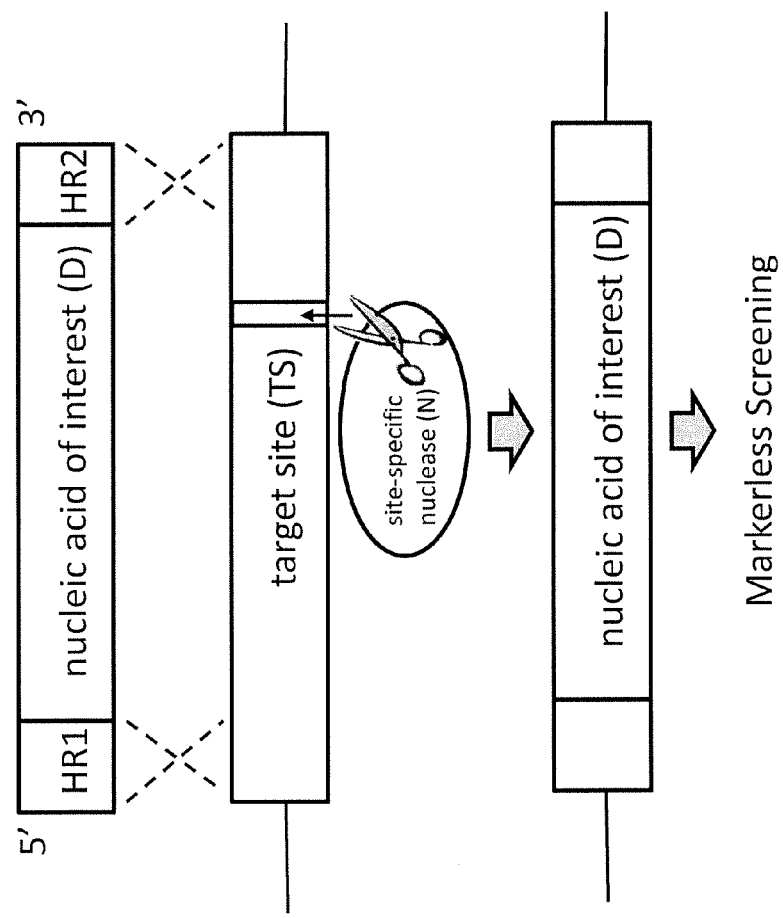

| | | | |
|---|---|---|---|
| 2010/0212035 A1* | 8/2010 | Buelow | A01K 67/0278 800/14 |
| 2011/0145940 A1 | 6/2011 | Voytas et al. | |
| 2012/0052582 A1* | 3/2012 | Benjamin | C12N 15/81 435/440 |
| 2014/0004608 A1 | 1/2014 | Cabaniols et al. | |

FOREIGN PATENT DOCUMENTS

| | | |
|---|---|---|
| WO | WO 99/25840 | 5/1999 |
| WO | WO 99/25841 | 5/1999 |
| WO | WO 99/25851 | 5/1999 |
| WO | WO 00/42219 A1 | 7/2000 |
| WO | WO 01/07572 A2 | 2/2001 |
| WO | WO 01/11058 A1 | 2/2001 |
| WO | WO 01/23545 A1 | 4/2001 |
| WO | WO 02/42459 A2 | 5/2002 |
| WO | WO 02/099084 A3 | 12/2002 |
| WO | WO 03/008045 A2 | 1/2003 |
| WO | WO 03/062455 A2 | 7/2003 |
| WO | WO 03/078619 A1 | 9/2003 |
| WO | WO 03/080809 A2 | 10/2003 |
| WO | WO 2004/031346 A2 | 4/2004 |
| WO | WO 2004/067736 A2 | 8/2004 |
| WO | WO 2004/067753 | 8/2004 |
| WO | WO 2004/067753 A2 | 8/2004 |
| WO | WO 2005/014791 A2 | 2/2005 |
| WO | WO 2005/084190 A2 | 9/2005 |
| WO | WO 2005/105989 A1 | 11/2005 |
| WO | WO 2006/097784 A1 | 9/2006 |
| WO | WO 2006/097853 A1 | 9/2006 |
| WO | WO 2006/097854 A1 | 9/2006 |
| WO | WO 2007/034262 A1 | 3/2007 |
| WO | WO 2007/049095 A1 | 5/2007 |
| WO | WO 2007/049156 A2 | 5/2007 |
| WO | WO 2007/057781 A2 | 5/2007 |
| WO | WO 2007/060495 A2 | 5/2007 |
| WO | WO 2008/021207 A2 | 2/2008 |
| WO | WO 2008/152524 A2 | 12/2008 |
| WO | WO 2009/001159 A1 | 12/2008 |
| WO | WO 2009/042186 A2 | 4/2009 |
| WO | WO 2009/054985 A1 | 4/2009 |
| WO | WO 2009/095742 A1 | 8/2009 |
| WO | WO 2009/095793 A1 | 8/2009 |
| WO | WO 2010/001189 A1 | 1/2010 |
| WO | WO 2010/015899 A2 | 2/2010 |
| WO | WO 2010/046786 A1 | 4/2010 |
| WO | WO 2010/065123 A1 | 6/2010 |
| WO | WO 2010/079430 A1 | 7/2010 |

OTHER PUBLICATIONS

Carroll (2004) "Using Nucleases to Stimulate Homologous Recombination" Methods Mol Biol 262:195-207.*
Kitazono et al (2002) "Marker-fusion PCR for one-step mutagenesis of essential genes in yeast" Yeast 19(2):141-149.*
Abremski & Hoess, Evidence for a second conserved arginine residue in the integrase family of recombination proteins. *Protein Eng.* (1992) 5:87-91.
Albert et al., Site-specific integration of DNA into wild-type and mutant *lox* sites placed in the plant genome. *Plant J.* (1995) 7:649-659.
Arnold et al., Mutants of Tn3 resolvase which do not require accessory binding sites for recombination activity. *EMBO J.* (1999) 18:1407-1414.
Basso et al. (2008) "Yeast selection for fuel ethanol production in Brazil," FEMS Yeast Res 8:1151-1163.
Bayer et al., Synthesis of methyl halides from biomass using engineered microbes. *J Am Chem Soc.* (2009) 131:6508-6515.
Beerli & Barbas, Engineering polydactyl zinc-finger transcription factors. *Nat Biotechnol.* (2002) 20:135-41.
Boch et al., Breaking the code of DNA binding specificity of TAL-type III effectors. *Science.* (2009) 326:1509-1512.

Buchholz & Stewart, Alteration of Cre recombinase site specificity by substrate-linked protein evolution. *Nat Biotechnol.* (2001) 19:1047-1052.
Capecchi, Altering the genome by homologous recombination. *Science.* (1989) 244:1288-1292.
Carroll et al., Design, construction and in vitro testing of zinc finger nucleases. *Nature Protocols.* (2006) 1:1329-1341.
Chames et al., In vivo selection of engineered homing endonucleases using double-strand break induced homologous recombination. *Nucleic Acids Res.* (2005) 33:e178.
Chen & Zhao, A highly sensitive selection method for directed evolution of homing endonucleases. *Nucleic Acids Res.* (2005) 33:e154.
Chevalier et al., Design, activity, and structure of a highly specific artificial endonuclease. *Mol. Cell.* (2002) 10:895-905.
Christ & Dröge, Alterations in the directionality of λ site-specific recombination catalyzed by mutant integrases in vivo. *J Mol Biol.* (1998) 288:825-836.
Chu et al., Characterization of the intron in the phage T4 thymidylate synthase gene and evidence for its self-excision from the primary transcript. *Cell.* (1986) 45:157-166.
Colleaux et al., The apocytochrome *b* gene of *Chlamydomonas smithii* contains a mobile intron related to both *Saccharomyces* and *Neurospora* introns. *Mol. Gen. Genet.* (1990) 223:288-296.
De Jonckheere, Evidence for the ancestral origin of group I introns in the SSUrDNA of *Naegleria* spp. *J. Eukaryot. Microbiol.* (1994) 41:457-463.
Dorgai et al., Identifying determinants of recombination specificity: construction and characterization of mutant bacteriophage integrases. (1995) *J Mol Biol.* 252:178-188.
Dorgai et al., Recognition of core binding sites by bacteriophage integrases. (1998) *J Mol Biol.* 277:1059-1070.
Dreier et al., Development of zinc finger domains for recognition of the 5'-ANN-3' family of DNA sequences and their use in the construction of artificial transcription factors. *J Biol Chem.* (2001) 276:29466-29478.
Dreier et al., Development of zinc finger domains for recognition of the 5'-CNN-3' family DNA sequences and their use in the construction of artificial transcription factors. *J Biol Chem* (2005) 280:35588-35597.
Dreier et al., Insights into the molecular recognition of the 5'-GNN-3' family of DNA sequences by zinc finger domains. *J Mol Biol* (2000) 303:489-502.
Durai et al., Zinc finger nucleases: custom-designed molecular scissors for genome engineering of plant and mammalian cells. *Nucleic Acids Res.* (2005) 33:5978-5990.
Eddy & Gold, The phage T4 *nrdB* intron: a deletion mutant of a version found in the wild. *Genes Dev.* (1991) 5: 1032-1041.
Elde et al., I-*NjaI*, a nuclear intron-encoded homing endonuclease from *Naegleria*, generates a pentanucleotide 3' cleavage-overhang within a 19 base-pair partially symmetric DNA recognition site. *Eur. J. Biochem.* (1999) 259:281-288.
Epinat et al., A novel engineered meganuclease induces homologous recombination in yeast and mammalian cells. *Nucleic Acids Res.* (2003) 31:2952-2962.
Esposito & Scocca, The integrase family of tyrosine recombinases: evolution of a conserved active site domain. *Nucleic Acids Res.* (1997) 25:3605-3614.
Foury et al., The complete sequence of the mitochondrial genome of *Saccharomyces cerevisiae*. *FEBS Lett.* (1998) 440:325-331.
Fujisawa et al., Sequence of the T4 recombination gene, *uvsX*, and its comparison with that of the *recA* gene of *Escherichia coli*. *Nucleic Acids Res.* (1985) 13:7473-7481.
Gimble et al., Assessing the plasticity of DNA target site recognition of the PI-*SceI* homing endonuclease using a bacterial two-hybrid selection system. *Mol Biol.* (2003) 334:993-1008.
Gloor et al., Targeted gene replacement in *Drosophila* via P element-induced gap repair. *Science.* (1991) 253:1110-1117.
Goodrich-Blair & Shub, Beyond homing: competition between intron endonucleases confers a selective advantage on flanking genetic markers. *Cell.* (1996) 84:211-221.

(56) References Cited

OTHER PUBLICATIONS

Goodrich-Blair et al., A self-splicing group I intron in the DNA polymerase gene of Bacillus subtilis bacteriophage SPO1. *Cell.* (1990) 63:417-424.

Griggs & Johnston, Regulated expression of the *GAL4* activator gene in yeast provides a sensitive genetic switch for glucose repression. *Proc. Natl. Acad. Sci.* (1991) 88:8597-8601.

Gruen, et al., An in vivo selection system for homing endonuclease activity. *Nucleic Acids Res.* (2002) 30:e29.

Gu et al., R gene expression induced by a type-III effector triggers disease resistance in rice. *Nature.* (2005) 435:1122-1125.

Guan et al., Heritable endogenous gene regulation in plants with designed polydactyl zinc finger transcription factors. *Proc Natl Acad Sci USA.* (2002) 99:13296-13301.

Guhan & Muniyappa, Structural and functional characteristics of homing endonucleases. *Crit Rev Biochem Mol Biol.* (2003) 38:199-248.

Hasty et al., The length of homology required for gene targeting in embryonic stem cells. *Mol Cell Biol.* (1991) 11:5586-5591.

Hirata et al., Molecular structure of a gene, *VMA1*, encoding the catalytic subunit of H(+)-translocating adenosine triphosphatase from vacuolar membranes of *Saccharomyces cerevisiae. J. Biol. Chem.* (1990) 265:6726-6733.

Hoess et al., the role of the *loxP* spacer region in P1 site-specific recombination. *Nucleic Acids Res.* (1986) 14:2287-2300.

Huang et al., A bacterial model system for chromosomal targeting. *Nucleic Acids Res.* (1991) 19:443-448.

International Search Report for PCT/US2012/035657 mailed Aug. 8, 2012, 6 pgs.

Jamieson et al., Drug discovery with engineered zinc-finger proteins. *Nature Rev Drug Discov.* (2003) 2:361-368.

Jasin, Genetic manipulation of genomes with rare-cutting endonucleases. *Trends Genet.* (1996) 12(6):224-228.

Johansen & Vogt, An intron in the nuclear ribosomal DNA of Didymium iridis codes for a group I ribozyme and a novel ribozyme that cooperate in self-splicing. *Cell.* (1994) 76:725-734.

Johansen et al., A family of nuclear homing endonucleases. *Nucleic Acids Res.* (1993) 21:4405.

Jurica & Stoddard, Homing endonucleases: structure, function and evolution. *Cell Mol Life Sci.* (1999) 55:1304-1326.

Kaliman et al., The nucleotide sequence of the region of bacteriophage T4 inh(lip)-hoc genes. *Nucleic Acids. Res.* (1990) 18:4277.

Kay et al., A bacterial effector acts as a plant transcription factor and induces a cell size regulator. *Science.* (2007) 318:648-651.

Kim et al. Hybrid restriction enzymes: zinc finger fusions to Fok I cleavage domain. *Proc. Natl. Acad. Sci. USA.* (1996) 93:1156-1160.

Klippel et al., Isolation and characterization of unusual *gin* mutants. *EMBO J.* (1988) 7:3983-3989.

Kodumal et al., Total synthesis of long DNA sequences: synthesis of a contiguous 32-kb polyketide synthase gene cluster. *Proc Natl Acad Sci USA.* (2004) 101:15573-15578.

Kuhlman & Cox, Site-specific chromosomal integration of large synthetic constructs. *Nucleic Acids Res.* (2010) 38:e92.

Lange-Gustafson & Nash, Purification and properties of Int-h, a variant protein involved in site-specific recombination of bacteriophage λ. *J Biol Chem.* (1984) 259:12724-12732.

Lee & Saito, Role of nucleotide sequences of *loxP* spacer region in Cre-mediated recombination. *Gene.* (1998) 216:55-65.

Li et al., "Modularly assembled designer TAL effector nucleases for targeted gene knockout and gene replacement in eukaryotes", Nucleic Acids Res. vol. 39, No. 14, pp. 6315-6325 (2011).

Liu et al., Validated zinc finger protein designs for all 16 GNN DNA triplet targets. *J Biol Chem.* (2002) 277:3850-3856.

Lorbach et al., Site-specific recombination in human cells catalyzed by phage λ integrase mutants. *J Mol Biol.* (2000) 296:1175-1181.

Lucas et al., Rapid evolution of the DNA-binding site in LAGLIDADG homing endonucleases. *Nucleic Acids Res.* (2001) 29:960-969.

Ma et al., Complete reconstitution of a highly reducing iterative polyketide synthase. *Science.* (2009) 326:589-592.

Malphettes et al., Highly efficient deletion of *FUT8* in CHO cell lines using zinc-finger nucleases yields cells that produce completely nonfucosylated antibodies. *Biotechnol Bioeng.* (2010) 106(5):774-783.

Martin et al., Engineering a mevalonate pathway in *Escherichia coli* for production of terpenoids. *Nat Biotechnol.* (2003) 21:796-802.

Millard et al. "An antisense RNA in a lytic cyanophage links *psbA* to a gene encoding a homing endonuclease," The ISME Journal, 2010, vol. 4, pp. 1121-1135.

Miller et al., *int*-h: an *int* mutation of phage λ that enhances site-specific recombination. *Cell.* (1980) 20:721-729.

Moran et al., Intron 5α of the *COXI* gene of yeast mitochondrial DNA is a mobile group I intron. *Nucleic Acids Res.* (1992) 20:4069-4076.

Moscou & Bogdanove, A simple cipher governs DNA recognition by TAL effectors. Science. (2009) 326:1501.

Moure, et al., Crystal structure of the intein homing endonuclease PI-*Sce*I bound to its recognition sequence. *Nat Struct Biol.* (2002) 9:764.

Muscarella et al., Characterization of I-*Ppo*, an intron-encoded endonuclease that mediates homing of a group I intron in the ribosomal DNA of *Physarum polycephalum. Mol. Cell. Biol.* (1990) 10:3386-3396.

Ordiz et al., Regulation of transgene expression in plants with polydactyl zinc finger transcription factors. *Proc Natl Acad Sci USA.* (2002) 99:13290-13295.

Pabo et al., Design and selection of novel $Cys_2His_2$ zinc finger proteins. *Ann Rev Biochem.* (2001) 70:313-340.

Porteus & Carroll, Gene targeting using zinc finger nucleases. *Nat Biotechnol.* (2005) 23:967-973.

Reyon et al., ZFNGenome: a comprehensive resource for locating zinc finger nuclease target sites in model organisms. *BMC Genomics.* (2011) 12:83.

Rochaix et al., The chloroplast ribosomal intron of *Chlamydomonas reinhardii* codes for a polypeptide related to mitochondrial maturases. *Nucleic Acids Res.* (1985) 13: 975-984.

Römer et al., Plant pathogen recognition mediated by promoter activation of the pepper *Bs3* resistance gene. *Science.* (2007) 318:645-648.

Rosen et al., Homing endonuclease I-CreI derivatives with novel DNA target specificities. *Nucleic Acids Res.* (2006) 34:4791-4800.

Sadowski, Site-specific genetic recombination: hops, flips, and flops. FASEB. (1993) 7:760-7.

Sanjana et al., A transcription activator-like effector toolbox for genome engineering. *Nature Protocols.* (2012) 7:171-192.

Santoro & Schultz, Directed evolution of the site specificity of Cre recombinase. *Proc Natl Acad Sci.* USA (2002) 99:4185-4190.

Sauer, Site-specific recombination: developments and applications. *Curr Op Biotechnol.* (1994) 5:521-527.

Saves et al., Identification of the first eubacterial endonuclease coded by an intein allele in the *pps1* gene of mycobacteria. *Nucleic Acids Res.* (2001) 29:4310-4318.

Schlake & Bode, Use of mutated FLP recognition target (FRT) sites for the exchange of expression cassettes at defined chromosomal loci. *Biochemistry.* (1994) 33:12746-12751.

Sclimenti et al., Directed evolution of a recombinase for improved genomic integration at a native human sequence. *Nucleic Acids Res.* (2001) 29:5044-5051.

Segal & Barbas, Custom DNA-binding proteins come of age: polydactyl zinc-finger proteins. *Curr Opin Biotechnol.* (2001) 12:632-637.

Segal et al., Evaluation of a modular strategy for the construction of novel polydactyl zinc finger DNA-binding proteins. *Biochemistry.* (2003) 42:2137-2148.

Segal, The use of zinc finger peptides to study the role of specific factor binding sites in the chromatin environment. *Methods.* (2002) 26:76-83.

Seibler & Bode, Double-reciprocal crossover mediated by FLP-recombinase: a concept and an assay. *Biochemistry.* (1997) 36:1740-1747.

Seligman et al., Mutations altering the cleavage specificity of a homing endonuclease. *Nucleic Acids Res.* (2002) 30:3870-3879.

(56) References Cited

OTHER PUBLICATIONS

Smith et al., A combinatorial approach to create artificial homing endonucleases cleaving chosen sequences. *Nucleic Acids Res.* (2006) 34:e149.
Steen et al., Microbial production of fatty-acid-derived fuels and chemicals from plant biomass. *Nature.* (2010) 463:559-562.
Stoddard, Homing endonuclease structure and function. *Q Rev Biophys.* (2006) 38:49-95.
Sugio et al., Two type III effector genes of *Xanthomonas oryzae* pv. *oryzae* control the induction of the host genes *OsTFIIAγ1* and *OsTFX1* during bacterial blight of rice. *Proc. Natl. Acad. Sci. USA.* (2007) 104:10720-10725.
Sussman et al., Isolation and characterization of new homing endonuclease specificities at individual target site positions. *J Mol Biol.* (2004) 342:31-41.
Takahashi et al., "Metabolic Engineering of Sesquiterpene Metabolism in Yeast", Biotechnology and Bioengineering vol. 97, No. 1 pp. 170-181 (2007).
Thomson et al., Mutational analysis of *LoxP* sites for efficient Cre-mediated insertion into genomic DNA. *Genesis.* (2003) 36:162-167.
Thyagarajan et al., Site-specific genomic integration in mammalian cells mediated by phage $\phi$C31 integrase. *Mol Cell Biol.* (2001) 21:3926-3934.
Tomaschewski & Rüger, Nucleotide sequence and primary structures of gene products coded for by the T4 genome between map positions 48.266 kb and 39.166 kb. *Nucleic Acids Res.* (1987) 15:3632-3633.
Turmel et al., Six group I introns and three internal transcribed spacers in the chloroplast large subunit ribosomal RNA gene of the green alga *Chlamydomonas eugametos*. *J .Mol. Biol.* (1991) 218:293-311.
Umlauf & Cox, The functional significance of DNA sequence structure in a site-specific genetic recombination reaction. *EMBO J.* (1988) 7:1845-1852.
Urnov et al., Genome editing with engineered zinc finger nucleases. *Nat Rev Genet.* (2010) 11:636-646.
Urnov et al., Highly efficient endogenous human gene correction using designed zinc-finger nucleases. *Nature.* (2005) 435:646-651.
Vergunst et al., VirB/D4-dependent protein translocation from *Agrobacterium* into plant cells. *Science.* (2000) 290:979-982.
Voziyanov et al., A dual reporter screening system identifies the amino acid at position 82 in Flp site-specific recombinase as a determinant for target specificity. *Nucleic Acids Res.* (2002) 30:1656-1663.
Voziyanov et al., Stepwise manipulation of DNA specificity in Flp recombinase: progressively adapting Flp to individual and combinatorial mutations in its target site. *J Mol Biol.* (2003) 326:65-76.
Wolfe et al., DNA recognition by $Cys_2His_2$ zinc finger proteins. *Ann Rev Biophys Biomol Struct.* (2000) 29:183-212.
Wright et al., High-frequency homologous recombination in plants mediated by zinc-finger nucleases. *Plant J.* (2005) 44:693-705.
Yagil et al., Identifying determinants of recombination specificity: construction and characterization of chimeric bacteriophage integrases. *J Mol Biol.* (1995) 252:163-177.
Yang et al., *Os8N3* is a host disease-susceptibility gene for bacterial blight of rice. *Proc. Natl. Acad. Sci. USA.* (2006) 103:10503-10508.
Zeng et al., A free-standing homing endonuclease targets an intron insertion site in the *psbA* gene of cyanophages. *Curr. Biol.* (2009) 19:218-222.
Abremski et al., Evidence for a second conserved arginine residue in the integrase family of recombination proteins. *Protein Eng.* (1992) 5:87-91.

Basso et al., Yeast selection for fuel ethanol production in Brazil. *FEMS Yeast Res* (2008) 8:1151-1163.
Beerli et al., Engineering polydactyl zinc-finger transcription factors. *Nat Biotechnol.* (2002) 20:135-41.
Buchholz et al., Alteration of Cre recombinase site specificity by substrate-linked protein evolution. *Nat Biotechnol.* (2001) 19:1047-1052.
Chen et al., A highly sensitive selection method for directed evolution of homing endonucleases. *Nucleic Acids Res.* (2005) 33:e154.
Christ et al., Alterations in the directionality of λ site-specific recombination catalyzed by mutant integrases in vivo. *J Mol Biol.* (1998) 288:825-836.
Eddy et al., The phage T4 *nrdB* intron: a deletion mutant of a version found in the wild. *Genes Dev.* (1991) 5: 1032-1041.
Esposito et al., The integrase family of tyrosine recombinases: evolution of a conserved active site domain. *Nucleic Acids Res.* (1997) 25:3605-3614.
Goodrich-Blair et al., Beyond homing: competition between intron endonucleases confers a selective advantage on flanking genetic markers. *Cell.* (1996) 84:211-221.
Griggs et al., Regulated expression of the *GAL4* activator gene in yeast provides a sensitive genetic switch for glucose repression. *Proc. Natl. Acad. Sci.* (1991) 88:8597-8601.
Guhan et al., Structural and functional characteristics of homing endonucleases. *Crit Rev Biochem Mol Biol.* (2003) 38:199-248.
Johansen et al., An intron in the nuclear ribosomal DNA of Didymium iridis codes for a group I ribozyme and a novel ribozyme that cooperate in self-splicing. *Cell.* (1994) 76:725-734.
Jurica et al., Homing endonucleases: structure, function and evolution. *Cell Mol Life Sci.* (1999) 55:1304-1326.
Kuhlman et al., Site-specific chromosomal integration of large synthetic constructs. *Nucleic Acids Res.* (2010) 38:e92.
Lange-Gustafson et al., Purification and properties of Int-h, a variant protein involved in site-specific recombination of bacteriophage λ. *J Biol Chem.* (1984) 259:12724-12732.
Lee et al., Role of nucleotide sequences of *loxP* spacer region in Cre-mediated recombination. *Gene.* (1998) 216:55-65.
Li et al., Modularly assembled designer TAL effector nucleases for targeted gene knockout and gene replacement in eukaryotes. *Nucleic Acids Res.* (2011) vol. 39, No. 14, pp. 6315-6325.
Moscou et al., A simple cipher governs DNA recognition by TAL effectors. *Science.* (2009) 326:1501.
Porteus et al., Gene targeting using zinc finger nucleases. *Nat Biotechnol.* (2005) 23:967-973.
Santoro et al., Directed evolution of the site specificity of Cre recombinase. *Proc Natl Aced Sci.* USA (2002) 99:4185-4190.
Schlake et al., Use of mutated FLP recognition target (FRT) sites for the exchange of expression cassettes at defined chromosomal loci. *Biochemistry.* (1994) 33:12746-12751.
Segal et al., Custom DNA-binding proteins come of age: polydactyl zinc-finger proteins. *Curr Opin Biotechnol.* (2001) 12:632-637.
Seibler et al., Double-reciprocal crossover mediated by FLP-recombinase: a concept and an assay. *Biochemistry.* (1997) 36:1740-1747.
Takahashi et al., Metabolic Engineering of Sesquiterpene Metabolism in Yeast. *Biotechnology and Bioengineering* (2007) vol. 97, No. 1 pp. 170-181.
Tomaschewski et al., Nucleotide sequence and primary structures of gene products coded for by the T4 genome between map positions 48.266 kb and 39.166 kb. *Nucleic Acids Res.* (1987) 15:3632-3633.
Umlauf et al., The functional significance of DNA sequence structure in a site-specific genetic recombination reaction. *EMBO J.* (1988) 7:1845-1852.

* cited by examiner

SEQUENCE LISTING

<160> NUMBER OF SEQ ID NOS: 66

<210> SEQ ID NO 1
<211> LENGTH: 741
<212> TYPE: DNA
<213> ORGANISM: Artificial Sequence
<220> FEATURE:
<223> OTHER INFORMATION: Synthetic: Wild-type Em.GFP coding sequence

<400> SEQUENCE: 1

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccttgaccta cggcgtgcag tgcttcgccc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaag gtctatatca ccgccgacaa gcagaagaac   480
ggcatcaagg tgaacttcaa gacccgccac aacatcgagg acggcagcgt gcagctcgcc   540
gaccactacc agcagaacac ccccatcggc gacggccccg tgctgctgcc cgacaaccac   600
tacctgagca cccagtccgc cctgagcaaa gaccccaacg agaagcgcga tcacatggtc   660
ctgctggagt tcgtgaccgc cgccgggatc actctcggca tggacgagct gtacaagtaa   720
ctcgagaagc ttgatccggc t                                             741
```

<210> SEQ ID NO 2
<211> LENGTH: 13
<212> TYPE: DNA
<213> ORGANISM: Artificial Sequence
<220> FEATURE:
<223> OTHER INFORMATION: Synthetic: EmGFP linker encoding premature stop
      codon

<400> SEQUENCE: 2

```
cgtctaaatc atg                                                       13
```

<210> SEQ ID NO 3
<211> LENGTH: 500
<212> TYPE: DNA
<213> ORGANISM: Artificial Sequence
<220> FEATURE:
<223> OTHER INFORMATION: Synthetic: HO upstream integration sequence

<400> SEQUENCE: 3

```
cgcaagtcct gtttctatgc ctttctctta gtaattcacg aaataaacct atggtttacg    60
aaatgatcca cgaaaatcat gttattattt acatcaacat atcgcgaaaa ttcatgtcat   120
gtccacatta acatcattgc agagcaacaa ttcattttca tagagaaatt tgctactatc   180
acccactagt actaccattg gtacctacta ctttgaattg tactaccgct gggcgttatt   240
aggtgtgaaa ccacgaaaag ttcaccataa cttcgaataa agtcgcggaa aaaagtaaac   300
agctattgct actcaaatga ggtttgcaga agcttgttga agcatgatga agcgttctaa   360
acgcactatt catcattaaa tatttaaagc tcataaaatt gtattcaatt cctattctaa   420
atggctttta tttctattac aactattagc tctaaatcca tatcctcata agcagcaatc   480
aattctatct atactttaaa                                               500
```

<210> SEQ ID NO 4
<211> LENGTH: 200
<212> TYPE: DNA
<213> ORGANISM: Artificial Sequence
<220> FEATURE:
<223> OTHER INFORMATION: Synthetic: HO downstream integration sequence

<400> SEQUENCE: 4

```
aatgtgtata ttagtttaaa aagttgtatg taataaaagt aaaatttaat attttggatg      60
aaaaaaacca tttttagact ttttcttaac tagaatgctg gagtagaaat acgccatctc     120
aagatacaaa aagcgttacc ggcactgatt tgtttcaacc agtatataga ttattattgg     180
gtcttgatca actttcctca                                                  200
```

<210> SEQ ID NO 5
<211> LENGTH: 490
<212> TYPE: DNA
<213> ORGANISM: Artificial Sequence
<220> FEATURE:
<223> OTHER INFORMATION: Synthetic: YGR250c upstream integration
      sequence

<400> SEQUENCE: 5

```
gtacgatgtt tctcccgctg atccgattac tagccgaaga cgtaaaattg gcgcttgatt      60
caatttatgc ccttcccggg aatagttgac caaagggcaa aaaaattcag tcggagattc     120
cctattgggc ggaatttagt agatctcttt ccgtgcataa cgcctgcccg ttagtcgtta     180
tttcacgtta acattttctt ggccactgcg ctatataaat aaatacatat atatatgtca     240
agcacaataa agaaacttcc cttaaatatt gaataagtaa ataatagttg aaaagtgcct     300
tttgttcgaa ggattagagt gttcttaatt ttagttcgtt caacggtctc aaaaaaagtg     360
tgaacaagta aagcatagca cacatcccaa attacaaggc accctgatta aaaatccaaa     420
aataaaccat aagttttatt ttactaaaaa cattatacgt gaaagacaaa ccgcatcaga     480
agtttcgagg                                                             490
```

<210> SEQ ID NO 6
<211> LENGTH: 185
<212> TYPE: DNA
<213> ORGANISM: Artificial Sequence
<220> FEATURE:
<223> OTHER INFORMATION: Synthetic: YGR250c downstream integration
      sequence

<400> SEQUENCE: 6

```
attgcatcag gtccataaaa tgttttgtc tgctttttttt tcttcatgta ttagttggtt      60
tttattttta tattttcatt tatcttattc atactttta ctccttttttt cttcattctt     120 tacgatcttg gacattcaac tagcctatgg taacttttct tattactttg ccctccttg      180 aggtg                                                                  185
```

<210> SEQ ID NO 7
<211> LENGTH: 504
<212> TYPE: DNA
<213> ORGANISM: Artificial Sequence
<220> FEATURE:
<223> OTHER INFORMATION: Synthetic: NDT80 upstream integration sequence

<400> SEQUENCE: 7

```
catcaagcgc tccaagctga cataaatcgc actttgtatc tacttttttt tattcgaaaa      60
caaggcacaa caatgaatct atcgccctgt gagattttca atctcaagtt tgtgtaatag     120
```
atagcgttat attatagaac tataaaggtc cttgaatata catagtgttt cattcctatt    180
actgtatatg tgactttaca ttgttacttc cgcggctatt tgacgttttc tgcttcaggt    240
gcggcttgga gggcaaagtg tcagaaaatc ggccaggccg tatgacacaa aagagtagaa    300
aacgagatct caaatatctc gaggcctgtc ctctatacaa ccgcccagct ctctgacaaa    360
gctccagaac ggttgtcttt tgtttcgaaa agccaaggtc ccttataatt gccctccatt    420
ttgtgtcacc tatttaagca aaaaattgaa agtttactaa ccttcatta aagagaaata    480 acaatattat aaaaagcgct taaa                                           504

<210> SEQ ID NO 8
<211> LENGTH: 202
<212> TYPE: DNA
<213> ORGANISM: Artificial Sequence
<220> FEATURE:
<223> OTHER INFORMATION: Synthetic: NDT80 downstream integration
      sequence

<400> SEQUENCE: 8
ataaactaat gattttaaat cgttaaaaaa atatgcgaat tctgtggatc gaacacagga    60
cctccagata acttgaccga agttttttct tcagtctggc gctctcccaa ctgagctaaa    120
tccgcttact atttgttatc agttcccttc atatctacat agaataggtt aagtattta     180 ttagttgcca gaagaactac tg                                             202

<210> SEQ ID NO 9
<211> LENGTH: 43
<212> TYPE: DNA
<213> ORGANISM: Artificial Sequence
<220> FEATURE:
<223> OTHER INFORMATION: Synthetic: Recognition sequence for ZFN.gfp

<400> SEQUENCE: 9
acaactacaa cagccacaac gtctatatca tggccgacaa gca                      43

<210> SEQ ID NO 10
<211> LENGTH: 31
<212> TYPE: DNA
<213> ORGANISM: Artificial Sequence
<220> FEATURE:
<223> OTHER INFORMATION: Synthetic: Forward primer specific to Em.GFP

<400> SEQUENCE: 10
caactacaac agccacaagg tctatatcac c                                   31

<210> SEQ ID NO 11
<211> LENGTH: 22
<212> TYPE: DNA
<213> ORGANISM: Artificial Sequence
<220> FEATURE:
<223> OTHER INFORMATION: Synthetic: Reverse primer for HO locus

<400> SEQUENCE: 11
ctctaacgct gttggtagat tg                                             22

<210> SEQ ID NO 12
<211> LENGTH: 39
<212> TYPE: DNA
<213> ORGANISM: Artificial Sequence
<220> FEATURE:
<223> OTHER INFORMATION: Synthetic: Reverse primer for NDT80 locus

<400> SEQUENCE: 12

```
accatgtgat aatacactac taatgtgact actagttga                         39
```

<210> SEQ ID NO 13
<211> LENGTH: 30
<212> TYPE: DNA
<213> ORGANISM: Artificial Sequence
<220> FEATURE:
<223> OTHER INFORMATION: Synthetic: Reverse primer for YGR250c locus

<400> SEQUENCE: 13

```
tcagacgcgt tcggaggaga gtgcattcac                                  30
```

<210> SEQ ID NO 14
<211> LENGTH: 5251
<212> TYPE: DNA
<213> ORGANISM: Artificial Sequence
<220> FEATURE:
<223> OTHER INFORMATION: Synthetic: Integration construct i8

<400> SEQUENCE: 14

```
ttgcctatgc tttgtttgct ttgaacactt gtttccgctc tccttttact tattggctac     60
taaaactacg tgtaaaagat cgcccagcgc aaaaaggtcc ggcggtttca ataatctcg     120 aactattcct ataatatgca aaatagtagg taggaacaag tcgactctag gcagataagg    180
aagatgtccg gtaaatggag actagtgctg accgggatag gcaatccaga gcctcagtac    240
gctggtaccc gtcacaatgt agggctatat atgctggagc tgctacgaaa gcggcttggt    300
ctgcagggga gaacttattc ccctgtgcct aatacgggcg gcaaagtgca ttatatagaa    360
gacgaacatt gtacgatact aagatcggat ggccagtaca tgaatctaag tggagaacag    420
gtgtgcaagg tctgggcccg gtacgccaag taccaagccc gacacgtagt tattcatgac    480
gagttaagtg tggcgtgtgg aaaagtgcag ctcagagccc ccagcaccag tattagaggt    540
cataatgggc tgcgaagcct gctaaaatgc agtggaggcc gtgtacccct tgccaaattg    600
gctattggaa tcggcagaga acctgggtcc cgttctagag accctgcgag cgtgtcccgg    660
tgggttctgg gagctctaac tccgcaggaa ctacaaacct tgcttacaca gagtgaacct    720
gctgcctggc gtgctctgac tcagtacatt tcatagtgga tggcggcgtt agtatcgaat    780
cgacagcagt atagcgacca gcattcacat acgattgacg catgatatta ctttctgcgc    840
acttaacttc gcatctgggc agatgatgtc gaggcgaaaa aaaatataaa tcacgctaac    900
atttgattaa aatagaacaa ctacaatata aaaaaactat acaaatgaca agttcttgaa    960
aacaagaatc ttttattgt cagtactgat tagaaaaact catcgagcat caaatgaaac     1020
tgcaatttat tcatatcagg attatcaata ccatattttt gaaaaagccg tttctgtaat    1080
gaaggagaaa actcaccgag gcagttccat aggatggcaa gatcctggta tcggtctgcg    1140
attccgactc gtccaacatc aatacaacct attaatttcc cctcgtcaaa ataaggtta    1200 tcaagtgaga atcaccatg agtgacgact gaatccggtg agaatggcaa agcttatgc     1260 atttctttcc agacttgttc aacaggccag ccattacgct cgtcatcaaa atcactcgca    1320
tcaaccaaac cgttattcat tcgtgattgc gcctgagcga gacgaaatac gcgatcgctg    1380
ttaaaaggac aattacaaac aggaatcgaa tgcaaccggc gcaggaacac tgccagcgca    1440
tcaacaatat tttcacctga atcaggatat tcttctaata cctggaatgc tgttttgccg    1500
gggatcgcag tggtgagtaa ccatgcatca tcaggagtac ggataaaatg cttgatggtc    1560
ggaagaggca taaattccgt cagccagttt agtctgacca tctcatctgt aacatcattg    1620
```

```
gcaacgctac ctttgccatg tttcagaaac aactctggcg catcgggctt cccatacaat    1680
cgatagattg tcgcacctga ttgcccgaca ttatcgcgag cccatttata cccatataaa    1740
tcagcatcca tgttggaatt taatcgcggc ctcgaaacgt gagtcttttc cttacccatg    1800
gttgtttatg ttcggatgtg atgtgagaac tgtatcctag caagattta aaaggaagta    1860 tatgaaagaa gaacctcagt ggcaaatcct aacctttat atttctctac aggggcgcgg    1920
cgtggggaca attcaacgcg tctgtgaggg gagcgtttcc ctgctcgcag gtctgcagcg    1980
aggagccgta atttttgctt cgcgccgtgc ggccatcaaa atgtatggat gcaaatgatt    2040
atacatgggg atgtatgggc taaatgtacg ggcgacagtc acatcatgcc cctgagctgc    2100
gcacgtcaag actgtcaagg agggtattct gggcctccat gtcgctggcc gggtgacccg    2160
gcggggacga ggcaagctaa acagatctga tcttgaaact gagtaagatg ctcagaatac    2220
ccgtcaagat aagagtataa tgtagagtaa tataccaagt attcagcata ttctcctctt    2280
cttttgtata aatcacggaa gggatgattt ataagaaaaa tgaatactat tacacttcat    2340
ttaccaccct ctgatctaga ttttccaacg atatgtacg agtggtataa ggtgaggggg    2400
tccacagata taacatcgtt taatttagta ctaacagaga cttttgtcac aactacatat    2460
aagtgtacaa atatagtaca gatatgacac acttgtagcg ccaacgcgca tcctacggat    2520
tgctgacaga aaaaaggtc acgtgaccag aaaagtcacg tgtaattttg taactcaccg    2580
cattctagcg gtccctgtcg tgcacactgc actcaacacc ataaaccttta gcaacctcca    2640 aaggaaatca ccgtataaca aagccacagt tttacaactt agtctcttat gaagttactt    2700
accaatgaga aatagaggct ctttctcgag aaatatgaat atggatatat atatatatat    2760
atatatatat atatatatat gtaaacttgg ttcttttta gcttgtgatc tctagcttgg    2820
gtctctctct gtcgtaacag ttgtgatatc ggaagaagag aaaagacgaa gagcagaagc    2880
ggaaaacgta tacacgtcac atatcacaca cacacaatgg gaaagctatt acaattggca    2940
ttgcatccgg tcgagatgaa ggcagctttg aagctgaagt tttgcagaac accgctattc    3000
tccatctatg atcagtccac gtctccatat ctcttgcact gtttcgaact gttgaacttg    3060
acctccagat cgtttgctgc tgtgatcaga gagctgcatc cagaattgag aaactgtgtt    3120
actctctttt atttgatttt aagggctttg gataccatcg aagacgatat gtccatcgaa    3180
cacgatttga aaattgactt gttgcgtcac ttccacgaga aattgttgtt aactaaatgg    3240
agtttcgacg gaaatgcccc cgatgtgaag gacagagccg ttttgacaga tttcgaatcg    3300
attcttattg aattccacaa attgaaacca gaatatcaag aagtcatcaa ggagatcacc    3360
gagaaaatgg gtaatggtat ggccgactac atcttagatg aaaattacaa cttgaatggg    3420
ttgcaaaccg tccacgacta cgacgtgtac tgtcactacg tagctggttt ggtcggtgat    3480
ggtttgaccc gtttgattgt cattgccaag tttgccaacg aatctttgta ttctaatgag    3540
caattgtatg aaagcatggg tctttttccta caaaaaacca acatcatcag agattacaat    3600
gaagatttgg tcgatggtag atccttctgg cccaaggaaa tctggtcaca atacgctcct    3660
cagttgaagg acttcatgaa acctgaaaac gaacaactgg ggttggactg tataaaccac    3720
ctcgtcttaa acgcattgag tcatgttatc gatgtgttga cttatttggc cggtatccac    3780
gagcaatcca ctttccaatt ttgtgccatt ccccaagtta tggccattgc aaccttggct    3840
ttggtattca acaaccgtga agtgctacat ggcaatgtaa agattcgtaa gggtactacc    3900
tgctatttaa ttttgaaatc aaggactttg cgtggctgtg tcgagatttt tgactattac    3960
ttacgtgata tcaaatctaa attggctgtg caagatccaa atttcttaaa attgaacatt    4020
```

```
caaatctcca agatcgaaca gtttatggaa gaaatgtacc aggataaatt acctcctaac    4080
gtgaagccaa atgaaactcc aatttcttg aaagttaaag aaagatccag atacgatgat     4140
gaattggttc caacccaaca agaagaagag tacaagttca atatggtttt atctatcatc    4200
ttgtccgttc ttcttgggtt ttattatata tacactttac acagagcgtg aagtctgcgc    4260
caaataacat aaacaaacaa ctccgaacaa taactaagta cttacataat aggtagaggc    4320
ctatccttaa agataacctt atatttcatt acatcaacta attcgacctt attatctttc    4380
gaattgaaat gcattatacc catcggtacg tctagctttg tcaccttccc cagtaaacgc    4440
tgtttcttgc cgacaaacaa tgtggccctc tctccgtcaa tctgtaacga cccaaatcgt    4500
attaaagttt cgccgtcctg ttcactgaac cttccctcat ttggagaatc tctcctcgcc    4560
agcgacgcaa agtccttagg caactctagt tcaccttgaa tctccagcat catcatccca    4620
agcggtgtta tcaccgtggt ctgcttttct cttgactgtg tcaacttctg ccattgacta    4680
gcatctatat ctacactagg cattcttttc agctgtttat tgggctgaat gatagtgata    4740 attcttttt ctatcactcc tttggctata ttagtggtta gcttactaaa aaagattaaa     4800
ggaaaaatga aattcaagat gctaacgttg acatgtatat tttaagaaaa caaaaatcat    4860
acaaagagga gatcggatat aaaagaataa cataaatatg tttagtgcat taggtaaatg    4920
ggtccgaggc tctcgcaatg ataaggactt tgtgacgaag tataccgcag atttatcaca    4980
aataacttca cagatccatc aattagatgt cgcgttaaag aaaagccaat ccatcttgag    5040
tcaatggcaa tcaaatctga ccttttatgg tattgcgtta acggtattgg ccctgagcta    5100
cacatattgg gagtaccatg gttatcgacc ataccttgtg gtgactgcgc tactatgcat    5160
aggctcgcta atcttgttca aatgggcatt aaccaaactc tatgcatttt ataacaacaa    5220
taggttacgc aagttggcaa aactccgtgc a                                   5251

<210> SEQ ID NO 15
<211> LENGTH: 70
<212> TYPE: DNA
<213> ORGANISM: Artificial Sequence
<220> FEATURE:
<223> OTHER INFORMATION: Synthetic: Primer 61-67-CPK066-G

<400> SEQUENCE: 15
ggtaagacgg ttgggtttta tcttttgcag ttggtactat taagaacaat cacaggaaac      60
agctatgacc                                                             70

<210> SEQ ID NO 16
<211> LENGTH: 70
<212> TYPE: DNA
<213> ORGANISM: Artificial Sequence
<220> FEATURE:
<223> OTHER INFORMATION: Synthetic: Primer 61-67-CPK067-G

<400> SEQUENCE: 16
ttgcgttttg tactttggtt cgctcaattt tgcaggtaga taatcgaaaa gttgtaaaac      60
gacggccagt                                                             70

<210> SEQ ID NO 17
<211> LENGTH: 4162
<212> TYPE: DNA
<213> ORGANISM: Artificial Sequence
<220> FEATURE:
<223> OTHER INFORMATION: Synthetic: Integration construct i32
```

```
<400> SEQUENCE: 17
gcctgtctac aggataaaga cgggtcggat acctgcacaa gcaatttggc acctgcatac      60
cccatttccc cagtagataa cttcaacaca cacatcaatg tccctcacca gtttatttcc     120
aaaagagacg cttttactcta cctgactaga ttttcatttt gtttcttttg gattgcgctt     180
gcctttgtag gtgtgtcgtt tatcctttac gttttgactt ggtgctcgaa gatgctttca     240
gagatggtgc ttatcctcat gtctttggg tttgtcttca atacggcagc cgttgtcttg      300
caaacggccg cctctgccat ggcaaagaat gctttccatg acgatcatcg tagtgcccaa     360
ttgggtgcct ctatgatggg tatggcttgg gcaagtgtct ttttatgtat cgtggaattt     420
atcctgctgg tcttctggtc tgttagggca aggttggcct ctacttactc catcgacaat     480
tcaagataca gaacctcctc cagatggaat cccttccata gagagaagga gcaagcaact     540
gacccaatat tgactgccac tggacctgaa gacatgcaac aaagtgcaag catagtgggg     600
ccttcttcca atgctaatcc ggtcactgcc actgctgcta cggaaaacca acctaaaggt     660
attaacttct tcactataag aaaatcacac gagcgcccgg acgatgtctc tgtttaaatg     720
gcgcaagttt tccgctttgt aatatatatt tatacccctt tcttctctcc cctgcaatat     780
aatagtttaa ttctaatatt aataatatcc tatattttct tcatttaccg gcgcactctc     840
gcccgaacga cctcaaaatg tctgctacat tcataataac caaaagctca taactttttt     900
ttttgaacct gaatatatat acatcacata tcactgctgg tccttgccga ccagcgtata     960
caatctcgat agttggtttc ccgttctttc cactcccgtc cacaggaaac agctatgacc    1020
atgattacgc caagctattt aggtgacact atagaatact caagctatgc atcaagcttg    1080
gtaccgagct cggatccact agtaacggcc gccagtgtgc tggaattcgc cctgtcgaca    1140
ctagtaatac acatcatcgt cctacaagtt catcaaagtg ttggacagac aactatacca    1200
gcatggatct cttgtatcgg ttcttttctc ccgctctctc gcaataacaa tgaacactgg    1260
gtcaatcata gcctacacag gtgaacagag tagcgtttat acagggttta tacggtgatt    1320
cctacggcaa aaattttcta tttctaaaaa aaaaagaaa aattttctt tccaacgcta     1380 gaaggaaaag aaaaatctaa ttaaattgat ttggtgattt tctgagagtt cccttttca     1440 tatatcgaat tttgaatata aaaggagatc gaaaaaattt ttctattcaa tctgttttct    1500 ggttttatt gatagttttt ttgtgtatta ttattatgga ttagtactgg tttatatggg     1560
tttttctgta taacttcttt ttattttagt ttgtttaatc ttattttgag ttacattata    1620
gttccctaac tgcaagagaa gtaacattaa aaatgaaaaa gcctgaactc accgcgacgt    1680
ctgtcgagaa gtttctgatc gaaaagttcg acagcgtctc cgacctgatg cagctctcgg    1740
agggcgaaga atctcgtgct ttcagcttcg atgtaggagg gcgtggatat gtcctgcggg    1800
taaatagctg cgccgatggt ttctacaaag atcgttatgt ttatcggcac tttgcatcgg    1860
ccgcgctccc gattccggaa gtgcttgaca ttggggaatt cagcgagagc ctgacctatt    1920
gcatctcccg ccgtgcacag ggtgtcacgt tgcaagacct gcctgaaacc gaactgcccg    1980
ctgttctgca gccggtcgcg gaggccatgg atgcgatcgc tgcggccgat cttagccaga    2040
cgagcgggtt cggcccattc ggaccgcaag gaatcggtca atacactaca tggcgtgatt    2100
tcatatgcgc gattgctgat ccccatgtgt atcactggca aactgtgatg gacgacaccg    2160
tcagtgcgtc cgtcgcgcag gctctcgatg agctgatgct ttgggccgag gactgccccg    2220
aagtccggca cctcgtgcac gcggatttcg gctccaacaa tgtcctgacg gacaatggcc    2280
gcataacagc ggtcattgac tggagcgagg cgatgttcgg ggattcccaa tacgaggtcg    2340
```

```
ccaacatctt cttctggagg ccgtggttgg cttgtatgga gcagcagacg cgctacttcg    2400
agcggaggca tccggagctt gcaggatcgc cgcggctccg ggcgtatatg ctccgcattg    2460
gtcttgacca actctatcag agcttggttg acggcaattt cgatgatgca gcttgggcgc    2520
agggtcgatg cgacgcaatc gtccgatccg gagccggact gtcgggcgt acacaaatcg     2580 cccgcagaag cgcggccgtc tggaccgatg gctgtgtaga agtactcgcc gatagtggaa    2640
accgacgccc cagcactcgt ccgagggcaa aggaataggt ttaacttgat actactagat    2700 ttttctctt catttataaa attttggtt ataattgaag ctttagaagt atgaaaaaat      2760 ccttttttt cattctttgc aaccaaaata agaagcttct tttattcatt gaatgatga     2820 atataaacct aacaaagaa aaagactcga atatcaaaca ttaaaaaaa ataaagagg       2880 ttatctgttt tcccatttag ttggagtttg cattttctaa tagatagaac tctcaattaa    2940
tgtggattta gtttctctgt tcgttttttt ttgttttgtt ctcactgtat ttacatttct    3000
atttagtatt tagttattca tataatctta acttctcgag gagctctaag ggcgaattct    3060
gcagatatcc atcacactgg cggccgctcg agcatgcatc tagagggccc aattcgccct    3120
atagtgagtc gtattacaat tcactggccg tcgttttaca acaagcatct tgccctgtgc    3180
ttggccccca gtgcagcgaa cgttataaaa acgaatactg agtatatatc tatgtaaaac    3240
aaccatatca tttcttgttc tgaactttgt ttacctaact agttttaaat ttccttttt    3300 cgtgcatgcg ggtgttctta tttattagca tactacattt gaaatatcaa atttccttag    3360
tagaaaagtg agagaaggtg cactgacaca aaaaataaaa tgctacgtat aactgtcaaa    3420
actttgcagc agcgggcatc cttccatcat agcttcaaac atattagcgt tcctgatctt    3480
catacccgtg ctcaaaatga tcaaacaaac tgttattgcc aagaaataaa cgcaaggctg    3540
ccttcaaaaa ctgatccatt agatcctcat atcaagcttc ctcatagaac gcccaattac    3600
aataagcatg ttttgctgtt atcaccgggt gataggtttg ctcaaccatg gaaggtagca    3660
tggaatcata atttggatac taatacaaat cggccatata atgccattag taaattgcgc    3720
tcccatttag gtggttctcc aggaatacta ataaatgcgg tgcatttgca aaatgaattt    3780
attccaaggc caaaacaaca cgatgaatgg ctttatttt ttgttattcc tgacatgaag     3840
ctttatgtaa ttaaggaaac ggacatcgag gaatttgcat cttttttaga tgaaggagct    3900
attcaagcac caaagctatc cttccaggat tatttaagcg gtaaggccaa ggcttcccaa    3960
caggttcatg aagtgcatca tagaaagctt acaaggtttc agggtgaaac ttttctaaga    4020
gattggaact tagtctgtgg gcattataag agagatgcta agtgtggaga aatgggaccc    4080
gacataattg cagcatttca agatgaaaag cttttttcctg agaataatct agccttaatt   4140
tctcatattg ggggtcatat tt                                             4162
```

<210> SEQ ID NO 18
<211> LENGTH: 7879
<212> TYPE: DNA
<213> ORGANISM: Artificial Sequence
<220> FEATURE:
<223> OTHER INFORMATION: Synthetic: Integration construct i33
<220> FEATURE:
<221> NAME/KEY: misc_feature
<222> LOCATION: (270)..(270)
<223> OTHER INFORMATION: n is a, c, g, or t

<400> SEQUENCE: 18

```
atgaattggc cagtttttc caattatgga acgcctgttc ctgatccacg gcctgcactt     60
```

-continued

```
gcgaccacaa ttccacacct gaggcgcctg cctctttcc agcatgtggc aactgtcccc      120
acgacagggc atcccagaat cctctggtaa atcttaaatg aaactgacgc gtggcagtag      180
attccaacaa tggtgggatg gcccgtggga aagtcgtgta gtgctcatac gcatcatatg      240
acatggatga tacggccggg tcaaacggtn cgattgcagt tggaatgcaa atgagagtag      300
cagatcattg ttgggcagcg gcttcaacac cagtgcttcg tcgtacggat accataaact      360
gtcatttata ccaatctgcg acaccgtgtc ttctgcgaac acacccagca gtagagtgcc      420
cagcatgaaa taggccagtg tgaggatcat cgtcgtcttg cctatgcttt gtttgctttg      480
aacacttgtt tccgctctcc ttttacttat tggctactaa aactacgtgt aaagatcgc      540
ccagcgcaaa aaggtccggc ggtttcaaat aatctcgaac tattcctata atatgcaaaa      600
tagtaggtag gaacaagtca actctaggca gataacgaag atgtccggta aatgagagact     660
agtgctgact gggataggca atccagagcc tcagtacgct ggcacccgtc acaatgtagg      720
gctatatatg ctggagctgc tacgaaagcg gcttggtctg caggggagaa cttattcccc      780
tgtgcctaat acgggcggca aagtgcatta tatagaagac gaacattgta cgatactaag      840
atcggatggc cagtacatga atctaagtgg agaacaggtg tgcaaggtct gggcccggta      900
cgccaagtac caagcccgac acgttgttat tcatgacgag ttaagtgtgg cgtgtggaaa      960
agtgcagctc agagccccca gcaccagtat tagaggtcat aatgggctgc gaagcctgct     1020
aaaatgcagt ggaggccgtg tacccttgc caaattgggct attggaatcg gcagagaacc     1080
tgggtcccgt tctagagacc ctgcgagcgt gtcccggtgg gttctgggag ctctaactcc     1140
gcaggaacta caaaccttgc ttacacagag tgaacctgct gcctggcgtg ctctgactca     1200
gtacatttca taggacagca ttcgcccagt attttttta ttctacaaac cttctataat      1260
ttcaaagtat ttacataatt ctgtatcagt ttaatcacca taatatcgtt ttctttgttt      1320
agtgcaatta attttttccta ttgttacttc gggcctttt ctgtttatg agctattttt      1380
tccgtcatcc ttccggatcc agattttcag cttcatctcc agattgtgtc tacgtaatgc     1440
acgccatcat tttaagagag acagagaag caagcctcct gaaagatgaa gctactgtct     1500
tctatcgaac aagcatgcga tatttgccga cttaaaaagc tcaagtgctc caagaaaaaa     1560
ccgaagtgcg ccaagtgtct gaagaacaac tgggagtgtc gctactctcc caaaaccaaa     1620
aggtctccgc tgactagggc acatctgaca gaagtggaat caaggctaga aagactggaa     1680
cagctatttc tactgatttt cctcgagaa gaccttgaca tgattttgaa aatggattct      1740
ttacaggata taaagcatt gttaacagga ttatttgtac aagataatgt gaataaagat      1800
gccgtcacag atagattggc ttcagtggag actgatatgc ctctaacatt gagacagcat     1860
agaataagtg cgacatcatc atcggaagag agtagtaaca aggtcaaag acagttgact      1920
gtatcgattg actcggcagc tcatcatgat aactccacaa ttccgttgga ttttatgccc     1980
agggatgctc ttcatggatt tgattggtct gaagaggatg acatgtcgga tggcttgccc     2040
ttcctgaaaa cggaccccaa caataatggg ttctttggcg acggttctct cttatgtatt     2100
cttcgatcta ttggctttaa accggaaaat tacacgaact ctaacgttaa caggctcccg     2160
accatgatta cggatagata cacgttggct tctagatcca caacatcccg tttacttcaa     2220
agttatctca ataattttca cccctactgc cctatcgtgc actcaccgac gctaatgatg     2280
ttgtataata accagattga aatcgcgtcg aaggatcaat ggcaaatcct ttttaactgc     2340
atattagcca ttggagcctg gtgtatagag ggggaatcta ctgatataga tgttttttac     2400
tatcaaaatg ctaaatctca tttgacgagc aaggtcttcg agtcaggttc cataatttg      2460
```

```
gtgacagccc tacatcttct gtcgcgatat acacagtgga ggcagaaaac aaatactagc    2520
tataattttc acagcttttc cataagaatg gccatatcat tgggcttgaa tagggacctc    2580
ccctcgtcct tcagtgatag cagcattctg gaacaaagac gccgaatttg gtggtctgtc    2640
tactcttggg agatccaatt gtccctgctt tatggtcgat ccatccagct ttctcagaat    2700
acaatctcct tcccttcttc tgtcgacgat gtgcagcgta ccacaacagg tcccaccata    2760
tatcatggca tcattgaaac agcaaggctc ttacaagttt tcacaaaaat ctatgaacta    2820
gacaaaacag taactgcaga aaaagtcct atatgtgcaa aaaatgctt gatgatttgt    2880 aatgagattg aggaggtttc gagacaggca ccaaagtttt tacaaatgga tatttccacc    2940
accgctctaa ccaatttgtt gaaggaacac ccttggctat cctttacaag attcgaactg    3000
aagtggaaac agttgtctct tatcatttat gtattaagag atttttttcac taattttacc    3060 cagaaaaagt cacaactaga acaggatcaa aatgatcatc aaagttatga agttaaacga    3120
tgctccatca tgttaagcga tgcagcacaa agaactgtta tgtctgtaag tagctatatg    3180
gacaatcata atgtcacccc atattttgcc tggaattgtt cttattactt gttcaatgca    3240
gtcctagtac cctaaaagac tctactctca aactcaaaat cgaatgctga gaataacgag    3300
accgcacaat tattacaaca aattaacact gttctgatgc tattaaaaaa actggccact    3360
tttaaaatcc agacttgtga aaaatacatt caagtactgg aagaggtatg tgcgccgttt    3420
ctgttatcac agtgtgcaat cccattaccg catatcagtt ataacaatag taatggtagc    3480
gccattaaaa atattgtcgg ttctgcaact atcgcccaat accctactct tccggaggaa    3540
aatgtcaaca atatcagtgt taaatatgtt tctcctggct cagtagggcc ttcacctgtg    3600
ccattgaaat caggagcaag tttcagtgat ctagtcaagc tgttatctaa ccgtccaccc    3660
tctcgtaact ctccagtgac aataccaaga agcacacctt cgcatcgctc agtcacgcct    3720
tttctagggc aacagcaaca gctgcaatca ttagtgccac tgaccccgtc tgctttgttt    3780
ggtggcgcca attttaatca aagtgggaat attgctgata gctcattgtc cttcactttc    3840
actaacagta gcaacggtcc gaacctcata acaactcaaa caaattctca agcgctttca    3900
caaccaattg cctcctctaa cgttcatgat aacttcatga ataatgaaat cacggctagt    3960
aaaattgatg atggtaataa ttcaaaacca ctgtcacctg gttggacgga ccaaactgcg    4020
tataacgcgt ttggaatcac tacagggatg tttaatacca ctacaatgga tgatgtatat    4080
aactatctat tcgatgatga agatacccca ccaaacccaa aaaaagagta aaatgaatcg    4140
tagatactga aaaccccgc aagttcactt caactgtgca tcgtgcacca tctcaatttc    4200
tttcatttat acatcgtttt gccttctttt atgtaactat actcctctaa gtttcaatct    4260
tggccatgta acctctgatc tatagaattt ttttaaatgac tagaattaat gcccatcttt    4320
tttttggacc taaattcttc atgaaaatat attacgaggg cttattcaga agcttcgctc    4380
agtcgacact agtaatacac atcatcgtcc tacaagttca tcaaagtgtt ggacagacaa    4440
ctataccagc atggatctct tgtatcggtt cttttctccc gctctctcgc aataacaatg    4500
aacactgggt caatcatagc ctacacaggt gaacagagta gcgtttatac agggtttata    4560
cggtgattcc tacggcaaaa attttttcatt tctaaaaaaa aaagaaaaa ttttttctttc    4620 caacgctaga aggaaaagaa aaatctaatt aaattgattt ggtgattttc tgagagttcc    4680 cttttttcata tatcgaattt tgaatataaa aggagatcga aaaaatttt ctattcaatc    4740 tgttttctgg ttttatttga tagttttttt gtgtattatt attatggatt agtactggtt    4800
```

```
tatatgggtt tttctgtata acttcttttt attttagttt gtttaatctt attttgagtt    4860
acattatagt tccctaactg caagagaagt aacattaaaa atgaccactc ttgacgacac    4920
ggcttaccgg taccgcacca gtgtcccggg ggacgccgag gccatcgagg cactggatgg    4980
gtccttcacc accgcacacg tcttccgcgt caccgccacc ggggacggct tcaccctgcg    5040
ggaggtgccg gtggacccgc ccctgaccaa ggtgttcccc gacgacgaat cggacgacga    5100
atcggacgcc ggggaggacg gcgacccgga ctcccggacg ttcgtcgcgt acggggacga    5160
cggcgacctg gcgggcttcg tggtcgtctc gtactccggc tggaaccgcc ggctgaccgt    5220
cgaggacatc gaggtcgccc cggagcaccg ggggcacggg gtcgggcgcg cgttgatggg    5280
gctcgcgacg gagttcgccc gcgagcgggg cgccgggcac ctctggctgg aggtcaccaa    5340
cgtcaacgca ccggcgatcc acgcgtaccg gcggatgggg ttcaccctct gcggcctgga    5400
caccgccctg tacgacggca ccgcctcgga cggcgagcag gcgctctaca tgagcatgcc    5460
ctgcccctga gtttaacttg atactactag atttttttctc ttcatttata aaattttttgg   5520 ttataattga agctttagaa gtatgaaaaa atccttttttt ttcattcttt gcaaccaaaa    5580
taagaagctt cttttattca ttgaaatgat gaatataaac ctaacaaaag aaaaagactc    5640
gaatatcaaa cattaaaaaa aaataaaaga ggttatctgt tttcccattt agttggagtt    5700
tgcattttct aatagataga actctcaatt aatgtggatt tagtttctct gttcgttttt    5760
ttttgttttg ttctcactgt atttacattt ctatttagta tttagttatt catataatct    5820
taacttctcg aggagctcga tcttgaaact gagtaagatg ctcagaatac ccgtcaagat    5880
aagagtataa tgtagagtaa tataccaagt attcagcata ttctcctctt cttttgtata    5940
aatcacggaa gggatgattt ataagaaaaa tgaatactat tacacttcat ttaccaccct    6000
ctgatctaga ttttccaacg atatgtacgt agtggtataa ggtgaggggg tccacagata    6060
taacatcgtt taatttagta ctaacagaga cttttgtcac aactacatat aagtgtacaa    6120
atatagtaca gatatgacac acttgtagcg ccaacgcgca tcctacggat tgctgacaga    6180
aaaaaaggtc acgtgaccag aaaagtcacg tgtaattttg taactcaccg cattctagcg    6240
gtccctgtcg tgcacactgc actcaacacc ataaaccttta gcaacctcca aaggaaatca    6300
ccgtataaca aagccacagt tttacaactt agtctcttat gaagtgtctc tctctgtcgt    6360
aacagttgtg atatcggaag aagagaaaag acgaagagca gaagcggaaa acgtatacac    6420
gtcacatatc acacacacac aatgggaaag ctattacaat tggcattgca tccggtcgag    6480
atgaaggcag ctttgaagct gaagttttgc agaacaccgc tattctccat ctatgatcag    6540
tccacgtctc catatctctt gcactgtttc gaactgttga acttgacctc cagatcgttt    6600
gctgctgtga tcagagagct gcatccagaa ttgagaaact gtgttactct cttttatttg    6660
attttaaggg ctttggatac catcgaagac gatatgtcca tcgaacacga tttgaaaatt    6720
gacttgttgc gtcacttcca cgagaaattg ttgttaacta atggagtttt cgacggaaat    6780
gcccccgatg tgaaggacag agccgttttg acagatttcg aatcgattct tattgaattc    6840
cacaaattga aaccagaata tcaagaagtc atcaaggaga tcaccgagaa aatgggtaat    6900
ggtatggccg actacatctt ggatgaaaat tacaacttga atgggttgca aaccgtccac    6960
gactacgacg tgtactgtca ctacgtagct ggtttggtcg gtgatggttt gacccgtttg    7020
attgtcattg ccaagtttgc caacgaatct ttgtattcta atgagcaatt gtatgaaagc    7080
atgggtcttt tcctacaaaa aaccaacatc atcagagact acaatgaaga tttggtcgat    7140
ggtagatcct tctggcccaa ggaaatctgg tcacaatacg ctcctcagtt gaaggacttc    7200
```

```
atgaaacctg aaaacgaaca actggggttg gactgtataa accacctcgt cttaaacgca    7260
ttgagtcatg ttatcgatgt gttgacttat ttggccagta tccacgagca atccactttc    7320
caattttgtg ccattcccca agttatggcc attgcaacct tggctttggt attcaacaac    7380
cgtgaagtgc tacatggcaa tgtaaagatt cgtaagggta ctacctgcta tttaattttg    7440
aaatcaagga ctttgcgtgg ctgtgtcgag attttgact attacttacg tgatatcaaa    7500
tctaaattgg ctgtgcaaga tccaaatttc ttaaaattga acattcaaat ctccaagatc    7560
gaacaattca tggaagaaat gtaccaggat aaattacctc ctaacgtgaa gccaaatgaa    7620
actccaattt tcttgaaagt taagaaaaga tccagatacg atgatgaatt ggtcccaacc    7680
caacaagaag aagagtacaa gttcaatatg gttttatcta tcatcttgtc cgttcttctt    7740
gggttttatt atatatacac tttcacagga gcgtgaagtc tgcgccaaat aacataaaca    7800
aacaactccg aacaataact aagtacttac ataataggta gaggcctatc cttaaagata    7860
accttatatt tcattacat                                                 7879
```

```
<210> SEQ ID NO 19
<211> LENGTH: 5714
<212> TYPE: DNA
<213> ORGANISM: Artificial Sequence
<220> FEATURE:
<223> OTHER INFORMATION: Synthetic: Integration construct i37

<400> SEQUENCE: 19
gcctgtctac aggataaaga cgggtcggat acctgcacaa gcaatttggc acctgcatac      60
cccatttccc cagtagataa cttcaacaca cacatcaatg tccctcacca gtttatttcc     120
aaaagagacg cttttttacta cctgactaga ttttcatttt gtttcttttg gattgcgctt    180
gcctttgtag gtgtgtcgtt tatcctttac gttttgactt ggtgctcgaa gatgctttca    240
gagatggtgc ttatcctcat gtcttttggg tttgtcttca atacggcagc cgttgtcttg    300
caaacggccg cctctgccat ggcaaagaat gctttccatg acgatcatcg tagtgcccaa    360
ttgggtgcct ctatgatggg tttaaacgta tggcttgggc aagtgtcttt ttatgtatcg    420
tggaatttat cctgctggtc ttctggtctg ttagggcaag gttggcctct acttactcca    480
tcgacaattc aagatacaga acctcctcca gatggaatcc cttccataga gagaaggagc    540
aagcaactga cccaatattg actgccactg gacctgaaga catgcaacaa agtgcaagca    600
tagtggggcc ttcttccaat gctaatccgg tcactgccac tgctgctacg gaaaaccaac    660
ctaaaggtat taacttcttc actataagaa aatcacacga gcgcccggac gatgtctctg    720
tttaaatggc gcaagttttc cgctttgtaa tatatattta tacccctttc ttctctcccc    780
tgcaatataa tagtttaatt ctaatattaa taatatccta tattttcttc atttaccggc    840
gcactctcgc ccgaacgacc tcaaaatgtc tgctacattc ataataacca aaagctcata    900
acttttttttt ttgaacctga atatatatac atcacatatc actgctggtc ctgagaagtt    960
aagattatat gaataactaa atactaaata gaaatgtaaa tacagtgaga acaaaacaaa    1020
aaaaaacgaa cagagaaact aaatccacat taattgagag ttctatctat tagaaaatgc    1080
aaactccaac taaatgggaa aacagataac ctcttttatt ttttttttaat gtttgatatt    1140
cgagtctttt tcttttgtta ggtttatatt catcatttca atgaataaaa gaagcttctt    1200
atttggttg caaagaatga aaaaaaagga tttttttcata cttctaaagc ttcaattata    1260
accaaaaatt ttataaatga agagaaaaaa tctagtagta tcaagttaaa cttagaaaaa    1320
```

```
ctcatcgagc atcaaatgaa actgcaattt attcatatca ggattatcaa taccatattt    1380
ttgaaaaagc cgtttctgta atgaaggaga aaactcaccg aggcagttcc ataggatggc    1440
aagatcctgg tatcggtctg cgattccgac tcgtccaaca tcaatacaac ctattaattt    1500
cccctcgtca aaataaggt tatcaagtga gaaatcacca tgagtgacga ctgaatccgg    1560
tgagaatggc aaaagcttat gcatttcttt ccagacttgt tcaacaggcc agccattacg    1620
ctcgtcatca aaatcactcg catcaaccaa accgttattc attcgtgatt gcgcctgagc    1680
gagacgaaat acgcgatcgc tgttaaaagg acaattacaa acaggaatcg aatgcaaccg    1740
gcgcaggaac actgccagcg catcaacaat atttcacct gaatcaggat attcttctaa    1800
tacctggaat gctgttttgc cggggatcgc agtggtgagt aaccatgcat catcaggagt    1860
acggataaaa tgcttgatgg tcggaagagg cataaattcc gtcagccagt ttagtctgac    1920
catctcatct gtaacatcat tggcaacgct acctttgcca tgtttcagaa acaactctgg    1980
cgcatcgggc ttcccataca atcgatagat tgtcgcacct gattgcccga cattatcgcg    2040
agcccattta tacccatata aatcagcatc catgttggaa tttaatcgcg gcctcgaaac    2100
gtgagtcttt tccttaccca ttttaatgt tacttctctt gcagttaggg aactataatg    2160
taactcaaaa taagattaaa caaactaaaa taaaagaag ttatacagaa aaacccatat    2220
aaaccagtac taatccataa taataataca caaaaaact atcaaataaa accagaaaac    2280
agattgaata gaaaaatttt ttcgatctcc ttttatattc aaaattcgat atatgaaaaa    2340
gggaactctc agaaaatcac caaatcaatt taattagatt tttcttttcc ttctagcgtt    2400
ggaaagaaaa attttctttt tttttttag aaatgaaaaa ttttgccgt aggaatcacc    2460 gtataaaccc tgtataaacg ctactctgtt cacctgtgta ggctatgatt gacccagtgt    2520
tcattgttat tgcgagagag cgggagaaaa gaaccgatac aagagatcca tgctggtata    2580
gttgtctgtc caacactttg atgaacttgt aggacgatga tgtgtattac tagtgtcgac    2640
accatataca tatccatatc taatcttact tatatgttgt ggaaatgtaa agagccccat    2700
tatcttagcc taaaaaaacc ttctcttttgg aactttcagt aatacgctta actgctcatt    2760
gctatattga agtacggatt agaagccgcc gagcgggcga cagccctccg acggaagact    2820
ctcctccgtg cgtcctggtc ttcaccggtc gcgttcctga aacgcagatg tgcctcgcgc    2880
cgcactgctc cgaacaataa agattctaca atactagctt ttatggttat gaagaggaaa    2940
aattggcagt aacctggccc cacaaacctt caaatcaacg aatcaaatta acaaccatag    3000
gataataatg cgattagttt tttagcctta tttctgggt aattaatcag cgaagcgatg    3060
atttttgatc tattaacaga tatataaatg caaaagctgc ataaccactt taactaatac    3120
tttcaacatt ttcggtttgt attacttctt attcaaatgt cataaaagta tcaacaaaaa    3180
attgttaata tacctctata ctttaacgtc aaggagaaaa aactataatg tcattaccgt    3240
tcttaacttc tgcaccggga aaggttatta ttttggtga acactctgct gtgtacaaca    3300
agcctgccgt cgctgctagt gtgtctgcgt tgagaaccta cctgctaata agcgagtcat    3360
ctgcaccaga tactattgaa ttggacttcc cggacattag ctttaatcat aagtggtcca    3420
tcaatgattt caatgccatc accgaggatc aagtaaactc ccaaaaattg gccaaggctc    3480
aacaagccac cgatggcttg tctcaggaac tcgttagtct tttggatccg ttgttagctc    3540
aactatccga atccttccac taccatgcag cgttttgttt cctgtatatg tttgtttgcc    3600
tatgccccca tgccaagaat attaagtttt ctttaaagtc tactttaccc atcggtgctg    3660
ggttgggctc aagcgcctct atttctgtat cactggcctt agctatggcc tacttggggg    3720
```

```
ggttaatagg atctaatgac ttggaaaagc tgtcagaaaa cgataagcat atagtgaatc    3780
aatgggcctt cataggtgaa aagtgtattc acgtaccccc ttcaggaata gataacgctg    3840
tggccactta tggtaatgcc ctgctatttg aaaaagactc acataatgga acaataaaca    3900
caaacaattt taagttctta gatgatttcc cagccattcc aatgatccta acctatacta    3960
gaattccaag gtctacaaaa gatcttgttg ctcgcgttcg tgtgttggtc accgagaaat    4020
ttcctgaagt tatgaagcca attctagatg ccatgggtga atgtgcccta caaggcttag    4080
agatcatgac taagttaagt aaatgtaaag gcaccgatga cgaggctgta gaaactaata    4140
atgaactgta tgaacaacta ttggaattga taagaataaa tcatggactg cttgtctcaa    4200
tcggtgtttc tcatcctgga ttagaactta ttaaaaatct gagcgatgat ttgagaattg    4260
gctccacaaa acttaccggt gctggtggcg gcggttgctc tttgactttg ttacgaagag    4320
acattactca agagcaaatt gacagtttca aaaagaaatt gcaagatgat tttagttacg    4380
agacatttga acagacttg gtgggactg gctgctgttt gttaagcgca aaaaatttga    4440
ataaagatct taaaatcaaa tccctagtat tccaattatt tgaaaataaa actaccacaa    4500
agcaacaaat tgacgatcta ttattgccag gaaacacgaa tttaccatgg acttcataag    4560
ctaatttgcg ataggcatta tttattagtt gtttttaatc ttaactgtgt atgaagtttt    4620
atgtaataaa gatagaaaga gaaacaaaaa aaaattttc gtagtatcaa ttcagctttc    4680
gaagacagaa tgaaatttaa gcagaccatc atcttgccct gtgcttggcc cccagtgcag    4740
cgaacgttat aaaaacgaat actgagtata tatctatgta aaacaaccat atcatttctt    4800
gttctgaact ttgtttacct aactagtttt aaatttccct ttttcgtgca tgcgggtgtt    4860
cttatttatt agcatactac atttgaaata tcaaatttcc ttagtagaaa agtgagagaa    4920
ggtgcactga cacaaaaaat aaaatgctac gtataactgt caaaactttg cagcagcggg    4980
catccttcca tcatagcttc aaacatatta gcgttcctga tcttcatacc cgtgctcaaa    5040
atgatcaaac aaactgttat tgccaagaaa taaacgcaag gctgccttca aaaactgatc    5100
cattagatcc tcatatcaag cttcctcata gaacgcccaa ttacaataag catgttttgc    5160
tgttatcacc gggtgatagg tttgctcaac catggaaggt agcatggaat cataatttgg    5220
atactaatac aaatcggcca tataatgcca ttagtaaatt gcgctcccat ttaggtggtt    5280
ctccaggcaa atttgaatac taataaatgc ggtgcatttg caaatgaat ttattccaag    5340 gccaaaacaa cacgatgaat ggctttattt ttttgttatt cctgacatga agctttatgt    5400
aattaaggaa acggacatcg aggaatttgc atcttttta gatgaaggag ctattcaagc    5460
accaaagcta tccttccagg attatttaag cggtaaggcc aaggcttccc aacaggttca    5520
tgaagtgcat catagaaagc ttacaaggtt tcagggtgaa acttttctaa gagattggaa    5580
cttagtctgt gggcattata agagagatgc taagtgtgga gaaatgggac ccgacataat    5640
tgcagcattt caagatgaaa agcttttttcc tgagaataat ctagccttaa tttctcatat    5700
tgggggtcat attt                                                      5714
```

<210> SEQ ID NO 20
<211> LENGTH: 7688
<212> TYPE: DNA
<213> ORGANISM: Artificial Sequence
<220> FEATURE:
<223> OTHER INFORMATION: Synthetic: Integration construct i301

<400> SEQUENCE: 20

-continued

```
gacggcacgg ccacgcgttt aaaccgccga gctattcgcg aacattcta gctcgtttgc    60 atcttcttgc atttggtagg ttttcaatag ttcggtaata ttaacggata cctactatta   120
tcccctagta ggctcttttc acggagaaat tcgggagtgt ttttttttccg tgcgcatttt   180 cttagctata ttcttccagc ttcgcctgct gcccggtcat cgttcctgtc acgtagtttt   240
tccggattcg tccggctcat ataataccgc aataaacacg gaatatctcg ttccgcggat   300
tcggttaaac tctcggtcgc ggattatcac agagaaagct tcgtggagaa ttttccaga    360 ttttccgctt tccccgatgt tggtatttcc ggaggtcatt atactgaccg ccattataat   420
gactgtacaa cgaccttctg gagaaagaaa caactcaata acgatgtggg acattggggg   480
cccactcaaa aaatctgggg actatatccc cagagaattt ctccagaaga aagaaaagt    540 caaagttttt tttcgcttgg gggttgcata taaagctcac acgcggccag ggggagccat   600
gaaaaagcct gaactcaccg cgacgtctgt cgagaagttt ctgatcgaaa agttcgacag   660
cgtctccgac ctgatgcagc tctcggaggg cgaagaatct cgtgctttca gcttcgatgt   720
aggagggcgt ggatatgtcc tgcgggtaaa tagctgcgcc gatggtttct acaaagatcg   780
ttatgtttat cggcactttg catcggccgc gctcccgatt ccggaagtgc ttgacattgg   840
ggaattcagc gagagcctga cctattgcat ctcccgccgt gcacagggtg tcacgttgca   900
agacctgcct gaaaccgaac tgcccgctgt tctgcagccg gtcgcggagg ccatggatgc   960
gatcgctgcg gccgatctta gccagacgag cgggttcggc ccattcggac cgcaaggaat  1020
cggtcaatac actacatggc gtgatttcat atgcgcgatt gctgatcccc atgtgtatca  1080
ctggcaaact gtgatggacg acaccgtcag tgcgtccgtc gcgcaggctc tcgatgagct  1140
gatgctttgg gccgaggact gccccgaagt ccggcacctc gtgcacgcgg atttcggctc  1200
caacaatgtc ctgacggaca atggccgcat aacagcggtc attgactgga gcgaggcgat  1260
gttcggggat tcccaatacg aggtcgccaa catcttcttc tggaggccgt ggttggcttg  1320
tatggagcag cagacgcgct acttcgagcg gaggcatccg gagcttgcag atcgccgcg    1380 gctccgggcg tatatgctcc gcattggtct tgaccaactc tatcagagct tggttgacgg  1440
caatttcgat gatgcagctt gggcgcaggg tcgatgcgac gcaatcgtcc gatccggagc  1500
cgggactgtc gggcgtacac aaatcgcccg cagaagcgcg gccgtctgga ccgatggctg  1560
tgtagaagta ctcgccgata gtggaaaccg acgcccagc actcgtccga gggcaaagga   1620
atagcgctcg tccaacgccg gcggacctcg ctcgtccaac gccggcggac tcttttaat    1680 tctgctgtaa cccgtacatg cccaaaatag ggggcgggtt acacagaata tataacatcg  1740
taggtgtctg ggtgaacagt ttattcctgg catccactaa atataatgga gcccgctttt  1800
taagctggca tccagaaaaa aaagaatcc cagcaccaaa atattgtttt cttcaccaac    1860
catcagttca taggtccatt tcttagcgc aactacagag aacaggggca caaacaggca   1920
aaaaacgggc acaacctcaa tggagtgatg caacctgcct ggagtaaatg atgcacaag    1980 gcaattgacc cacgcatgta tctatctcat tttcttacac cttctattac cttctgctct  2040
ctctgatttg gaaaaagctg aaaaaaaagg ttgaaaccag ttccctgaaa ttattcccct   2100
acttgactaa taagtatata aagacggtag gtattgattg taattctgta aatctatttc   2160
ttaaacttct taaattctac ttttatagtt agtcttttt ttagttttaa aacaccaaga    2220
acttagtttc gatccccgcg tgcttggccg gccgtatccc cgcgtgcttg gccggccgta   2280
tgtctcagaa cgtttacatt gtatcgactg ccagaaccc aattggttca ttccaggggt    2340
ctctatcctc caagacagca gtggaattgg gtgctgttgc tttaaaggc gccttggcta    2400
```

```
aggttccaga attggatgca tccaaggatt ttgacgaaat tattttttggt aacgttcttt    2460 ctgccaattt gggccaagct ccggccagac aagttgcttt ggctgccggt ttgagtaatc    2520
atatcgttgc aagcacagtt aacaaggtct gtgcatccgc tatgaaggca atcattttgg    2580
gtgctcaatc catcaaatgt ggtaatgctg atgttgtcgt agctggtggt tgtgaatcta    2640
tgactaacgc accatactac atgccagcag cccgtgcggg tgccaaattt ggccaaactg    2700
ttcttgttga tggtgtcgaa agagatgggt tgaacgatgc gtacgatggt ctagccatgg    2760
gtgtacacgc agaaaagtgt gcccgtgatt gggatattac tagagaacaa caagacaatt    2820
ttgccatcga atcctaccaa aaatctcaaa aatctcaaaa ggaaggtaaa ttcgacaatg    2880
aaattgtacc tgttaccatt aagggattta gaggtaagcc tgatactcaa gtcacgaagg    2940
acgaggaacc tgctagatta cacgttgaaa aattgagatc tgcaaggact gttttccaaa    3000
aagaaaacgg tactgttact gccgctaacg cttctccaat caacgatggt gctgcagccg    3060
tcatcttggt ttccgaaaaa gttttgaagg aaaagaattt gaagcctttg gctattatca    3120
aaggttgggg tgaggccgct catcaaccag ctgattttac atgggctcca tctcttgcag    3180
ttccaaaggc ttttgaaaca tgctggcatc gaagacatca attctgttgat tactttgaat    3240 tcaatgaagc cttttcggtt gtcggtttgg tgaacactaa gattttgaag ctagacccat    3300
ctaaggttaa tgtatatggt ggtgctgttg ctctaggtca cccattgggt tgttctggtg    3360
ctagagtggt tgttacactg ctatccatct tacagcaaga aggaggtaag atcggtgttg    3420
ccgccatttg taatggtggt ggtggtgctt cctctattgt cattgaaaag atatgattac    3480
gttctgcgat tttctcatga tcttttttcat aaaatacata aatatataaa tggctttatg    3540
tataacaggc ataatttaaa gttttatttg cgattcatcg ttttttcaggt actcaaacgc    3600 tgaggtgtgc cttttgactt acttttccgc cttggcaagc tggccgggtg atacttgcac    3660
aagttccact aattactgac atttgtggta ttaactcgtt tgactgctct acaattgtag    3720
gatgttaatc aatgtcttgg ctgcctaacc tgcaggccgc gagcgccgat atgctatgta    3780
atagacaata aaaccatgtt tatataaaaa aaattcaaaa tagaaaacga ttctgtacaa    3840
ggagtatttt tttttttgttc tagtgtgttt atattatcct tggctaagag gcactgcgta    3900
tacttcaagg taccccctgtg ttttgaaaaa aaacaacagt aaaataggaa ctccgcgagg    3960
ttcaggaacc tgaaacaaaa tcaataaaaa cattatatgc gtttcgaaca aaattaaaga    4020
aaaagaataa atatagatta aaaaaaaaaa gaagaaatta aaagaatttc tactaaatcc    4080
caattgttat atatttgtta aatgccaaaa aagtttataa aaaatttaga atgtataaat    4140
aataataaac taagtaacgc gatcgccgac gccgccgata tctccctcgc cagcggccgc    4200
cttatggcta agaatgttgg aattttggcc atggacatct acttcccacc aacttgtgtt    4260
cagcaggagg ctttagaagc acatgacgga gcctcaaagg gtaagtacac aatcggatta    4320
ggacaggatt gcttagcatt ctgcactgaa ttggaggacg tcatctcaat gtctttcaac    4380
gccgtcacct cattgttaga gaagtacaaa atcgacccaa accagatcgg aaggttggaa    4440
gtcggttctg aaaccgtcat cgacaagtct aaatcaatca agactttcgt tatgcagttg    4500
ttcgaaaagt gcggtaatac tgacgtcgag ggtgtagact ctactaacgc ttgttatggt    4560
ggtaccgcag ctttattgaa ctgcgtaaac tgggttgagt caaactcatg ggatggtagg    4620 tacgattag tcatttgcac cgattctgcc gtctacgccg agggtccagc aaggccaacc    4680
ggtggagctg cagctattgc tatgttaatc ggaccagatg cccctatagt cttcgagtct    4740
```

```
aagttgaggg gttcacacat ccctaacgtc tacgacttct acaagccaaa cttggcctca    4800
gagtatccag ttgtcgacgg aaagttatct cagacatgct acttgatggc cttagattca    4860
tgttacaagc acttatgcaa caagttcgaa aagttggagg gaaaggagtt ctcaattaac    4920
gacgccgact acttcgtttt tcactctcca tacaacaaat tggtccagaa gtcattcgcc    4980
aggttattgt acaacgattt tttgagaaac gcatcatcta tcgatgaggc cgccaaggag    5040
aaattcaccc catattcttc tttgtcattg gacgagtctt accagtctag ggacttggag    5100
aaggtatcac agcaattggc taaaaccttc tatgacgcca agttcagcc aaccaccttg     5160 gtccctaaac aggtcggaaa tatgtatact gcatctttgt atgccgcctt tgcctctttg    5220
atccacaaca agcacaacga tttagtcgga aaaagggttg tcatgttttc ttacggtgcc    5280
ggatctactg ccactatgtt ctcattgagg ttatgcgaaa accagtcacc attttcattg    5340
tctaacatcg cctcagtcat ggacgtaggt gtctcacctg agaagttcgt agaaaccatg    5400
aagttgatgg agcacagata cggtgccaaa gaattcgtca cttcaaaaga gggaatcttg    5460
gatttgttgg ccccaggaac ctactatttg aaggaggtcg actctttgta cagaaggttc    5520
tatggaaaga agggagacga cggatctgtc gcaaacggtc agtaaatcgg cggcgtcggc    5580
gatcgcgtta aggcggccgc tggcgaggga gatatttcaa cctgggccta acagtaaaga    5640
tatcctcctc aaaactggtg cacttaatcg ctgaatttgt tctggcttct cttctttttc    5700
tttattcccc ccatgggcca aaaaaaatag tactatcagg aatttggcgc cgggtcacga    5760
tatacgtgta cagtgaccta ggcgacgcca caaggaaaaa ggaaaaaaac agaaaaaaca    5820
acaaaaacta aaacaaacac gaaaacttta atagatctaa gtgaagtagt ggtgaggcaa    5880
ttggagtgac atagcagcta ctacaactac aaaaaaggcg cgccacggtc gtgcggatat    5940
gaaagaggtc gttatagctt ctgccgtcag gaccgccatc ggatcttacg gtaagtcatt    6000 aaggacgtc cctgccgttg atttaggagc caccgcaatt aaagaggccg ttaaaaaggc     6060
aggtataaag ccagaggacg tcaacgaggt catcttggga aatgtcttac aagccggatt    6120
aggtcaaaac ccagcaagac aagcatcatt caaagccggt ttacctgtcg agatacctgc    6180
aatgaccatc aacaaggttt gcggttcagg attaaggacc gtttctttag cagcacagat    6240
cattaaggct ggagatgcag acgttatcat tgctggtggt atggaaaaca tgtcaagagc    6300
cccatacttg gctaataacg ccaggtgggg atataggatg ggaaacgcca agtttgtcga    6360
cgaaatgatt actgacggat tgtgggacgc cttcaatgac tatcacatgg gtataaccgc    6420
agaaaacatt gccgagaggt ggaatatctc aagagaagaa caggatgagt ttgcattggc    6480
ctcacagaaa aaagcagagg aggcaataaa gtcaggtcag tttaaggatg aaatcgtccc    6540
agtcgtcatc aagggaagaa agggtgagac agttgtcgac accgacgaac ccctagatt    6600 tggttcaacc atcgagggat tagcaaagtt gaagccagcc ttcaagaaag acggaaccgt    6660
aaccgccggt aatgcatctg gattgaacga ttgcgcagca gttttggtca taatgtcagc    6720
cgagaaagct aaggagttgg gtgtcaagcc attggcaaaa attgtttcat acggatcagc    6780
cggtgtcgac cctgccatca tgggttacgg accttttttac gccaccaagg ctgcaatcga    6840
aaaggccggt tggaccgtag atgaattgga tttgatcgag tcaaacgagg cctttgccgc    6900
ccaatcattg gctgtcgcca aggacttgaa gttcgacatg aacaaggtca acgtcaacgg    6960
tggtgccatc gcattgggtc accctatcgg agcctctggt gccaggatct tggttacctt    7020
ggtccacgcc atgcagaaga gggacgcaaa gaagggtttg gccaccttgt gcatcggtgg    7080
aggtcaggga acagctatct tgttagagaa atgcagcccc tcagccccc tagcgtcgaa     7140
```

```
taaaagacat tggtacatga tatcaaacag aattttaaca tttcttgatc cagtttgtaa    7200
acaaaacaaa caattttttct accatttaac ttcataccat cggcgagagc cgaacaggaa    7260
aaaaaagaag tctccggtta tcgtaagcag tatcaaataa taagaatgta tgtgtgtgca    7320
atttgttata cccacgaaga agtgcgcagt agagttagaa aaccaactga gtaatcttta    7380
ctcccgacaa tcgtccaata atcctcttgt tgctaggaac gtgatgatgg atttcgtttg    7440
aaatccggac ggaaaactca aaagaagtcc aaccaccaac cattttcgag cctcaagaat    7500
ctctaagcag gtttctttac taaggggatg gcctttctgt cctggacatt ttttccttcc    7560
ttttttcatt tccttgaaag gaacagattt tttttgactt tgccacaca gctgcactat    7620 ctcaacccct tttacatttt aagttttcgg gttgaatggc cggtgtttaa accccagcgc    7680
ctggcggg                                                              7688

<210> SEQ ID NO 21
<211> LENGTH: 5025
<212> TYPE: DNA
<213> ORGANISM: Artificial Sequence
<220> FEATURE:
<223> OTHER INFORMATION: Synthetic: Integration construct i476

<400> SEQUENCE: 21
caggatccga cggcacggcc acgcgtttaa accgcctggg ataggatagt agcaactctt      60
ggaggagagc attgtcagtt gtccagtctc tgaagttaag tagtaagttt gcggagtcaa     120 aggggggatgg cttttgccat ttgtgagagt tgtgcggcag catcttattc aaatagagct     180
gtattctgaa gacctcttgt agaacatcat ccatactaaa aagtaaatcg tcctgtccca     240
ttacgagctg tattagtgct gtgaccctct gtatatttac gttgccatga agaaggtaat     300
gggcgatatt ttgatacaat tcctgagttg catgttggat tgagtttacg aagggtcgcc     360
agacggccag aaacctccag gcggagttaa caactagtaa tacggcatcc atgtttgcat     420
cagcgccgag cctataccag tcactgagta gacgttttct tgctcttttt atgtcctgac     480
ttcttttgac gagggggcat tctctagaga cacaggcagt tgcttccagc aactgccgta     540
cggccgttct catgctgtcg aggatttttt ttggacgat attgtcatta tagggcagtg     600
tgtgacttat gaattgttgt agaaggacgt ctgtgatgtt ggagatatgt attttgttaa     660
ctcttcttga gacgatttgg ccctggatag cgaagcgtgc ggttacaaat aggtcgtctt     720
gttcaagaag gtaggcgagg acattatcta tcagtacaaa catcttagta gtgtctgagg     780
agagggttga ttgtttatgt attttttgcga aatatatata tatatattct acacagatat     840
atacatattt gttttcgggg ctcattcttt cttcttttgcc agaggctcac cgctcaagag     900
gtccgctaat tctggagcga ttgttattgt ttttttcttt cttcttctat cgaaaccca      960 gttttttgatt tgaatgcgag ataaactggt attcttcatt agattctcta ggcccttggt    1020
atctagatat gggttctcga tgttctttgc aaaccaactt tctagtattc ggacattttc    1080
ttttgtaaac cggtgtcctc tgtaaggttt agtactttg tttatcatat cttgagttac    1140
cacattaaat accaacccat ccgccgattt attttttctgt gtaagttgat aattacttct    1200
atcgttttct atgctgcgca tttctttgag taatacagta atggtagtag tgagttgaga    1260
tgttgtttgc aacaacttct tctcctcatc actaatctta cggttttgt tggccctaga    1320 taagaatcct aatatatccc ttaattcaac ttcttcttct gttgttacac tctctggtaa    1380
cttaggtaaa ttacagcaaa tagaaaagag ctttttattt atgtctagta tgctggattt    1440
```

```
aaactcatct gtgatttgtg gatttaaaag gtctttaatg ggtattttat tcatttttc    1500 ttgcttatct tccttttttt cttgcccact tctaagctga tttcaatctc tcctttatat    1560 atattttaa gttccaacat tttatgtttc aaaacattaa tgatgtctgg gttttgtttg     1620
ggatgcaatt tattgcttcc caatgtagaa aagtacatca tatgaaacaa cttaaactct    1680
taactacttc ttttaacctt cacttttat gaaatgtatc aaccatatat aataacttaa     1740
tagacgacat tcacaatatg tttacttcga agcctgcttt caaaattaag aacaaagcat    1800
ccaaatcata cagaaacaca gcggtttcaa aaaagctgaa agaaaaacgt ctagctgagc    1860
atgtgaggcc aagctgcttc aatattattc gaccactcaa gaaagatatc cagattcctg    1920
ttccttcctc tcgatttta aataaaatcc aaattcacag gatagcgtct ggaagtcaaa     1980
atactcagtt tcgacagttc aataagacat ctataaaatc ttcaaagaaa tatttaaact    2040
catttatggc ttttagagca tattactcac agtttggctc cggtgtaaaa caaaatgtct    2100
tgtcttctct gctcgctgaa gaatggcacg cggacaaaat gcagcacgga atatgggact    2160
acttcgcgca acagtataat tttataaacc ctggttttgg ttttgtagag tggttgacga    2220
ataattatgc tgaagtacgt ggtgacggat attgggaaga tgtgtttgta catttggcct    2280
tatagagtgt ggtcgtggcg gaggttgttt atctttcgag tactgaatgt tgtcagtata    2340
gctatcctat ttgaaactcc ccatcgtctt gctcttgttc ccaatgtttg tttatacact    2400
catatggcta tacccttatc tacttgcctc ttttgtttat gtctatgtat ttgtataaaa    2460
tatgatatta ctcagactca agcaaacaat caatgctcac acgcggccag ggggagcctc    2520
gacactagta atacacatca tcgtcctaca agttcatcaa agtgttggac agacaactat    2580
accagcatgg atctcttgta tcggttcttt tctcccgctc tctcgcaata acaatgaaca    2640
ctgggtcaat catagcctac acaggtgaac agagtagcgt ttatacaggg tttatacggt    2700
gattcctacg gcaaaaattt ttcatttcta aaaaaaaaaa gaaaaatttt tctttccaac    2760
gctagaagga aaagaaaaat ctaattaaat tgatttggtg attttctgag agttcccttt    2820
ttcatatatc gaattttgaa tataaaagga gatcgaaaaa attttctat tcaatctgtt     2880 ttctggtttt atttgatagt tttttttgtgt attattatta tggattagta ctggtttata    2940 tgggttttc tgtataactt ctttttattt tagtttgttt aatcttattt tgagttacat     3000
tatagttccc taactgcaag agaagtaaca ttaaaaatga aaaagcctga actcaccgcg    3060
acgtctgtcg agaagtttct gatcgaaaag ttcgacagcg tctccgacct gatgcagctc    3120
tcggagggcg aagaatctcg tgctttcagc ttcgatgtag agggcgtgg atatgtcctg     3180 cgggtaaata gctgcgccga tggtttctac aaagatcgtt atgtttatcg gcactttgca    3240
tcggccgcgc tcccgattcc ggaagtgctt gacattgggg aattcagcga gagcctgacc    3300
tattgcatct cccgccgtgc acagggtgtc acgttgcaag acctgcctga aaccgaactg    3360
cccgctgttc tgcagccggt cgcggaggcc atggatgcga tcgctgcggc cgatcttagc    3420
cagacgagcg ggttcggccc attcggaccg caaggaatcg gtcaatacac tacatggcgt    3480
gatttcatat gcgcgattgc tgatccccat gtgtatcact ggcaaactgt gatggacgac    3540
accgtcagtg cgtccgtcgc gcaggctctc gatgagctga tgctttgggc cgaggactgc    3600
cccgaagtcc ggcacctcgt gcacgcggat ttcggctcca acaatgtcct gacggacaat    3660
ggccgcataa cagcggtcat tgactggagc gaggcgatgt tcggggattc ccaatacgag    3720
gtcgccaaca tcttcttctg gaggccgtgg ttggcttgta tggagcagca gacgcgctac    3780
ttcgagcgga ggcatccgga gcttgcagga tcgccgcggc tccgggcgta tatgctccgc    3840
```

| | |
|---|---:|
| attggtcttg accaactcta tcagagcttg gttgacggca atttcgatga tgcagcttgg | 3900 |
| gcgcagggtc gatgcgacgc aatcgtccga tccggagccg ggactgtcgg gcgtacacaa | 3960 |
| atcgcccgca gaagcgcggc cgtctggacc gatggctgtg tagaagtact cgccgatagt | 4020 |
| ggaaaccgac gccccagcac tcgtccgagg gcaaaggaat aggtttaact tgatactact | 4080 |
| agattttttc tcttcattta taaaattttt ggttataatt gaagctttag aagtatgaaa | 4140 |
| aaatcctttt ttttcattct ttgcaaccaa aataagaagc ttcttttatt cattgaaatg | 4200 |
| atgaatataa acctaacaaa agaaaaagac tcgaatatca acattaaaa aaaaataaaa | 4260 |
| gaggttatct gtttttccat ttagttggag tttgcatttt ctaatagata gaactctcaa | 4320 |
| ttaatgtgga tttagtttct ctgttcgttt ttttttgttt tgttctcact gtatttacat | 4380 |
| ttctatttag tatttagtta ttcatataat cttaacttct cgaggagctc cgctcgtcca | 4440 |
| acgccggcgg acctcggagg ttgtttatct ttcgagtact gaatgttgtc agtatagcta | 4500 |
| tcctatttga aactccccat cgtcttgctc ttgttcccaa tgtttgttta tacactcata | 4560 |
| tggctatacc cttatctact tgcctctttt gtttatgtct atgtatttgt ataaaatatg | 4620 |
| atattactca gactcaagca aacaatcaat tcttagcatc attctttgtt cttatcttaa | 4680 |
| ccataaacga tcttgatgtg acttttgtaa tttgaacgaa ttggctatac gggacggatg | 4740 |
| acaaatgcac cattactcta ggttgttgtt ggatcttaac aaaccgtaaa ggtaaactgc | 4800 |
| ccatgcggtt cacatgactt tgactttcc tttgtttgct agttaccttc ggcttcacaa | 4860 |
| tttgtttttc cacttttcta acaggtttat caccttcaa acttatcttt atcttattcg | 4920 |
| ccttcttggg tgcctccaca gtagaggtta cttccttttt aatatgtact tttaggatac | 4980 |
| tttcacgctt tataacacgg tgtttaaacc ccagcgcctg gcggg | 5025 |

<210> SEQ ID NO 22
<211> LENGTH: 3665
<212> TYPE: DNA
<213> ORGANISM: Artificial Sequence
<220> FEATURE:
<223> OTHER INFORMATION: Synthetic: Integration construct i477

<400> SEQUENCE: 22

| | |
|---|---:|
| agctcgagga cggcacggcc acgcgtttaa accgccaagc ttttcaattc atctttttt | 60 |
| tttttgttct ttttttgat tccggtttct ttgaaatttt tttgattcgg taatctccga | 120 |
| gcagaaggaa gaacgaagga aggagcacag acttagattg gtatatatac gcatatgtgg | 180 |
| tgttgaagaa acatgaaatt gcccagtatt cttaacccaa ctgcacagaa caaaaacctg | 240 |
| caggaaacga agataaatca tgtcgaaagc tacatataag gaacgtgctg ctactcatcc | 300 |
| tagtcctgtt gctgccaagc tatttaatat catgcacgaa aagcaaacaa acttgtgtgc | 360 |
| ttcattggat gttcgtacca ccaaggaatt actggagtta gttgaagcat taggtcccaa | 420 |
| aatttgttta ctaaaaacac atgtggatat cttgactgat ttttccatgg agggcacagt | 480 |
| taagccgcta aaggcattat ccgccaagta caattttttta ctcttcgaag acagaaaatt | 540 |
| tgctgacatt ggtaatacag tcaaattgca gtactctgcg ggtgtataca gaatagcaga | 600 |
| atgggcagac attacgaatg cacacggtgt ggtgggccca ggtattgtta gcggtttgaa | 660 |
| gcaggcggca gaagaagtaa caaaggaacc tagaggcctt tgatgttag cagaattgtc | 720 |
| atgcaagggc tccctatcta ctggagaata tactaagggt actgttgaca ttgcgaagag | 780 |
| tgacaaagat tttgttatcg gctttattgc tcaaagagac atgggtggaa gagatgaagg | 840 |

| | | |
|---|---|---|
| ttacgattgg ttgattatga cacccggtgt gggtttagat gacaagggag acgcattggg | 900 |
| tcaacagtat agaaccgtgg atgatgtggt ctctacagga tctgacatta ttattgttgg | 960 |
| aagcgctcgt ccaacgccgg cggacctatg gcgcaagttt ccgctttgt aatatatatt | 1020 |
| tataccccctt tcttctctcc cctgcaatat aatagtttaa ttctaatatt aataatatcc | 1080 |
| tatattttct tcatttaccg gcgcactctc gcccgaacga cctcaaaatg tctgctacat | 1140 |
| tcataataac caaaagctca taacttttttt ttttgaacct gaatatatat acatcacata | 1200 |
| tcactgctgg tccttgccga ccagcgtata caatctcgat agttggtttc ccgttctttc | 1260 |
| cactcccgtc atggactaca acaagagatc ttcggtctca accgtgccta atgcagctcc | 1320 |
| cataagagtc ggattcgtcg gtctcaacgc agccaaagga tgggcaatca agacacatta | 1380 |
| ccccgccata ctgcaactat cgtcacaatt tcaaatcact gccttataca gtccaaaaat | 1440 |
| tgagacttct attgccacca tccagcgtct aaaattgagt aatgccactg cttttcccac | 1500 |
| tttagagtca tttgcatcat cttccactat agatatgata gtgatagcta tccaagtggc | 1560 |
| cagtcattat gacgttgtta tgcctctctt ggaattctcc aaaaataatc cgaacctcaa | 1620 |
| gtatcttttc gtagaatggg cccttgcatg ttcactagat caagccgaat ccatttataa | 1680 |
| ggctgctgct gaacgtgggg ttcaaaccat catctcttta caaggtcgta aatcaccata | 1740 |
| tattttgaga gcaaaagaat taatatctca aggctatatc ggcgacatta attctatcga | 1800 |
| gattgctgga aatggcggtt ggtacggcta cgaaaggcct gttaaatcac caaaatacat | 1860 |
| ctatgaaatc gggaacggtg tagatctggt aaccacaaca tttggtcaca caatcgatat | 1920 |
| tttacaatac atgacaagtt cgtacttttc caggataaat gcaatggttt tcaataatat | 1980 |
| tccagagcaa gagctgatag atgagcgtgg taaccgattg ggccagcgag tcccaaagac | 2040 |
| agtaccggat catcttttat tccaaggcac attgttaaat ggcaatgttc cagtgtcatg | 2100 |
| cagtttcaaa ggtggcaaac ctaccaaaaa atttaccaaa aatttggtca ttgatattca | 2160 |
| cggtaccaag ggagatttga aacttgaagg cgatgccgga ttcgcagaaa tttcaaatct | 2220 |
| ggtcctttac tacagtggaa ctagagcaaa cgacttcccg ctagctaatg gacaacaagc | 2280 |
| tcctttagac ccggggtatg atgcaggtaa agaaatcatg gaagtatatc atttacgaaa | 2340 |
| ttataatgcc attgtcggta atattcatcg actgtatcaa tctatctctg acttccactt | 2400 |
| caatacaaag aaaattcctg aattaccctc acaatttgta atgcaaggtt tcgatttcga | 2460 |
| aggctttccc accttgatgg atgctctgat attacacagg ttaatcgaga gcgtttataa | 2520 |
| aagtaacatg atgggctcca cattaaacgt tagcaatatc tcgcattata gtttataaaa | 2580 |
| gcatcttgcc ctgtgcttgg cccccagtgc agcgaacgtt ataaaaacga atactgagta | 2640 |
| tatatctatg taaaacaacc atatcatttc ttgttctgaa cttttgtttac ctaactagtt | 2700 |
| ttaaatttcc cttttttcgtg catgcgggtg ttcttattta ttagcatact acatttgaaa | 2760 |
| tatcaaattt ccttagtaga aaagtgagag aaggtgcact gacacaaaaa ataaaatccc | 2820 |
| cgcgtgcttg gccggccgtc ttcattggat gttcgtacca ccaaggaatt actggagtta | 2880 |
| gttgaagcat taggtcccaa aatttgttta ctaaaaacac atgtggatat cttgactgat | 2940 |
| ttttccatgg agggcacagt taagccgcta aaggcattat ccgccaagta caatttttta | 3000 |
| ctcttcgaag acagaaaatt tgctgacatt ggtaatacag tcaaattgca gtactctgcg | 3060 |
| ggtgtataca gaatagcaga atgggcagac attacgaatg cacacggtgt ggtgggccca | 3120 |
| ggtattgtta gcggtttgaa gcaggcggca gaagaagtaa caaaggaacc tagaggcctt | 3180 |
| ttgatgttag cagaattgtc atgcaagggc tccctatcta ctggagaata tactaagggt | 3240 |

-continued

```
actgttgaca ttgcgaagag tgacaaagat tttgttatcg gctttattgc tcaaagagac   3300
atgggtggaa gagatgaagg ttacgattgg ttgattatga cacccggtgt gggtttagat   3360
gacaagggag acgcattggg tcaacagtat agaaccgtgg atgatgtggt ctctacagga   3420
tctgacatta ttattgttgg aagaggacta tttgcaaagg gaagggatgc taaggtagag   3480
ggtgaacgtt acagaaaagc aggctgggaa gcatatttga agatgcgg ccagcaaaac   3540 taaaaaactg tattataagt aaatgcatgt atactaaact cacaaattag agcttcaatt   3600
taattatatc agttattacc cgggaatctc ggtgtttaaa ccccagcgcc tggcgggtct   3660
agatc                                                              3665
```

<210> SEQ ID NO 23
<211> LENGTH: 10623
<212> TYPE: DNA
<213> ORGANISM: Artificial Sequence
<220> FEATURE:
<223> OTHER INFORMATION: Synthetic: Integration construct i94

<400> SEQUENCE: 23

```
atgagtgata gggaattcgt cacggtagat cccgtcacta tcataatcaa agaatgcatt     60
aatttatcga cagcgatgcg gaaatactct aaatttacct ctcaatctgg agtggccgct    120
ttgctggggg gaggaagtga atatttagc aatcaagatg actacttggc tcacacattc    180
aacaatttga ataccaacaa gcacaatgat ccatttttat ctggattcat tcagttaaga    240
cttatgttga ataaactgaa aaatctagat aatatagatt cactaaccat attgcagcca    300
tttttattaa ttgtgagtac aagttccatt tctggttaca tcacttccct ggccctggac    360
tctttgcaga aattctttac cttgaatatc atcaatgaat catcgcaaaa ctatattggt    420
gcacacaggg cgacggtaaa tgctctaaca cattgtaggt ttgaaggatc tcaacaactt    480
tctgatgatt cagttctttt gaaagtcgtg ttttttactgc gttcaatcgt cgactcacct    540
tacggagatt tattatcaaa ctctatcata tatgacgtat tgcaaacgat tctttcattg    600
gcttgtaata acagaaggag cgaagtcctt aggaatgctg cacaatcaac aatgatagcc    660
gttaccgtaa agatttctc aaaactaaag actattgagc ctgttaatgt gaatcaaata    720
tacatcaatg atgaaagtta cacaaatgat gtattgaagg ccgatacaat tggcacaaat    780
gtagaatcca aagaagaagg aagtcaagaa gatcccatcg gcatgaaagt gaataatgag    840
gaagctatta gcgaggacga tggcattgaa gaagagcata ttcattcaga gaagagcaca    900 aatgcgccg acaactaga tattgtgcaa aaaacaacaa gatcaaattc caggatccaa    960
gcgtatgctg atgataacta tggattgccc gtggttaggc aatatttaaa cttattacta   1020
tcattgattg cgccagaaaa tgaattaaaa cattcatact ccactagaat atttggccta   1080
gagttaattc aaacggcatt agaaatttca ggtgatcgat tgcagctata cccacggctt   1140
tttacactga tatcagatcc tatttttcaaa agcattttgt ttatcataca gaacactaca   1200
aaattatcac tacttcaagc tacattgcag ctatttacta ctctagttgt tatattgggc   1260
aacaacttac aattacagat cgagctcact ctaacaagaa tattttctat tcttttagat   1320
gatggtaccg caaataactc gagttctgaa ataagaaca agccatcaat aataaggaa   1380 cttctaattg agcaaatatc catcttatgg actaggtcgc catctttttt tacttctact   1440
tttatcaatt tcgattgtaa tctcgatagg gcagacgttt ccataaactt tttgaaggct   1500
ttgactaaat tggccttacc agaatccgcc ttaactacca cagaaagtgt accacccatt   1560
```

```
tgccttgagg gattggtctc cctagtcgat gatatgttcg atcacatgaa ggacattgac    1620
agagaagaat ttggcaggca aaagaatgaa atggaaatct taaaaaagag ggaccgtaaa    1680
acagagttta ttgaatgtac caatgcattc aatgaaaagc ccaaaaaggg tattccgatg    1740
ttaatagaaa aaggtttcat tgcttccgac tccgataaag atattgcgga gtttcttttc    1800
aataataaca accgtatgaa taaaaaaaca atcggtttgc tactttgcca tccggacaaa    1860
gtaagcttgt tgaatgaata tattcgtttg tttgatttt cagggttaag ggtcgatgaa     1920
gctattagaa ttttgttgac gaaatttagg ttgcctggtg aatcgcaaca aattgaaaga    1980
atcatcgaag ccttctcgtc tgcgtattgt gaaaatcaag attacgatcc atccaaaatc    2040
agtgacaacg cggaggatga catttctact gttcaaccag acgctgattc tgttttcatt    2100
ttaagttatt caattattat gttgaacact gacctacata accctcaagt gaaggaacac    2160
atgtcatttg aagattactc tggtaactta aagggatgct gtaatcacaa agacttccca    2220
ttctggtatt tggatagaat ttactgttca atcagagata agaaattgt tatgcctgaa     2280 gagcaccacg gcaacgaaaa gtggtttgaa gatgcttgga ataacttgat atcttcaact    2340
actgttataa ctgaaataaa aaagacaca caatctgtca tggataaaatt aacacccttg    2400 gagcttttga ctttgatag agcaattttt aaacaagttg gcccaagtat tgtcagtact     2460
ttattcaaca tttacgtagt tgcatctgat gaccatatat ctaccagaat gataacaagt    2520
ttggacaaat gttcctatat ttccgcattt tttgacttca aagatctctt taatgatata    2580
ctaaactcca ttgctaaggg cactactttg attaattcaa gccatgacga tgaactttca    2640
actttagctt ttgaatatgg cccaatgcca ctggtgcaaa ttaaattcga agacactaac    2700
actgagatcc cggttagtac agatgctgtt agatttggta gatcatttaa gggtcaacta    2760
aatacagttg ttttttccg gattattcgc aggaacaaag atcctaaaat tttctccaag    2820
gaattatggt taaacattgt taatattata ctaacattgt acgaagactt gattttgtct    2880
cctgatattt tccctgattt acaaaaaaga ctgaaattaa gcaacttgcc taagccatct    2940
cctgaaattt ctattaacaa gagcaaagaa agcaaaggtc tcttatcaac atttgcttct    3000
tatttaaaag gtgatgaaga acccacagaa gaggaaatca atcctcaaa aaaagcgatg     3060 gagtgcataa agtcgagtaa tattgccgcc tctgtctttg gaaatgaatc aaatataaca    3120
gcggatttaa taaaaacttt actagactcc gccaaaactg agaaaaacgc agataattcc    3180
aggtattttg aagcagaact tttatttatc atcgaattga ctattgcatt atttctatt     3240 tgcaaagagg agaaagaatt aggaaagttc atacttcaaa aagttttcca actttctcac    3300
acgaaaggcc tcacgaaaag gactgttcgt agaatgctaa catacaaaat tttgttaatt    3360
tcgttatgtg cggatcagac ggagtacttg tccaaattaa taaacgatga gctgttaaaa    3420 aaggggggata ttttaccca aaaatttttt gcaactaatc aaggtaagga atttttgaag    3480
agactatttt cattgaccga atcagagttt tatagaggat ttttactagg aaatgagaat    3540
ttttggaaat tttaagaaa agttacagca atgaaagagc agagcgagag cattttttgaa    3600 tatttaaatg aatcgatcaa gacagacagc aatattttga caaatgagaa cttcatgtgg    3660
gtcctaggac tattagatga aatttcatca atgggtgccg ttggaaatca ctgggaaata    3720
gaatacaaga aattgacaga aagtggtcat aaaattgata aggagaatcc atacaagaaa    3780
tcgatcgaat tatcattgaa atccattcaa ctaacatcac acttgctgga agataataac    3840
gatctgcgta aaaacgagat attcgctatt attcaagctt tggcacatca atgcatcaat    3900
ccgtgtaagc agataagtga atttgcagtg gtaacgctag agcagacgct catcaataaa    3960
```

```
atcgaaattc caactaatga gatggaatcg gtagaagaat taattgaggg cggattacta    4020
ccgttgctaa attcgagtga aacacaggaa gaccagaaaa tcctcatttc atccatatta    4080
acaataattt caaatgttta tttgcattat ttgaaactag ggaagacaag caacgaaacg    4140
tttttgaaaa ttttgagtat tttcaataaa tttgtagagg actcagatat tgaaaaaaag    4200
ctacagcaat taatacttga taagaagagt attgagaagg caacggttc atcatctcat     4260 ggatctgcac atgaacaaac accagagtca aacgacgttg aaattgaggc tactgcgcca    4320
attgatgaca atacagacga tgataacaaa ccgaagttat ctgatgtaga aaaggattaa    4380
agatgctaag agatagtgat gatatttcat aaataatgta attctatata tgttaattac    4440
cttttttgcg aggcatattt atggtgaagg ataagttttg accatcaaag aaggttaatg    4500
tggctgtggt ttcagggtcc atacccggga gttatgacaa ttacaacaac agaattcttt    4560
ctatatatgc acgaacttgt aatatggaag aaattatgac gtacaaacta taaagtaaat    4620
attttacgta acacatggtg ctgttgtgct tcttttcaa gagaatacca atgacgtatg     4680
actaagttta ggatttaatg caggtgacgg acccatcttt caaacgattt atatcagtgg    4740
cgtccaaatt gttaggtttt gttggttcag caggtttcct gttgtgggtc atatgacttt    4800
gaaccaaatg gccggctgct agggcagcac ataaggataa ttcacctgcc aagacggcac    4860
aggcaactat tcttgctaat tgacgtgcgt tggtaccagg agcggtagca tgtgggcctc    4920
ttacacctaa taagtccaac atggcaccct tgtggtctag aacagtacca ccaccgatgg    4980
tacctacttc gatggatggc atggatacgg aaattctcaa atcaccgtcc acttctttca    5040
tcaatgttat acagttggaa ctttcgacat tttgtgcagg atcttgtcct aatgccaaga    5100
aaacagctgt cactaaatta gctgcatgtg cgttaaatcc accaacagac ccagccattg    5160
cagatccaac caaattctta gcaatgttca actcaaccaa tgcggaaaca tcacttttta    5220 acactttttct gacaacatca ccaggaatag tagcttctgc gacgacactc ttaccacgac    5280
cttcgatcca gttgatggca gctggttttt tgtcggtaca gtagttacca gaaacggaga    5340
caacctccat atcttcccag ccatactctt ctaccatttg ctttaatgag tattcgacac    5400
ccttagaaat catattcata cccattgcgt caccagtagt tgttctaaat ctcatgaaga    5460
gtaaatctcc tgctagacaa gtttgaatat gttgcagacg tgcaaatctt gatgtagagt    5520
taaaagcttt tttaattgcg ttttgtccct cttctgagtc taaccatatc ttacaggcac    5580
cagatctttt caaagttggg aaacggacta ctgggcctct tgtcatacca tccttagtta    5640
aaacagttgt tgcaccaccg ccagcattga ttgccttaca gccacgcatg gcagaagcta    5700
ccaaacaacc ctctgtagtt gccattggta tatgataaga gtgtaccatcg ataaccaagg   5760 ggcctataac accaacgggc aaaggcatgt aacctataac attttcacaa caagcgccaa    5820
atacgcggtc gtagtcataa ttttatatg gtaaacgatc agatgctaat acaggagctt      5880
ctgccaaaat tgaaagagcc ttcctacgta ccgcaaccgc tctcgtagta tcacctaatt    5940
ttttctccaa agcgtacaaa ggtaacttac cgtgaataac caaggcagcg acctctttgt    6000
tcttcaattg ttttgtattt ccactactta ataatgcttc taattcttct aaaggacgta    6060
ttttcttatc caagctttca atatcgcggg aatcatcttc tcactagat gatgaaggtc      6120 ctgatgagct cgattgcgca gatgataaac ttttgacttt cgatccagaa atgactgttt    6180
tattggttaa aactggtgta gaagcctttt gtacaggagc agtaaaagac ttcttggtga    6240
cttcagtctt caccaattgg tctgcagcca ttatagtttt ttctccttga cgttaaagta    6300
```

```
tagaggtata ttaacaattt tttgttgata cttttatgac atttgaataa gaagtaatac    6360
aaaccgaaaa tgttgaaagt attagttaaa gtggttatgc agcttttgca tttatatatc    6420
tgttaataga tcaaaaatca tcgcttcgct gattaattac cccagaaata aggctaaaaa    6480
actaatcgca ttattatcct atggttgtta atttgattcg ttgatttgaa ggtttgtggg    6540
gccaggttac tgccaatttt tcctcttcat aaccataaaa gctagtattg tagaatcttt    6600
attgttcgga gcagtgcggc gcgaggcaca tctgcgtttc aggaacgcga ccggtgaaga    6660
ccaggacgca cggaggagag tcttccgtcg gagggctgtc gcccgctcgg cggcttctaa    6720
tccgtacttc aatatagcaa tgagcagtta agcgtattac tgaaagttcc aagagaagg    6780 ttttttagg ctaagataat ggggctcttt acatttccac aacatataag taagattaga    6840
tatggatatg tatatggtgg tattgccatg taatatgatt attaaacttc tttgcgtcca    6900
tccaaaaaaa aagtaagaat ttttgaaaat tcaatataaa tgaaactctc aactaaactt    6960
tgttggtgtg gtattaaagg aagcttagg ccgcaaaagc aacaacaatt acacaataca    7020
aacttgcaaa tgactgaact aaaaaaacaa aagaccgctg aacaaaaaac cagacctcaa    7080
aatgtcggta ttaaggtat ccaaatttac atcccaactc aatgtgtcaa ccaatctgag    7140
ctagagaaat ttgatggcgt ttctcaaggt aaatacacaa ttggtctggg ccaaaccaac    7200 atgtctttg tcaatgacag agaagatatc tactcgatgt ccctaactgt tttgtctaag    7260
ttgatcaaga gttacaacat cgacaccaac aaaattggta gattagaagt cggtactgaa    7320
actctgattg acaagtccaa gtctgtcaag tctgtcttga tgcaattgtt tggtgaaaac    7380
actgacgtcg aaggtattga cacgcttaat gcctgttacg gtggtaccaa cgcgttgttc    7440
aactctttga actggattga atctaacgca tgggatggta gagacgccat tgtagtttgc    7500
ggtgatattg ccatctacga taagggtgcc gcaagaccaa ccggtggtgc cggtactgtt    7560
gctatgtgga tcggtcctga tgctccaatt gtatttgact ctgtaagagc ttcttacatg    7620
gaacacgcct acgattttta caagccagat ttcaccagcg aatatcctta cgtcgatggt    7680 cattttcat taacttgtta cgtcaaggct cttgatcaag tttacaagag ttattccaag    7740
aaggctattt ctaaagggtt ggttagcgat cccgctggtt cggatgcttt gaacgttttg    7800
aaatatttcg actacaacgt tttccatgtt ccaacctgta aattggtcac aaaatcatac    7860
ggtagattac tatataacga tttcagagcc aatcctcaat tgttcccaga agttgacgcc    7920
gaattagcta ctcgcgatta tgacgaatct ttaaccgata agaacattga aaaaactttt    7980
gttaatgttg ctaagccatt ccacaaagag agagttgccc aatctttgat tgttccaaca    8040
aacacaggta acatgtacac cgcatctgtt tatgccgcct ttgcatctct attaaactat    8100
gttggatctg acgacttaca aggcaagcgt gttggtttat tttcttacgg ttccggttta    8160
gctgcatctc tatattcttg caaaattgtt ggtgacgtcc aacatattat caaggaatta    8220
gatattacta caaattagc caagagaatc accgaaactc caaaggatta cgaagctgcc    8280
atcgaattga gagaaaatgc ccatttgaag aagaacttca accctcaagg ttccattgag    8340
catttgcaaa gtggtgttta ctacttgacc aacatcgatg acaaatttag aagatcttac    8400
gatgttaaaa ataatcttc ccccatcgat tgcatcttgc tgaacccct tcataaatgc    8460 tttatttttt tggcagcctg cttttttag ctctcattta atagagtagt ttttaatct    8520 atatactagg aaaactcttt atttaataac aatgatatat atatattcca gtggtgcatg    8580
aacgcatgag aaagccccg gaagatcatc ttccgggggc ttttttttg gcgcgcgata    8640 cagaccggtt cagacaggat aaagaggaac gcagaatgtt agacaacacc cgcttacgca    8700
```

```
tagctattca gaaatcaggc cgtttaagcg atgattcacg agaattgctg gcccgctgcg   8760
gcataaaaat taatttacac actcagcgcc tgattgcgat ggcggaaaac atgccgattg   8820
atatcctgcg cgtgcgtgat gatgacattc cgggtctggt aatggatggc gtggtcgatc   8880
tcggtattat cggcgaaaac gtgctggaag aagagctact caaccgccgc gcacagggcg   8940
aagatccacg ctatttaacc ctgcgccgtc ttgacttcgg cggctgccgt ttatcgctgg   9000
caacaccggt tgacgaagcc tgggacggcc cggccgcgct ggacggtaaa cgtatcgcta   9060
cctcatatcc gcacctcctc aaacgctacc tcgaccagaa aggcgtctct tttaaatcgt   9120
gtctgttaaa tggttctgtc gaagtcgcgc gcgcgcggg gctggccgac gctatctgcg    9180
atttggtctc taccggcgcg acgcttgaag ctaacggcct gcgtgaagtc gaagttatct   9240
accgctctaa agcctgtctg attcagcgcg acggtgagat ggcacagagc aagcaagagc   9300
tgatcgataa attgctgacc cgtattcagg gcgtgattca ggcgcgcgaa tcgaaataca   9360
tcatgatgca cgcgccaagt gaacgcctgg aagaggttat cgccctgctg ccaggcgccg   9420
aaaggccgac aattctgccg ctggcaggcg agcaacagcg cgtggcgatg cacatggtca   9480
gcagcgaaac gttgttctgg gaaaccatgg agaaactgaa agcgcttggc gccagctcga   9540
ttctggtact gccgatcgag aagatgatgg agtgatctga cgcctgatgg cgctgcgctt   9600
atcaggccta cgtaatgcgt tgaaaaactg tattataagt aaatgcatgt atactaaact   9660
cacaaattag agcttcaatt taattatatc agttattacc cgggaatctc ggtcgtaatg   9720
atttctataa tgacgaaaaa aaaaaaattg gaaagaaaaa gcttcatggc ctttataaaa   9780
aggaactatc caatacctcg ccagaaccaa gtaacagtat tttacggggc acaaatcaag   9840
aacaataaga caggactgta agatggacg cattgaactc caagaacaa caagagttcc     9900 aaaaagtagt ggaacaaaag caaatgaagg atttcatgcg tttgtactct aatctggtag   9960
aaagatgttt cacagactgt gtcaatgact tcacaacatc aaagctaacc aataaggaac  10020
aaacatgcat catgaagtgc tcagaaaagt tcttgaagca tagcgaacgt gtagggcagc  10080
gtttccaaga acaaaacgct gccttgggac aaggcttggg ccgataaggt gtactggcgt  10140
atatatatct aattatgtat ctctggtgta gcccattttt agcatgtaaa tataagagaa  10200
aaccatatct aatctaacca aatccaaaca aaattcaata gttactatcg ctttttttctt 10260 tctgtatcgc aaataagtga aaattaaaaa agaaagatta aattggaagt tggatatggg  10320
ctggaacagc agcagtaatc ggtatcgggt tcgccactaa tgacgtccta cgattgcact  10380
caacagacct tgacgctcac gccgtagcgg gcgacaagtc aaacggaaca accgttgccg  10440
ttcccatcgg agtccgacct aggccgaact ccgtgaattt ctgataacaa cggtcggtaa  10500
agactggttc cccagtatat ttcttctctc aggagcaggg gccaatgcca aaagcgacat  10560
taacccggag acaaggctc cactgtgttc caccgaattt cccacctgat aatatctgat    10620
aac                                                                10623
```

`<210>` SEQ ID NO 24
`<211>` LENGTH: 8479
`<212>` TYPE: DNA
`<213>` ORGANISM: Artificial Sequence
`<220>` FEATURE:
`<223>` OTHER INFORMATION: Synthetic: Integration construct i467

`<400>` SEQUENCE: 24

```
gacggcacgg ccacgcgttt aaaccgccct ccaagctgac ataaatcgca ctttgtatct     60
```

```
acttttttttt attcgaaaac aaggcacaac aatgaatcta tcgccctgtg agattttcaa    120
tctcaagttt gtgtaataga tagcgttata ttatagaact ataaaggtcc ttgaatatac    180
atagtgtttc attcctatta ctgtatatgt gactttacat tgttacttcc gcggctattt    240
gacgttttct gcttcaggtg cggcttggag ggcaaagtgt cagaaaatcg gccaggccgt    300
atgacacaaa agagtagaaa acgagatctc aaatatctcg aggcctgtcc tctatacaac    360
cgcccagctc tctgacaaag ctccagaacg gttgtctttt gtttcgaaaa gccaaggtcc    420
cttataattg ccctccattt tgtgtcacct atttaagcaa aaaattgaaa gtttactaac    480
cttttcattaa agagaaataa caatattata aaaagcgctt aaagctcaca cgcggccagg    540
gggagccgtt catcatctca tggatctgca catgaacaaa caccagagtc aaacgacgtt    600
gaaattgagg ctactgcgcc aattgatgac aatacagacg atgataacaa accgaagtta    660
tctgatgtag aaaaggatta aagatgctaa gagatagtga tgatatttca taaataatgt    720
aattctatat atgttaatta ccttttttgc gaggcatatt tatggtgaag ataagttttt    780
gaccatcaaa gaaggttaat gtggctgtgg tttcagggtc cataaagctt ttcaattcat    840
cttttttttt tttgttcttt ttttgattc cggtttcttt gaatttttt tgattcggta    900
atctccgagc agaaggaaga acgaaggaag gagcacagac ttagattggt atatatacgc    960
atatgtggtg ttgaagaaac atgaaattgc ccagtattct taacccaact gcacagaaca   1020
aaaacctgca ggaaacgaag ataaatcatg tcgaaagcta catataagga acgtgctgct   1080
actcatccta gtcctgttgc tgccaagcta tttaatatca tgcacgaaaa gcaaacaaac   1140
ttgtgtgctt cattggatgt tcgtaccacc aaggaattac tggagttagt tgaagcatta   1200
ggtcccaaaa tttgtttact aaaaacacat gtggatatct tgactgattt ttccatggag   1260
ggcacagtta agccgctaaa ggcattatcc gccaagtaca attttttact cttcgaagac   1320
agaaaatttg ctgacattgg taatacagtc aaattgcagt actctgcggg tgtatacaga   1380
atagcagaat gggcagacat tacgaatgca cacggtgtgg tgggcccagg tattgttagc   1440
ggtttgaagc aggcggcaga agaagtaaca aaggaaccta gaggcctttt gatgttagca   1500
gaattgtcat gcaagggctc cctatctact ggagaatata ctaagggtac tgttgacatt   1560
gcgaagagtg acaaagattt tgttatcggc tttattgctc aaagagacat gggtggaaga   1620
gatgaaggtt acgattggtt gattatgaca cccggtgtgg gtttagatga caagggagac   1680
gcattgggtc aacagtatag aaccgtggat gatgtggtct ctacaggatc tgacattatt   1740
attgttggaa gaggactatt tgcaaaggga agggatgcta aggtagaggg tgaacgttac   1800
agaaaagcag gctgggaagc atatttgaga agatgcggcc agcaaaacta aaaaactgta   1860
ttataagtaa atgcatgtat actaaactca caaattagag cttcaattta attatatcag   1920
ttattacccg ggaatctcgg tcgtaatgat ttctataatg acgaaaaaaa aaaaattgga   1980
aagaaaaagc ttcatggcct ttataaaaag gaactatcca atacctcgcc agaaccaagt   2040
aacagtattt tacgggcac aaatcaagaa caataagaca ggactgtaaa gatggacgca   2100
tcgctcgtcc aacgccggcg gacctgtttt caatagttcg gtaatattaa cggatacctta   2160
ctattatccc ctagtaggct cttttcacgg agaaattcgg gagtgttttt tttccgtgcg   2220
cattttctta gctatattct tccagcttcg cctgctgccc ggtcatcgtt cctgtcacgt   2280
agtttttccg gattcgtccg gctcatataa taccgcaata aacacggaat atctcgttcc   2340
gcggattcgg ttaaactctc ggtcgcggat tatcacagag aaagcttcgt ggagaatttt   2400
tccagatttt ccgctttccc cgatgttggt atttccggag gtcattatac tgaccgccat   2460
```

```
tataatgact gtacaacgac cttctggaga aagaaacaac tcaataacga tgtgggacat   2520
tgggggccca ctcaaaaaat ctggggacta tatccccaga gaatttctcc agaagagaag   2580
aaaagtcaaa gttttttttc gcttgggggt tgcatataaa tacaggcgct gttttatctt   2640
cagcatgaat attccataat tttacttaat agcttttcat aaataataga atcacaaaca   2700
aaatttacat ctgagttaaa caatcatgac aatcaaggaa cataaagtag tttatgaagc   2760
tcacaacgta aaggctctta aggctcctca acatttttac aacagccaac ccggcaaggg   2820
ttacgttact gatatgcaac attatcaaga aatgtatcaa caatctatca atgagccaga   2880
aaaattcttt gataagatgg ctaaggaata cttgcattgg gatgctccat acaccaaagt   2940
tcaatctggt tcattgaaca atggtgatgt tgcatggttt ttgaacggta aattgaatgc   3000
atcatacaat tgtgttgaca gacatgcctt tgctaatccc gacaagccag ctttgatcta   3060
tgaagctgat gacgaatccg acaacaaaat catcacattt ggtgaattac tcagaaaagt   3120
ttcccaaatc gctggtgtct taaaaagctg gggcgttaag aaaggtgaca cagtggctat   3180
ctatttgcca atgattccag aagcggtcat tgctatgttg gctgtggctc gtattggtgc   3240
tattcactct gttgtctttg ctgggttctc cgctggttcg ttgaaagatc gtgtcgttga   3300
cgctaattct aaagtggtca tcacttgtga tgaaggtaaa agaggtggta agaccatcaa   3360
cactaaaaaa attgttgacg aaggtttgaa cggagtcgat ttggtttccc gtatcttggt   3420
tttccaaaga actggtactg aaggtattcc aatgaaggcc ggtagagatt actggtggca   3480
tgaggaggcc gctaagcaga gaacttacct acctcctgtt tcatgtgacg ctgaagatcc   3540
tctattttta ttatacactt ccggttccac tggttctcca aagggtgtcg ttcacactac   3600
aggtggttat ttattaggtg ccgctttaac aactagatac gttttgata ttcacccaga    3660 agatgttctc ttcactgccg gtgacgtcgg ctggatcacg ggtcacacct atgctctata   3720
tggtccatta accttgggta ccgcctcaat aattttcgaa tccactcctg cctacccaga   3780
ttatggtaga tattggagaa ttatccaacg tcacaaggct acccatttct atgtggctcc   3840
aactgcttta agattaatca aacgtgtagg tgaagccgaa attgccaaat atgacacttc   3900
ctcattacgt gtcttgggtt ccgtcggtga accaatctct ccagacttat gggaatggta   3960
tcatgaaaaa gtgggtaaca aaaactgtgt catttgtgac actatgtggc aaacagagtc   4020
tggttctcat ttaattgctc ctttggcagg tgctgtccca acaaaacctg gttctgctac   4080
cgtgccattc tttggtatta acgcttgtat cattgaccct gttacaggtg tggaattaga   4140
aggtaatgat gtcgaaggtg tccttgccgt taaatcacca tggccatcaa tggctagatc   4200
tgtttggaac caccacgacc gttacatgga tacttacttg aaaccttatc ctggtcacta   4260
tttcacaggt gatggtgctg gtagagatca tgatggttac tactggatca ggggtagagt   4320
tgacgacgtt gtaaatgttt ccggtcatag attatccaca tcagaaattg aagcatctat   4380
ctcaaatcac gaaaacgtct cggaagctgc tgttgtcggt attccagatg aattgaccgg   4440
tcaaaccgtc gttgcatatg tttccctaaa agatggttat ctacaaaaca acgctactga   4500
aggtgatgca gaacacatca caccagataa tttacgtaga gaattgatct tacaagttag   4560
gggtgagatt ggtccttttcg cctcaccaaa aaccattatt ctagttagag atctaccaag   4620
aacaaggtca ggaaagatta tgagaagagt tctaagaaag gttgcttcta acgaagccga   4680
acagctaggt gacctaacta cttttggcca cccagaagtt gtacctgcca tcatttctgc   4740
tgtagagaac caattttctc tcaaaaaaa gaaataaatt gaattgaatt gaaatcgata   4800
```

```
gatcaatttt tttcttttct ctttccccat cctttacgct aaaataatag tttattttat    4860
tttttgaata ttttttattt atatacgtat atatagacta ttatttatct tttaatgatt    4920
attaagattt ttattaaaaa aaaattcgct cctcttttaa tgcctttatg cagttttttt    4980
ttcccattcg atatttctat gttcgggttc agcgtatttt aagtttaata actcgaaaat    5040
tctgcgttcg ttaaagcttt cgagaaggat attatttcga aataaaccgt gttgtgtaag    5100
cttgaagcct ttttgcgctg ccaatattct tatccatcta ttgtactctt tagatccagt    5160
atagtgtatt cttcctgctc caagctcatc ccatcccgc gtgcttggcc ggccgttttg     5220
ccagcttact atccttcttg aaaatatgca ctctatatct tttagttctt aattgcaaca    5280
catagatttg ctgtataacg aatttttatgc tatttttttaa atttggagtt cagtgataaa   5340
agtgtcacag cgaatttcct cacatgtagg gaccgaattg tttacaagtt ctctgtacca    5400
ccatggagac atcaaaaatt gaaatctat ggaaagatat ggacggtagc aacaagaata     5460
tagcacgagc cgcggagttc atttcgttac ttttgatatc actcacaact attgcgaagc    5520
gcttcagtga aaaaatcata aggaaaagtt gtaaatatta ttggtagtat tcgtttggta    5580
aagtagaggg ggtaattttt ccccttattt ttgttcatac attcttaaat tgctttgcct    5640 ctcctttttgg aaagctatac ttcggagcac tgttgagcga aggctcatta gatatatttt   5700
ctgtcatttt ccttaaccca aaaataaggg aaagggtcca aaaagcgctc ggacaactgt    5760
tgaccgtgat ccgaaggact ggctatacag tgttcacaaa atagccaagc tgaaaataat    5820
gtgtagctat gttcagttag tttggctagc aaagatataa aagcaggtcg gaaatattta    5880
tgggcattat tatgcagagc atcaacatga taaaaaaaaa cagttgaata ttccctcaaa    5940
aatgtcttac accgtcggaa cctacttggc cgagaggttg gtccagatcg gattgaagca    6000
ccacttcgcc gtcgccggtg actacaactt ggtcttgttg acaacttgt tgttgaacaa     6060 gaacatggag caggtctatt gctgcaacga gttgaactgc ggtttctcag cagaaggtta    6120
tgcaagagca aagggagcag ccgctgccgt cgtcacctac tcagtcggtg cattatcagc    6180
attcgatgca attggaggtg cttacgctga gaacttgcca gtcatcttga tctctggagc    6240
acctaacaac aacgaccatg ctgctggtca cgtattgcac cacgccttgg gtaaaacaga    6300
ctaccactac cagttggaaa tggcaaaaaa tattaccgca gccgcagagg ccatctacac    6360
cccagaggaa gcacctgcca aaattgacca cgtcataaag accgctttga gagagaagaa    6420
gcctgtttac ttggagatcg cctgcaacat cgcttctatg ccatgcgccg cacctggtcc    6480
agcctctgct tgttcaacg acgaggcctc tgacgaagct tcattgaacg ccgcagtcga    6540
agagacatta aagttcatcg ccaacaggga caaagttgcc gtcttagtcg gttcaaagtt    6600
gagggccgct ggtgccgaag aggcagctgt caagttcgct gacgccttgg gaggagccgt    6660
cgccaccatg gccgcagcaa aatctttctt tcctgaggag aacccacatt acatcggaac    6720
ctcatggggt gaagtatcat atcctggagt agaaaaaacc atgaaagagg ccgatgccgt    6780
aatagcattg gctcctgtct tcaacgacta ctcaaccaca ggatggactg ataaccaga    6840 tccaaagaaa ttagtcttgg ctgagcctag gtctgtcgtc gtaaacggta tcaggttccc    6900
ttctgttcat ttgaaggact acttaacaag attggcccaa aaggtatcta aaagactgg    6960 tgccttggac ttcttcaagt cattaaacgc aggagaattg aaaaaagcag caccagccga    7020
tccatcagcc ccattagtta acgctgaaat cgctagacaa gtagaggctt tgttgactcc    7080
aaacactacc gtcatagctg agacaggtga ctccttggtt caacgcacaga gaatgaaatt    7140 gccaaatggt gccagggtcg agtatgaaat gcagtgggga catataggtt ggtcagtccc    7200
```

```
agccgccttt ggatacgcag taggtgcccc tgagaggagg aacatattga tggttggtga    7260
tggttcattc caattaacag cccaggaggt agcccaaatg gtcaggttga agttgcctgt    7320
catcatcttc ttgatcaaca attacgata caccatcgag gtcatgatcc acgacggacc     7380
ttacaacaac atcaaaaact gggactacgc cggtttgatg gaggttttca acggtaacgg    7440
tggttatgac tcaggagccg gtaagggatt aaaggctaag accggtggtg aattggctga    7500
agcaattaag gtcgcattgg ccaacaccga tggacctaca ttgattgaat gcttcatcgg    7560
aagggaggac tgcaccgagg aattggttaa atggggtaaa agggtagccg ctgctaattc    7620
aagaaaacca gttaataaat tattataata agtgaattta ctttaaatct tgcatttaaa    7680
taaattttct ttttatagct ttatgactta gtttcaattt atatactatt ttaatgacat    7740
tttcgattca ttgattgaaa gctttgtgtt ttttcttgat gcgctattgc attgttcttg    7800 tcttttcgc cacatgtaat atctgtagta gataccctgat acattgtgga tgctgagtga    7860
aattttagtt aataatggag gcgctcttaa taattttggg gatattggct taacctgcag    7920
gccgcgagcg ccgatataaa ctaatgattt taaatcgtta aaaaaatatg cgaattctgt    7980
ggatcgaaca caggacctcc agataacttg accgaagttt tttcttcagt ctggcgctct    8040
cccaactgag ctaaatccgc ttactatttg ttatcagttc ccttcatatc tacatagaat    8100
aggttaagta ttttattagt tgccagaaga actactgata gttgggaata tttggtgaat    8160
aatgaagatt gggtgaataa tttgataatt ttgagattca attgttaatc aatgttacaa    8220
tattatgtat acagagtata ctagaagttc tcttcggaga tcttgaagtt cacaaaaggg    8280
aatcgatatt tctacataat attatcatta cttcttcccc atcttatatt tgtcattcat    8340
tattgattat gatcaatgca ataatgattg gtagttgcca aacatttaat acgatcctct    8400
gtaatatttc tatgaataat tatcacagca acgttcaatt atcttcaatt ccggtgttta    8460
aaccccagcg cctggcggg                                                 8479
```

<210> SEQ ID NO 25
<211> LENGTH: 5628
<212> TYPE: DNA
<213> ORGANISM: Artificial Sequence
<220> FEATURE:
<223> OTHER INFORMATION: Synthetic: URA3 FcphI target site cassette

<400> SEQUENCE: 25

```
gcctgtctac aggataaaga cgggtcggat acctgcacaa gcaatttggc acctgcatac      60
cccatttccc cagtagataa cttcaacaca cacatcaatg tccctcacca gtttatttcc    120
aaaagagacg cttttactac cctgactaga ttttcatttt gttctttttg gattgcgctt    180 gccttgtag gtgtgtcgtt tatcctttac gttttgactt ggtgctcgaa gatgctttca    240
gagatggtgc ttatcctcat gtcttttggg tttgtcttca atacggcagc cgttgtcttg    300
caaacggccg cctctgccat ggcaaagaat gctttccatg acgatcatcg tagtgcccaa    360
ttgggtgcct ctatgatggg tttaaacgta tggcttgggc aagtgtcttt ttatgtatcg    420
tggaatttat cctgctggtc ttctggtctg ttagggcaag gttggcctct acttactcca    480
tcgacaattc aagatacaga acctcctcca gatggaatcc cttccataga gagaaggagc    540
aagcaactga cccaatattg actgccactg gacctgaaga catgcaacaa agtgcaagca    600
tagtggggcc ttcttccaat gctaatccgg tcactgccac tgctgctacg gaaaaccaac    660
ctaaaggtat taacttcttc actataagaa aatcacacga gcgcccggac gatgtctctg    720
```

```
tttaaatggc gcaagttttc cgctttgtaa tatatattta taccccttttc ttctctcccc    780
tgcaatataa tagtttaatt ctaatattaa taatatccta tattttcttc atttaccggc    840
gcactctcgc ccgaacgacc tcaaaatgtc tgctacattc ataataacca aaagctcata    900
acttttttt ttgaacctga atatatatac atcacatatc actgctggtc ctttgtgagc    960
gttgcgctcg tgcatcatgc gtccatcttt acagtcctgt cttattgttc ttgatttgtg   1020
ccccgtaaaa tactgttact tggttctggc gaggtattgg atagttcctt tttataaagg   1080
ccatgaagct ttttctttcc aatttttttt ttttcgtcat tatagaaatc attacgaccg   1140
agattcccgg gtaataactg ataataattaa attgaagctc taatttgtga gtttagtata  1200
catgcattta cttataatac agttttttag ttttgctggc cgcatcttct caaatatgct   1260
tcccagcctg cttttctgta acgttcaccc tctaccttag catcccttcc ctttgcaaat   1320
agtcctcttc caacaataat aatgtcagat cctgtagaga ccacatcatc cacggttcta   1380
tactgttgac ccaatgcgtc tcccttgtca tctaaaccca caccgggtgt cataatcaac   1440
caatcgtaac cttcatctct tccacccatg tctctttgag caataaagcc gataacaaaa   1500
tctttgtcac tcttcgcaat gtcaacagta cccttagtat attctccagt agataggggag  1560
cccttgcatg acaattctgc taacatcaaa aggcctctag gttcctttgt tacttcttct   1620
gccgcctgct tcaaaccgct aacaatacct gggcccacca caccgtgtgc attcgtaatg   1680
tctgcccatt ctgctattct gtatacaccc gcagagtact gcaatttgac tgtattacca   1740
atgtcagcaa attttctgtc ttcgaagagt aaaaaattgt acttggcgga taatgccttt   1800
agcggcttaa ctgtgccctc catggaaaaa tcagtcaaga tatccacatg tgtttttagt   1860
aaacaaattt tgggacctaa tgcttcaact aactccagta attccttggt ggtacgaaca   1920
tccaatgaag cacacaagtt tgtttgcttt tcgtgcatga tattaaatag cttggcagca   1980
acaggactag gatgagtagc agcacgttcc ttatatgtag cttttcgacat gatttatctt   2040
cgtttcctgc aggtttttgt tctgtgcagt tgggttaaga atactgggca atttcatgtt   2100
tcttcaacac cacatatgcg tatatatacc aatctaagtc tgtgctcctt ccttcgttct   2160
tccttctgct cggagattac cgaatcaaaa aaatttcaaa gaaaccggaa tcaaaaaaaa   2220
gaacaaaaaa aaaaagatg aattgaaaag ctttatggac cctgaaacca cagccacatt    2280
aaccttctt gatggtcaaa acttatcctt caccataaat atgcctcgca aaaaggtaa     2340
ttaacatata tagaattaca ttatttatga aatatcatca ctatctctta gcatctttaa   2400
tccttttcta catcagataa cttcggtttg ttatcatcgt ctgtattgtc atcaattggc   2460
gcagtagcct caatttcaac gtcgtttgac tctggtgttt gttcatgtgc agatccatga   2520
gatgatgaac ttgtgagcgt tgcgctcgtg catcaccata tacatatcca tatctaatct   2580
tacttatatg ttgtggaaat gtaaagagcc ccattatctt agcctaaaaa aaccttctct   2640
ttggaacttt cagtaatacg cttaactgct cattgctata ttgaagtacg gattagaagc   2700
cgccgagcgg gcgacagccc tccgacggaa gactctcctc cgtgcgtcct ggtcttcacc   2760
ggtcgcgttc ctgaaacgca gatgtgcctc gcgccgcact gctccgaaca ataaagattc   2820
tacaatacta gctttatgg ttatgaagag gaaaaattgg cagtaacctg gccccacaaa    2880
ccttcaaatc aacgaatcaa attaacaacc ataggataat aatgcgatta gttttttagc   2940
cttatttctg gggtaattaa tcagcgaagc gatgattttt gatctattaa cagatatata   3000
aatgcaaaag ctgcataacc actttaacta atactttcaa cattttcggt ttgtattact   3060
tcttattcaa atgtcataaa agtatcaaca aaaaattgtt aatatacctc tatactttaa   3120
```

```
cgtcaaggag aaaaaactat aatgtcatta ccgttcttaa cttctgcacc gggaaaggtt    3180 attattttg gtgaacactc tgctgtgtac aacaagcctg ccgtcgctgc tagtgtgtct     3240
gcgttgagaa cctacctgct aataagcgag tcatctgcac cagatactat tgaattggac   3300
ttcccggaca ttagctttaa tcataagtgg tccatcaatg atttcaatgc catcaccgag   3360
gatcaagtaa actcccaaaa attggccaag gctcaacaag ccaccgatgg cttgtctcag   3420
gaactcgtta gtcttttgga tccgttgtta gctcaactat ccgaatcctt ccactaccat   3480
gcagcgtttt gtttcctgta tatgtttgtt tgcctatgcc cccatgccaa gaatattaag   3540
ttttctttaa agtctacttt acccatcggt gctgggttgg gctcaagcgc ctctatttct   3600
gtatcactgg ccttagctat ggcctacttg gggggttaa taggatctaa tgacttggaa    3660
aagctgtcag aaaacgataa gcatatagtg aatcaatggg ccttcatagg tgaaaagtgt   3720
attcacggta cccccttcagg aatagataac gctgtggcca cttatggtaa tgccctgcta  3780
tttgaaaaag actcacataa tggaacaata aacacaaaca attttaagtt cttagatgat   3840
ttcccagcca ttccaatgat cctaacctat actagaattc caaggtctac aaaagatctt  3900
gttgctcgcg ttcgtgtgtt ggtcaccgag aaatttcctg aagttatgaa gccaattcta  3960
gatgccatgg gtgaatgtgc cctacaaggc ttagagatca tgactaagtt aagtaaatgt  4020
aaaggcaccg atgacgaggc tgtagaaact aataatgaac tgtatgaaca actattggaa 4080
ttgataagaa taaatcatgg actgcttgtc tcaatcggtg tttctcatcc tggattagaa  4140
cttattaaaa atctgagcga tgatttgaga attggctcca caaaacttac cggtgctggt 4200
ggcggcggtt gctctttgac tttgttacga agagacatta ctcaagagca aattgacagt 4260
ttcaaaaaga aattgcaaga tgattttagt tacgagacat ttgaaacaga cttgggtggg  4320
actggctgct gtttgttaag cgcaaaaaat ttgaataaag atcttaaaat caaatcccta  4380
gtattccaat tatttgaaaa taaaactacc acaaagcaac aaattgacga tctattattg  4440
ccaggaaaca cgaatttacc atggacttca taagctaatt tgcgataggc attatttatt  4500
agttgttttt aatcttaact gtgtatgaag ttttatgtaa taaagataga aagagaaaca 4560
aaaaaaaatt tttcgtagta tcaattcagc tttcgaagac agaatgaaat ttaagcagac  4620
catcatcttg ccctgtgctt ggcccccagt gcagcgaacg ttataaaaac gaatactgag   4680
tatatatcta tgtaaaacaa ccatatcatt tcttgttctg aactttgttt acctaactag   4740
ttttaaattt ccctttttcg tgcatgcggg tgttcttatt tattagcata ctacatttga   4800
aatatcaaat ttccttagta gaaaagtgag agaaggtgca ctgacacaaa aaataaaatg   4860
ctacgtataa ctgtcaaaac tttgcagcag cgggcatcct tccatcatag cttcaaacat   4920
attagcgttc ctgatcttca tacccgtgct caaaatgatc aaacaaactg ttattgccaa   4980
gaaataaacg caaggctgcc ttcaaaaact gatccattag atcctcatat caagcttcct   5040
catagaacgc ccaattacaa taagcatgtt ttgctgttat caccgggtga taggtttgct  5100
caaccatgga aggtagcatg gaatcataat ttggatacta atacaaatcg ccatataat   5160 gccattagta aattgcgctc ccatttaggt ggttctccag gcaaatttga atactaataa   5220
atgcggtgca tttgcaaaat gaatttattc caaggccaaa acaacacgat gaatggcttt   5280 attttttgt tattcctgac atgaagcttt atgtaattaa ggaaacggac atcgaggaat   5340
ttgcatcttt tttagatgaa ggagctattc aagcaccaaa gctatccttc caggattatt    5400
taagcggtaa ggccaaggct tcccaacagg ttcatgaagt gcatcataga aagcttacaa   5460
```

```
ggtttcaggg tgaaactttt ctaagagatt ggaacttagt ctgtgggcat tataagagag    5520
atgctaagtg tggagaaatg ggacccgaca taattgcagc atttcaagat gaaaagcttt    5580
ttcctgagaa taatctagcc ttaatttctc atattggggg tcatattt                 5628
```

<210> SEQ ID NO 26
<211> LENGTH: 10019
<212> TYPE: DNA
<213> ORGANISM: Artificial Sequence
<220> FEATURE:
<223> OTHER INFORMATION: Synthetic: HXT3 FcphI target site cassette

<400> SEQUENCE: 26

```
accggtatat caaatggcgg tgtagtttga aaagtacact gtatgtccat taataaaatt      60
acgccgaaga acactgacta gctataaatt ctcttccggc gtccaatttc aacctaaggc     120
aagtattgtt aatcaataat gcgtgttggt aaatatgaag cccgatgttg attaagaaga     180
attattcgta taagaattaa gcaagcaaaa ttaaggaaaa ttttttcttt cctattcgtc     240
atcgcagaca gccttcatct tctcgagata cacctggag gaggagcaat gaaatgaaag      300
gaaaaaaaaa tactttcttt ttcttgaaaa agaaaaaaa ttgtaagatg agctattcgc      360
ggaacattct agctcgtttg catcttcttg catttggtag gttttcaata gttcggtaat     420
attaacggat acctactatt atcccctagt aggctctttt cacggagaaa ttcgggagtg     480
ttttttttcc gtgcgcattt tcttagctat attcttccag cttcgcctgc tgcccggtca     540
tcgttcctgt cacgtagttt ttccggattc gtccggctca tataataccg caataaacac     600
ggaatatctc gttccgcgga ttcggttaaa ctctcggtcg cggattatca cagagaaagc     660
ttcgtggaga atttttccag attttccgct ttccccgatg ttggtatttc cggaggtcat     720
tatactgacc gccattataa tgactgtaca acgaccttct ggagaaagaa acaactcaat     780
aacgatgtgg acattgggg gcccactcaa aaaatctggg gactatatcc ccagagaatt      840
tctccagaag agaagaaaag tcaaagtttt ttttcgcttg ggggttgcat ataaattgtg     900
agcgttgcgc tcgtgcatcg tcgacactag taatacacat catcgtccta caagttcatc     960
aaagtgttgg acagacaact ataccagcat ggatctcttg tatcggttct tttctcccgc    1020
tctctcgcaa taacaatgaa cactgggtca atcatagcct acacaggtga acagagtagc    1080
gtttatacag ggtttatacg gtgattccta cggcaaaaat ttttcatttc taaaaaaaaa    1140
aagaaaaatt tttctttcca acgctagaag gaaaagaaaa atctaattaa attgatttgg    1200
tgattttctg agagttccct ttttcatata tcgaattttg aatataaaag gagatcgaaa    1260
aaatttttct attcaatctg ttttctggtt ttatttgata gtttttttgt gtattattat    1320
tatggattag tactggttta tatgggtttt tctgtataac ttcttttat tttagttgt      1380 ttaatcttat tttgagttac attatagttc cctaactgca agagaagtaa cattaaaaat    1440
gaccactctt gacgacacgg cttaccggta ccgcaccagt gtcccggggg acgccgaggc    1500
catcgaggca ctggatgggt ccttcaccac cgacaccgtc ttccgcgtca ccgccaccgg    1560
ggacggcttc accctgcggg aggtgccggt ggacccgccc ctgaccaagg tgttccccga    1620
cgacgaatcg gacgacgaat cggacgccgg ggaggacggc gacccggact cccgacgtt     1680 cgtcgcgtac ggggacgacg gcgacctggc gggcttcgtg gtcgtctcgt actccggctg    1740
gaaccgccgg ctgaccgtcg aggacatcga ggtcgccccg gagcaccggg ggcacggggt    1800 cggggcgcgcg ttgatggggc tcgcgacgga gttcgcccgc gagcggggcg ccgggcacct    1860
ctggctggag gtcaccaacg tcaacgcacc ggcgatccac gcgtaccggc ggatgggtt     1920
```

```
caccctctgc ggcctggaca ccgccctgta cgacggcacc gcctcggacg gcgagcaggc    1980
gctctacatg agcatgccct gccccctgagt ttaacttgat actactagat tttttctctt    2040
catttataaa attttttggtt ataattgaag ctttagaagt atgaaaaaat ccttttttt    2100 cattctttgc aaccaaaata agaagcttct tttattcatt gaaatgatga atataaacct    2160
aacaaaagaa aaagactcga atatcaaaca ttaaaaaaaa ataaaagagg ttatctgttt    2220
tcccatttag ttggagtttg cattttctaa tagatagaac tctcaattaa tgtggattta    2280
gtttctctgt tcgtttttttt ttgttttgtt ctcactgtat ttacatttct atttagtatt    2340
tagttattca tataatctta acttctcgag gagctcgatg cgtccatctt tacagtcctg    2400
tcttattgtt cttgatttgt gccccgtaaa atactgttac ttggttctgg cgaggtattg    2460
gatagttcct tttataaag gccatgaagc ttttctttc caattttttt tttttcgtca    2520
ttatagaaat cattacgacc gagattcccg ggtaataact gatataatta aattgaagct    2580
ctaatttgtg agtttagtat acatgcattt acttataata cagtttttta gttttgctgg    2640
ccgcatcttc tcaaatatgc ttcccagcct gcttttctgt aacgttcacc ctctacctta    2700
gcatcccttc cctttgcaaa tagtcctctt ccaacaataa taatgtcaga tcctgtagag    2760
accacatcat ccacggttct atactgttga cccaatgcgt ctcccttgtc atctaaaccc    2820
acaccgggtg tcataatcaa ccaatcgtaa ccttcatctc ttccacccat gtctctttga    2880
gcaataaagc cgataacaaa atctttgtca ctcttcgcaa tgtcaacagt acccttagta    2940
tattctccag tagataggga gcccttgcat gacaattctg ctaacatcaa aaggcctcta    3000
ggttcctttg ttacttcttc tgccgcctgc ttcaaaccgc taacaatacc tgggcccacc    3060
acaccgtgtg cattcgtaat gtctgcccat tctgctattc tgtatacacc cgcagagtac    3120
tgcaatttga ctgtattacc aatgtcagca aattttctgt cttcgaagag taaaaaattg    3180
tacttggcgg ataatgcctt tagcggctta actgtgccct ccatggaaaa atcagtcaag    3240
atatccacat gtgtttttag taaacaaatt ttgggaccta atgcttcaac taactccagt    3300
aattccttgg tggtacgaac atccaatgaa gcacacaagt ttgtttgctt ttcgtgcatg    3360
atattaaata gcttggcagc aacaggacta ggatgagtag cagcacgttc cttatatgta    3420
gctttcgaca tgatttatct tcgtttcctg caggtttttg ttctgtgcag ttgggttaag    3480
aatactgggc aatttcatgt ttcttcaaca ccacatatgc gtatatatac caatctaagt    3540
ctgtgctcct tccttcgttc ttccttctgc tcggagatta ccgaatcaaa aaaatttcaa    3600
agaaaccgga atcaaaaaaa agaacaaaaa aaaaaagat gaattgaaaa gctttatgga    3660
ccctgaaacc acagccacat taaccttctt tgatggtcaa aacttatcct tcaccataaa    3720
tatgcctcgc aaaaaaggta attaacatat atagaattac attatttatg aaatatcatc    3780
actatctctt agcatcttta atccttttct acatcagata acttcggttt gttatcatcg    3840
tctgtattgt catcaattgg cgcagtagcc tcaatttcaa cgtcgtttga ctctggtgtt    3900
tgttcatgtg cagatccatg agatgatgaa cttgtgagcg ttgcgctcgt gcatccgctc    3960
gtccaacgcc ggcggacctc gctcgtccaa cgccggcgga cctcttttaa ttctgctgta    4020
acccgtacat gcccaaaata gggggcgggt tacacagaat atataacatc gtaggtgtct    4080
gggtgaacag tttattcctg gcatccacta aatataatgg agcccgcttt ttaagctggc    4140
atccagaaaa aaaagaatc ccagcaccaa aatattgttt tcttcaccaa ccatcagttc    4200
ataggtccat tctcttagcg caactacaga gaacaggggc acaaacaggc aaaaaacggg    4260
```

```
cacaacctca atggagtgat gcaacctgcc tggagtaaat gatgacacaa ggcaattgac    4320
ccacgcatgt atctatctca ttttcttaca ccttctatta ccttctgctc tctctgattt    4380
ggaaaaagct gaaaaaaaag gttgaaacca gttccctgaa attattcccc tacttgacta    4440
ataagtatat aaagacggta ggtattgatt gtaattctgt aaatctattt cttaaacttc    4500
ttaaattcta cttttatagt tagtcttttt tttagtttta aaacaccaag aacttagttt    4560
cgatccccgc gtgcttggcc ggccgtatcc ccgcgtgctt ggccggccgt atgtctcaga    4620
acgtttacat tgtatcgact gccagaaccc caattggttc attccagggt tctctatcct    4680
ccaagacagc agtggaattg ggtgctgttg ctttaaaagg cgccttggct aaggttccag    4740
aattggatgc atccaaggat tttgacgaaa ttattttttgg taacgttctt tctgccaatt    4800
tgggccaagc tccggccaga caagttgctt tggctgccgg tttgagtaat catatcgttg    4860
caagcacagt taacaaggtc tgtgcatccg ctatgaaggc aatcattttg ggtgctcaat    4920
ccatcaaatg tggtaatgct gatgttgtcg tagctggtgg ttgtgaatct atgactaacg    4980
caccatacta catgccagca gcccgtgcgg gtgccaaatt tggccaaact gttcttgttg    5040
atggtgtcga aagagatggg ttgaacgatg cgtacgatgg tctagccatg ggtgtacacg    5100
cagaaaagtg tgcccgtgat tgggatatta ctagagaaca acaagacaat tttgccatcg    5160
aatcctacca aaaatctcaa aaatctcaaa aggaaggtaa attcgacaat gaaattgtac    5220
ctgttaccat taagggattt agaggtaagc ctgatactca agtcacgaag gacgaggaac    5280
ctgctagatt acacgttgaa aaattgagat ctgcaaggac tgttttccaa aagaaaacg    5340 gtactgttac tgccgctaac gcttctccaa tcaacgatgg tgctgcagcc gtcatcttgg    5400
tttccgaaaa agttttgaag gaaagaatt tgaagccttt ggctattatc aaaggtttggg    5460 gtgaggccgc tcatcaacca gctgatttta catgggctcc atctcttgca gttccaaagg    5520 cttttgaaaca tgctggcatc gaagacatca attctgttga ttactttgaa ttcaatgaag    5580
ccttttcggt tgtcggtttg gtgaacacta agatttttgaa gctagaccca tctaaggtta    5640
atgtatatgg tggtgctgtt gctctaggtc acccattggg ttgttctggt gctagagtgg    5700
ttgttacact gctatccatc ttacagcaag aaggaggtaa gatcggtgtt gccgccattt    5760
gtaatggtgg tggtggtgct tcctctattg tcattgaaaa gatatgatta cgttctgcga    5820
ttttctcatg atcttttttca taaaatacat aaatatataa atggctttat gtataacagg    5880
cataatttaa agttttattt gcgattcatc gttttttcagg tactcaaacg ctgaggtgtg    5940 cctttttgact tacttttccg ccttggcaag ctggccgggt gatacttgca caagttccac    6000
taattactga catttgtggt attaactcgt ttgactgctc tacaattgta ggatgttaat    6060
caatgtcttg gctgcctaac ctgcaggccg cgagcgccga tatgcgtatgt aatagacaat    6120 aaaaccatgt ttatataaaa aaaattcaaa atagaaaacg attctgtaca aggagtattt    6180 ttttttttgtt ctagtgtgtt tatattatcc ttggctaaga ggcactgcgt atacttcaag    6240
gtacccctgt gttttgaaaa aaaacaacag taaaatagga actccgcgag gttcaggaac    6300
ctgaaacaaa atcaataaaa acattatatg cgtttcgaac aaaattaaag aaaaagaata    6360
aatatagatt aaaaaaaaaa agaagaaatt aaagaatttt ctactaaatc ccaattgtta    6420
tatatttgtt aaatgccaaa aaagtttata aaaaatttag aatgtataaa taataataaa    6480
ctaagtaacg cgatcgccga cgccgccgat atctccctcg ccagcggccg ccttatggct    6540
aagaatgttg gaattttggc catggacatc tacttcccac caacttgtgt tcagcaggag    6600 gcttttagaag cacatgacgg agcctcaaag ggtaagtaca caatcggatt aggacaggat    6660
```

```
tgcttagcat tctgcactga attggaggac gtcatctcaa tgtctttcaa cgccgtcacc    6720
tcattgttag agaagtacaa aatcgaccca aaccagatcg gaaggttgga agtcggttct    6780
gaaaccgtca tcgacaagtc taaatcaatc aagactttcg ttatgcagtt gttcgaaaag    6840
tgcggtaata ctgacgtcga gggtgtagac tctactaacg cttgttatgg tggtaccgca    6900
gctttattga actgcgtaaa ctgggttgag tcaaactcat gggatggtag gtacggatta    6960
gtcatttgca ccgattctgc cgtctacgcc gagggtccag caaggccaac cggtggagct    7020
gcagctattg ctatgttaat cggaccagat gcccctatag tcttcgagtc taagttgagg    7080
ggttcacaca tccctaacgt ctacgacttc tacaagccaa acttggcctc agagtatcca    7140
gttgtcgacg gaaagttatc tcagacatgc tacttgatgg ccttagattc atgttacaag    7200
cacttatgca acaagttcga aaagttggag ggaaaggagt tctcaattaa cgacgccgac    7260
tacttcgttt ttcactctcc atacaacaaa ttggtccaga agtcattcgc caggttattg    7320
tacaacgatt ttttgagaaa cgcatcatct atcgatgagg ccgccaagga gaaattcacc    7380
ccatattctt ctttgtcatt ggacgagtct taccagtcta gggacttgga gaaggtatca    7440
cagcaattgg ctaaaacctt ctatgacgcc aaagttcagc caaccacctt ggtccctaaa    7500
caggtcggaa atatgtatac tgcatctttg tatgccgcct ttgcctcttt gatccacaac    7560
aagcacaacg atttagtcgg aaaaagggtt gtcatgtttt cttacggtgc cggatctact    7620
gccactatgt tctcattgag gttatgcgaa aaccagtcac cattttcatt gtctaacatc    7680
gcctcagtca tggacgtagg tgtctcacct gagaagttcg tagaaaccat gaagttgatg    7740
gagcacagat acggtgccaa agaattcgtc acttcaaaag agggaatctt ggatttgttg    7800
gccccaggaa cctactattt gaaggaggtc gactctttgt acagaaggtt ctatggaaag    7860
aagggagacg acggatctgt cgcaaacggt cagtaaatcg gcggcgtcgg cgatcgcgtt    7920
aaggcggccg ctggcgaggg agatatttca acctgggcct aacagtaaag atatcctcct    7980
caaaactggt gcacttaatc gctgaatttg ttctggcttc tcttcttttt ctttattccc    8040
cccatgggcc aaaaaaaata gtactatcag gaatttggcg ccgggtcacg atatacgtgt    8100
acagtgacct aggcgacgcc acaaggaaaa aggaaaaaaa cagaaaaaac aacaaaaact    8160
aaaacaaaca cgaaaacttt aatagatcta agtgaagtag tggtgaggca attggagtga    8220
catagcagct actacaacta caaaaaaggc gcgccacggt cgtgcggata tgaaagaggt    8280
cgttatagct tctgccgtca ggaccgccat cggatcttac ggtaagtcat taaaggacgt    8340
ccctgccgtt gatttaggag ccaccgcaat taaagaggcc gttaaaaagg caggtataaa    8400
gccagaggac gtcaacgagg tcatcttggg aaatgtctta caagccggat taggtcaaaa    8460
cccagcaaga caagcatcat tcaaagccgg tttacctgtc gagatacctg caatgaccat    8520
caacaaggtt tgcggttcag gattaaggac cgtttcttta gcagcacaga tcattaaggc    8580
tggagatgca gacgttatca ttgctggtgg tatggaaaac atgtcaagag ccccatactt    8640
ggctaataac gccaggtggg gatataggat gggaaacgcc aagtttgtcg acgaaatgat    8700
tactgacgga ttgtgggacg ccttcaatga ctatcacatg gtataaccg cagaaaacat    8760 tgccgagagg tggaatatct caagagaaga acaggatgag tttgcattgg cctcacagaa    8820
aaaagcagag gaggcaataa agtcaggtca gtttaaggat gaaatcgtcc cagtcgtcat    8880
caagggaaga aagggtgaga cagttgtcga caccgacgaa cacccctagat ttggttcaac    8940 catcgaggga ttagcaaagt tgaagccagc cttcaagaaa gacggaaccg taaccgccgg    9000
```

```
taatgcatct ggattgaacg attgcgcagc agttttggtc ataatgtcag ccgagaaagc      9060
taaggagttg ggtgtcaagc cattggcaaa aattgtttca tacggatcag ccggtgtcga      9120
ccctgccatc atgggttacg gaccttttta cgccaccaag gctgcaatcg aaaaggccgg      9180
ttggaccgta gatgaattgg atttgatcga gtcaaacgag gcctttgccg cccaatcatt      9240
ggctgtcgcc aaggacttga agttcgacat gaacaaggtc aacgtcaacg gtggtgccat      9300
cgcattgggt caccctatcg gagcctctgg tgccaggatc ttggttacct tggtccacgc      9360
catgcagaag agggacgcaa agaagggttt ggccaccttg tgcatcggtg gaggtcaggg      9420
aacagctatc ttgttagaga atgcagccc ctcagccccc ctagcgtcga ataaaagaca      9480
ttggtacatg atatcaaaca gaattttaac atttcttgat ccagtttgta aacaaaacaa      9540
acaatttttc taccatttaa cttcatacca tcggcgagag ccgaacagga aaaaaaagaa      9600
gtctccggtt atcgtaagca gtatcaaata ataagaatgt atgtgtgtgc aatttgttat      9660
acccacgaag aagtgcgcag tagagttaga aaaccaactg agtaatcttt actcccgaca      9720
atcgtccaat aatcctcttg ttgctaggaa cgtgatgatg gatttcgttt gaaatccgga      9780
cggaaaactc aaaagaagtc caaccaccaa ccattttcga gcctcaagaa tctctaagca      9840
ggtttcttta ctaaggggat ggcctttctg tcctggacat ttttccttc ctttttttcat      9900 ttccttgaaa ggaacagatt tttttgact tttgccacac agctgcacta tctcaaccc      9960 ttttacattt taagttttcg ggtgaatgg ccggtgttta accccagcg cctggcggg    10019
```

<210> SEQ ID NO 27
<211> LENGTH: 5027
<212> TYPE: DNA
<213> ORGANISM: Artificial Sequence
<220> FEATURE:
<223> OTHER INFORMATION: Synthetic: Mat alpha FcphI target site cassette

<400> SEQUENCE: 27

```
tgatgtctgg gttttgtttg ggatgcaatt tattgcttcc caatgtagaa aagtacatca        60
tatgaaacaa cttaaactct taactacttc ttttaacctt cacttttat gaaatgtatc        120 aaccatatat aataacttaa tagacgacat tcacaatatg tttacttcga agcctgcttt        180
caaaattaag aacaaagcat ccaaatcata cagaaacaca gcggtttcaa aaaagctgaa        240
agaaaaacgt ctagctgagc atgtgaggcc aagctgcttc aatattattc gaccactcaa        300
gaaagatatc cagattcctg ttccttcctc tcgattttta aataaaatcc aaattcacag        360
gatagcgtct ggaagtcaaa atactcagtt tcgacagttc aataagacat ctataaaatc        420
ttcaaagaaa tatttaaact catttatggc ttttagagca tattactcac agtttggctc        480
cggtgtaaaa caaatgtct tgtcttctct gctcgctgaa gaatggcacg cggacaaaat        540
gcagcacgga atatgggact acttcgcgca acagtataat tttataaacc ctggttttgg        600
ttttgtagag tggttgacga ataattatgc tgaagtacgt ggtgacggat attgggaaga        660
tgtgtttgta catttggcct tatagagtgt ggtcgtggcg gaggttgttt atcttttcgag       720 tactgaatgt tgtcagtata gctatcctat ttgaaactcc ccatcgtctt gctcttgttc        780
ccaatgtttg tttatacact catatggcta tacccttatc tacttgcctc ttttgttat        840 gtctatgtat ttgtataaaa tatgatatta ctcagactca agcaaacaat caatttgtga        900
gcgttgcgct cgtgcatcga gaagttaaga ttatatgaat aactaaatac taaatagaaa        960
tgtaaataca gtgagaacaa acaaaaaaa acgaacaga gaaactaaat ccacattaat       1020
tgagagttct atctattaga aaatgcaaac tccaactaaa tgggaaaaca gataacctct      1080
```

```
tttattttttt tttaatgttt gatattcgag tcttttctt tgttaggtt tatattcatc     1140 atttcaatga ataaaagaag cttcttattt tggttgcaaa gaatgaaaaa aaaggatttt     1200
ttcatacttc taaagcttca attataacca aaaattttat aaatgaagag aaaaaatcta     1260
gtagtatcaa gttaaactta gaaaaactca tcgagcatca aatgaaactg caatttattc     1320
atatcaggat tatcaatacc atattttga aaaagccgtt tctgtaatga aggagaaaac     1380
tcaccgaggc agttccatag gatggcaaga tcctggtatc ggtctgcgat tccgactcgt     1440
ccaacatcaa tacaacctat taatttcccc tcgtcaaaaa taaggttatc aagtgagaaa     1500
tcaccatgag tgacgactga atccggtgag aatggcaaaa gcttatgcat ttctttccag     1560
acttgttcaa caggccagcc attacgctcg tcatcaaaat cactcgcatc aaccaaaccg     1620
ttattcattc gtgattgcgc ctgagcgaga cgaaatacgc gatcgctgtt aaaaggacaa     1680
ttacaaacag gaatcgaatg caaccggcgc aggaacactg ccagcgcatc aacaatattt     1740
tcacctgaat caggatattc ttctaatacc tggaatgctg ttttgccggg gatcgcagtg     1800
gtgagtaacc atgcatcatc aggagtacgg ataaaatgct tgatggtcgg aagaggcata     1860
aattccgtca gccagtttag tctgaccatc tcatctgtaa catcattggc aacgctacct     1920
ttgccatgtt tcagaaacaa ctctggcgca tcgggcttcc catacaatcg atagattgtc     1980
gcacctgatt gcccgacatt atcgcgagcc catttatacc catataaatc agcatccatg     2040
ttggaattta atcgcggcct cgaaacgtga gtcttttcct tacccatttt taatgttact     2100
tctcttgcag ttagggaact ataatgtaac tcaaaataag attaaacaaa ctaaaataaa     2160
aagaagttat acagaaaaac ccatataaac cagtactaat ccataataat aatacacaaa     2220
aaaactatca aataaaacca gaaaacagat tgaatagaaa aatttttcg atctcctttt     2280 atattcaaaa ttcgatatat gaaaagggga actctcagaa aatcaccaaa tcaatttaat     2340
tagatttttc ttttccttct agcgttggaa agaaaaattt ttcttttttt tttagaaat     2400 gaaaaatttt tgccgtagga atcaccgtat aaaccctgta taaacgctac tctgttcacc     2460
tgtgtaggct atgattgacc cagtgttcat tgttattgcg agagagcggg agaaaagaac     2520
cgatacaaga gatccatgct ggtatagttg tctgtccaac actttgatga acttgtagga     2580
cgatgatgtg tattactagt gtcgacatgc gtccatcttt acagtcctgt cttattgttc     2640
ttgatttgtg ccccgtaaaa tactgttact tggttctggc gaggtattgg atagttcctt     2700
tttataaagg ccatgaagct ttttcttttcc aattttttt ttttcgtcat tatagaaatc     2760
attacgaccg agattcccgg gtaataactg atataattaa attgaagctc taatttgtga     2820
gtttagtata catgcatta cttataatac agtttttag ttttgctggc cgcatcttct     2880
caaatatgct tccagcctg ctttctgta acgttcaccc tctaccttag catcccttcc     2940
ctttgcaaat agtcctcttc caacaataat aatgtcagat cctgtagaga ccacatcatc     3000
cacggttcta tactgttgac ccaatgcgtc tcccttgtca tctaaaccca caccgggtgt     3060
cataatcaac caatcgtaac cttcatctct tccacccatg tctctttgag caataaagcc     3120
gataacaaaa tctttgtcac tcttcgcaat gtcaacagta cccttagtat attctccagt     3180
agatagggag cccttgcatg acaattctgc taacatcaaa aggcctctag gttcctttgt     3240
tacttcttct gccgcctgct tcaaaccgct aacaatacct gggcccacca caccgtgtgc     3300
attcgtaatg tctgcccatt ctgctattct gtatacaccc gcagagtact gcaatttgac     3360
tgtattacca atgtcagcaa attttctgtc ttcgaagagt aaaaaaattgt acttggcgga     3420
```

```
taatgccttt agcggcttaa ctgtgccctc catggaaaaa tcagtcaaga tatccacatg    3480 tgttttagt aaacaaattt tgggacctaa tgcttcaact aactccagta attccttggt    3540
ggtacgaaca tccaatgaag cacacaagtt tgtttgcttt tcgtgcatga tattaaatag    3600
cttggcagca acaggactag gatgagtagc agcacgttcc ttatatgtag ctttcgacat    3660
gatttatctt cgtttcctgc aggttttgt tctgtgcagt tgggttaaga atactgggca    3720
atttcatgtt tcttcaacac cacatatgcg tatatatacc aatctaagtc tgtgctcctt    3780
ccttcgttct tccttctgct cggagattac cgaatcaaaa aaatttcaaa gaaaccggaa    3840
tcaaaaaaaa gaacaaaaaa aaaaagatg aattgaaaag ctttatggac cctgaaacca    3900
cagccacatt aaccttcttt gatggtcaaa acttatcctt caccataaat atgcctcgca    3960
aaaaaggtaa ttaacatata tagaattaca ttatttatga aatatcatca ctatctctta    4020
gcatctttaa tccttttcta catcagataa cttcggtttg ttatcatcgt ctgtattgtc    4080
atcaattggc gcagtagcct caatttcaac gtcgtttgac tctggtgttt gttcatgtgc    4140
agatccatga gatgatgaac ttgtgagcgt tgcgctcgtg catccggagg ttgtttatct    4200
ttcgagtact gaatgttgtc agtatagcta tcctatttga aactccccat cgtcttgctc    4260
ttgttcccaa tgtttgttta tacactcata tggctatacc cttatctact tgcctctttt    4320
gtttatgtct atgtatttgt ataaatatg atattactca gactcaagca aacaatcaat    4380
tcttagcatc attctttgtt cttatcttaa ccataaacga tcttgatgtg acttttgtaa    4440
tttgaacgaa ttggctatac gggacggatg acaaatgcac cattactcta ggttgttgtt    4500
ggatcttaac aaaccgtaaa ggtaaactgc ccatgcggtt cacatgactt ttgactttcc    4560
tttgtttgct agttaccttc ggcttcacaa tttgtttttc cacttttcta acaggtttat    4620
cacctttcaa acttatcttt atcttattcg ccttcttggg tgcctccaca gtagaggtta    4680
cttccttttt aatatgtact tttaggatac tttcacgctt tataacaata tcaagtttac    4740
cttcttcatt actattcatc ttcgccacaa gtcttctctc ccttggtgtt tccaatctaa    4800
ctacaaaact gttgattagg gtgtacatca ccctaacaag atcatgtatt tgcttcctct    4860
ggtacaagct aagaacaggt aaattcaaaa catcccagag taatatcttc aaagggctat    4920 acccttaaa catatctcgg catatttgta ttaacccact aatattttga cggccaatct    4980
tttctatttt tattttcata tcatcgacgt aatgaccact taaaaac                 5027
```

<210> SEQ ID NO 28
<211> LENGTH: 6126
<212> TYPE: DNA
<213> ORGANISM: Artificial Sequence
<220> FEATURE:
<223> OTHER INFORMATION: Synthetic: ADS_GAL80 donor cassette

<400> SEQUENCE: 28

```
gcctgtctac aggataaaga cgggtcggat acctgcacaa gcaatttggc acctgcatac      60
cccatttccc cagtagataa cttcaacaca cacatcaatg tccctcacca gtttatttcc     120
aaaagagacg cttttactac cctgactaga ttttcatttt gtttctttg gattgcgctt     180 gcctttgtag gtgtgtcgtt tatccttttac gttttgactt ggtgctcgaa gatgctttca     240
gagatggtgc ttatcctcat gtcttttggg tttgtcttca atacggcagc cgttgtcttg     300
caaacggccg cctctgccat ggcaaagaat gctttccatg acgatcatcg tagtgcccaa     360
ttgggtgcct ctatgatggg tttaaacgta tggcttgggc aagtgtcttt ttatgtatcg     420
tggaatttat cctgctggtc ttctggtctg ttagggcaag gttggcctct acttactcca     480
```

```
tcgacaattc aagatacaga acctcctcca gatggaatcc cttccataga gagaaggagc    540
aagcaactga cccaatattg actgccactg gacctgaaga catgcaacaa agtgcaagca    600
tagtggggcc ttcttccaat gctaatccgg tcactgccac tgctgctacg gaaaaccaac    660
ctaaaggtat taacttcttc actataagaa aatcacacga gcgcccggac gatgtctctg    720
tttaaatggc gcaagttttc cgctttgtaa tatatattta taccccttc ttctctcccc     780 tgcaatataa tagtttaatt ctaatattaa taatatccta tattttcttc atttaccggc    840
gcactctcgc ccgaacgacc tcaaaatgtc tgctacattc ataataacca aaagctcata    900 acttttttt ttgaacctga atatatatac atcacatatc actgctggtc ctcttcgagc     960
gtcccaaaac cttctcaagc aaggttttca gtaatgtt acatgcgtac acgcgtctgt     1020
acagaaaaaa aagaaaaatt tgaaatataa ataacgttct taatactaac ataactataa   1080
aaaaataaat agggacctag acttcaggtt gtctaactcc ttccttttcg gttagagcgg   1140
atcttagcta gcttaaatag acatgggata aactaataaa gacttaatta aatgcttgta   1200
ctcatctccc atacgagtga agttatcttt acccgcgtac tgcacttcca ggaattgaca   1260
aagatagata actgccatca gtaatggtct gggtatgttt ttagtggtca agtattctct   1320
gtttatgtcc ttccaaacgt cttcgacttc cttgtatatg agggtttgtg cgtattcctc   1380
atttacatta tattccttca tataagattc tagagaagat gatgagtgct ttctctcctg   1440
ttctgccttg tgcgtcatca agtcgtttag acgacgaccc aaaataccag aataccggaa   1500
tagtggtggc gctgacacgg cccattcaac tgattcttta gtgaaaatat ctgacatccc   1560
caggtaacat gtggttgtca gtaggttcgc tccaccagtt ataataacaa ctggatcgtg   1620
ttcttcagtg gtcggtatgt gcccttcgtt tgcccacttt gcttcgacca tgagattccg   1680
tacaaattcc ttaacaaact cttttccgca attaaataaa tctgttctcc cttcttttgc   1740
aagaaattcc tccatttctg tatacgtatc catgaataat ttatagatag gcttcatgta   1800
ttctggcagc gtatcaaggc aggtaatcga ccaacgttct acagcttcag tgaaaatttt   1860
taattcttca tatgttccat aagcatcgta agtatcatca atcagggtta taacggctac   1920
cactttggtg aagaaaactc gtgctcttga atattgtggt tcataaccag aacctaaacc   1980
ccagaaataa cactctacaa tgcggtcgcg caaacaaggt gcgttctttt ttatatcaaa   2040
tgctttccac catttacaga cgtggctaag ctcctccttg tgcaaagatt gcagcaggtt   2100
gaattctaat tttgctaatt ttaaaagcgt cttattatga gagtcttgtt gttggtagaa   2160
aggaatatac tgagcagctt ctatgcgggg aagacgcttc cataaaggtt gttttaatgc   2220
tctttgtatt tcggtaaaca aagccggatt agtggagaat gcatccttag tcattataga   2280
taatcgactt ctagtaaacc caagcgcgtc ttccaaaata atttcgcctg gaacccgcat   2340
ggaagtcgcc tcatataact ctaataaccc ttccacatca ttagccaatg attgtttaaa   2400
agcaccgttt ttatctttgt aattattgaa aacatcacag gtcacgtagt agccttgctt   2460
cctcatcaag cgaaaccata gtgaactgcg atctccattc cagttgtctc cgtatgtctc   2520
gtaaatacat tgaagagcat ggtcaatttc cctttcaaaa tggtatggaa ttcctagtct   2580
ctgtatttca tctattaatt ttaacaaatt agcatgcttc ataggaatgt ctaaggcttc   2640
cttcaggagc tgtcttactt cttcttcag atcgtttaca atttgttcga cccttgttc    2700 tacttgtttc tcataaatga gaaactgatc accccaaata gagggaggga aattggctat   2760
aggtctaatc ggtttctcct cggttagtgc catggatcct tcagttacag taaatgtttt   2820
```

```
agttgcatcg tcataggtcc attcaccatc aacaccatta tcattagcat attgcttaaa    2880
gaccttttcg gctgttgctg catctactgc ttcggtagta gtttcaccct tcaaagtttt    2940
accattcaaa attaatttat attgacccat ttatattgaa ttttcaaaaa ttcttacttt    3000
ttttttggat ggacgcaaag aagtttaata atcatattac atggcattac caccatatac    3060
atatccatat ctaatcttac ttatatgttg tggaaatgta aagagcccca ttatcttagc    3120
ctaaaaaaac cttctctttg gaactttcag taatacgctt aactgctcat tgctatattg    3180
aagtacggat tagaagccgc cgagcgggcg acagccctcc gacggaagac tctcctccgt    3240
gcgtcctcgt cttcaccggt cgcgttcctg aaacgcagat gtgcctcgcg ccgcactgct    3300
ccgaacaata aagattctac aatactagct tttatggtta tgaagaggaa aaattggcag    3360
taacctggcc ccacaaacct tcaaattaac gaatcaaatt aacaaccata ggatgataat    3420
gcgattagtt ttttagcctt atttctgggg taattaatca gcgaagcgat gattttttgat    3480 ctattaacag atatataaat ggaaaagctg cataaccact ttaactaata ctttcaacat    3540
tttcagtttg tattacttct tattcaaatg tcataaaagt atcaacaaaa aattgttaat    3600
atacctctat actttaacgt caaggagaaa aaactataat gtcattaccg ttcttaactt    3660
ctgcaccggg aaaggttatt attttttggtg aacactctgc tgtgtacaac aagcctgccg    3720
tcgctgctag tgtgtctgcg ttgagaacct acctgctaat aagcgagtca tctgcaccag    3780
atactattga attggacttc ccggacatta gctttaatca taagtggtcc atcaatgatt    3840
tcaatgccat caccgaggat caagtaaact cccaaaaatt ggccaaggct caacaagcca    3900
ccgatggctt gtctcaggaa ctcgttagtc ttttggatcc gttgttagct caactatccg    3960
aatccttcca ctaccatgca gcgttttgtt tcctgtatat gtttgtttgc ctatgccccc    4020
atgccaagaa tattaagttt tctttaaagt ctactttacc catcggtgct gggttgggct    4080
caagcgcctc tatttctgta tcactggcct tagctatggc ctacttgggg gggttaatag    4140
gatctaatga cttggaaaag ctgtcagaaa acgataagca tatagtgaat caatgggcct    4200
tcataggtga aaagtgtatt cacggtaccc cttcaggaat agataacgct gtggccactt    4260
atggtaatgc cctgctattt gaaaaagact cacataatgg aacaataaac acaaacaatt    4320
ttaagttctt agatgatttc ccagccattc caatgatcct aacctatact agaattccaa    4380
ggtctacaaa agatcttgtt gctcgcgttc gtgtgttggt caccgagaaa tttcctgaag    4440
ttatgaagcc aattctagat gccatggggtg aatgtgccct acaaggctta gagatcatga    4500
ctaagttaag taaatgtaaa ggcaccgatg acgaggctgt agaaactaat aatgaactgt    4560
atgaacaact attggaattg ataagaataa atcatggact gcttgtctca atcggtgttt    4620
ctcatcctgg attagaactt attaaaaatc tgagcgatga tttgagaatt ggctccacaa    4680
aacttaccgg tgctggtggc ggcggttgct ctttgacttt gttacgaaga gacattactc    4740
aagagcaaat tgacagtttc aaaaagaaat tgcaagatga ttttagttac gagacatttg    4800
aaacagactt gggtgggact ggctgctgtt tgttaagcgc aaaaaatttg aataaagatc    4860
ttaaaatcaa atccctagta ttccaattat ttgaaaataa aactaccaca agcaacaaa    4920 ttgacgatct attattgcca ggaaacacga atttaccatg gacttcataa gctaatttgc    4980
gataggcatt atttattagt tgtttttaat cttaactgtg tatgaagttt tatgtaataa    5040
agatagaaag agaaacaaaa aaaaattttt cgtagtatca attcagcttt cgaagacaga    5100
atgaaattta agcagaccat tcatcttgcc ctgtgcttgg cccccagtgc agcgaacgtt    5160
ataaaaacga atactgagta tatatctatg taaaacaacc atatcatttc ttgttctgaa    5220
```

```
ctttgtttac ctaactagtt ttaaatttcc cttttcgtg catgcgggtg ttcttattta      5280
ttagcatact acatttgaaa tatcaaattt ccttagtaga aaagtgagag aaggtgcact      5340
gacacaaaaa ataaaatgct acgtataact gtcaaaactt tgcagcagcg ggcatccttc      5400
catcatagct tcaaacatat tagcgttcct gatcttcata cccgtgctca aaatgatcaa      5460
acaaactgtt attgccaaga aataaacgca aggctgcctt caaaaactga tccattagat      5520
cctcatatca agcttcctca tagaacgccc aattacaata agcatgtttt gctgttatca      5580
ccgggtgata ggtttgctca accatggaag gtagcatgga atcataattt ggatactaat      5640
acaaatcggc catataatgc cattagtaaa ttgcgctccc atttaggtgg ttctccaggc      5700
aaatttgaat actaataaat gcggtgcatt tgcaaaatga atttattcca aggccaaaac      5760
aacacgatga atggctttat ttttttgtta ttcctgacat gaagctttat gtaattaagg      5820
aaacggacat cgaggaattt gcatcttttt tagatgaagg agctattcaa gcaccaaagc      5880
tatccttcca ggattattta agcggtaagg ccaaggcttc ccaacaggtt catgaagtgc      5940
atcatagaaa gcttacaagg tttcagggtg aaacttttct aagagattgg aacttagtct      6000
gtgggcatta taagagagat gctaagtgtg gagaaatggg acccgacata attgcagcat      6060
ttcaagatga aaagcttttt cctgagaata atctagcctt aatttctcat attggggggtc      6120 atattt                                                                 6126

<210> SEQ ID NO 29
<211> LENGTH: 9550
<212> TYPE: DNA
<213> ORGANISM: Artificial Sequence
<220> FEATURE:
<223> OTHER INFORMATION: Synthetic: ADS_HXT3 donor cassette

<400> SEQUENCE: 29
accggtatat caaatggcgg tgtagtttga aaagtacact gtatgtccat taataaaatt        60
acgccgaaga acactgacta gctataaatt ctcttccggc gtccaattc aacctaaggc        120 aagtattgtt aatcaataat gcgtgttggt aaatatgaag cccgatgttg attaagaaga        180
attattcgta taagaattaa gcaagcaaaa ttaaggaaaa ttttttcttt cctattcgtc        240
atcgcagaca gccttcatct tctcgagata cacctggag gaggagcaat gaaatgaaag        300
gaaaaaaaaa tactttcttt ttcttgaaaa aagaaaaaaa ttgtaagatg agctattcgc        360
ggaacattct agctcgtttg catcttcttg catttggtag gttttcaata gttcggtaat        420
attaacggat acctactatt atccctagt aggctctttt cacggagaaa ttcgggagtg        480 ttttttttc gtgcgcattt tcttagctat attcttccag cttcgcctgc tgcccggtca        540
tcgttcctgt cacgtagttt ttccggattc gtccggctca tataataccg caataaacac        600
ggaatatctc gttccgcgga ttcggttaaa ctctcggtcg cggattatca cagagaaagc        660
ttcgtggaga atttttccag attttccgct tccccgatg ttggtatttc cggaggtcat        720
tatactgacc gccattataa tgactgtaca acgaccttct ggagaaagaa acaactcaat        780
aacgatgtgg gacattgggg gcccactcaa aaaatctggg gactatatcc ccagagaatt        840
tctccagaag agaagaaaag tcaaagtttt ttttcgcttg ggggttgcat ataaacttcg        900
agcgtcccaa aaccttctca agcaaggttt tcagtataat gttacatgcg tacacgcgtc        960
tgtacagaaa aaaagaaaa atttgaaata taaataacgt tcttaatact aacataacta       1020
taaaaaaata aatagggacc tagacttcag gttgtctaac tccttccttt tcggttagag       1080
```

```
cggatcttag atagacatag ggtagaccaa caaagactta attaagtgct tatattcgtc    1140
acccattctg gtgaaattgt ctttaccagc gtattgaact tctaagaatt gacataaata    1200
gataacagcc attaacaatg gacgtggaat attttggtg gtcaagtatt ctctgttaat     1260
atctttccaa acgtcttcaa cttccttgta aatcaaagtt tgagcgtatt cttcgttaac    1320
gttgtattcc ttcatgtaag attctaagga agaggaggag tgctttcttt cttgctcagc   1380
cttgtgagtc atcaaatcgt ttaatcttct acccaaaata ccagagtatc tgaacaaagg   1440
tggagcggaa acggcccatt caacagattc cttggtgaaa atatcagaca tacctaagta   1500
acaagtagta gtcaacaagt tagcaccacc agtaatgata acgactggat cgtgttcttc   1560
agtagttgga atatgacctt cgttagccca tttagcttca accatcaagt tacgaacgaa   1620
ttccttaacg aattccttac cacaattgaa caagtcggta cgaccttcct tagccaagaa   1680
ttcttccatt tcggtgtaag tgtccatgaa caacttataa attggcttca tgtattctgg   1740
taaagtatct aaacaggtaa tggaccatct ttcgacagct tcagtgaaaa tcttcaattc   1800
ttcgtaggta ccgtaagcgt cgtaagtgtc gtcaatcaag gtaataacag caaccacctt   1860
agtaaagaaa actctagctc tagagtattg tggttcgtaa ccggaaccca accccagaa    1920 gtaacattcg acaattctat ctctcaaaca tggagcgttc ttcttaatat cgaaggcttt   1980
ccaccactta caaacgtgag acaattcttc cttgtgcaag gattgcaaca agttaaattc   2040 caattagcc aatttcaaca aggttttgtt gtgagagtct tgttgttggt agaatgggat     2100
gtattgagca gcttcgattc ttggcaaacg cttccacaat ggttgtttca agctctttg    2160 gatttcagtg aacaaagctg ggttagtaga gaaggcatct ttagtcatga tggacaatct   2220
agatctagta aaacccaaag cgtcttccaa gatgatttca ccaggaactc tcatggaggt   2280
ggcttcatac aattctaaca aaccttcaac atcgttggcc aaagattgct taaaagcacc   2340
attcttatct ttgtagttgt tgaaaacgtc acaagtaacg tagtaacctt gctttctcat   2400
taatctgaac cataaggaag atctgtcacc gttccagtta tcaccgtaag tttcgtaaat   2460
acattgcaaa gcgtgatcaa tttctctttc gaaatggtat ggaataccta atctttggat   2520
ttcgtcgatt aatttcaata agttagcgtg cttcattggg atgtccaaag cttccttcaa   2580
caattgtcta acttccttct tcaaatcgtt aacgatttgt tcaacacctt gctcaacttg   2640
cttttcgtag atcaagaatt ggtcacccca gatagaaggt ggaaaattag caattggtct   2700
gattggtttt tcttcagtca aagccatgga tccttcagtt acagtaaatg ttttagttgc   2760
atcgtcatag gtccattcac catcaacacc attatcatta gcatattgct taaagacctt   2820
ttcggctgtt gctgcatcta ctgcttcggt agtagtttca cccttcaaag ttttaccatt   2880
caaaattaat ttatattgac ccatttatat tgaattttca aaaattctta ctttttttt    2940 ggatggacgc aaagaagttt aataatcata ttacatggca ttaccaccat atacatatcc   3000
atatctaatc ttacttatat gttgtggaaa tgtaaagagc cccattatct agcctaaaa    3060 aaaccttctc tttggaactt tcagtaatac gcttaactgc tcattgctat attgaagtac   3120
ggattagaag ccgccgagcg ggcgacagcc ctccgacgga agactctcct ccgtgcgtcc   3180
tcgtcttcac cggtcgcgtt cctgaaacgc agatgtgcct cgcgccgcac tgctccgaac   3240
aataaagatt ctacaatact agcttttatg gttatgaaga ggaaaaattg gcagtaacct   3300
ggccccacaa accttcaaat taacgaatca aattaacaac cataggatga taatgcgatt   3360
agttttttag ccttatttct gggtaatta atcagcgaag cgatgatttt tgatctatta    3420
acagatatat aaatggaaaa gctgcataac cactttaact aatactttca acattttcag   3480
```

```
tttgtattac ttcttattca aatgtcataa aagtatcaac aaaaaattgt taatatttta     3540
attctgctgt aacccgtaca tgcccaaaat aggggcggg ttacacagaa tatataacat      3600
cgtaggtgtc tgggtgaaca gtttattcct ggcatccact aaatataatg gagcccgctt    3660
tttaagctgg catccagaaa aaaaagaat cccagcacca aaatattgtt ttcttcacca     3720
accatcagtt cataggtcca ttctcttagc gcaactacag agaacagggg cacaaacagg    3780
caaaaaacgg gcacaacctc aatggagtga tgcaacctgc ctggagtaaa tgatgacaca   3840
aggcaattga cccacgcatg tatctatctc attttcttac accttctatt accttctgct   3900
ctctctgatt tggaaaaagc tgaaaaaaaa ggttgaaacc agttccctga aattattccc   3960
ctacttgact aataagtata taaagacggt aggtattgat tgtaattctg taaatctatt   4020
tcttaaactt cttaaattct acttttatag ttagtctttt ttttagtttt aaaacaccaa   4080
gaacttagtt tcgatccccg cgtgcttggc cggccgtatc cccgcgtgct ggccggccg    4140 tatgtctcag aacgtttaca ttgtatcgac tgccagaacc ccaattggtt cattccaggg   4200
ttctctatcc tccaagacag cagtggaatt gggtgctgtt gctttaaaag gcgccttggc   4260
taaggttcca gaattggatg catccaagga ttttgacgaa attatttttg gtaacgttct   4320
ttctgccaat ttgggccaag ctccggccag acaagttgct ttggctgccg gtttgagtaa   4380
tcatatcgtt gcaagcacag ttaacaaggt ctgtgcatcc gctatgaagg caatcatttt   4440
gggtgctcaa tccatcaaat gtggtaatgc tgatgttgtc gtagctggtg gttgtgaatc   4500
tatgactaac gcaccatact acatgccagc agcccgtgcg ggtgccaaat ttggccaaac   4560
tgttcttgtt gatggtgtcg aaagagatgg gttgaacgat gcgtacgatg gtctagccat   4620
gggtgtacac gcagaaaagt gtgcccgtga ttgggatatt actagagaac aacaagacaa   4680
ttttgccatc gaatcctacc aaaaatctca aaaatctcaa aaggaaggta aattcgacaa   4740
tgaaattgta cctgttacca ttaagggatt tagaggtaag cctgatactc aagtcacgaa   4800
ggacgaggaa cctgctagat tacacgttga aaaattgaga tctgcaagga ctgttttcca   4860
aaaagaaaac ggtactgtta ctgccgctaa cgcttctcca atcaacgatg gtgctgcagc   4920
cgtcatcttg gtttccgaaa aagttttgaa ggaaaagaat ttgaagcctt tggctattat   4980
caaaggttgg ggtgaggccg ctcatcaacc agctgatttt acatgggctc catctcttgc   5040
agttccaaag gctttgaaac atgctggcat cgaagacatc aattctgttg attactttga   5100
attcaatgaa gccttttcgg ttgtcggttt ggtgaacact aagatttga agctagaccc    5160 atctaaggtt aatgtatatg gtggtgctgt tgctctaggt cacccattgg ttgttctgg    5220 tgctagagtg gttgttacac tgctatccat cttacagcaa gaaggaggta agatcggtgt   5280
tgccgccatt tgtaatggtg gtggtggtgc ttcctctatt gtcattgaaa agatatgatt   5340
acgttctgcg attttctcat gatcttttc ataaaataca taaatatata aatggcttta   5400
tgtataacag gcataattta aagttttatt tgcgattcat cgttttcag gtactcaaac    5460 gctgaggtgt gccttttgac ttacttttcc gccttggcaa gctggccggg tgatacttgc   5520
acaagttcca ctaattactg acatttgtgg tattaactcg tttgactgct ctacaattgt   5580
aggatgttaa tcaatgtctt ggctgcctaa cctgcaggcc gcgagcgccg atatgctatg   5640
taatagacaa taaaaccatg tttatataaa aaaaattcaa aatagaaaac gattctgtac   5700
aaggagtatt tttttttgt tctagtgtgt ttatatttatc cttggctaag aggcactgcg   5760
tatacttcaa ggtaccccctg tgtttgaaa aaaaacaaca gtaaaatagg aactccgcga   5820
```

```
ggttcaggaa cctgaaacaa aatcaataaa aacattatat gcgtttcgaa caaaattaaa    5880
gaaaaagaat aaatatagat taaaaaaaaa aagaagaaat taaaagaatt tctactaaat    5940
cccaattgtt atatatttgt taaatgccaa aaaagtttat aaaaaattta gaatgtataa    6000
ataataataa actaagtaac gcgatcgccg acgccgccga tatctccctc gccagcggcc    6060
gccttatggc taagaatgtt ggaattttgg ccatggacat ctacttccca ccaacttgtg    6120
ttcagcagga ggctttagaa gcacatgacg gagcctcaaa gggtaagtac acaatcggat    6180
taggacagga ttgcttagca ttctgcactg aattggagga cgtcatctca atgtctttca    6240
acgccgtcac ctcattgtta gagaagtaca aaatcgaccc aaaccagatc ggaaggttgg    6300
aagtcggttc tgaaaccgtc atcgacaagt ctaaatcaat caagactttc gttatgcagt    6360
tgttcgaaaa gtgcggtaat actgacgtcg agggtgtaga ctctactaac gcttgttatg    6420
gtggtaccgc agctttattg aactgcgtaa actgggttga gtcaaactca tgggatggta    6480
ggtacggatt agtcatttgc accgattctg ccgtctacgc cgagggtcca gcaaggccaa    6540
ccggtggagc tgcagctatt gctatgttaa tcggaccaga tgcccctata gtcttcgagt    6600
ctaagttgag gggttcacac atccctaacg tctacgactt ctacaagcca aacttggcct    6660
cagagtatcc agttgtcgac ggaaagtttat ctcagacatg ctacttgatg gccttagatt    6720
catgttacaa gcacttatgc aacaagttcg aaaagttgga gggaaaggag ttctcaatta    6780
acgacgccga ctacttcgtt tttcactctc catacaacaa attggtccag aagtcattcg    6840
ccaggttatt gtacaacgat tttttgagaa acgcatcatc tatcgatgag gccgccaagg    6900
agaaattcac cccatattct tctttgtcat tggacgagtc ttaccagtct agggacttgg    6960
agaaggtatc acagcaattg gctaaaacct tctatgacgc caaagttcag ccaaccacct    7020
tggtccctaa acaggtcgga aatatgtata ctgcatcttt gtatgccgcc tttgcctctt    7080
tgatccacaa caagcacaac gatttagtcg aaaaagggt tgtcatgttt tcttacggtg    7140
ccggatctac tgccactatg ttctcattga ggttatgcga aaaccagtca ccattttcat    7200
tgtctaacat cgcctcagtc atggacgtag gtgtctcacc tgagaagttc gtagaaacca    7260
tgaagttgat ggagcacaga tacggtgcca aagaattcgt cacttcaaaa gagggaatct    7320
tggatttgtt ggccccagga acctactatt tgaaggaggt cgactctttg tacagaaggt    7380
tctatggaaa gaagggagac gacggatctg tcgcaaacgg tcagtaaatc ggcggcgtcg    7440
gcgatcgcgt taaggcggcc gctggcgagg gagatatttc aacctgggcc taacagtaaa    7500
gatatcctcc tcaaaactgg tgcacttaat cgctgaattt gttctggctt ctcttctttt    7560
tctttattcc ccccatgggc caaaaaaat agtactatca ggaatttggc gccgggtcac    7620
gatatacgtg tacagtgacc taggcgacgc cacaaggaaa aaggaaaaaa acagaaaaaa    7680
caacaaaaac taaaacaaac acgaaaactt taatagatct aagtgaagta gtggtgaggc    7740
aattggagtg acatagcagc tactacaact acaaaaaagg cgcgccacgg tcgtgcggat    7800
atgaaagagg tcgttatagc ttctgccgtc aggaccgcca tcggatctta cggtaagtca    7860
ttaaaggacg tccctgccgt tgatttagga gccaccgcaa ttaagaggc cgttaaaaag    7920
gcaggtataa agccgagga cgtcaacgag gtcatcttgg gaaatgtctt acaagccgga    7980
ttaggtcaaa acccagcaag acaagcatca ttcaaagccg gtttacctgt cgagatacct    8040
gcaatgacca tcaacaaggt ttgcggttca ggattaagga ccgtttcttt agcagcacag    8100
atcattaagg ctggagatgc agacgttatc attgctggtg gtatggaaaa catgtcaaga    8160
gccccatact tggctaataa cgccaggtgg ggatatagga tgggaaacgc caagtttgtc    8220
```

```
gacgaaatga ttactgacgg attgtgggac gccttcaatg actatcacat gggtataacc      8280
gcagaaaaca ttgccgagag gtggaatatc tcaagagaag aacaggatga gtttgcattg      8340
gcctcacaga aaaagcaga ggaggcaata aagtcaggtc agtttaagga tgaaatcgtc       8400
ccagtcgtca tcaagggaag aaagggtgag acagttgtcg acaccgacga cacccctaga      8460
tttggttcaa ccatcgaggg attagcaaag ttgaagccag ccttcaagaa agacggaacc      8520
gtaaccgccg gtaatgcatc tggattgaac gattgcgcag cagttttggt cataatgtca      8580
gccgagaaag ctaaggagtt gggtgtcaag ccattggcaa aaattgtttc atacggatca      8640
gccggtgtcg accctgccat catgggttac ggaccttttt acgccaccaa ggctgcaatc      8700
gaaaaggccg gttggaccgt agatgaattg gatttgatcg agtcaaacga ggcctttgcc      8760
gcccaatcat tggctgtcgc caaggacttg aagttcgaca tgaacaaggt caacgtcaac      8820
ggtggtgcca tcgcattggg tcaccctatc ggagcctctg gtgccaggat cttggttacc      8880
ttggtccacg ccatgcagaa gagggacgca agaagggtt tggccacctt gtgcatcggt       8940
ggaggtcagg gaacagctat cttgttagag aaatgcagcc cctcagcccc cctagcgtcg      9000
aataaaagac attggtacat gatatcaaac agaattttaa catttcttga tccagtttgt      9060
aaacaaaaca aacaattttt ctaccattta acttcatacc atcggcgaga gccgaacagg      9120
aaaaaaaaga agtctccggt tatcgtaagc agtatcaaat aataagaatg tatgtgtgtg      9180
caatttgtta tacccacgaa gaagtgcgca gtagagttag aaaaccaact gagtaatctt      9240
tactcccgac aatcgtccaa taatcctctt gttgctagga acgtgatgat ggatttcgtt      9300
tgaaatccgg acggaaaact caaagaagt ccaaccacca accattttcg agcctcaaga       9360
atctctaagc aggtttcttt actaagggga tggccttct gtcctggaca tttttttcctt      9420
ccttttttca tttccttgaa aggaacagat ttttttgac ttttgccaca cagctgcact       9480
atctcaaccc cttttacatt ttaagttttc gggttgaatg gccggtgttt aaacccagc       9540
gcctggcggg                                                            9550

<210> SEQ ID NO 30
<211> LENGTH: 4429
<212> TYPE: DNA
<213> ORGANISM: Artificial Sequence
<220> FEATURE:
<223> OTHER INFORMATION: Synthetic: ADS_Mat alpha donor cassette

<400> SEQUENCE: 30
tgatgtctgg gttttgtttg ggatgcaatt tattgcttcc caatgtagaa aagtacatca       60
tatgaaacaa cttaaactct taactacttc ttttaacctt cacttttat gaaatgtatc       120
aaccatatat aataacttaa tagacgacat tcacaatatg tttacttcga agcctgcttt      180
caaaattaag aacaaagcat ccaaatcata cagaaacaca gcggtttcaa aaaagctgaa      240
agaaaaacgt ctagctgagc atgtgaggcc aagctgcttc aatattattc gaccactcaa      300
gaaagatatc cagattcctg ttccttcctc tcgattttta aataaaatcc aaattcacag      360
gatagcgtct ggaagtcaaa atactcagtt tcgacagttc aataagacat ctataaaatc      420
ttcaaagaaa tatttaaact catttatggc ttttagagca tattactcac agtttggctc      480
cggtgtaaaa caaaatgtct tgtcttctct gctcgctgaa gaatggcacg cggacaaaat      540
gcagcacgga atatgggact acttcgcgca acagtataat tttataaacc ctggttttgg      600
ttttgtagag tggttgacga ataattatgc tgaagtacgt ggtgacggat attgggaaga      660
```

```
tgtgtttgta catttggcct tatagagtgt ggtcgtggcg gaggttgttt atctttcgag   720
tactgaatgt tgtcagtata gctatcctat ttgaaactcc ccatcgtctt gctcttgttc   780
ccaatgtttg tttatacact catatggcta taccctttatc tacttgcctc ttttgtttat   840
gtctatgtat ttgtataaaa tatgatatta ctcagactca agcaaacaat caattttcaa   900
aaattcttac tttttttttg gatggacgca aagaagttta ataatcatat tacatggcat   960
taccaccata tacatatcca tatacatatc catatctaat cttacttata tgttgtggaa  1020
atgtaaagag ccccattatc ttagcctaaa aaaaccttct ctttggaact ttcagtaata  1080
cgcttaactg ctcattgcta tattgaagta cggattagaa gccgccgagc gggtgacagc  1140
cctccgaagg aagactctcc tccgtgcgtc ctcgtcttca ccggtcgcgt tcctgaaacg  1200
cagatgtgcc tcgcgccgca ctgctccgaa caataaagat tctacaatac tagcttttat  1260
ggttatgaag aggaaaaatt ggcagtaacc tggccccaca aaccttcaaa tgaacgaatc  1320
aaattaacaa ccataggatg ataatgcgat tagtttttta gccttatttc tggggtaatt  1380
aatcagcgaa gcgatgattt tgatctatt aacagatata taaatgcaaa aactgcataa  1440
ccactttaac taatactttc aacattttcg gtttgtatta cttcttattc aaatgtaata  1500
aaagtatcaa caaaaaattg ttaatatacc tctatacttt aacgtcaagg agaaaaaacc  1560
ccggatccat gggtcaatat aaattaattt tgaatggtaa actttgaag ggtgaaacta   1620
ctaccgaagc agtagatgca gcaacagccg aaaaggtctt taagcaatat gctaatgata  1680
atggtgttga tggtgaatgg acctatgacg atgcaactaa acatttact gtaactgaag   1740
gatccatggc cttaacagaa gagaagccaa tcagacccat agccaacttc cctccatcaa  1800
tatggggtga tcaattctt atatacgaaa agcaagttga acaaggtgtc gaacaaatcg    1860
tcaacgatct aaagaaggag gtcaggcagt tattaaaaga agctctggac ataccgatga  1920
aacatgctaa tctactaaaa ttaattgatg agattcaaag attgggcatc ccttatcact  1980
tcgagagaga gattgatcat gcattgcaat gtatatacga gacgtacggt gataactgga  2040
acggagatag gagtagtcta tggttcaggt tgatgagaaa gcaaggctac tatgtgacat  2100
gcgatgtctt taataactat aaggacaaaa atggtgcatt taagcaatct ctagccaacg  2160
atgttgaagg tttattagaa ttatatgaag ccacaagcat gagagtccca ggagagatca  2220
tattggaaga tgctctaggg ttcacacgtt ctagattgtc aataatgacc aaggacgcat  2280
tcagtactaa ccctgcgtta ttcactgaaa tccaaggggc actaaagcaa cctctttgga  2340
aaagattgcc tcgtattgaa gcagcacaat atatacccctt ctatcagcag caggactctc  2400
acaacaaaac tctacttaaa ttagcaaagt tagaattcaa tttgttgcaa agtttacata  2460
aggaagaatt atctcacgta tgcaaatggt ggaaagcttt cgatattaag aagaacgccc  2520
catgcctgag agacagaata gttgagtgtt atttctgggg tctggttcc ggttatgaac   2580
cacaatattc tagggccaga gtcttttta ccaaagttgt cgcggtcata actttaatcg   2640
acgatactta tgatgcttat ggtacctacg aggagttaaa gatattcacc gaagctgtgg  2700
aaaggtggtc tataacttgc ttggacaccc taccagaata tatgaaacca atttacaaat  2760
tgtttatgga tacttatact gaaatggagg aattcctggc aaaagaaggt agaactgatt  2820
tgtttaattg cggtaaggaa tttgtgaagg aattcgtaag aaacttaatg gtcgaggcaa  2880
aatgggccaa cgaaggacac attccaacaa ccgaagagca tgatcctgtc gtgataatca  2940
ccggtggcgc taacctacta accactacct gctacctagg tatgtctgat atcttcacaa  3000
aagagagtgt tgaatgggca gttagtgctc cgcctttgtt caggtatagc ggtatacttg  3060
```

```
gcaggcgttt aaatgatctt atgacccata aagccgaaca agaaagaaaa cactcaagct    3120
cctctcttga atcctatatg aaggaataca atgttaacga ggaatatgcg caaactttaa    3180
tatacaagga ggtggaagat gtgtggaaag atatcaacag agaatatctt actacaaaga    3240 acatacccg tccactttg atggcagtga tttacttgtg tcagttctta gaggtacaat      3300
acgctggtaa ggataacttt acaagaatgg gcgacgaata caaacatttg atcaagtcat    3360
tattagttta tcccatgtcc atctaagcta gctaagatcc gctctaaccg aaaaggaagg    3420
agttagacaa cctgaagtct aggtccctat ttatttttt atagttatgt tagtattaag     3480
aacgttattt atatttcaaa ttttctttt tttctgtac agacgcgtgt acgcatgtaa       3540
cattatactg aaaaccttgc ttgagaaggt tttgggacgc tcgaagcgga ggttgtttat    3600
ctttcgagta ctgaatgttg tcagtatagc tatcctattt gaaactcccc atcgtcttgc    3660
tcttgttccc aatgtttgtt tatacactca tatggctata cccttatcta cttgcctctt    3720
ttgtttatgt ctatgtattt gtataaaata tgatattact cagactcaag caaacaatca    3780
attcttagca tcattctttg ttcttatctt aaccataaac gatcttgatg tgacttttgt    3840
aatttgaacg aattggctat acgggacgga tgacaaatgc accattactc taggttgttg    3900
ttggatctta acaaaccgta aaggtaaact gcccatgcgg ttcacatgac ttttgacttt    3960
cctttgtttg ctagttacct tcggcttcac aatttgtttt tccactttc taacaggttt     4020 atcacctttc aaacttatct ttatcttatt cgccttcttg ggtgcctcca cagtagaggt    4080
tacttccttt ttaatatgta ctttaggat actttcacgc tttataacaa tatcaagttt     4140
accttcttca ttactattca tcttcgccac aagtcttctc tcccttggtg tttccaatct    4200
aactacaaaa ctgttgatta gggtgtacat caccctaaca agatcatgta tttgcttcct    4260
ctggtacaag ctaagaacag gtaaattcaa aacatcccag agtaatatct tcaagggct    4320 ataccctta aacatatctc ggcatatttg tattaaccca ctaatatttt gacggccaat    4380
cttttctatt tttattttca tatcatcgac gtaatgacca cttaaaaac                4429
```

```
<210> SEQ ID NO 31
<211> LENGTH: 23
<212> TYPE: DNA
<213> ORGANISM: Artificial Sequence
<220> FEATURE:
<223> OTHER INFORMATION: Synthetic: Primer CUT24

<400> SEQUENCE: 31
gtttcttttg gattgcgctt gcc                                             23

<210> SEQ ID NO 32
<211> LENGTH: 20
<212> TYPE: DNA
<213> ORGANISM: Artificial Sequence
<220> FEATURE:
<223> OTHER INFORMATION: Synthetic: Primer ART12

<400> SEQUENCE: 32
tactgacaac cacatgttac                                                 20

<210> SEQ ID NO 33
<211> LENGTH: 29
<212> TYPE: DNA
<213> ORGANISM: Artificial Sequence
<220> FEATURE:
<223> OTHER INFORMATION: Synthetic: Primer ART45
```

<400> SEQUENCE: 33
tactgcttcg gtagtagttt cacccttca                29

<210> SEQ ID NO 34
<211> LENGTH: 20
<212> TYPE: DNA
<213> ORGANISM: Artificial Sequence
<220> FEATURE:
<223> OTHER INFORMATION: Synthetic: Primer ART210

<400> SEQUENCE: 34
gggaagtcca attcaatagt                20

<210> SEQ ID NO 35
<211> LENGTH: 25
<212> TYPE: DNA
<213> ORGANISM: Artificial Sequence
<220> FEATURE:
<223> OTHER INFORMATION: Synthetic: Primer HJ207

<400> SEQUENCE: 35
catcttctcg agataacacc tggag                25

<210> SEQ ID NO 36
<211> LENGTH: 19
<212> TYPE: DNA
<213> ORGANISM: Artificial Sequence
<220> FEATURE:
<223> OTHER INFORMATION: Synthetic: Primer KB349

<400> SEQUENCE: 36
acgcgtgtac gcatgtaac                19

<210> SEQ ID NO 37
<211> LENGTH: 20
<212> TYPE: DNA
<213> ORGANISM: Artificial Sequence
<220> FEATURE:
<223> OTHER INFORMATION: Synthetic: Primer HJ602

<400> SEQUENCE: 37
caattggggt tctggcagtc                20

<210> SEQ ID NO 38
<211> LENGTH: 30
<212> TYPE: DNA
<213> ORGANISM: Artificial Sequence
<220> FEATURE:
<223> OTHER INFORMATION: Synthetic: Primer CUT76

<400> SEQUENCE: 38
gaagcctgct ttcaaaatta agaacaaagc                30

<210> SEQ ID NO 39
<211> LENGTH: 30
<212> TYPE: DNA
<213> ORGANISM: Artificial Sequence
<220> FEATURE:
<223> OTHER INFORMATION: Synthetic: Primer HJ362

<400> SEQUENCE: 39
gaatttacct gttcttagct tgtaccagag                30

<210> SEQ ID NO 40
<211> LENGTH: 6523

<212> TYPE: DNA
<213> ORGANISM: Artificial Sequence
<220> FEATURE:
<223> OTHER INFORMATION: Synthetic: ADS_HIS3 donor cassette

<400> SEQUENCE: 40

```
attgtgaggg tcagttattt catccagata aacccgaga ggaaacttct tagcgtctgt      60
tttcgtacca taaggcagtt catgaggtat attttcgtta ttgaagccca gctcgtgaat     120
gcttaatgct gctgaactgg tgtccatgtc gcctaggtac gcaatctcca caggctgcaa    180
aggttttgtc tcaagagcaa tgttattgtg caccccgtaa ttggtcaaca agtttaatct    240
gtgcttgtcc accagctctg tcgtaacctt cagttcatcg actatctgaa gaaatttact    300
aggaatagtg ccatggtaca gcaaccgaga atggcaattt ctactcgggt tcagcaacgc    360
tgcataaacg ctgttggtgc cgtagacata ttcgaagata ggattatcat tcataagttt    420
cagagcaatg tccttattct ggaacttgga tttatggctc ttttggttta atttcgcctg    480
attcttgatc tcctttagct tctcgacgtg ggccttttc ttgccatatg gatccgctgc     540
acggtcctgt tccctagcat gtacgtgagc gtatttcctt taaaccacg acgctttgtc    600
ttcattcaac gtttcccatt gttttttttct actattgctt tgctgtggga aaaacttatc    660
gaaagatgac gactttttct taattctcgt tttaagagct tggtgagcgc taggagtcac    720
tgccaggtat cgtttgaaca cggcattagt cagggaagtc ataacacagt cctttcccgc    780
aattttcttt ttctattact cttggcctcc tctagtacac tctatatttt tttatgcctc    840
ggtaatgatt tcatttttt tttttccac ctagcggatg actctttttt tttcttagcg      900
attggcatta tcacataatg aattatacat tatataaagt aatgtgattt cttcgaagaa    960
tatactaaaa aaatcgttat tgtcttgaag gtgaaattc tactcttatt aatggtgaac    1020
gttaagctga tgctatgatg gaagctgatt ggtcttaact tgcttgtcat cttgctaatg   1080
gtcattggct cgtgttatta cttaagttat ttgtactcgt tttgaacgta atgctaatga   1140
tcatcttatg gaataatagt gagtggtttc agggtccata aagctttca attcatcttt    1200
tttttttttg ttcttttttt tgattccggt ttctttgaaa ttttttttgat tcggtaatct   1260
ccgagcagaa ggaagaacga aggaaggagc acagacttag attggtatat atacgcatat   1320
gtggtgttga agaaacatga aattgcccag tattcttaac ccaactgcac agaacaaaaa   1380
cctgcaggaa acgaagataa atcatgtcga aagctacata taaggaacgt gctgctactc   1440
atcctagtcc tgttgctgcc aagctatttta atatcatgca cgaaaagcaa acaaacttgt   1500
gtgcttcatt ggatgttcgt accaccaagg aattactgga gttagttgaa gcattaggtc    1560
ccaaaatttg tttactaaaa acacatgtgg atatcttgac tgatttttcc atggagggca   1620
cagttaagcc gctaaaggca ttatccgcca agtacaattt tttactcttc gaagacagaa   1680
aatttgctga cattggtaat acagtcaaat tgcagtactc tgcgggtgta tacagaatag   1740
cagaatgggc agacattacg aatgcacacg gtgtggtggg cccaggtatt gttagcggtt   1800
tgaagcaggc ggcggaagaa gtaacaaagg aacctagagg cctttgatg ttagcagaat     1860
tgtcatgcaa gggctcccta gctactggag aatatactaa gggtactgtt gacattgcga   1920
agagtgacaa agattttgtt atcggcttta ttgctcaaag agacatgggt ggaagagatg   1980
aaggttacga ttggttgatt atgacacccg gtgtgggttt agatgacaag ggagacgcat   2040
tgggtcaaca gtatagaacc gtggatgatg tggtctctac aggatctgac attattattg   2100
ttggaagagg actatttgca aagggaaggg atgctaaggt agagggtgaa cgttacagaa   2160
```

| | |
|---|---|
| aagcaggctg ggaagcatat ttgagaagat gcggccagca aaactaaaaa actgtattat | 2220 |
| aagtaaatgc atgtatacta aactcacaaa ttagagcttc aatttaatta tatcagttat | 2280 |
| taccacgaaa atcgttattg tcttgaaggt gaaatttcta ctcttattaa tggtgaacgt | 2340 |
| taagctgatg ctatgatgga agctgattgg tcttaacttg cttgtcatct tgctaatggt | 2400 |
| catatggctc gtgttattac ttaagttatt tgtactcgtt ttgaacgtaa tgctaatgat | 2460 |
| catcttatgc ttcgagcgtc ccaaaacctt ctcaagcaag gttttcagta taatgttaca | 2520 |
| tgcgtacacg cgtctgtaca gaaaaaaaag aaaaatttga atataaata acgttcttaa | 2580 |
| tactaacata actataaaaa aataaatagg gacctagact tcaggttgtc taactccttc | 2640 |
| cttttcggtt agagcggatc ttagctagct tagctagctt agatagacat agggtagacc | 2700 |
| aacaaagact taattaagtg cttatattcg tcacccattc tggtgaaatt gtctttacca | 2760 |
| gcgtattgaa cttctaagaa ttgacataaa tagataacag ccattaacaa tggacgtgga | 2820 |
| atattttttgg tggtcaagta ttctctgtta atatctttcc aaacgtcttc aacttccttg | 2880 |
| taaatcaaag tttgagcgta ttcttcgtta acgttgtatt ccttcatgta agattctaag | 2940 |
| gaagaggagg agtgctttct ttcttgctca gccttgtgag tcatcaaatc gtttaatctt | 3000 |
| ctacccaaaa taccagagta tctgaacaaa ggtggagcgg aaacggccca ttcaacagat | 3060 |
| tccttggtga aaatatcaga catacctaag taacaagtag tagtcaacaa gttagcacca | 3120 |
| ccagtaatga taacgactgg atcgtgttct tcagtagttg gaatatgacc ttcgttagcc | 3180 |
| catttagctt caaccatcaa gttacgaacg aattccttaa cgaattcctt accacaattg | 3240 |
| aacaagtcgg tacgaccttc cttagccaag aattcttcca tttcggtgta agtgtccatg | 3300 |
| aacaacttat aaattggctt catgtattct ggtaaagtat ctaaacaggt aatggaccat | 3360 |
| cttttcgacag cttcagtgaa aatcttcaat tcttcgtagg taccgtaagc gtcgtaagtg | 3420 |
| tcgtcaatca aggtaataac agcaacagcc ttagtaaaga aaactctagc tctagagtat | 3480 |
| tgtggttcgt aaccggaacc caaaccccag aagtaacatt cgacaattct atctctcaaa | 3540 |
| catggagcgt tcttcttaat atcgaaggct ttccaccact acaaacgtg agacaattct | 3600 |
| tccttgtgca aggattgcaa caagttaaat tccaatttag ccaatttcaa caaggttttg | 3660 |
| ttgtgagagt cttgttgttg gtagaatggg atgtattgag cagcttcgat tcttggcaaa | 3720 |
| cgcttccaca atggttgttt caaagctctt tggatttcag tgaacaaagc tgggttagta | 3780 |
| gagaaggcat ctttagtcat gatggacaat ctagatctag taaaacccaa agcgtcttcc | 3840 |
| aagatgattt caccaggaac tctcatggag gtggcttcat acaattctaa caaaccttca | 3900 |
| acatcgttgg ccaaagattg cttaaaagca ccattcttat ctttgtagtt gttgaaaacg | 3960 |
| tcacaagtaa cgtagtaacc ttgctttctc attaatctga accataagga agatctgtca | 4020 |
| ccgttccagt tatcaccgta agtttcgtaa atacattgca aagcgtgatc aatttctctt | 4080 |
| tcgaaatggt atggaatacc taatctttgg atttcgtcga ttaatttcaa taagttagcg | 4140 |
| tgcttcattg ggatgtccaa agcttccttc aacaattgtc taacttcctt cttcaaatcg | 4200 |
| ttaacgattt gttcaacacc ttgctcaact tgcttttcgt agatcaagaa ttggtcaccc | 4260 |
| cagatagaag gtggaaaatt agcaattggt ctgattggtt tttcttcagt caaagccatg | 4320 |
| gatccttcag ttacagtaaa tgttttagtt gcatcgtcat aggtccattc accatcaaca | 4380 |
| ccattatcat tagcatattg cttaaagacc ttttcggctg ttgctgcatc tactgcttcg | 4440 |
| gtagtagttt caccccttcaa agttttacca ttcaaaatta atttatattg acccattata | 4500 |
| gtttttctc cttgacgtta aagtatagag gtatattaac aatttttttgt tgatactttt | 4560 |

```
attacatttg aataagaagt aatacaaacc gaaaatgttg aaagtattag ttaaagtggt    4620
tatgcagttt ttgcatttat atatctgtta atagatcaaa aatcatcgct tcgctgatta    4680
attaccccag aaataaggct aaaaaactaa tcgcattatc atcctatggt tgttaatttg    4740
attcgttcat ttgaaggttt gtggggccag gttactgcca attttttcctc ttcataacca    4800 taaaagctag tattgtagaa tctttattgt tcggagcagt gcggcgcgag gcacatctgc    4860
gtttcaggaa cgcgaccggt gaagacgagg acgcacggag gagagtcttc cttcggaggg    4920
ctgtcacccg ctcggcggct tctaatccgt acttcaatat agcaatgagc agttaagcgt    4980
attactgaaa gttccaaaga gaaggttttt ttaggctaag ataatggggc tctttacatt    5040
tccacaacat ataagtaaga ttagatatgg atatgtatat ggatatgtat atggtggtaa    5100
tgccatgtaa tatgattatt aaacttcttt gcgtccatcc aaaaaaaaag taagaatttt    5160
tgaaaattca atataaatgt ctcagaacgt ttacattgta tcgactgcca gaaccccaat    5220
tggttcattc cagggttctc tatcctccaa gacagcagtg gaattgggtg ctgttgcttt    5280
aaaaggcgcc ttggctaagg ttccagaatt ggatgcatcc aaggattttg acgaaattat    5340
ttttggtaac gttctttctg ccaatttggg ccaagctccg gccagacaag ttgctttggc    5400
tgccggtttg agtaatcata tcgttgcaag cacagttaac aaggtctgtg catccgctat    5460
gaaggcaatc attttgggtg ctcaatccat caaatgtggt aatgctgatg ttgtcgtagc    5520
tggtggttgt gaatctatga ctaacgcacc atactacatg ccagcagccc gtgcgggtgc    5580
caaatttggc caaactgttc ttgttgatgg tgtcgaaaga gatgggttga acgatgcgta    5640
cgatggtcta gccatgggtg tacacgcaga aaagtgtgcc cgtgattggg atattactag    5700
agaacaacaa gacaattttg ccatcgaatc ctaccaaaaa tctcaaaaat ctcaaaagga    5760
aggtaaattc gacaatgaaa ttgtacctgt taccattaag ggatttagag gtaagcctga    5820
tactcaagtc acgaaggacg aggaacctgc tagattacac gttgaaaaat tgagatctgc    5880
aaggactgtt ttccaaaaag aaaacggtac tgttactgcc gctaacgctt ctccaatcaa    5940
cgatggtgct gcagccgtca tcttggtttc cgaaaaagtt ttgaaggaaa agaatttgaa    6000
gcctttggct attatcaaag gttggggtga ggccgctcat caaccagctg attttacatg    6060
ggctccatct cttgcagttc caaaggcttt gaaacatgct ggcatcgaag acatcaattc    6120
tgttgattac tttgaattca atgaagcctt ttcggttgtc ggtttggtga acactaagat    6180
tttgaagcta gacccatcta aggttaatgt atatggtggt gctgttgctc taggtcaccc    6240
attgggttgt tctggtgcta gagtggttgt tacactgcta tccatcttac agcaagaagg    6300
aggtaagatc ggtgttgccg ccatttgtaa tggtggtggt ggtgcttcct ctattgtcat    6360 tgaaagata tgattacgtt ctgcgatttt ctcatgatct ttttcataaa atacataaat    6420
atataaatgg ctttatgtat aacaggcata atttaaagtt ttatttgcga ttcatcgttt    6480
ttcaggtact caaacgctga ggtgtgcctt ttgacttact ttt    6523

<210> SEQ ID NO 41
<211> LENGTH: 10379
<212> TYPE: DNA
<213> ORGANISM: Artificial Sequence
<220> FEATURE:
<223> OTHER INFORMATION: Synthetic: ADS_FS.1 donor cassette

<400> SEQUENCE: 41
atattgtttt ttccctagct gttttcggtt tggttatgaa cgcattgtct gcgaaaagaa    60
```

-continued

```
acgtggataa gtattataga acagcactt cttcggccaa caatatcacg caaattgagc    120
aagatagtgc tataaaaggt cttttgccct tttttgccta ttatgcaagc attgctttac    180
tagtgtggat gcaaccaagc tttattacac tctctttcat cctttccgtt ggtttcacgg    240
gagcatttac cgtcggaaga ataatcgttt gccatttaac taagcagagc tttcccatgt    300
tcaatgcacc catgttaatt cctttgtgcc agatagtatt gtacaaaata tgtctatccc    360
tttggggaat tgagtctaat aaaatcgtct ttgccctatc ttggcttggg ttcggtctct    420
cactaggtgt tcacattatg tttatgaatg acattatcca tgaatttact gagtacctgg    480
acgtttatgc tttatccatc aagcgctcca agctgacata aatcgcactt tgtatctact    540
tttttttatt cgaaaacaag gcacaacaat gaatctatcg ccctgtgaga ttttcaatct    600
caagtttgtg taatagatag cgttatatta tagaactata aaggtccttg aatatacata    660
gtgtttcatt cctattactg tatatgtgac tttacattgt tacttccgcg gctatttgac    720
gttttctgct tcaggtgcgg cttggagggc aaagtgtcag aaaatcggcc aggccgtatg    780
acacaaaaga gtagaaaacg agatctcaaa tatctcgagg cctgtcctct atacaaccgc    840
ccagctctct gacaaagctc cagaacggtt gtcttttgtt tcgaaaagcc aaggtccctt    900
ataattgccc tccattttgt gtcacctatt aagcaaaaaa attgaaagtt tactaacctt    960
tcattaaaga gaaataacaa tattataaaa agcgcttaaa tatacctgag aaagcaacct   1020
gacctacagg aaagagttac tcaagaataa gaattttcgt tttaaaacct aagagtcact   1080 ttaaatttg tatacactta ttttttttat aacttattta ataataaaaa tcataaatca    1140
taagaaattc gcttatttag aagtgtcaac aacgtatcta ccaacgattt gacccttttc   1200
catcttttcg taaatttctg gcaaggtaga caagccgaca accttgattg gagacttgac   1260
caaacctctg gcgaagaatt gttaattaag agctcagatc ttatcgtcgt catccttgta   1320
atccatcgat actagtgcgg ccgccctta gtgagggttg aattcgaatt ttcaaaaatt    1380 cttactttt ttttggatgg acgcaaagaa gtttaataat catattacat ggcattacca    1440
ccatatacat atccatatac atatccatat ctaatcttac ttatatgttg tggaaatgta   1500
aagagcccca ttatcttagc ctaaaaaaac cttctctttg gaactttcag taatacgctt   1560
aactgctcat tgcgccgccg agcgggtgac agccctccga aggaagactc tcctccgtgc   1620
gtcctcgtct tcaccggtcg cgttcctgaa acgcagatgt gcctcgcgcc gcactgctcc   1680
gaacaataaa gattctacaa tactagcttt tatggttatg aagaggaaaa attggcagta   1740
acctggcccc acaaaccttc aaatgaacga atcaaattaa caaccatagg atgataatgc   1800
gattagtttt ttagccttat ttctggggta attaatcagc gaagcgatga ttttgatct    1860 attaacagat atataaatgc aaaaactgca taaccacttt aactaatact ttcaacattt   1920
tcggtttgta ttacttctta ttcaaatgta ataaaagtat caacaaaaaa ttgttaatat   1980
acctctatac tttaacgtca aggagaaaaa actataatgg gtcaatataa attaattttg   2040
aatggtaaaa ctttgaaggg tgaaactact accgaagcag tagatgcagc aacagccgaa   2100
aaggtcttta agcaatatgc taatgataat ggtgttgatg gtgaatggac ctatgacgat   2160
gcaactaaaa catttactgt aactgaagga tccatggctt tgactgaaga aaaaccaatc   2220
agaccaattg ctaattttcc accttctatc tggggtgacc aattcttgat ctacgaaaag   2280
caagttgagc aaggtgttga acaaatcgtt aacgatttga agaaggaagt tagacaattg   2340
ttgaaggaag ctttggacat cccaatgaag cacgctaact tattgaaatt aatcgacgaa   2400
atccaaagat taggtattcc ataccatttc gaaagagaaa ttgatcacgc tttgcaatgt   2460
```

```
atttacgaaa cttacggtga taactggaac ggtgacagat cttccttatg gttcagatta    2520
atgagaaagc aaggttacta cgttacttgt gacgttttca acaactacaa agataagaat    2580 ggtgcttta  agcaatcttt ggccaacgat gttgaaggtt tgttagaatt gtatgaagcc    2640
acctccatga gagttcctgg tgaaatcatc ttggaagacg ctttgggttt tactagatct    2700
agattgtcca tcatgactaa agatgccttc tctactaacc cagctttgtt cactgaaatc    2760
caaagagctt tgaaacaacc attgtggaag cgtttgccaa gaatcgaagc tgctcaatac    2820
atcccattct accaacaaca agactctcac aacaaaacct tgttgaaatt ggctaaattg    2880
gaatttaact tgttgcaatc cttgcacaag gaagaattgt ctcacgtttg taagtggtgg    2940
aaagccttcg atattaagaa gaacgctcca tgtttgagag atagaattgt cgaatgttac    3000
ttctggggtt tgggttccgg ttacgaacca caatactcta gagctagagt tttctttact    3060
aaggtggttg ctgttattac cttgattgac gacacttacg acgcttacgg tacctacgaa    3120
gaattgaaga ttttcactga agctgtcgaa agatggtcca ttacctgttt agatacttta    3180
ccagaataca tgaagccaat ttataagttg ttcatggaca cttacaccga aatggaagaa    3240
ttcttggcta aggaaggtcg taccgacttg ttcaattgtg gtaaggaatt cgttaaggaa    3300
ttcgttcgta acttgatggt tgaagctaaa tgggctaacg aaggtcatat tccaactact    3360
gaagaacacg atccagtcgt tatcattact ggtggtgcta acttgttgac tactacttgt    3420
tacttaggta tgtctgatat tttccaccaag gaatctgttg aatgggccgt ttccgctcca    3480
cctttgttca gatactctgg tattttgggt agaagattaa acgatttgat gactcacaag    3540
gctgagcaag aaagaaagca ctcctcctct tccttagaat cttacatgaa ggaatacaac    3600
gttaacgaag aatacgctca aactttgatt tacaaggaag ttgaagacgt ttggaaagat    3660
attaacagag aatacttgac caccaaaaat attccacgtc cattgttaat ggctgttatc    3720
tatttatgtc aattcttaga agttcaatac gctggtaaag acaatttcac cagaatgggt    3780
gacgaatata agcacttaat taagtctttg ttggtctacc ctatgtctat ctaagatccg    3840
ctctaaccga aaaggaagga gttagacaac ctgaagtcta ggtccctatt tattttttta    3900
tagttatgtt agtattaaga acgttattta tatttcaaat ttttcttttt tttctgtaca    3960
gacgcgtgta cgcatgtaac attatactga aaaccttgct tgagaaggtt ttgggacgct    4020
cgaaggtttt caatagttcg gtaatattaa cggataccta ctattatccc ctagtaggct    4080
cttttcacgg agaaattcgg gagtgttttt tttccgtgcg cattttctta gctatattct    4140
tccagcttcg cctgctgccc ggtcatcgtt cctgtcacgt agttttttccg gattcgtccg    4200 gctcatataa taccgcaata aacacggaat atctcgttcc gcggattcgg ttaaactctc    4260
ggtcgcggat tatcacagag aaagcttcgt ggagaattt tccagatttt ccgctttccc    4320
cgatgttggt atttccggag gtcattatac tgaccgccat tataatgact gtacaacgac    4380
cttctggaga aagaaacaac tcaataacga tgtgggacat tgggggccca ctcaaaaaat    4440
ctggggacta tatccccaga gaatttctcc agaagagaag aaaagtcaaa gttttttttc    4500
gcttgggggt tgcatataaa tacaggcgct gttttatctt cagcatgaat attccataat    4560
tttacttaat agcttttcat aaataataga atcacaaaca aatttacat  ctgagttaaa    4620 caatcatgac aatcaaggaa cataaagtag tttatgaagc tcacaacgta aaggctctta    4680
aggctcctca acattttac  aacagccaac ccggcaaggg ttacgttact gatatgcaac    4740
attatcaaga aatgtatcaa caatctatca atgagccaga aaaattcttt gataagatgg    4800
```

```
ctaaggaata cttgcattgg gatgctccat acaccaaagt tcaatctggt tcattgaaca      4860
atggtgatgt tgcatggttt ttgaacggta aattgaatgc atcatacaat tgtgttgaca      4920
gacatgcctt tgctaatccc gacaagccag ctttgatcta tgaagctgat gacgaatccg      4980
acaacaaaat catcacattt ggtgaattac tcagaaaagt ttcccaaatc gctggtgtct      5040
taaaaagctg gggcgttaag aaaggtgaca cagtggctat ctatttgcca atgattccag      5100
aagcggtcat tgctatgttg gctgtggctc gtattggtgc tattcactct gttgtctttg      5160
ctgggttctc cgctggttcg ttgaaagatc gtgtcgttga cgctaattct aaagtggtca      5220
tcacttgtga tgaaggtaaa agaggtggta agaccatcaa cactaaaaaa attgttgacg      5280
aaggtttgaa cggagtcgat ttggtttccc gtatcttggt tttccaaaga actggtactg      5340
aaggtattcc aatgaaggcc ggtagagatt actggtggca tgaggaggcc gctaagcaga      5400
gaacttacct acctcctgtt tcatgtgacg ctgaagatcc tctattttta ttatacactt      5460
ccggttccac tggttctcca aagggtgtcg ttcacactac aggtggttat ttattaggtg      5520
ccgctttaac aactagatac gtttttgata ttcacccaga agatgttctc ttcactgccg      5580
gtgacgtcgg ctggatcacg ggtcacacct atgctctata tggtccatta accttgggta      5640
ccgcctcaat aattttcgaa tccactcctg cctacccaga ttatggtaga tattggagaa      5700
ttatccaacg tcacaaggct acccatttct atgtggctcc aactgcttta agattaatca      5760
aacgtgtagg tgaagccgaa attgccaaat atgcacttc ctcattacgt gtcttgggtt      5820
ccgtcggtga accaatctct ccagacttat gggaatggta tcatgaaaaa gtgggtaaca      5880
aaaactgtgt catttgtgac actatgtggc aaacagagtc tggttctcat ttaattgctc      5940
ctttggcagg tgctgtccca acaaaacctg gttctgctac cgtgccattc tttggtatta      6000
acgcttgtat cattgaccct gttacaggtg tggaattaga aggtaatgat gtcgaaggtg      6060
tccttgccgt taaatcacca tggccatcaa tggctagatc tgtttggaac caccacgacc      6120
gttacatgga tacttacttg aaaccttatc ctggtcacta tttcacaggt gatggtgctg      6180
gtagagatca tgatggttac tactggatca ggggtagagt tgacgacgtt gtaaatgttt      6240
ccggtcatag attatccaca tcagaaattg aagcatctat ctcaaatcac gaaaacgtct      6300
cggaagctgc tgttgtcggt attccagatg aattgaccgg tcaaaccgtc gttgcatatg      6360 tttcccctaaa agatggttat ctacaaaaca acgctactga aggtgatgca gaacacatca      6420
caccagataa tttacgtaga gaattgatct tacaagttag gggtgagatt ggtccttcg      6480 cctcaccaaa aaccattatt ctagttagag atctaccaag aacaaggtca ggaaagatta      6540
tgagaagagt tctaagaaag gttgcttcta acgaagccga acagctaggt gacctaacta      6600
ctttggccaa cccagaagtt gtacctgcca tcatttctgc tgtagagaac caattttct      6660 ctcaaaaaaa gaaataaatt gaattgaatt gaaatcgata gatcaatttt tttctttcct      6720
ctttccccat cctttacgct aaaataatag tttatttat tttttgaata tttttattt      6780 atatacgtat atatagacta ttatttatct tttaatgatt attaagattt ttattaaaaa      6840
aaaattcgct cctcttttaa tgcctttatg cagttttttt ttcccattcg atatttctat      6900
gttcgggttc agcgtatttt aagtttaata actcgaaaat tctgcgttcg ttaaagcttt      6960
cgagaaggat attatttcga aataaaccgt gttgtgtaag cttgaagcct ttttgcgctg      7020
ccaatattct tatccatcta ttgtactctt tagatccagt atagtgtatt cttcctgctc      7080
caagctcatc ccatccccgc gtgcttggcc ggccgttttg ccagcttact atccttcttg      7140
aaaatatgca ctctatatct tttagttctt aattgcaaca catagatttg ctgtataacg      7200
```

| | |
|---|---|
| aattttatgc tattttttaa atttggagtt cagtgataaa agtgtcacag cgaatttcct | 7260 |
| cacatgtagg gaccgaattg tttacaagtt ctctgtacca ccatggagac atcaaaaatt | 7320 |
| gaaaatctat ggaaagatat ggacggtagc aacaagaata tagcacgagc cgcggagttc | 7380 |
| atttcgttac ttttgatatc actcacaact attgcgaagc gcttcagtga aaaaatcata | 7440 |
| aggaaaagtt gtaaatatta ttggtagtat tcgtttggta aagtagaggg ggtaattttt | 7500 |
| cccctttatt ttgttcatac attcttaaat tgctttgcct ctccttttgg aaagctatac | 7560 |
| ttcggagcac tgttgagcga aggctcatta gatatatttt ctgtcatttt ccttaaccca | 7620 |
| aaaataaggg aaagggtcca aaagcgctc ggacaactgt tgaccgtgat ccgaaggact | 7680 |
| ggctatacag tgttcacaaa atagccaagc tgaaaataat gtgtagctat gttcagttag | 7740 |
| tttggctagc aaagatataa aagcaggtcg gaaatattta tgggcattat tatgcagagc | 7800 |
| atcaacatga taaaaaaaaa cagttgaata ttccctcaaa aatgtcttac accgtcggaa | 7860 |
| cctacttggc cgagaggttg gtccagatcg gattgaagca ccacttcgcc gtcgccggtg | 7920 |
| actacaactt ggtcttgttg gacaacttgt tgttgaacaa gaacatggag caggtctatt | 7980 |
| gctgcaacga gttgaactgc ggtttctcag cagaaggtta tgcaagagcc aagggagcag | 8040 |
| ccgctgccgt cgtcacctac tcagtcggtg cattatcagc attcgatgca attggaggtg | 8100 |
| cttacgctga gaacttgcca gtcatcttga tctctggagc acctaacaac aacgaccatg | 8160 |
| ctgctggtca cgtattgcac cacgccttgg gtaaaacaga ctaccactac cagttggaaa | 8220 |
| tggcaaaaaa tattaccgca gccgcagagg ccatctacac cccagaggaa gcacctgcca | 8280 |
| aaattgacca cgtcataaag accgctttga gagagaagaa gcctgtttac ttggagatcg | 8340 |
| cctgcaacat cgcttctatg ccatgcgccg cacctggtcc agcctctgct ttgttcaacg | 8400 |
| acgaggcctc tgacgaagct tcattgaacg ccgcagtcga agagacatta aagttcatcg | 8460 |
| ccaacaggga caaagttgcc gtcttagtcg gttcaaagtt gagggccgct ggtgccgaag | 8520 |
| aggcagctgt caagttcgct gacgccttgg gaggagccgt cgccaccatg gccgcagcaa | 8580 |
| aatctttctt tcctgaggag aacccacatt acatcggaac ctcatggggt gaagtatcat | 8640 |
| atcctggagt agaaaaaacc atgaaagagg ccgatgccgt aatagcattg gctcctgtct | 8700 |
| tcaacgacta ctcaaccaca ggatggactg atataccaga tccaaagaaa ttagtcttgg | 8760 |
| ctgagcctag gtcgtcgtc gtaaacggta tcaggttccc ttctgttcat ttgaaggact | 8820 |
| acttaacaag attggcccaa aaggtatcta aaaagactgg tgccttggac ttcttcaagt | 8880 |
| cattaaacgc aggagaattg aaaaaagcag caccagccga tccatcagcc ccattagtta | 8940 |
| acgctgaaat cgctagacaa gtagaggctt tgttgactcc aaacactacc gtcatagctg | 9000 |
| agacaggtga ctcttggttc aacgcacaga gaatgaaatt gccaaatggt gccagggtcg | 9060 |
| agtatgaaat gcagtgggga catataggtt ggtcagtccc agccgccttt ggatacgcag | 9120 |
| taggtgcccc tgagaggagg aacatattga tggttggtga tggttcattc caattaacag | 9180 |
| cccaggaggt agcccaaatg gtcaggttga agttgcctgt catcatcttc ttgatcaaca | 9240 |
| attacggata caccatcgag gtcatgatcc acgacggacc ttacaacaac atcaaaaact | 9300 |
| gggactacgc cggtttgatg gaggttttca acggtaacgg tggttatgac tcaggagccg | 9360 |
| gtaagggatt aaaggctaag accggtggtg aattggctga agcaattaag gtcgcattgg | 9420 |
| ccaacaccga tggacctaca ttgattgaat gcttcatcgg aagggaggac tgcaccgagg | 9480 |
| aattggttaa atggggtaaa agggtagccg ctgctaattc aagaaaacca gttaataaat | 9540 |

| | | | |
|---|---|---|---|
| tattataata agtgaattta ctttaaatct tgcatttaaa taaattttct ttttatagct | 9600 |
| ttatgactta gtttcaattt atatactatt ttaatgacat tttcgattca ttgattgaaa | 9660 |
| gctttgtgtt ttttcttgat gcgctattgc attgttcttg tcttttcgc cacatgtaat | 9720 |
| atctgtagta gataccctgat acattgtgga tgctgagtga aattttagtt aataatggag | 9780 |
| gcgctcttaa taattttggg gatattggct taacctgcag gccgcgagcg ccgatataaa | 9840 |
| ctaatgattt taaatcgtta aaaaaatatg cgaattctgt ggatcgaaca caggacctcc | 9900 |
| agataacttg accgaagttt tttcttcagt ctggcgctct cccaactgag ctaaatccgc | 9960 |
| ttactatttg ttatcagttc ccttcatatc tacatagaat aggttaagta ttttattagt | 10020 |
| tgccagaaga actactgata gttgggaata tttggtgaat aatgaagatt gggtgaataa | 10080 |
| tttgataatt ttgagattca attgttaatc aatgttacaa tattatgtat acagagtata | 10140 |
| ctagaagttc tcttcggaga tcttgaagtt cacaaaggg aatcgatatt tctacataat | 10200 |
| attatcatta cttcttcccc atcttatatt tgtcattcat tattgattat gatcaatgca | 10260 |
| ataatgattg gtagttgcca aacatttaat acgatcctct gtaatatttc tatgaataat | 10320 |
| tatcacagca acgttcaatt atcttcaatt ccggtgttta aaccccagcg cctggcgggg | 10379 |

<210> SEQ ID NO 42
<211> LENGTH: 4140
<212> TYPE: DNA
<213> ORGANISM: Artificial Sequence
<220> FEATURE:
<223> OTHER INFORMATION: Synthetic: ADS_FS.2 donor cassette

<400> SEQUENCE: 42

| | | |
|---|---|---|
| tcctcttgtg gtccgtggct tgtaattttc gggaaagata gaaatcactg cattcatcga | 60 |
| aagaagtgaa aataaattgt atcggggaag taatgagggg tggaatacgt aattgcttct | 120 |
| caatttgata atacaagtta cagtcttttt attgagagtc cctggaagga aaattattga | 180 |
| tgtttacctt ttttttgcgac gcgcgtctgg ccataaataa aagggttctc ttgccaagaa | 240 |
| aaaataaaaa ggcgccttaa gggaccttct atgacaaata tggtgaggta tgcaacctca | 300 |
| atgaagagca atgagaaaat ttaagggggta agtaagcatc ggaatttgtt gtttcctaac | 360 |
| aatttgtcta atttactcaa taatatcagg agaattgatc gaaaaaagca aaccaggaac | 420 |
| ccctcacaaa taagggaaca taagtaatt gctcgtctttt acatacatgg cactcaatcc | 480 |
| cagacgtcgc gtgctaaaaa tccttatatt attggcccct caggagttta tttgaattttt | 540 |
| gattgcattg ctttcagtgg acagtatatc ataaaatttg caagggcata gtgcctgccc | 600 |
| tacgatgttg taaaacaatt tctgaaaata ggttcagaat caaaaatgat gtataaatat | 660 |
| tgaaataaat tttcacataa attgtgctcc tccgcaaagt cttgactaaa taaacaattt | 720 |
| gttaatatcc tttcaaaaat tcttactttt tttttggatg gacgcaaaga agtttaataa | 780 |
| tcatattaca tggcattacc accatataca tatccatata catatccata tctaatctta | 840 |
| cttatatgtt gtggaaatgt aaagagcccc attatcttag cctaaaaaaa ccttctcttt | 900 |
| ggaactttca gtaatacgct taactgctca ttgctatatt gaagtacgga ttagaagccg | 960 |
| ccgagcgggt gacagccctc cgaaggaaga ctctcctccg tgcgtcctcg tcttcaccgg | 1020 |
| tcgcgttcct gaaacgcaga gtgtgcctcgc gccgcactgc tccgaacaat aaagattcta | 1080 |
| caatactagc ttttatggtt atgaagagga aaaattggca gtaacctggc cccacaaacc | 1140 |
| ttcaaatgaa cgaatcaaat taacaaccat aggatgataa tgcgattagt tttttagcct | 1200 |
| tatttctggg gtaattaatc agcgaagcga tgattttga tctattaaca gatatataaa | 1260 |

```
tgcaaaaact gcataaccac tttaactaat actttcaaca ttttcggttt gtattacttc    1320
ttattcaaat gtaataaaag tatcaacaaa aaattgttaa tatacctcta tactttaacg    1380
tcaaggagaa aaaccccgg atccatgggt caatataaat taattttgaa tggtaaaact    1440
ttgaagggtg aaactactac cgaagcagta gatgcagcaa cagccgaaaa ggtctttaag    1500
caatatgcta atgataatgg tgttgatggt gaatggacct atgacgatgc aactaaaaca    1560
tttactgtaa ctgaaggatc catggctttg actgaagaaa aaccaatcag accaattgct    1620
aattttccac cttctatctg gggtgaccaa ttcttgatct acgaaaagca agttgagcaa    1680
ggtgttgaac aaatcgttaa cgatttgaag aaggaagtta dacaattgtt gaaggaagct    1740
ttggacatcc caatgaagca cgctaactta tgaaattaa tcgacgaaat ccaaagatta    1800
ggtattccat accatttcga aagagaaatt gatcacgctt gcaatgtat ttacgaaact    1860 tacggtgata actggaacgg tgacagatct tccttatggt tcagattaat gagaaagcaa    1920
ggttactacg ttacttgtga cgttttcaac aactacaaag ataagaatgg tgcttttaag    1980
caatctttgg ccaacgatgt tgaaggttgg ttagaattgt atgaagccac ctccatgaga    2040
gttcctggtg aaatcatctt ggaagacgct ttgggtttta ctagatctag attgtccatc    2100
atgactaaag atgccttctc tactaaccca gctttgttca ctgaaatcca aagagctttg    2160
aaacaaccat tgtggaagcg tttgccaaga atcgaagctg ctcaatacat cccattctac    2220
caacaacaag actctcacaa caaaaccttg ttgaaattgg ctaaattgga atttaacttg    2280
ttgcaatcct tgcacaagga agaattgtct cacgtttgta agtggtggaa agccttcgat    2340
attaagaaga acgctccatg tttgagagat agaattgtcg aatgttactt ctggggtttg    2400
ggttccggtt acgaaccaca atactctaga gctagagttt tctttactaa ggtggttgct    2460
gttattacct tgattgacga cacttacgac gcttacggta cctacgaaga attgaagatt    2520
ttcactgaag ctgtcgaaag atggtccatt acctgtttag atactttacc agaatacatg    2580
aagccaattt ataagttgtt catggacact tacaccgaaa tggaagaatt cttggctaag    2640
gaaggtcgta ccgacttgtt caattgtggt aaggaattcg ttaaggaatt cgttcgtaac    2700
ttgatggttg aagctaaatg ggctaacgaa ggtcatattc caactactga gaacacgat    2760 ccagtcgtta tcattactgg tggtgctaac ttgttgacta ctacttgtta cttaggtatg    2820
tctgatattt tcaccaagga atctgttgaa tgggccgttt ccgctccacc tttgttcaga    2880
tactctggta ttttgggtag aagattaaac gatttgatga ctcacaaggc tgagcaagaa    2940
agaaagcact cctcctcttc cttagaatct tacatgaagg aatacaacgt taacgaagaa    3000
tacgctcaaa ctttgattta caaggaagtt gaagacgttt ggaaagatat taacagagaa    3060
tacttgacca ccaaaaatat tccacgtcca ttgttaatgg ctgttatcta tttatgtcaa    3120
ttcttagaag ttcaatacgc tggtaaagac aatttcacca gaatgggtga cgaatataag    3180
cacttaatta agtctttgtt ggtctaccct atgtctatct aagatccgct ctaaccgaaa    3240
aggaaggagt cagacaacct gaagtctagg tccctattta ttttttttata gttatgttag    3300 tattaagaac gttatttata tttcaaattt ttctttttttt tctgtacaga cgcgtgtacg    3360
catgtaacat tatactgaaa accttgcttg agaaggtttt gggacgctcg aagctacctt    3420
tttgttcttt tacttaaaca ttagttagtt cgttttcttt ttctcatttt tttatgtttc    3480 cccccaaag ttctgatttt ataatatttt atttcacaca attccattta acagagggg     3540 aatagattct ttagcttaga aaattagtga tcaatatata tttgcctttc ttttcatctt    3600
```

```
ttcagtgata ttaatggttt cgagacactg caatggccct agttgtctaa gaggatagat    3660
gttactgtca aagatgatat tttgaatttc aattgacgta attaatgata ctattaataa    3720
tacagagcgt atatgaagta ttgcaaataa catgcacagt tcttttggga tgagaatgat    3780
aatgaaaggc gaaggcgggc gttcagaaaa gcgttgcgga gtaacaagtg attaaatagc    3840
acccaaataa tcttctttga tactaccgat tgcgtgaata gaactcactt gactgataca    3900
accttcaatt ttaactctaa ttctactttt tatggtgatg acatcctcgg aactttggta    3960
tgatggtggg tttgaacccg cattaaaggt taaatcttga ggcatcagat gctttgtcac    4020
aaatactttc attggaccta cttgcacttc gaacccgtgc tgagaacatg aaacgactgt    4080
gccgtccact acttcccctt taaatggttt gaaaactaca gctctatatt tcacgttgaa    4140
```

<210> SEQ ID NO 43
<211> LENGTH: 4475
<212> TYPE: DNA
<213> ORGANISM: Artificial Sequence
<220> FEATURE:
<223> OTHER INFORMATION: Synthetic: ADS_FS.3 donor cassette

<400> SEQUENCE: 43

```
attgaagcac ctgtggagta tttaaaaact gcggttacat ggcctacaga tgaaatatgt      60
gctcaactaa tgacacaatt cccaccagga acgccgacca gtgtcctgct gcagactatt     120
tcagatgagc tagagaaaag ttctgacaac ctgttcacgt tatctgattt aaagagcaaa     180
ctgaaagtta ttggcttatt cgagcacatg aagatatcc attttttcga caagctgaaa     240
ctaagcaatg cgcccgtgaa ggacatgcct atggtcacaa aggcgttcac caaattttgc     300
gaaacaatag caaaaaggca tacaagaggc ctactgtcat accgattacc ttttaaccta     360
ctggactaca attgcatacc gaatgagagt tattcattag aggtttatga gtcattgtac     420
aacatcatta ctctatactt ctggctcagc aacaggtacc caaactactt cattgacatg     480
gaatctgcta aagatttgaa gtatttctgt gagatgatta ttttcgagaa acttgatcga     540
ttaaagaaga atccttacgc acataagccc tttggttcta caagaggtca cctctcatct     600
tcgagaagaa gattgcgtac ataatctacg atatatcctg taaatagaaa cagctacact     660
gcttgaaagc cttaacatga tacatttctg gtatgatgcc attgttgtgc cctgccgggt     720
ttatcgtttc ctaacaggca cgtcacttat aacgaggtgc ctgtcgttta ccgcccaagc     780
cggttttttc gctggagagt acggtactac tagcccacca cacgttcgtg gccaggttga     840
taggccaccg ttgagcaaag ggcagtaaaa tatataaaag aggaacaagc gcttccatta     900
agagcactgc taagcctact cgttttctag ttctctgaaa aaaggtagcc taaaacaagc     960
gccatatcat atatatttat acagattaga cgtactcaaa attcttactt tttttttgga    1020
tggacgcaaa gaagtttaat aatcatatta catggcatta ccaccatata catatccata    1080
tacatatcca tatctaatct tacttatatg ttgtggaaat gtaaagagcc ccattatctt    1140
agcctaaaaa aaccttctct ttggaacttt cagtaatacg cttaactgct cattgcgccg    1200
ccgagcgggt gacagccctc cgaaggaaga ctctcctccg tgcgtcctcg tcttcaccgg    1260
tcgcgttcct gaaacgcaga tgtgcctcgc gccgcactgc tccgaacaat aaagattcta    1320
caatactagc ttttatggtt atgaagagga aaaattggca gtaacctggc cccacaaacc    1380
ttcaaatgaa cgaatcaaat taacaaccat aggatgataa tgcgattagt ttttagcct    1440 tatttctggg gtaattaatc agcgaagcga tgattttga tctattaaca gatatataaa    1500
tgcaaaaact gcataaccac tttaactaat actttcaaca ttttcggttt gtattacttc    1560
```

```
ttattcaaat gtaataaaag tatcaacaaa aaattgttaa tatacctcta tactttaacg    1620
tcaaggagaa aaactataa tgggtcaata taaattaatt ttgaatggta aaactttgaa     1680
gggtgaaact actaccgaag cagtagatgc agcaacagcc gaaaaggtct ttaagcaata    1740
tgctaatgat aatggtgttg atggtgaatg gacctatgac gatgcaacta aaacatttac   1800
tgtaactgaa ggatccatgg ctttgactga agaaaaacca atcagaccaa ttgctaattt   1860
tccaccttct atctggggtg accaattctt gatctacgaa aagcaagttg agcaaggtgt   1920
tgaacaaatc gttaacgatt tgaagaagga agttagacaa ttgttgaagg aagctttgga   1980
catcccaatg aagcacgcta acttattgaa attaatcgac gaaatccaaa gattaggtat   2040
tccataccat ttcgaaagag aaattgatca cgctttgcaa tgtatttacg aaacttacgg   2100
tgataactgg aacggtgaca gatcttcctt atggttcaga ttaatgagaa agcaaggtta   2160
ctacgttact tgtgacgttt tcaacaacta caaagataag aatggtgctt ttaagcaatc   2220
tttggccaac gatgttgaag gtttgttaga attgtatgaa gccacctcca tgagagttcc   2280
tggtgaaatc atcttggaag acgctttggg ttttactaga tctagattgt ccatcatgac   2340
taaagatgcc ttctctacta acccagcttt gttcactgaa atccaaagag ctttgaaaca   2400
accattgtgg aagcgtttgc caagaatcga agctgctcaa tacatcccat tctaccaaca   2460
acaagactct cacaacaaaa ccttgttgaa attggctaaa ttggaattta acttgttgca   2520
atccttgcac aaggaagaat tgtctcacgt ttgtaagtgg tggaaagcct tcgatattaa   2580
gaagaacgct ccatgtttga gagatagaat tgtcgaatgt tacttctggg gtttgggttc   2640
cggttacgaa ccacaatact ctagagctag agttttcttt actaaggtgg ttgctgttat   2700
taccttgatt gacgacactt acgacgctta cggtacctac gaagaattga agattttcac   2760
tgaagctgtc gaaagatggt ccattacctg tttagatact ttaccagaat acatgaagcc   2820
aatttataag ttgttcatgg acacttacac cgaaatggaa gaattcttgg ctaaggaagg   2880
tcgtaccgac ttgttcaatt gtggtaagga attcgttaag gaattcgttc gtaacttgat   2940
ggttgaagct aaatgggcta acgaaggtca tattccaact actgaagaac acgatccagt   3000
cgttatcatt actggtggtg ctaacttgtt gactactact tgttacttag gtatgtctga   3060
tattttcacc aaggaatctg ttgaatgggc cgtttccgct ccaccttgt tcagatactc    3120 tggtattttg ggtagaagat taaacgattt gatgactcac aaggctgagc aagaaagaaa   3180
gcactcctcc tcttccttag aatcttacat gaaggaatac aacgttaacg aagaatacgc   3240
tcaaactttg atttacaagg aagttgaaga cgtttggaaa gatattaaca gagaatactt   3300
gaccaccaaa aatattccac gtccattgtt aatggctgtt atctatttat gtcaattctt   3360
agaagttcaa tacgctggta agacaatttc accagaatgg ggtgacgaat ataagcactt   3420
aattaagtct tgttggtct accctatgtc tatctaagat ccgctctaac cgaaaaggaa    3480
ggagttagac aacctgaagt ctaggtccct atttattttt ttatagttat gttagtatta   3540
agaacgttat ttatatttca aatttttctt tttttttctgt acagacgcgt gtacgcatgt   3600
aacattatac tgaaaacctt gcttgagaag gttttgggac gctcgaagga tacttgcaca   3660
agttccacta attactgaca tttgtggtat taactcgttt gactgctcta caattgtagg   3720
atgttaatca atgtcttggc tgccttcatt ctcttcaggc tctattaatt ttaaccgtta   3780
taagttcctt ttctccccttg gaagcaaaca tcaactgcct taaaatctgg tggcgaggaa   3840
agaggaaatg gcatgtacta atgatggtcc taataaatat cccgaaattg tgagtgttaa   3900
```

| | |
|---|---|
| gcacctgttc caacattcgg gatccaagca tgaatttagt gctggtaaac gattttcaaa | 3960 |
| atccattggt aaatattca aacgaaactc tgctttgaaa acttctagaa ctgaaacggc | 4020 |
| aaatcataaa atggaattga aaaaagaga gggtgttacc ttattgccac ctgtcccaga | 4080 |
| atcattatta cataaactca attcttggtt ggaaactttt tcttccacca agaacatgaa | 4140 |
| aatcgaagaa aacaaaattg ttattaatga aaaagagatt cgggattcag tctcttacta | 4200 |
| ccctgataag aatggaggaa gtgctgtatt ttgttacttg cccgaccttg tgctatatta | 4260 |
| taagccgcct ataaaagtca caggcaagca atgtccaata aagagaagtc cttgggaatc | 4320 |
| gatggaaatc caatatcaaa agtttatgta ccccttagaa aggttggaaa gacagtttga | 4380 |
| ggaagttcca tttaggcccct ggtattttgc aatgcgatta aaggaacttt acagatgctg | 4440 |
| tgaaaggtct tttactaacg cggcaaatag aggaa | 4475 |

<210> SEQ ID NO 44
<211> LENGTH: 8247
<212> TYPE: DNA
<213> ORGANISM: Artificial Sequence
<220> FEATURE:
<223> OTHER INFORMATION: Synthetic: 9XFS_URA3_FS.4 donor cassette

<400> SEQUENCE: 44

| | |
|---|---|
| attgctattg agtaagttcg atccgtttgg cgtctttggg ggtgtaacgc caaacttatt | 60 |
| acttttccta tttgaggttg gtattgattg ttgtcaaaga atgaaaatat acacaaacgc | 120 |
| cacaatatac gtaccaggtt cacgaaaact gatcgtatgg ttcataccct gacttggcaa | 180 |
| acctaatgtg accgtcgctg attagcggat cacgaaaagt gatctcgata caattagagg | 240 |
| atccacgaaa atgatgtgaa tgaatacatg aaagattcat gagatctgac aacatggtag | 300 |
| acgtgtgtgt ctcatggaaa ttgatgcagt tgaagacatg tgcgtcacga aaaagaaat | 360 |
| caatcctaca cagggcttaa gggcaaatgt attcatgtgt gtcacgaaaa gtgatgtaac | 420 |
| taaatacacg attaccatgg aaattaacgt acctttttg tgcgtgtatt gaaatattat | 480 |
| gacatattac agaaagggtt cgcaagtcct gtttctatgc ctttctctta gtaattcacg | 540 |
| aaataaacct atggtttacg aaatgatcca cgaaaatcat gttattattt acatcaacat | 600 |
| atcgcgaaaa ttcatgtcat gtccacatta acatcattgc agagcaacaa ttcattttca | 660 |
| tagagaaatt tgctactatc acccactagt actaccattg gtacctacta ctttgaattg | 720 |
| tactaccgct gggcgttatt aggtgtgaaa ccacgaaaag ttccaccataa cttcgaataa | 780 |
| agtcgcggaa aaaagtaaac agctattgct actcaaatga ggtttgcaga agcttgttga | 840 |
| agcatgatga agcgttctaa acgcactatt catcattaaa tatttaaagc tcataaaatt | 900 |
| gtattcaatt cctattctaa atggctttta tttctattac aactattagc tctaaatcca | 960 |
| tatcctcata agcagcaatc aattctatct atactttaaa agtaaaattc ttgagggaac | 1020 |
| tttcaccatt atgggaaatg gttcaagaag gtattgactt aaactccatc aaatggtcag | 1080 |
| gtcattgagt gttttttatt tgttgtattt tttttttttt agagaaaatc ctccaatatc | 1140 |
| aaattaggaa tcgtagtttc atgattttct gttacaccta actttttgtg tggtgccctc | 1200 |
| ctccttgtca atattaatgt taagtgcaa ttctttttcc ttatcacgtt gagccattag | 1260 |
| tatcaatttg cttacctgta ttcctttact atcctccttt ttctccttct tgataaatgt | 1320 |
| atgtagattg cgtatatagt ttcgtctacc ctatgaacat attccatttt gtaatttcgt | 1380 |
| gtcgtttcta ttatgaattt catttataaa gtttatgtac aaatatcata aaaaagaga | 1440 |
| atctttttaa gcaaggattt tcttaacttc ttcggcgaca gcatcaccga cttcggtggt | 1500 |

```
actgttggaa ccacctaaat caccagttct gatacctgca tccaaaacct ttttaactgc    1560
atcttcaatg gccttacctt cttcaggcaa gttcaatgac aatttcaaca tcattgcagc    1620
agacaagata gtggcgatag ggtcaacctt attctttggc aaatctggag cagaaccgtg    1680
gcatggttcg tacaaaccaa atgcggtgtt cttgtctggc aaagaggcca aggacgcaga    1740
tggcaacaaa cccaaggaac ctgggataac ggaggcttca tcggagatga tatcaccaaa    1800
catgttgctg gtgattataa taccatttag gtgggttggg ttcttaacta ggatcatggc    1860
ggcagaatca atcaattgat gttgaacctt caatgtaggg aattcgttct tgatggtttc    1920
ctccacagtt tttctccata atcttgaaga ggccaaaaca ttagctttat ccaaggacca    1980
aataggcaat ggtggctcat gttgtagggc catgaaagcg gccattcttg tgattctttg    2040
cacttctgga acggtgtatt gttcactatc ccaagcgaca ccatcaccat cgtcttcctt    2100
tctcttacca aagtaaatac ctcccactaa ttctctgaca acaacgaagt cagtaccttt    2160
agcaaattgt ggcttgattg gagataagtc taaaagagag tcggatgcaa agttacatgg    2220
tcttaagttg gcgtacaatt gaagttcttt acggattttt agtaaacctt gttcaggtct    2280
aacactaccg gtaccccatt taggaccacc cacagcacct aacaaaacgg catcaacctt    2340
cttggaggct ccagcgcct catctggaag tgggacacct gtagcatcga tagcagcacc    2400
accaattaaa tgattttcga aatcgaactt gacattggaa cgaacatcag aaatagcttt    2460
aagaaccta atggcttcgg ctgtgatttc ttgaccaacg tggtcacctg caaaacgac    2520
gatcttctta ggggcagaca taggggcaga cattagaatg gtatatcctt gaaatatata    2580
tatatattgc tgaaatgtaa aaggtaagaa aagttagaaa gtaagacgat tgctaaccac    2640
ctattggaaa aaacaatagg tccttaaata atattgtcaa cttcaagtat tgtgatgcaa    2700
gcattagtc atgaacgctt ctctattcta tatgaaaagc cggttccggc ctctcacctt    2760
tccttttct cccaattttt cagttgaaaa aggtatatgc gtcaggcgac ctctgaaatt    2820
aacaaaaaat ttccagtcat cgaatttgat tctgtgcgat agcgccctg tgtgttctcg    2880
ttatgttgag gaaaaaaata atggttgcta agagattcga actcttgcat cttacgatac    2940
ctgagtattc ccacagttaa ctgcggtcaa gatatttctt gaatcaggcg ccttagaccg    3000
ctcggccaaa caaccaatta cttgttgaga aatagagtat aattatccta taaatataac    3060
gtttttgaac acacatgaac aaggaagtac aggacaattg attttgaaga gaatgtggat    3120
tttgatgtaa ttgttgggat tccattttta ataaggcaat aatattaggt atgtggatat    3180
actagaagtt ctcctcgacc gtaataatca tattacatgg cattaccacc atatacatat    3240
ccatatacat atccatatct aatcttactt atatgttgtg gaaatgtaaa gagccccatt    3300
atcttagcct aaaaaaacct tctctttgga actttcagta atacgcttaa ctgctcattg    3360
cgccgccgag cgggtgacag ccctccgaag gaagactctc ctccgtgcgt cctcgtcttc    3420
accggtcgcg ttcctgaaac gcagatgtgc ctcgcgccgc actgctccga acaataaaga    3480
ttctacaata ctagctttta tggttatgaa gaggaaaaat tggcagtaac ctggccccac    3540
aaaccttcaa atgaacgaat caaattaaca accataggat gataatgcga ttagtttttt    3600
agccttattt ctggggtaat taatcagcga agcgatgatt tttgatctat aacagatat    3660
ataaatgcaa aaactgcata accactttaa ctaatacttt caacattttc ggtttgtatt    3720
acttcttatt caaatgtaat aaaagtatca acaaaaaatt gttaatatac ctctatactt    3780
taacgtcaag gagaaaaaac tataatgtcc actttgccta tttcctctgt ttcttcctct    3840
```

```
ccatctactt ccccaattgt tgtcgatgat aaggattcta ccaagccaga cgttattaga    3900
cataccgcta acttcaacgc ttccatttgg ggtgatcaat ttttgactta cgatgaacca    3960
gaggacttgg ttatgaagaa gcaattagtc gaagagttaa aggaggaagt taagaaggaa    4020
ttgattacta ttaagggttc taacgaacct atgcaacatg ttaagttgat cgaattaatc    4080
aatgctgttc aacgtttagg tattgcttac cattttgaag aagaaatcga agaagcttta    4140
caacatatcc atgtcactta cggtgaacaa tgggtcgata aggaaaattt acaatctatc    4200
tccttgtggt ttcgtttgtt gcgtcaacaa ggtttcaatg tctcctctgg tgttttcaag    4260
gactttatgg acgaaaaagg taaatttaag gaatctttgt gtaacgacgc tcaaggtatc    4320
ttggccttgt acgaagctgc tttcatgaga gtcgaagatg aaaccatctt ggacaacgct    4380
ttggaattct ctaaggttca cttggacatt attgccaagg atccatcttg tgactcttcc    4440
ttaagaaccc aaatccacca agccttgaag caaccattga gaagaagatt ggccagaatc    4500
gaagctttac actatatgcc aatttaccaa caagaaactt ctcacgacga ggttttgttg    4560
aagttggcta agttagattt ctctgttttg caatccatgc ataagaaaga attgtctcac    4620
atctgcaagt ggtggaaaga tttagacttg caaaacaaat tgccattcgt tcgtgataga    4680
gttgtcgaag gttacttctg gatttttgtct attactatg aaccacaaca tgccagaacc    4740
agaatgttct tgatgaagtc ttgtatgtgg ttggtcgttt tggatgatac cttcgacaac    4800
tacggtacct acgaagaatt ggaaattttc actcaagccg ttgagaagtg gtccatttct    4860
tgtttggaca tgttgccaga atacatgaag ttgatctacc aagaattggt taacttgcac    4920
gttgaaatgg aagaatcttt agaaaaggaa ggtaaggctt atcaaatcca ctacgttaag    4980
gaaatggcta aggaattggt cagaaactac ttggttgaag ccagatggtt gaaagaaggt    5040
tacatgccta ctttggaaga gtacatgtct gtttccatgg ttaccggtac ctacggtttg    5100
atcactgcta gatcttacgt tggtagaggt gacattgtta acgaggacac ttttaaatgg    5160
gtttcttcct acccacctat tgttgaagct tcttgtgtta tcattagatt gatggatgat    5220
attgtctctc ataaagaaga acaagaaaga ggtcatgttg cctcctccat cgaatgttat    5280
tctaaggaat ccggtgcttc tgaagaagaa gcctgtgaat acatctctag aaaagtcgaa    5340
gacgcctgga aggttattaa cagagaatct ttgagaccaa ccgccgttcc attcccttg    5400
ttaatgccag ctatcaactt ggctagaatg tgtgaagttt tatactctgt taacgatggt    5460
ttcactcacg ccgaaggtga catgaaatct tacatgaagt ccttctttgt ccatccaatg    5520
gtcgtttgag cgaatttctt atgatttatg attttatta ttaaataagt tataaaaaaa    5580
ataagtgtat acaaatttta aagtgactct taggttttaa aacgaaaatt cttattcttg    5640
agtaactctt tcctgtaggt caggttgctt tctcaggtat agcatgaggt cgctcatgcg    5700
tccatcttta cagtcctgtc ttattgttct tgatttgtgc cccgtaaaat actgttactt    5760
ggttctggcg aggtattgga tagttccttt ttataaaggc catgaagctt tttctttcca    5820
attttttttt tttcgtcatt atagaaatca ttacgaccga gattcccggg taataactga    5880
tataattaaa ttgaagctct aatttgtgag tttagtatac atgcatttac ttataataca    5940
gttttttagt tttgctggcc gcatcttctc aaatatgctt cccagcctgc ttttctgtaa    6000
cgttcaccct ctaccttagc atcccttccc tttgcaaata gtcctcttcc aacaataata    6060
atgtcagatc ctgtagagac cacatcatcc acggttctat actgttgacc caatgcgtct    6120
cccttgtcat ctaaacccac accgggtgtc ataatcaacc aatcgtaacc ttcatctctt    6180
ccacccatgt ctctttgagc aataaagccg ataacaaaat ctttgtcact cttcgcaatg    6240
```

```
tcaacagtac ccttagtata ttctccagta gatagggagc ccttgcatga caattctgct    6300
aacatcaaaa ggcctctagg ttcctttgtt acttcttctg ccgcctgctt caaaccgcta    6360
acaatacctg gcccaccac accgtgtgca ttcgtaatgt ctgcccattc tgctattctg    6420
tatacacccg cagagtactg caatttgact gtattaccaa tgtcagcaaa ttttctgtct    6480
tcgaagagta aaaaattgta cttggcggat aatgccttta gcggcttaac tgtgccctcc    6540
atggaaaaat cagtcaagat atccacatgt gtttttagta aacaaatttt gggacctaat    6600
gcttcaacta actccagtaa ttccttggtg gtacgaacat ccaatgaagc acacaagttt    6660
gtttgctttt cgtgcatgat attaaatagc ttggcagcaa caggactagg atgagtagca    6720
gcacgttcct tatatgtagc tttcgacatg atttatcttc gtttcctgca ggttttttgtt    6780 ctgtgcagtt gggttaagaa tactgggcaa tttcatgttt cttcaacacc acatatgcgt    6840
atatatacca atctaagtct gtgctccttc cttcgttctt ccttctgctc ggagattacc    6900
gaatcaaaaa aatttcaaag aaaccggaat caaaaaaaag aacaaaaaaa aaaaagatga    6960
attgaaaagc tttatggacc ctgaaaccac agccacatta accttctttg atggtcaaaa    7020
cttatccttc accataaata tgcctcgcaa aaaaggtaat taacatatat agaattacat    7080
tatttatgaa atatcatcac tatctcttag catctttaat ccttttctac atcagataac    7140
ttcggtttgt tatcatcgtc tgtattgtca tcaattggcg cagtagcctc aatttcaacg    7200
tcgtttgact ctggtgtttg ttcatgtgca gatccatgag atgatgaaat gtgtatatta    7260
gtttaaaaag ttgtatgtaa taaaagtaaa atttaatatt ttggatgaaa aaaaccatt    7320 ttagactttt tcttaactag aatgctggag tagaaatacg ccatctcaag atacaaaaag    7380
cgttaccggc actgatttgt ttcaaccagt atatagatta ttattgggtc ttgatcaact    7440
ttcctcagac atatcagtaa cagttatcaa gctaaatatt tacgcgaaag aaaaacaaat    7500
attttaattg tgatacttgt gaatttttatt ttattaagga tacaaagtta agagaaaaca    7560
aaatttatat acaatataag taatattcat atatatgtga tgaatgcagt cttaacgaga    7620
agacatggcc ttggtgacaa ctctcttcaa accaacttca gcctttctca attcatcagc    7680
agatgggtct tcgatttgca aagcagccaa agcatcggac aaagcagctt caatcttgga    7740
cttggaacct ctcttcaatt tagaagacaa gactgggtca gtgacagttt gttcgatgga    7800
ggcaacgtag gattccaatc tttgtctagc ttcgtgcttc ttggcaaaag cttcatcggc    7860
agccttgaac tcttcagctt ggttaaccat cttttcaatt tcttcagaag acaatctacc    7920
aacagcgtta gagatagtga tgttagaaga cttaccggta gacttttcga cggcagtaac    7980
cttcaagata ccgttagcat caacttcgaa gatagcttcc aagactggtt caccagctgg    8040
catcattggg atgttcttca agtcgaattc acccaacaaa gtgttttctt tacagttaac    8100
acgttcacct tggtagactg ggaattgaac ggtggttggg ttgtcagcac atgtagtaaa    8160
ggttcttctc ttgatggttg gaacagtagt gtttcttgga acaacgatac cgaacatgtc    8220
accttgcata ccaacaccta gagataa                                        8247
```

<210> SEQ ID NO 45
<211> LENGTH: 49
<212> TYPE: DNA
<213> ORGANISM: Artificial Sequence
<220> FEATURE:
<223> OTHER INFORMATION: Synthetic: Recognition sequence for FS-specific TALEN

<400> SEQUENCE: 45

```
tagtggagga attaaaagag gaagttaaga aggaattgat aactatcaa        49
```

<210> SEQ ID NO 46
<211> LENGTH: 26
<212> TYPE: DNA
<213> ORGANISM: Artificial Sequence
<220> FEATURE:
<223> OTHER INFORMATION: Synthetic: Primer HJ272

<400> SEQUENCE: 46

```
ataacaatat tataaaaagc gcttaa                                 26
```

<210> SEQ ID NO 47
<211> LENGTH: 29
<212> TYPE: DNA
<213> ORGANISM: Artificial Sequence
<220> FEATURE:
<223> OTHER INFORMATION: Synthetic: Primer ART45

<400> SEQUENCE: 47

```
tactgcttcg gtagtagttt cacccttca                              29
```

<210> SEQ ID NO 48
<211> LENGTH: 22
<212> TYPE: DNA
<213> ORGANISM: Artificial Sequence
<220> FEATURE:
<223> OTHER INFORMATION: Synthetic: Primer HJ643

<400> SEQUENCE: 48

```
aaaatcctta tattattggc cc                                     22
```

<210> SEQ ID NO 49
<211> LENGTH: 19
<212> TYPE: DNA
<213> ORGANISM: Artificial Sequence
<220> FEATURE:
<223> OTHER INFORMATION: Synthetic: Primer HJ799

<400> SEQUENCE: 49

```
gtagcctaaa acaagcgcc                                         19
```

<210> SEQ ID NO 50
<211> LENGTH: 9
<212> TYPE: PRT
<213> ORGANISM: Artificial Sequence
<220> FEATURE:
<223> OTHER INFORMATION: Synthetic: Homing endonuclease family conserved
      motif

<400> SEQUENCE: 50

Leu Ala Gly Leu Ile Asp Ala Asp Gly
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic: Homing endonuclease family conserved
      motif

<400> SEQUENCE: 51

Gly Ile Tyr Tyr Ile Gly
1               5

<210> SEQ ID NO 52
<211> LENGTH: 18
<212> TYPE: DNA
<213> ORGANISM: Artificial Sequence
<220> FEATURE:
<223> OTHER INFORMATION: Synthetic: Recognition sequence for I-SceI

<400> SEQUENCE: 52
tagggataac agggtaat                                                        18

<210> SEQ ID NO 53
<211> LENGTH: 31
<212> TYPE: DNA
<213> ORGANISM: Artificial Sequence
<220> FEATURE:
<223> OTHER INFORMATION: Synthetic: Recognition sequence for VDE
      (PI-SceI)

<400> SEQUENCE: 53
tatgtcgggt gcggagaaag aggtaatgaa a                                         31

<210> SEQ ID NO 54
<211> LENGTH: 24
<212> TYPE: DNA
<213> ORGANISM: Artificial Sequence
<220> FEATURE:
<223> OTHER INFORMATION: Synthetic: Recognition sequence for F-CphI

<400> SEQUENCE: 54
gatgcacgag cgcaacgctc acaa                                                 24

<210> SEQ ID NO 55
<211> LENGTH: 24
<212> TYPE: DNA
<213> ORGANISM: Artificial Sequence
<220> FEATURE:
<223> OTHER INFORMATION: Synthetic: Recognition sequence for PI-MgaI

<400> SEQUENCE: 55
gcgtagctgc ccagtatgag tcag                                                 24

<210> SEQ ID NO 56
<211> LENGTH: 40
<212> TYPE: DNA
<213> ORGANISM: Artificial Sequence
<220> FEATURE:
<223> OTHER INFORMATION: Synthetic: Recognition sequence for PI-MtuII

<400> SEQUENCE: 56
acgtgcacta cgtagagggt cgcaccgcac cgatctacaa                                40

<210> SEQ ID NO 57
<211> LENGTH: 4300
<212> TYPE: DNA
<213> ORGANISM: Artificial Sequence
<220> FEATURE:
<223> OTHER INFORMATION: Synthetic: ADE2_SFC1 donor cassette

<400> SEQUENCE: 57
ccggtggtgc ttatactgtt tctactgcag ctgccgctac tgttagatct accatcagaa          60
gattaagaga aatggttgaa gcttaaactt ctttcattca ttttctcttg gctttcacta         120
ggtatatcta ttccataacg actatgtttt gtatttgtta atttacataa aaccatatca         180
gtacatcaac gaactgtaaa aaagaaactt tagcataatt attgcggata tttaaactca         240

```
cttgcaggta agagcaaaag gcgattgatt tccagtccgc ctcttgtcac gtgatttagt      300
aagaaatttt gacagcaccc tcggtttaat ggaaaagagg ggcgttttc gatgaacccg       360 aggggagact agagaatcat ctcggttgaa tggagcatta ttttttagt agcgcccgcc       420 cggagaaatg gacgttggcg aatgagccat gaattattaa ccgcccatgt ctaccagata      480
gacggcacgg ccacgcgttt aaaccgcccc acatcgtatg acagtaccag cctagtcccg      540
gtaaaccgca aacggacctt aattgtgacg aagggcccaa atttgatggg tcggtgttaa      600
tgattagtcc tcattgtcat aataaagtgt gatgatggag gcaatgatga tatacggtag     660
tactactgct cgaggtgcta tcttttaacc aatcctttga gattcttgtc gccacggagt      720
tactaccttt tacaaaccgt aatgtcacat tttgcatata tcttatgtat aaatatatag      780
ttcacttact acttgttctc gttttgttaa cttttcttgtt gtagttcttc ttgttcttgg    840
cgtttccccc tttgttttct atctgcttca taagtaaagt gcaaagcatt ttggaagata     900
ttatcaattg agtcattgaa agaaacttgg catcttccct attactaaaa ctaagaatac     960
ttgattcaag aaagaagttt atattagttt tagccgtaag ataacataac aaagaagaag   1020
aaagaaaatt cttgaataat acataacttt tcttaaaaga atcaaagaca gataaaattt   1080
aagagatatt aaatattagt gagaagccga gaattttgta acaccaacat aacactgaca    1140
tcttaaacaa cttttaatta tgatacattt cttacgtcat gattgattat tacagctatg    1200
ctgacaaatg actcttgttg catggctacg aaccgggtaa tactaagtga ttgactcttg    1260 ctgaccttt attaagaact aaatggacaa tattatggag catttcatgt ataaattggt     1320
gcgtaaaatc gttggatctc tcttctaagt acatcctact ataacaatca agaaaaacaa    1380
gaaaatcgga caaaacaatc aagtatggat tctagaacag ttggtatatt aggaggggga    1440
caattgggac gtatgattgt tgaggcagca acaggctca acattaagac ggtaatacta    1500
gatgctgaaa attctcctgc caaacaaata agcaactcca atgaccacgt taatggctcc    1560
ttttccaatc ctcttgatat cgaaaaacta gctgaaaaat gtgatgtgct aacgattgag    1620
attgagcatg ttgatgttcc tacactaaag aatcttcaag taaacatcc caaattaaaa    1680 atttacccctt ctccagaaac aatcagattg atacaagaca aatatattca aaaagagcat   1740
ttaatcaaaa atggtatagc agttacccaa agtgttcctg tggaacaagc cagtgagacg   1800
tccctattga atgttggaag agatttgggt tttccattcg tcttgaagtc gaggactttg    1860
gcatacgatg gaagaggtaa cttcgttgta aagaataagg aaatgattcc ggaagctttg   1920
gaagtactga aggatcgtcc tttgtacgcc gaaaaatggg caccattac taaagaatta    1980 gcagtcatga ttgtgaggtc tgttaacggt ttagtgtttt cttacccaat tgtagagact   2040
atccacaagg acaatatttg tgacttatgt tatgcgcctg ctagagttcc ggactccgtt    2100
caacttaagg cgaagttgtt ggcagaaaat gcaatcaaat cttttcccgg ttgtggtata    2160
tttggtgtgg aaatgttcta tttagaaaca ggggaattgc ttattaacga aattgcccca   2220
aggcctcaca actctggaca ttataccatt gatgcttgcg tcacttctca atttgaagct    2280
catttgagat caatattgga tttgccaatg ccaaagaatt tcacatcttt ctccaccatt    2340
acaacgaacg ccattatgct aaatgttctt ggagacaaac atacaaaaga taagagcta    2400 gaaacttgcg aaagagcatt ggcgactcca ggttcctcag tgtacttata tggaaaagag   2460
tctagaccta acagaaaagt aggtcacata aatattattg cctccagtat ggcggaatgt   2520
gaacaaaggc tgaactacat tacaggtaga actgatattc caatcaaaat ctctgtcgct    2580
caaaagttgg acttggaagc aatggtcaaa ccattggttg gaatcatcat gggatcagac    2640
```

```
tctgacttgc cggtaatgtc tgccgcatgt gcggttttaa aagattttgg cgttccattt      2700
gaagtgacaa tagtctctgc tcatagaact ccacatagga tgtcagcata tgctatttcc      2760
gcaagcaagc gtggaattaa acaattatc gctggagctg gtgggctgc tcacttgcca        2820 ggtatggtgg ctgcaatgac accacttcct gtcatcggtg tgcccgtaaa aggttcttgt      2880
ctagatggag tagattcttt acattcaatt gtgcaaatgc ctagaggtgt tccagtagct      2940
accgtcgcta ttaataatag tacgaacgct gcgctgttgg ctgtcagact gcttggcgct      3000
tatgattcaa gttatacaac gaaaatggaa cagttttat taaagcaaga agaagaagtt       3060
cttgtcaaag cacaaaagtt agaaactgtc ggttacgaag cttatctaga aacaagtaa       3120 tatataagtt tattgatata cttgtacagc aaataattat aaaatgatat acctattttt     3180
taggctttgt tatgattaca tcaaatgtgg acttcataca tagaaatcaa cgcttacagg      3240
tgtccttttt taagaatttc atacataaga tcatgatgaa caatgggact acaaaatgaa      3300
ataaagaaaa aatagaaata gaatagaaga tcaattatta atcgccctat tcttccttat      3360
tacctacaca aaataaagca gcaacataag aaacaaaaac aaaatgaaaa caaaccaaat      3420
aaatctatgt aagcatactc atttcaattt gatattcatt acttgacttt tttgtcctta     3480
tttgaggctc cataagcgcg ccattttccc ctactccctt ttttcgtaaa tagtaataat     3540
gtgctgaaaa gaacaatgaa gtagttatca tacatattcc gtcgtgtcga tatgagggga     3600
ggtgtctctt tctttcatcc cttgtcgcaa cctccaatat ataagagcat aagcaactga     3660
tcttacttta gtaattaact tagcatacct ggcccgaagg aagaaaaaaa attcacctca     3720
acaacatggt tcctaagttt tacaaacttt caaacggctt caaaatccca agcattgctt     3780
tgggaaccta ccggtgttta accccagcg cctggcgggg atattccaag atcgcaaaca     3840
gccgaaattg tgtatgaagg tgtcaagtgc ggctaccgtc atttcgatac tgctgttctt    3900
tatggtaatg agaaggaagt tggcgatggt atcattaaat ggttgaacga agatccaggg    3960
aaccataaac gtgaggaaat cttctacact actaaattat ggaattcgca aaacggatat    4020
aaaagagcta aagctgccat tcagcaagt ttgaatgaag tctcgggctt gcaatacatc    4080
gatcttcttt tgattcattc gccactggaa ggttctaaat taaggttgga aacttggcgc    4140
gccatgcaag aagcggttga tgaaggattg gttaagtcta taggggtttc caactatggg    4200
aaaaagcaca ttgatgaact tttgaactgg ccagaactga agcacaagcc agtggtcaac    4260
caaatcgaga tatcaccttg gattatgaga caagaattag                          4300
```

<210> SEQ ID NO 58
<211> LENGTH: 3586
<212> TYPE: DNA
<213> ORGANISM: Artificial Sequence
<220> FEATURE:
<223> OTHER INFORMATION: Synthetic: GFP_SFC1 donor cassette

<400> SEQUENCE: 58

```
ccggtggtgc ttatactgtt tctactgcag ctgccgctac tgttagatct accatcagaa        60
gattaagaga aatggttgaa gcttaaactt cttttcattca ttttctcttg gctttcacta      120
ggtatatcta ttccataacg actatgtttt gtatttgtta atttacataa aaccatatca       180
gtacatcaac gaactgtaaa aagaaactt tagcataatt attgcggata tttaaactca        240
cttgcaggta agagcaaaag gcgattgatt tccagtccgc ctcttgtcac gtgatttagt       300
aagaaatttt gacagcaccc tcggtttaat ggaaaagagg ggcgttttc gatgaacccg        360
```

```
agggagact agagaatcat ctcggttgaa tggagcatta ttttttttagt agcgcccgcc      420 cggagaaatg gacgttggcg aatgagccat gaattattaa ccgcccatgt ctaccagata      480
gacggcacgg ccacgcgttt aaaccgcccc acatcgtatg acagtaccag cctagtcccg      540
gtaaaccgca aacggacctt aattgtgacg aagggcccaa atttgatggg tcggtgttaa      600
tgattagtcc tcattgtcat aataaagtgt gatgatggag gcaatgatga tatacggtag      660
tactactgct cgaggtgcta tcttttaacc aatcctttga gattcttgtc gccacggagt      720
tactaccttt tacaaaccgt aatgtcacat tttgcatata tcttatgtat aaatatatag      780
ttcacttact acttgttctc gttttgttaa cttttcttgtt gtagttcttc ttgttcttgg      840
cgtttccccc tttgttttct atctgcttca taagtaaagt gcaaagcatt ttggaagata      900
ttatcaattg agtcattgaa agaaacttgg catcttccct attactaaaa ctaagaatac      960
ttgattcaag aaagaagttt atattagttt tagccgtaag ataacataac aaagaagaag     1020
aaagaaaaac acaattacag taacaataac aagaggacag atactaccaa aatgtgtggg     1080
gaagcgggta agctgccaca gcaattaatg cacaacattt aacctacatt cttccttatc     1140
ggatcctcaa aacccttaaa aacatatgcc tcaccctaac atattttcca attaaccctc     1200
aatatttctc tgtcacccgg cctctatttt ccatttctt ctttacccgc cacgcgtttt      1260
tttcttccaa atttttttct tcttttcttct ttttcttcca cgtcctcttg cataaataaa     1320
taaaccgttt tgaaaccaaa ctcgcctctc tctctccttt ttgaaatatt tttgggtttg     1380
tttgatcctt tccttcccaa tctctcttgt ttaatatata ttcattttata tcacgctctc     1440 ttttatctt ccttttttttc ctctctcttg tattcttcct tcccctttct actcaaacca     1500
agaagaaaaa gaaaaggtca atctttgtta agaataggga tcttctacta catcagctt     1560 tagatttttc acgcttactg cttttttcttt cccaagatcg aaaatttact gaattaacaa     1620
tggtgagcaa gggcgaggag ctgttcaccg gggtggtgcc catcctggtc gagctggacg     1680
gcgacgtaaa cggccacaag ttcagcgtgt ccggcgaggg cgagggcgat gccacctacg     1740
gcaagctgac cctgaagttc atctgcacca ccggcaagct gcccgtgccc tggcccaccc     1800
tcgtgaccac cttgacctac ggcgtgcagt gcttcgcccg ctaccccgac cacatgaagc     1860
agcacgactt cttcaagtcc gccatgcccg aaggctacgt ccaggagcgc accatcttct     1920
tcaaggacga cggcaactac aagacccgcg ccgaggtgaa gttcgagggc gacaccctgg     1980
tgaaccgcat cgagctgaag ggcatcgact tcaaggagga cggcaacatc ctggggcaca     2040
agctggagta caactacaac agccacaagg tctatatcac cgccgacaag cagaagaacg     2100
gcatcaaggt gaacttcaag acccgccaca acatcgagga cggcagcgtg cagctcgccg     2160
accactacca gcagaacacc cccatcggcg acggccccgt gctgctgccc gacaaccact     2220
acctgagcac ccagtccgcc ctgagcaaag accccaacga gaagcgcgat cacatggtcc     2280
tgctggagtt cgtgaccgcc gccgggatca ctctcggcat ggacgagctg tacaagtaac     2340
tcgagaagct tgatccggct gcgaatttct tatgatttat gattttattt attaaataag     2400
ttataaaaaa aataagtgta tacaaatttt aaagtgactc ttaggtttta aaacgaaaat     2460
tcttattctt gagtaactct ttcctgtagg tcaggttgct ttctcaggta tagcatgagg     2520
tcgctcttat tgaccacacc tctaccggca tgccgagcat gatgaacaat gggactacaa     2580
aatgaaataa agaaaaaata gaaatagaat agaagatcaa ttattaatcg ccctattctt     2640
ccttattacc tacacaaaat aaagcagcaa cataagaaac aaaaacaaaa tgaaaacaaa     2700
ccaaataaat ctatgtaagc atactcattt caatttgata ttcattactt gactttttttg     2760
```

```
tccttatttg aggctccata agcgcgccat tttcccctac tcccttttt  cgtaaatagt   2820 aataatgtgc tgaaaagaac aatgaagtag ttatcataca tattccgtcg tgtcgatatg   2880
aggggaggtg tctctttctt tcatcccttg tcgcaacctc caatatataa gagcataagc   2940
aactgatctt actttagtaa ttaacttagc ataccctggcc cgaaggaaga aaaaaaattc   3000
acctcaacaa catggttcct aagttttaca aactttcaaa cggcttcaaa atcccaagca   3060
ttgctttggg aacctaccgg tgtttaaacc ccagcgcctg gcggggatat tccaagatcg   3120
caaacagccg aaattgtgta tgaaggtgtc aagtgcggct accgtcattt cgatactgct   3180
gttctttatg gtaatgagaa ggaagttggc gatggtatca ttaaatggtt gaacgaagat   3240
ccagggaacc ataaacgtga ggaaatcttc tacactacta aattatggaa ttcgcaaaac   3300
ggatataaaa gagctaaagc tgccattcag caatgtttga atgaagtctc gggcttgcaa   3360
tacatcgatc ttcttttgat tcattcgcca ctggaaggtt ctaaattaag gttggaaact   3420
tggcgcgcca tgcaagaagc ggttgatgaa ggattggtta agtctatagg ggttccaac   3480 tatgggaaaa agcacattga tgaactttg aactggccag aactgaagca caagccagtg   3540
gtcaaccaaa tcgagatatc accttggatt atgagacaag aattag              3586
```

```
<210> SEQ ID NO 59
<211> LENGTH: 4300
<212> TYPE: DNA
<213> ORGANISM: Artificial Sequence
<220> FEATURE:
<223> OTHER INFORMATION: Synthetic: ADE2_YJR030C donor cassette

<400> SEQUENCE: 59
```

```
ggaactttat gaacatatta agtctgcttg atgaaatgtc atgtgcaggt gccgttggca     60
caaaatggga acaaaattat gaaaattcag tcgaggatgg gtgtgaagca cctgaatcca    120
atccataccg ttctattatt gatctttcta gtcgttccat taatataact gcagacctac    180
tttcgactgt tgggaggagt aattcagcac tcaacaagaa tgagattata gctgctattc    240
aaggtctcgc ccatcaatgc ctcaatccct gtgacgaact aggtatgcaa gcattgcaag    300
cattagagaa cattctgtta tctcgagcaa gtcaactacg tacggaaaaa gttgcggtgg    360
ataacctact agagacagga ttattaccga tttttgagtt ggatgaaatc caagatgtca    420
agatgaaacg aattactagc attttatccg ttctttctaa aatgacggca cggccacgcg    480
tttaaaccgc ccttcttggg tcaacttgtg gaaggcgtaa caagtaacga aacttttttg    540
agagtgctta acgtatttaa caagtatgta gatgatccta cggtggaaag gcagttgcaa    600
gagttgatta tttctaagag ggaaatcgag aaggagtaga ccaacgataa tgtaactata    660
ccaagaaact tagtatgatg gaattttttc aaggagtcgt aaattagatt ttcgcaggta    720
ataatgcgat atataagcaa tctcatttaa atatcgacgg tggcatttat accatcattt    780
actgttatat ttatctaacg cgtcgcgacg cgttagataa aatacaacaa gattttttt    840 tcgtgtcacc aatggcatga aagcttcgag aataatttga aggaaatttc acttaatggg    900
aaaaataaaa atgtaccctt atcgagatta ctcttttacc ctcagttcaa ttaaaattca    960
tcatgaacca agtaaaagtt cctctaatta cgaacgagca agcaaattag tattgtgtgg   1020
gagacgggtt cttgaataat acataacttt tcttaaaaga atcaaagaca gataaaattt   1080
aagagatatt aaatattagt gagaagccga gaatttttgta acaccaacat aacactgaca   1140 tcttttaacaa cttttaatta tgatacattt cttacgtcat gattgattat tacagctatg   1200
```

```
ctgacaaatg actcttgttg catggctacg aaccgggtaa tactaagtga ttgactcttg    1260 ctgaccttt  attaagaact aaatggacaa tattatggag catttcatgt ataaattggt    1320
gcgtaaaatc gttggatctc tcttctaagt acatcctact ataacaatca agaaaaacaa    1380
gaaaatcgga caaaacaatc aagtatggat tctagaacag ttggtatatt aggagggga    1440 caattgggac gtatgattgt tgaggcagca acaggctca  acattaagac ggtaatacta    1500
gatgctgaaa attctcctgc caaacaaata agcaactcca atgaccacgt taatggctcc    1560
ttttccaatc ctcttgatat cgaaaaacta gctgaaaaat gtgatgtgct aacgattgag    1620
attgagcatg ttgatgttcc tacactaaag aatcttcaag taaaacatcc caaattaaaa    1680 atttacccctt ctccagaaac aatcagattg atacaagaca aatatattca aaaagagcat    1740
ttaatcaaaa atggtatagc agttacccaa agtgttcctg tggaacaagc cagtgagacg    1800
tccctattga atgttggaag agatttgggt tttccattcg tcttgaagtc gaggactttg    1860
gcatacgatg aagaggtaa cttcgttgta agaataagg aaatgattcc ggaagctttg    1920
gaagtactga aggatcgtcc tttgtacgcc gaaaaatggg caccatttac taaagaatta    1980
gcagtcatga ttgtgaggtc tgttaacggt ttagtgtttt cttacccaat tgtagagact    2040
atccacaagg acaatatttg tgacttatgt tatgcgcctg ctagagttcc ggactccgtt    2100
caacttaagg cgaagttgtt ggcagaaaat gcaatcaaat cttttcccgg ttgtggtata    2160
tttggtgtgg aaatgttcta tttagaaaca ggggaattgc ttattaacga aattgcccca    2220
aggcctcaca actctggaca ttataccatt gatgcttgcg tcacttctca atttgaagct    2280
catttgagat caatattgga tttgccaatg ccaaagaatt tcacatcttt ctccaccatt    2340
acaacgaacg ccattatgct aaatgttctt ggagacaaac atacaaaaga taaagagcta    2400
gaaacttgcg aaagagcatt ggcgactcca ggttcctcag tgtacttata tggaaaagag    2460
tctagaccta acagaaaagt aggtcacata atattattg  cctccagtat ggcggaatgt    2520
gaacaaaggc tgaactacat tacaggtaga actgatattc caatcaaaat ctctgtcgct    2580
caaaagttgg acttggaagc aatggtcaaa ccattggttg gaatcatcat gggatcagac    2640
tctgacttgc cggtaatgtc tgccgcatgt gcggttttaa aagatttggg cgttccattt    2700
gaagtgacaa tagtctctgc tcatagaact ccacatagga tgtcagcata tgctatttcc    2760
gcaagcaagc gtggaattaa aacaattatc gctggagctg gtggggctgc tcacttgcca    2820
ggtatggtgg ctgcaatgac accacttcct gtcatcggtg tgcccgtaaa aggttcttgt    2880
ctagatggag tagattcttt acattcaatt gtgcaaatgc ctagaggtgt tccagtagct    2940
accgtcgcta ttaataatag tacgaacgct gcgctgttgg ctgtcagact gcttggcgct    3000
tatgattcaa gttatacaac gaaaatggaa cagttttat  taaagcaaga agaagaagtt    3060
cttgtcaaag cacaaaagtt agaaactgtc ggttacgaag cttatctaga aacaagtaa    3120 tatataagtt tattgatata cttgtacagc aaataattat aaaatgatat acctatttt    3180 taggctttgt tatgattaca tcaaatgtgg acttcataca tagaaatcaa cgcttacagg    3240 tgtcctttt  taagaatttc atacataaga tcatgttgag ataattgttg ggattccatt    3300
gttgataaag gctataatat taggtataca gaatatacta gaagttctcc tcgaggatat    3360
aggaatcctc aaaatggaat ctatatttct acatactaat attacgatta ttcctcattc    3420
cgttttatat gttatattc  attgatccta ttcattatc  aatccttgcg tttcagcttc    3480
ctctaacttc gatgacagct tctcataact tatgtcatca tcttaacacc gtatatgata    3540
atatattgat aatataacta ttagttgata gacgatagtg gatttttatt ccaacatacc    3600
```

-continued

| | |
|---|---|
| acccataatg taatagatct aatgaatcca tttgtttgtt aatagtttga atgttttat | 3660 |
| cggaagaggt ttggtcatta cgtctgcaat attcttttg gtttcgatat agcatacgtg | 3720 |
| cagatgattt cctgatactt catctctcaa tctcattgct ttagtaccaa aaaatctgtt | 3780 |
| cctaaatttc cggtgtttaa accccagcgc ctggcgggtc ttcattattg gatataatta | 3840 |
| tactgattgt agatttactg tcggttagta atcctttggt aattggtttc ttgtcaagtt | 3900 |
| cttgtatcag gtaacttaga ttatttaata atgggacaga ttcacttatc gcgtgtattt | 3960 |
| ctgcttccgt agttgaagta catgttaatg aagccttggt ggactttcct ccaattacct | 4020 |
| ttccattaag taaatatatg ttgccaattt gtgatttata atacggttgg ttgccatacg | 4080 |
| aggcatcgct tataacaact aatttatttg ttggcttaac aggtttgctt ttgtgccata | 4140 |
| ttaattgctt atctctcgta ttccatatga actgtatcaa ttcatatgtc atatctaaca | 4200 |
| cttgcttgga cggaaatagt atatgttgtg caagtgtgtt gatgtagtat aataggtcaa | 4260 |
| atctaaattt atatccaaca tatgatgcta gacctatcag | 4300 |

<210> SEQ ID NO 60
<211> LENGTH: 3586
<212> TYPE: DNA
<213> ORGANISM: Artificial Sequence
<220> FEATURE:
<223> OTHER INFORMATION: Synthetic: GFP_YJR030C donor cassette

<400> SEQUENCE: 60

| | |
|---|---|
| ggaactttat gaacatatta agtctgcttg atgaaatgtc atgtgcaggt gccgttggca | 60 |
| caaaatggga acaaaattat gaaaattcag tcgaggatgg gtgtgaagca cctgaatcca | 120 |
| atccataccg ttctattatt gatctttcta gtcgttccat taatataact gcagacctac | 180 |
| tttcgactgt tgggaggagt aattcagcac tcaacaagaa tgagattata gctgctattc | 240 |
| aaggtctcgc ccatcaatgc ctcaatccct gtgacgaact aggtatgcaa gcattgcaag | 300 |
| cattagagaa cattctgtta tctcgagcaa gtcaactacg tacggaaaaa gttgcggtgg | 360 |
| ataacctact agagacagga ttattaccga tttttgagtt ggatgaaatc caagatgtca | 420 |
| agatgaaacg aattactagc atttatccg ttctttctaa aatgacggca cggccacgcg | 480 |
| tttaaaccgc ccttcttggg tcaacttgtg gaaggcgtaa caagtaacga aactttttg | 540 |
| agagtgctta acgtatttaa caagtatgta gatgatccta cggtggaaag gcagttgcaa | 600 |
| gagttgatta tttctaagag ggaaatcgag aaggagtaga ccaacgataa tgtaactata | 660 |
| ccaagaaact tagtatgatg gaattttttc aaggagtcgt aaattagatt ttcgcaggta | 720 |
| ataatgcgat atataagcaa tctcatttaa atatcgacgg tggcatttat accatcattt | 780 |
| actgttatat ttatctaacg cgtcgcgacg cgttagataa aatacaacaa gattttttt | 840 |
| tcgtgtcacc aatggcatga aagcttcgag aataatttga aggaaatttc acttaatggg | 900 |
| aaaaataaaa atgtacccctt atcgagatta ctcttttacc ctcagttcaa ttaaaattca | 960 |
| tcatgaacca agtaaaagtt cctctaatta cgaacgagca agcaaattag tattgtgtgg | 1020 |
| gagacgggac acaattacag taacaataac aagaggacag atactaccaa aatgtgtggg | 1080 |
| gaagcgggta agctgccaca gcaattaatg cacaacattt aacctacatt cttccttatc | 1140 |
| ggatcctcaa aacccttaaa aacatatgcc tcaccctaac atattttcca attaaccctc | 1200 |
| aatatttctc tgtcacccgg cctctatttt ccattttctt ctttacccgc cacgcgtttt | 1260 |
| tttctttcaa attttttct tctttcttct tttttcttcca cgtcctcttg cataaataaa | 1320 |

-continued

```
taaaccgttt tgaaaccaaa ctcgcctctc tctctccttt tgaaatatt tttgggtttg    1380 tttgatcctt tccttcccaa tctctcttgt ttaatatata ttcatttata tcacgctctc    1440
tttttatctt cctttttttc ctctctcttg tattcttcct tccccttttct actcaaacca    1500 agaagaaaaa gaaaaggtca atctttgtta agaatagga tcttctacta catcagcttt    1560
tagatttttc acgcttactg cttttttctt cccaagatcg aaaatttact gaattaacaa    1620
tggtgagcaa gggcgaggag ctgttcaccg gggtggtgcc catcctggtc gagctggacg    1680
gcgacgtaaa cggccacaag ttcagcgtgt ccggcgaggg cgagggcgat gccacctacg    1740
gcaagctgac cctgaagttc atctgcacca ccggcaagct gcccgtgccc tggcccaccc    1800
tcgtgaccac cttgacctac ggcgtgcagt gcttcgcccg ctaccccgac cacatgaagc    1860
agcacgactt cttcaagtcc gccatgcccg aaggctacgt ccaggagcgc accatcttct    1920
tcaaggacga cggcaactac aagacccgcg ccgaggtgaa gttcgagggc gacaccctgg    1980
tgaaccgcat cgagctgaag ggcatcgact tcaaggagga cggcaacatc ctggggcaca    2040
agctggagta caactacaac agccacaagg tctatatcac cgccgacaag cagaagaacg    2100
gcatcaaggt gaacttcaag acccgccaca acatcgagga cggcagcgtg cagctcgccg    2160
accactacca gcagaacacc cccatcggcg acggccccgt gctgctgccc gacaaccact    2220
acctgagcac ccagtccgcc ctgagcaaag accccaacga gaagcgcgat cacatggtcc    2280
tgctggagtt cgtgaccgcc gccgggatca ctctcggcat ggacgagctg tacaagtaac    2340
tcgagaagct tgatccggct gcgaatttct tatgatttat gattttattt attaaataag    2400
ttataaaaaa aataagtgta tacaaatttt aaagtgactc ttaggtttta aaacgaaaat    2460
tcttattctt gagtaactct ttcctgtagg tcaggttgct ttctcaggta tagcatgagg    2520
tcgctcttat tgaccacacc tctaccggca tgccgagcat gttgagataa ttgttgggat    2580
tccattgttg ataaaggcta atatattagg tatacagaat atactagaag ttctcctcga    2640
ggatatagga atcctcaaaa tggaatctat atttctacat actaatatta cgattattcc    2700
tcattccgtt ttatatgttt atattcattg atcctattac attatcaatc cttgcgtttc    2760
agcttcctct aacttcgatg acagcttctc ataacttatg tcatcatctt aacaccgtat    2820
atgataatat attgataata taactattag ttgatagacg atagtggatt tttattccaa    2880
cataccaccc ataatgtaat agatctaatg aatccatttg tttgttaata gtttgaatgt    2940
ttttatcgga agaggtttgg tcattacgtc tgcaatattc ttttttggttt cgatatagca    3000 tacgtgcaga tgatttcctg atacttcatc tctcaatctc attgctttag taccaaaaaa    3060
tctgttccta aatttccggt gtttaaaccc cagcgcctgg cgggtcttca ttattggata    3120
taattatact gattgtagat ttactgtcgg ttagtaatcc tttggtaatt ggtttcttgt    3180
caagttcttg tatcaggtaa cttagattat ttaataatgg gacagattca cttatcgcgt    3240
gtatttctgc ttccgtagtt gaagtacatg ttaatgaagc cttggtggac tttcctccaa    3300
ttacctttcc attaagtaaa tatatgttgc caatttgtga tttataatac ggttggttgc    3360
catacgaggc atcgcttata acaactaatt tatttgttgg cttaacaggt ttgcttttgt    3420
gccatattaa ttgcttatct ctcgtattcc atatgaactg tatcaattca tatgtcatat    3480
ctaacacttg cttggacgga aatagtatat gttgtgcaag tgtgttgatg tagtataata    3540
ggtcaaatct aaatttatat ccaacatatg atgctagacc tatcag                   3586
```

<210> SEQ ID NO 61
<211> LENGTH: 43

```
<212> TYPE: DNA
<213> ORGANISM: Artificial Sequence
<220> FEATURE:
<223> OTHER INFORMATION: Synthetic: Recognition sequence for ZFN.YJR030C

<400> SEQUENCE: 61
cccggtatca gcaaccccccc atgacgataa cgttgatgaa acg                43

<210> SEQ ID NO 62
<211> LENGTH: 40
<212> TYPE: DNA
<213> ORGANISM: Artificial Sequence
<220> FEATURE:
<223> OTHER INFORMATION: Synthetic: Recognition sequence for ZFN.SFC1

<400> SEQUENCE: 62
cacctttacc gtttatgaat atgtaaggga gcatttagaa                     40

<210> SEQ ID NO 63
<211> LENGTH: 27
<212> TYPE: DNA
<213> ORGANISM: Artificial Sequence
<220> FEATURE:
<223> OTHER INFORMATION: Synthetic: Primer CUT351

<400> SEQUENCE: 63
gcgaatgagc catgaattat taaccgc                                   27

<210> SEQ ID NO 64
<211> LENGTH: 33
<212> TYPE: DNA
<213> ORGANISM: Artificial Sequence
<220> FEATURE:
<223> OTHER INFORMATION: Synthetic: Primer CUT350

<400> SEQUENCE: 64
agatgaaacg aattactagc attttatccg ttc                            33

<210> SEQ ID NO 65
<211> LENGTH: 47
<212> TYPE: DNA
<213> ORGANISM: Artificial Sequence
<220> FEATURE:
<223> OTHER INFORMATION: Synthetic: Primer CUT371

<400> SEQUENCE: 65
taactaccat tactcagtgt acttgattgt tttgtccgat tttcttg             47

<210> SEQ ID NO 66
<211> LENGTH: 22
<212> TYPE: DNA
<213> ORGANISM: Artificial Sequence
<220> FEATURE:
<223> OTHER INFORMATION: Synthetic: Primer HJ788

<400> SEQUENCE: 66
gccgggtgac agagaaatat tg                                        22
```

METHODS FOR GENOMIC MODIFICATION

1. CROSS REFERENCE TO RELATED APPLICATIONS

This application is a divisional of U.S. application Ser. No. 13/459,034, filed Apr. 27, 2012, which claims benefit of priority of U.S. Provisional Application No. 61/479,821, filed on Apr. 27, 2011; U.S. Provisional Application No. 61/500,741, filed on Jun. 24, 2011; and U.S. Provisional Application No. 61/539,389, filed on Sep. 26, 2011, the contents of each of which are hereby incorporated by reference in their entirety.

2. FIELD OF THE INVENTION

The methods and compositions provided herein generally relate to the fields of molecular biology and genetic engineering.

3. BACKGROUND

Genetic engineering techniques to introduce and integrate exogenous nucleic acids into a host cell genome are needed in a variety of fields. For example, in the field of synthetic biology, the fabrication of a genetically modified strain requires the insertion of customized DNA sequences into a chromosome of the host cell, and commonly, industrial scale production requires the introduction of dozens of genes into the host organism. Optimized designs for the industrial strain are arrived at empirically, requiring construction and in vivo testing of many DNA assemblies, alone and/or in concert with other biosynthetic pathway components.

Genetic engineering is highly reliant on gene targeting, which utilizes an extrachromosomal fragment of donor template DNA and invokes a cell's homologous recombination (HR) machinery to exchange a chromosomal sequence with an exogenous donor sequence. See, e.g., Capecchi, *Science* 244:1288-1292 (1989). Gene targeting is limited in its efficiency; in plant and mammalian cells, only ~1 in $10^6$ cells provided with excess template sequences undergo the desired gene modification. Yeast demonstrates an increased capacity for homologous recombination. However, the successful incorporation of exogenous DNA into yeast genomes is still a comparatively rare event (~1 in $10^5$), and requires the use of a selectable marker to screen for recombinant cells which usually comprise only a single genomic modification. In addition, since only a limited cache of selectable markers are available for use in yeast, selectable marker(s) must be removed from a recombinant strain to allow for additional genomic modifications using the same markers, and in some instances, prior to releasing the host cell in a manufacturing or natural environment. Thus, independent of the efficiency at which integration can be achieved at any single locus, the one-at-a-time serial nature of genomic engineering requires that making changes at multiple loci requires as many engineering cycles as there are loci to be modified.

The efficiency of gene targeting can be improved when combined with a targeted genomic double-stranded break (DSB) introduced near the intended site of integration. See e.g., Jasin, M., *Trends Genet* 12(6):224-228 (1996); and Urnov et al., *Nature* 435(7042):646-651 (2005). So called "designer nucleases" are enzymes that can be tailored to bind to a specific "target" sequence of DNA in vivo and introduce a double-strand break thereto. Such targeted double-strand breaks can be effected, for instance, by transforming a host cell with a plasmid containing a gene that encodes the designer nuclease. The host cell repairs these double-strand breaks by either homology-directed DNA repair or non-homologous end joining. In the course of the repair, either mechanism may be utilized to incorporate an exogenous donor DNA at the target site. If the nuclease is introduced into the cell at the same time as the donor DNA is introduced, the cell can integrate the donor DNA at the target loci.

The advent of designer nucleases has enabled the introduction of transgenes into particular target loci in crops (Wright et al., *Plant J* 44:693-705 (2005)), to improve mammalian cell culture lines expressing therapeutic antibodies (Malphettes et al., *Biotechnol Bioeng* 106(5):774-783 (2010)), and even to edit the human genome to evoke resistance to HIV (Urnov et al., *Nat Rev Genet* 11(9):636-646 (2010)). While impactful, DSB-mediated HR has yet to be exploited to reduce the multiple rounds of engineering needed to integrate multiple DNA assemblies, for example, towards the construction of functional metabolic pathways in industrial microbes.

Thus, there exists a need for methods and compositions that allow for the simultaneous integration of a plurality of exogenous nucleic acids into specific regions of a host cell genome.

4. SUMMARY

Provided herein are methods and compositions for integrating one or more exogenous nucleic acids into specified genomic loci of a host cell. In some embodiments, a plurality of exogenous nucleic acids is simultaneously integrated with a single transformation reaction. In some embodiments, the methods comprise the introduction of one or more nucleases and one or more donor DNA assemblies into the cell to facilitate integration of the donor DNA at specified locations in the genome. The methods and compositions utilize the native homologous recombination machinery of the host cell, which recombination is further enhanced by inducing targeted double-strand breaks in the host cell's genome at the intended sites of integration.

Thus, in one aspect, provided herein is a method for integrating a plurality of exogenous nucleic acids into a host cell genome, the method comprising:
  (a) contacting a host cell with:
  (i) a plurality of exogenous nucleic acids, wherein each exogenous nucleic acid $(ES)_x$, comprises a first homology region $(HR1)_x$ and a second homology region $(HR2)_x$, wherein $(HR1)_x$ and $(HR2)_x$ are capable of initiating host cell mediated homologous recombination of $(ES)_x$ at a target site $(TS)_x$ of said host cell genome; and
  (ii) for each said target site $(TS)_x$, a nuclease $(N)_x$ capable of cleaving at $(TS)_x$, whereupon said cleaving results in homologous recombination of $(ES)_x$ at $(TS)_x$; and
  (b) recovering a host cell wherein each selected exogenous nucleic acid $(ES)_x$ has integrated at each selected target sequence $(TS)_x$,
  wherein x is any integer from 1 to n wherein n is at least 2.

In some embodiments, $(HR1)_x$ is homologous to a 5' region of $(TS)_x$, and $(HR2)_x$ is homologous to a 3' region of $(TS)_x$.

In some embodiments, $(N)_x$ is capable of cleaving at a region positioned between said 5' and 3' regions of $(TS)_x$.

In some embodiments, a single nuclease is capable of cleaving each $(TS)_x$.

In some embodiments, n=3, 4, 5, 6, 7, 8, 9 or 10. In some embodiments, n>10.

In some embodiments, said recovering does not require integration of a selectable marker. In some embodiments, said recovering occurs at a higher frequency as compared to not contacting the host cell with a nuclease capable of cleaving at said target site. In some embodiments, said recovering occurs at a frequency of about one every 10, 9, 8, 7, 6, 5, 4, 3, or 2 contacted host cells, or clonal populations thereof, screened. In some embodiments, said recovering comprises identifying said integrations by at least one method selected from the group consisting of PCR, Southern blot, restriction mapping, and DNA sequencing.

In some embodiments, $(N)_x$ is capable of cleaving an endogenous host genomic sequence, e.g., a native loci within $(TS)_x$. In some embodiments, $(N)_x$ is capable of cleaving an exogenous sequence, e.g., an introduced loci within $(TS)_x$.

In some embodiments, $(ES)_x$ further comprises a nucleic acid of interest $(D)_x$ positioned 3' of $(HR1)_x$ and 5' of $(HR2)_x$. In some embodiments, $(D)_x$ is selected from the group consisting of a promoter, a nucleic acid sequence encoding an epitope tag, a gene of interest, a reporter gene, and a nucleic acid sequence encoding a termination codon.

In some embodiments, $(ES)_x$ is linear. In some embodiments, $(N)_x$ is provided as an expression vector comprising the nucleic acid sequence encoding $(N)_x$. In some embodiments, $(N)_x$ is transformed into the host cell as a purified protein. In some embodiments, $(N)_x$ is transformed into the host cell as purified RNA.

In some embodiments, the host cell comprises one or more heterologous nucleotide sequences encoding one or more enzymes of a biosynthetic pathway. In some embodiments, the one or more heterologous nucleotide sequences encoding one or more enzymes of a biosynthetic pathway are genomically integrated. In some embodiments, each exogenous nucleic acid $(ES)_x$ comprises a nucleic acid of interest $(D)_x$ positioned 3' of $(HR1)_x$ and 5' of $(HR2)_x$, encoding an enzyme of a biosynthetic pathway. In some embodiments, $(D)_x$ is a member of a library $(L)_x$ comprising a plurality of nucleic acid molecules that encode variants of an enzyme of a biosynthetic pathway.

In some embodiments, the host cell comprises one or more heterologous nucleotide sequences encoding one or more enzymes of a mevalonate (MEV) pathway for making isopentenyl pyrophosphate. In some embodiments, the one or more enzymes of the mevaloante pathway are selected from acetyl-CoA thiolase, HMG-CoA synthase, HMG-CoA reductase, mevalonate kinase, phosphomevalonate kinase and mevalonate pyrophosphate decarboxylase. In some embodiments, the host cell comprises a plurality of heterologous nucleic acids encoding all of the enzymes of a MEV pathway. In other words, the plurality of heterologous nucleic acids, taken together, encodes at least one enzyme of each class of enzymes of the MEV pathway listed above. In some embodiments, each exogenous nucleic acid $(ES)_x$ comprises a nucleic acid of interest $(D)_x$ positioned 3' of $(HR1)_x$ and 5' of $(HR2)_x$, encoding a terpene synthase. In some embodiments, the terpene synthase is selected from the group consisting of a monoterpene synthase, a diterpene synthase, a sesquiterpene synthase, a sesterterpene synthase, a triterpene synthase, a tetraterpene synthase, and a polyterpene synthase.

In some embodiments, $(N)_x$ is selected from the group consisting of an endonuclease, e.g., a meganuclease, a zinc finger nuclease, a TAL-effector DNA binding domain-nuclease fusion protein (TALEN) a transposase, and a site-specific recombinase, wherein x is 1 or any integer from 1 to n. In some embodiments, the zinc finger nuclease is a fusion protein comprising the cleavage domain of a TypeIIS restriction endonuclease fused to an engineered zinc finger binding domain. In some embodiments, the TypeIIS restriction endonuclease is selected from the group consisting of HO endonuclease and Fok I endonuclease. In some embodiments, the zinc finger binding domain comprises 3, 5 or 6 zinc fingers. In some embodiments, the endonuclease is a homing endonuclease selected from the group consisting of: an LAGLIDADG homing endonuclease, an HNH homing endonuclease, a His-Cys box homing endonuclease, a GIY-YIG homing endonuclease, and a cyanobacterial homing endonuclease. In some embodiments, the endonuclease is selected from the group consisting of: H-DreI, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, Pi-PspI, F-SceI, F-SceII, F-SuvI, F-CphI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp68031, I-SthPhiJP, I-SthPhiST3P, I-SthPhiSTe3bP, I-TdeIP, I-TevI, I-TevII, I-TevIII, i-UarAP, i-UarHGPAIP, I-UarHGPA13P, I-VinIP, I-ZbiIP, PI-MgaI, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, or PI-TliII. In particular embodiments, the endonuclease is Fcph-I.

In some embodiments, the endonuclease is modified to specifically bind an endogenous host cell genomic sequence, wherein the modified endonuclease no longer binds to its wild type endonuclease recognition sequence. In some embodiments, the modified endonuclease is derived from a homing endonuclease selected from the group consisting of: an LAGLIDADG homing endonuclease, an HNH homing endonuclease, a His-Cys box homing endonuclease, a GIY-YIG homing endonuclease, and a cyanobacterial homing endonuclease. In some embodiments, the modified endonuclease is derived from an endonuclease selected from the group consisting of: H-DreI, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, Pi-PspI, F-SceI, F-SceII, F-SuvI, F-CphI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp68031, I-SthPhiJP, I-SthPhiST3P, I-SthPhiSTe3bP, I-TdeIP, I-TevI, I-TevII, I-TevIII, i-UarAP, i-UarHGPAIP, I-UarHGPA13P, I-VinIP, I-ZbiIP, PI-MgaI, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, or PI-TliII.

In some embodiments, the host cell is a fungal cell, a bacterial cell, a plant cell, an animal cell, or a human cell. In particular embodiments, the host cell is a yeast cell. In some embodiments, the yeast cell is a haploid yeast cell. In some embodiments, the yeast cell is a *Saccharomyces cerevisiae* cell. In some embodiments, the *Saccharomyces cerevisiae* cell is of the Baker's yeast, Mauri, Santa Fe, IZ-1904, TA, BG-1, CR-1, SA-1, M-26, Y-904, PE-2, PE-5, VR-1, BR-1, BR-2, ME-2, VR-2, MA-3, MA-4, CAT-1, CB-1, NR-1, BT-1 or AL-1 strain.

In another aspect, provided herein is a method for markerless integration of an exogenous nucleic acid into a target site of a yeast cell genome, the method comprising:
(a) contacting a host yeast cell with:
(i) an exogenous nucleic acid (ES) comprising a first homology region (HR1) and a second homology region (HR2), wherein (HR1) and (HR2) are capable of initiating host cell mediated homologous recombination at said target site (TS); and
(ii) a nuclease (N) capable of cleaving at (TS), whereupon said cleaving results in homologous recombination of (ES) at (TS);
and
(b) recovering a host cell having (ES) integrated at (TS), wherein said recovering does not require integration of a selectable marker.

In another aspect, provided herein is a modified host cell generated by any of the methods of genomically integrating one or more exogenous nucleic acids described herein. In some embodiments, the modified host cell comprises:
(a) a plurality of exogenous nucleic acids, wherein each exogenous nucleic acid $(ES)_x$ comprises a first homology region $(HR1)_x$ and a second homology region $(HR2)_x$, wherein $(HR1)_x$ and $(HR2)_x$ are capable of initiating host cell mediated homologous recombination of $(ES)_x$ at a target site $(TS)_x$ of said host cell genome; and
(b) for each said target site $(TS)_x$, a nuclease $(N)_x$ capable of cleaving at $(TS)_x$, whereupon said cleaving results in homologous recombination of $(ES)_x$ at $(TS)_x$;
wherein x is any integer from 1 to n wherein n is at least 2.

In some embodiments, the modified host cell is a yeast cell and comprises:
(a) an exogenous nucleic acid (ES) comprising a first homology region (HR1) and a second homology region (HR2), wherein (HR1) and (HR2) are capable of initiating host cell mediated homologous recombination at a target site (TS) of the host cell genome; and
(b) a nuclease (N) capable of cleaving at (TS), whereupon said cleaving results in homologous recombination of (ES) at (TS);
wherein (ES) does not comprise a selectable marker.

In another aspect, provided herein is a composition comprising:
(a) a yeast cell;
(b) a plurality of exogenous nucleic acids, wherein each exogenous nucleic acid $(ES)_x$ comprises:
(i) a first homology region $(HR1)_x$ and a second homology region $(HR2)_x$, wherein $(HR1)_x$ and $(HR2)_x$ are capable of initiating host cell mediated homologous recombination of $(ES)_x$ at a selected target site $(TS)_x$ of a yeast cell genome; and
(ii) a nucleic acid of interest $(D)_x$ positioned 3' of $(HR1)_x$ and 5' of $(HR2)_x$;
(c) a plurality of nucleases, wherein each nuclease $(N)_x$ capable of cleaving at $(TS)_x$, whereupon said cleaving results in homologous recombination of $(ES)_x$ at $(TS)_x$;
wherein x is any integer from 1 to n wherein n is at least 2.

In another aspect, provided herein is a kit useful for performing the methods for genomically integrating one or more exogenous nucleic acids described herein. In some embodiments, the kit comprises:

(a) a plurality of exogenous nucleic acids, wherein each exogenous nucleic acid $(ES)_x$ comprises:
(i) a first homology region $(HR1)_x$ and a second homology region $(HR2)_x$, wherein $(HR1)_x$ and $(HR2)_x$ are capable of initiating host cell mediated homologous recombination of $(ES)_x$ at a selected target site $(TS)_x$ of a yeast cell genome; and
(ii) a nucleic acid of interest $(D)_x$ positioned 3' of $(HR1)_x$ and 5' of $(HR2)_x$;
(b) a plurality of nucleases, wherein each nuclease $(N)_x$ capable of cleaving at $(TS)_x$, whereupon said cleaving results in homologous recombination of $(ES)_x$ at $(TS)_x$;
wherein x is any integer from 1 to n wherein n is at least 2.

In some embodiments, $(D)_x$ is selected from the group consisting of a selectable marker, a promoter, a nucleic acid sequence encoding an epitope tag, a gene of interest, a reporter gene, and a nucleic acid sequence encoding a termination codon. In some embodiments, the kit further comprises a plurality of primer pairs $(P)_x$, wherein each primer pair is capable of identifying integration of $(ES)_x$ at $(TS)_x$ by PCR. In some embodiments, $(ES)_x$ is linear. In some embodiments, $(ES)_x$ is circular.

In a particular embodiment, the kit enables site-specific integration of an exogenous nucleic acid at a unique target site within any of the approximately 6000 genetic loci of the yeast genome. In these embodiments, n≥6000, wherein each $(TS)_x$ is unique to a specific locus of the yeast cell genome.

5. BRIEF DESCRIPTION OF THE FIGURES

FIG. 1 provides an exemplary embodiment of markerless genomic integration of an exogenous nucleic acid using a site-specific nuclease.

Figure 2:
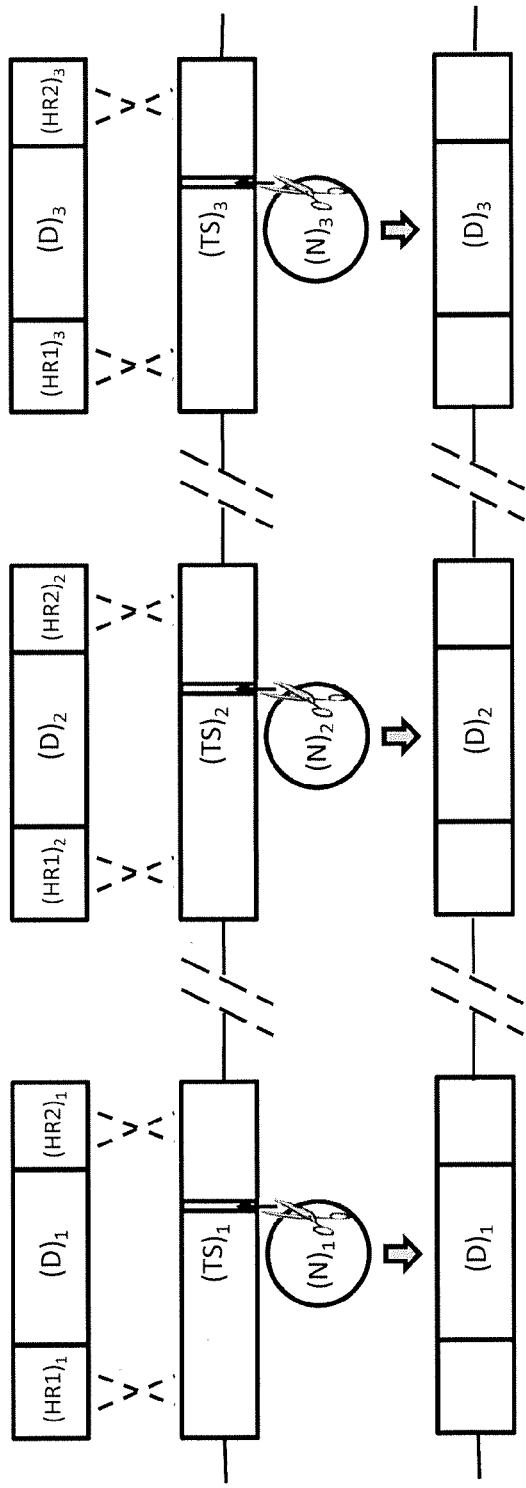

FIG. 2 provides an exemplary embodiment of simultaneous genomic integration of a plurality of exogenous nucleic acids using a plurality of site-specific nucleases. HR1—upstream homology region; HR2—downstream homology region; TS—target site; N—site-specific nuclease; D—nucleic acid of interest.

Figure 3:
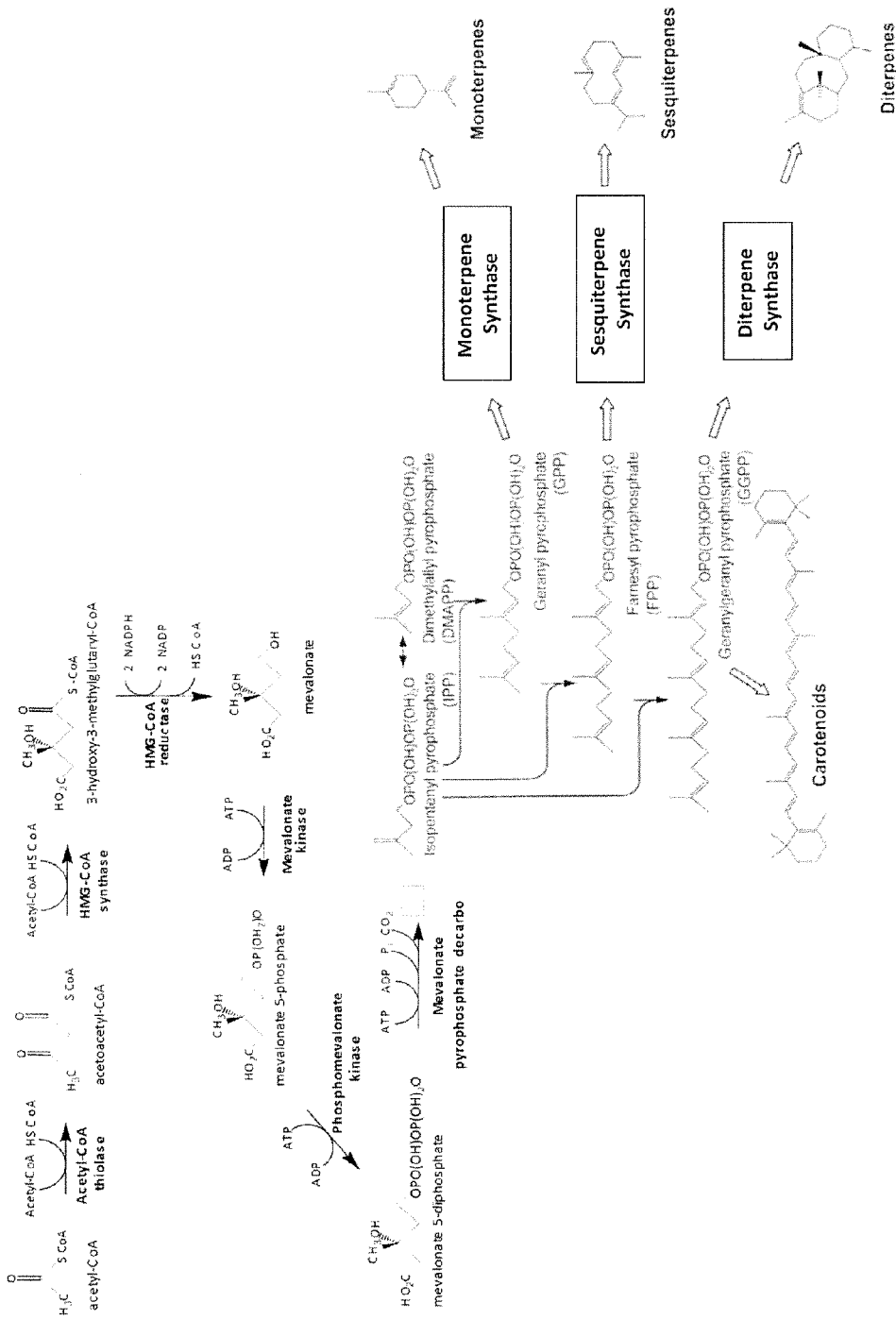

FIG. 3 provides a schematic representation of the MEV pathway for isoprenoid production.

Figure 4:
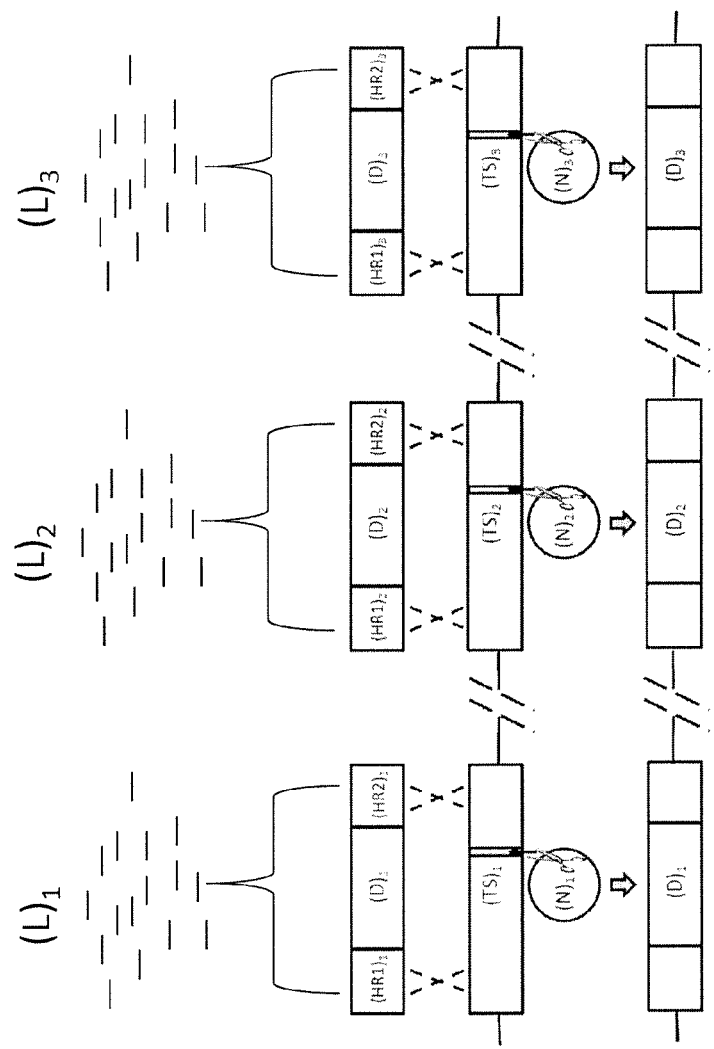

FIG. 4 provides an exemplary embodiment of the methods of generating combinatorial integration libraries provided herein. The hatch marks represent individual exogenous nucleic acid members of each library $(L)_x$.

Figure 5:
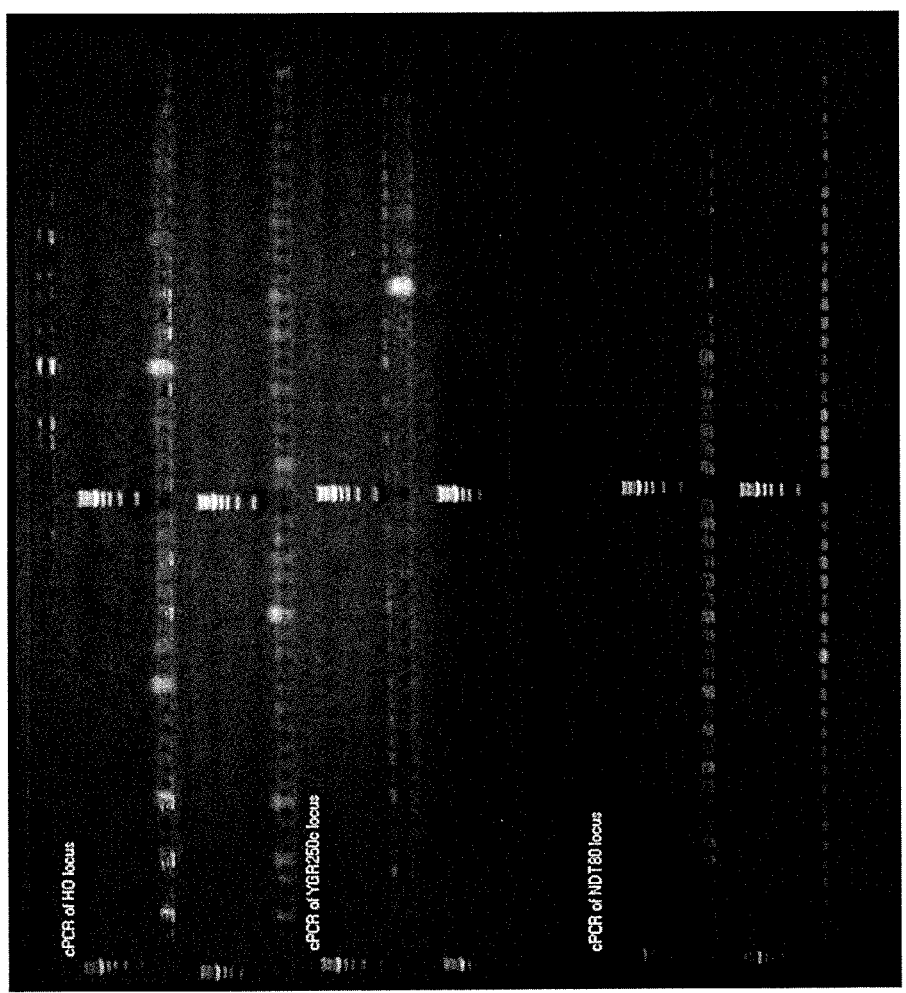

FIG. 5 provides results of colony PCR of 96 colonies of yeast cells transformed with empty vector DNA and linear "donor" DNA encoding functional EmGFP. The yeast cells comprised copies of "target" nucleic acid encoding a truncated, non-functional EmGFP genomically integrated at each of the HO, YGR250c, and NDT80 loci. Separate PCR reactions were performed to probe the HO, YGR250c, and NDT80 loci with primers specific to nucleic acid encoding functional EmGFP. No PCR products were observed, indicating that no replacements of the target nucleic acid encoding non-functional EmGFP with donor nucleic acid encoding functional EmGFP occurred.

Figure 6:
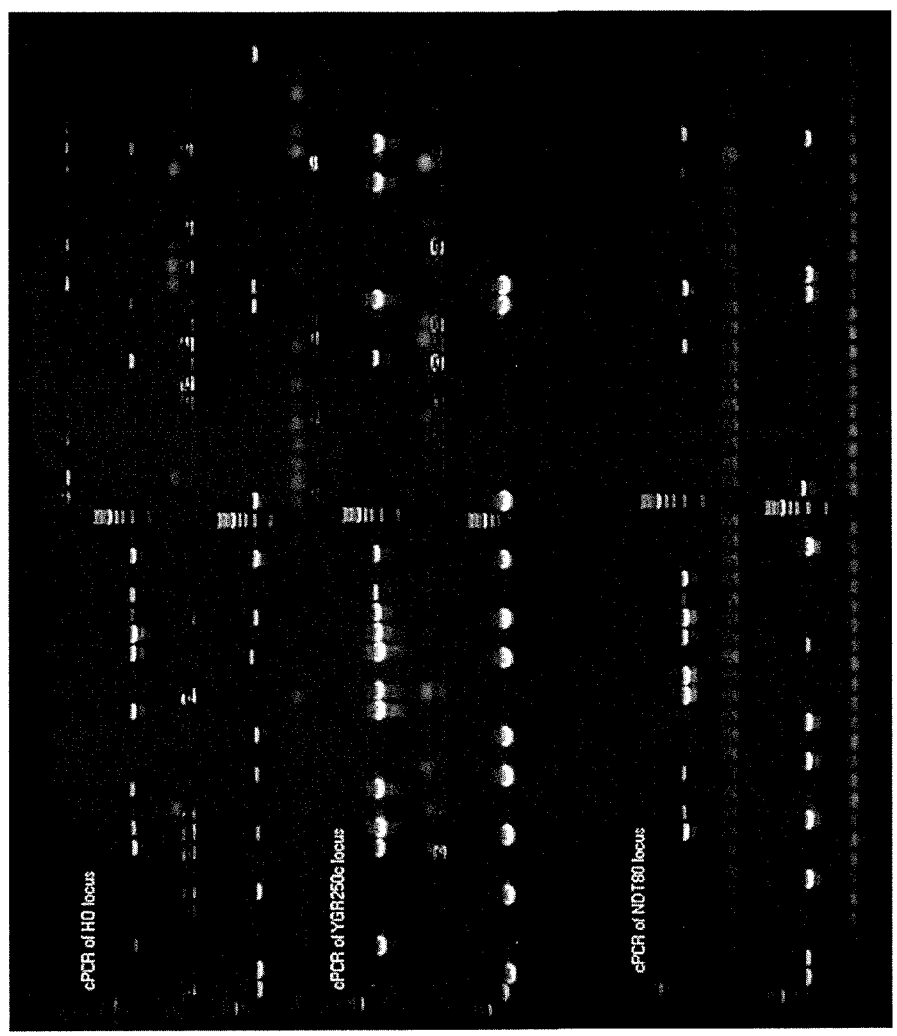

FIG. 6 provides results of colony PCR of 96 colonies of yeast cells transformed with pZFN.gfp DNA and linear "donor" DNA encoding functional EmGFP. The yeast cells comprised copies of "target" nucleic acid encoding a truncated, non-functional EmGFP genomically integrated at each of the HO, YGR250c, and NDT80 loci. pZFN.gfp encodes a zinc finger nuclease which recognizes and cleaves a nucleic acid sequence specific to the non-functional EmGFP coding sequence. Separate PCR reactions were performed to probe the HO, YGR250c, and NDT80 loci with primers specific to nucleic acid encoding functional EmGFP. Numerous PCR products were observed, indicating successful replacement of the non-functional EmGFP integrations with DNA expressing functional EmGFP. 23 colonies have all 3 loci replaced.

Figure 7:
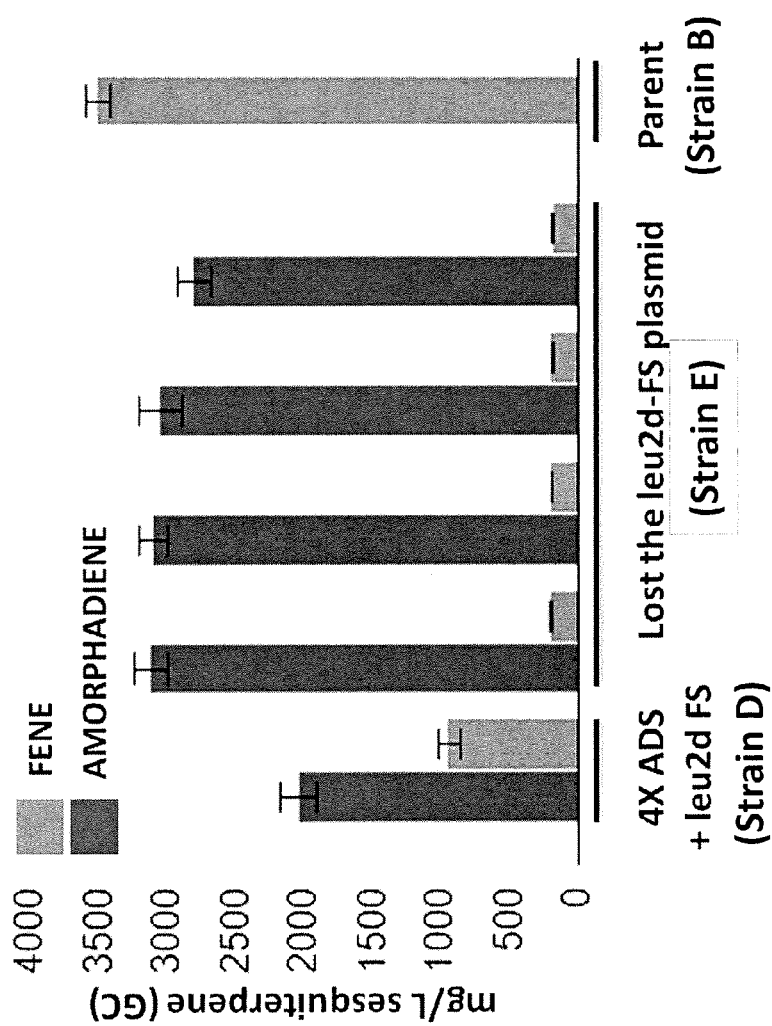

FIG. 7 provides the sequiterpene titers of Strain B, a parental farnesene-producing yeast strain comprising enzymes of the mevalonate pathway and a plasmid encoding farnesene synthase (FS); Strain D, a derivative strain of Strain B in which 4 copies of amorphadiene synthase (ADS) have been genomically integrated; and Strain E, a derivative strain of Strain D in which the plasmid encoding FS has been lost. Nearly 100% of the sesquiterpene capacity of parental Strain B is maintained in Strains D and E with only the addition of multiple copies of ADS.

Figure 8:
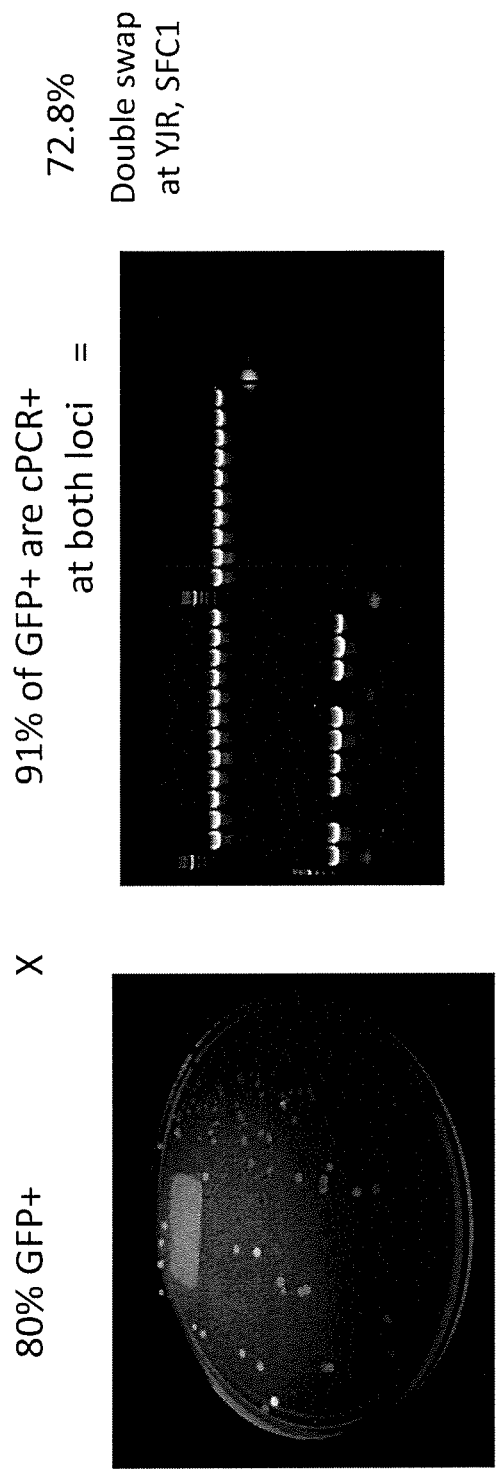

FIG. 8, provides results for cells co-transformed with linear donor DNAs for the SFC1 (GFP donor DNA) and YJR030c (ADE2 donor DNA) loci, the YJR030c endonuclease plasmid (pCUT006) and SFC1 endonuclease plasmid (pCUT058). 80% of colonies selected on URA dropout+Kan agar plates were GFP positive. Of these colonies, 91% were positive for ADE2 integration. In total, 72.8% of colonies had successfully integrated the markerless donor DNA at both loci.

6. DETAILED DESCRIPTION OF THE EMBODIMENTS

6.1 Definitions

As used herein, the terms "cleaves," "cleavage" and/or "cleaving" with respect to a nuclease, e.g. a homing endonuclease, zinc-finger nuclease or TAL-effector nuclease, refer to the act of creating a double-stranded break (DSB) in a particular nucleic acid. The DSB can leave a blunt end or sticky end (i.e., 5' or 3' overhang), as understood by those of skill in the art.

As used herein, the term "engineered host cell" refers to a host cell that is generated by genetically modifying a parent cell using genetic engineering techniques (i.e., recombinant technology). The engineered host cell may comprise additions, deletions, and/or modifications of nucleotide sequences to the genome of the parent cell.

As used herein, the term "heterologous" refers to what is not normally found in nature. The term "heterologous nucleotide sequence" refers to a nucleotide sequence not normally found in a given cell in nature. As such, a heterologous nucleotide sequence may be: (a) foreign to its host cell (i.e., is "exogenous" to the cell); (b) naturally found in the host cell (i.e., "endogenous") but present at an unnatural quantity in the cell (i.e., greater or lesser quantity than naturally found in the host cell); or (c) be naturally found in the host cell but positioned outside of its natural locus.

As used herein, the term "homology" refers to the identity between two or more nucleic acid sequences, or two or more amino acid sequences. Sequence identity can be measured in terms of percentage identity (or similarity or homology); the higher the percentage, the more near to identical the sequences are to each other. Homologs or orthologs of nucleic acid or amino acid sequences possess a relatively high degree of sequence identity when aligned using standard methods. Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. Biosc.* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations. The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

As used herein, the term "markerless" refers to integration of a donor DNA into a target site within a host cell genome without accompanying integration of a selectable marker. In some embodiments, the term also refers to the recovery of such a host cell without utilizing a selection scheme that relies on integration of selectable marker into the host cell genome. For example, in certain embodiments, a selection marker that is episomal or extrachromasomal may be utilized to select for cells comprising a plasmid encoding a nuclease capable of cleaving a genomic target site. Such use would be considered "markerless" so long as the selectable marker is not integrated into the host cell genome.

As used herein, the term "polynucleotide" refers to a polymer composed of nucleotide units as would be understood by one of skill in the art. Preferred nucleotide units include but are not limited to those comprising adenine (A), guanine (G), cytosine (C), thymine (T), and uracil (U). Useful modified nucleotide units include but are not limited to those comprising 4-acetylcytidine, 5-(carboxyhydroxylmethyl)uridine, 2-O-methylcytidine, 5-carboxymethylaminomethyl-2-thiouridine, 5-carboxymethylamino-methyluridine, dihydrouridine, 2-O-methylpseudouridine, 2-O-methylguanosine, inosine, N6-isopentyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, 5-methoxyuridine, 5-methoxycarbonylmethyl-2-thiouridine, 5-methoxycarbonylmethyluridine, 2-methylthio-N6-isopentyladenosine, uridine-5-oxyacetic acid-methylester, uridine-5-oxyacetic acid, wybutoxosine, wybutosine, pseudouridine, queuosine, 2-thiocytidine, 5-methyl-2-thiouridine, 2-thiouridine, 4-thiouridine, 5-methyluridine, 2-O-methyl-5-methyluridine, 2-O-methyluridine, and the like. Polynucleotides include naturally occurring nucleic acids, such as deoxyribonucleic acid ("DNA") and ribonucleic acid ("RNA"), as well as nucleic acid analogs. Nucleic acid analogs include those that include non-naturally occurring bases, nucleotides that engage in linkages with other nucleotides other than the naturally occurring phosphodiester bond or that include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

As used herein, the term "simultaneous," when used with respect to multiple integration, encompasses a period of time beginning at the point at which a host cell is co-transformed with a nuclease, e.g. a plasmid encoding a nuclease, and more than one donor DNA to be integrated into the host cell genome, and ending at the point at which the transformed host cell, or clonal populations thereof, is screened for successful integration of the donor DNAs at their respective target loci. In some embodiments, the period of time encompassed by "simultaneous" is at least the amount of time required for the nuclease to bind and cleave its target sequence within the host cell's chromosome(s). In some embodiments, the period of time encompassed by "simultaneous" is at least 6, 12, 24, 36, 48, 60, 72, 96 or more than 96 hours, beginning at the point at which the a host cell is co-transformed with a nuclease, e.g. a plasmid encoding a nuclease, and more than one donor DNA.

6.2 Methods of Integrating Exogenous Nucleic Acids

Provided herein are methods of integrating one or more exogenous nucleic acids into one or more selected target sites of a host cell genome. In certain embodiments, the methods comprise contacting the host cell with one or more integration polynucleotides, i.e., donor DNAs, comprising an exogenous nucleic acid to be integrated into the genomic target site, and one or more nucleases capable of causing a double-strand break near or within the genomic target site. Cleavage near or within the genomic target site greatly increases the frequency of homologous recombination at or near the cleavage site.

In a particular aspect, provided herein is a method for markerless integration of an exogenous nucleic acid into a target site of a host cell genome, the method comprising:
 (a) contacting a host cell with:
  (i) an exogenous nucleic acid (ES) comprising a first homology region (HR1) and a second homology region (HR2), wherein (HR1) and (HR2) are capable of initiating host cell mediated homologous recombination at said target site (TS); and
  (ii) a nuclease (N) capable of cleaving at (TS), whereupon said cleaving results in homologous recombination of (ES) at (TS);
 and
 (b) recovering a host cell having (ES) integrated at (TS), wherein said recovering does not require integration of a selectable marker.

FIG. 1 provides an exemplary embodiment of markerless genomic integration of an exogenous nucleic acid using a site-specific nuclease. A donor polynucleotide is introduced to a host cell, wherein the polynucleotide comprises a nucleic acid of interest (D) flanked by a first homology region (HR1) and a second homology region (HR2). HR1 and HR2 share homology with 5' and 3' regions, respectively, of a genomic target site (TS). A site-specific nuclease (N) is also introduced to the host cell, wherein the nuclease is capable of recognizing and cleaving a unique sequence within the target site. Upon induction of a double-stranded break within the target site by the site-specific nuclease, endogenous homologous recombination machinery integrates the nucleic acid of interest at the cleaved target site at a higher frequency as compared to a target site not comprising a double-stranded break. This increased frequency of integration obviates the need to co-integrate a selectable marker in order to select transformants having undergone a recombination event. By eliminating the need for selectable markers, for example, during construction of an engineered microbe, the time needed to build a strain comprising a complete and functional biosynthetic pathway is greatly reduced. In addition, engineering strategies are no longer limited by the need to recycle selectable markers due to there being a limited cache of markers available for a given host organism.

In some embodiments, markerless recovery of a transformed cell comprising a successfully integrated exogenous nucleic acid occurs within a frequency of about one every 1000, 900, 800, 700, 600, 500, 400, 300, 200 or 100 contacted host cells, or clonal populations thereof, screened. In particular embodiments, markerless recovery of a transformed cell comprising a successfully integrated exogenous nucleic acid occurs within a frequency of about one every 90, 80, 70, 60, 50, 40, 30, 20, or 10 contacted host cells, or clonal populations thereof, screened. In more particular embodiments, markerless recovery of a transformed cell comprising a successfully integrated exogenous nucleic acid occurs within a frequency of about one every 9, 8, 7, 6, 5, 4, 3, or 2 contacted host cells, or clonal populations thereof, screened. In more particular embodiments, the host cell is a yeast cell, and the increased frequency of integration derives from yeast's increased capacity for homologous recombination relative to other host cell types.

A variety of methods are available to identify those cells having an altered genome at or near the target site without the use of a selectable marker. In some embodiments, such methods seek to detect any change in the target site, and include but are not limited to PCR methods, sequencing methods, nuclease digestion, e.g., restriction mapping, Southern blots, and any combination thereof.

In another aspect, provided herein is a method for integrating a plurality of exogenous nucleic acids into a host cell genome, the method comprising:
 (a) contacting a host cell with:
  (i) a plurality of exogenous nucleic acids, wherein each exogenous nucleic acid $(ES)_x$ comprises a first homology region $(HR1)_x$ and a second homology region $(HR2)_x$, wherein $(HR1)_x$ and $(HR2)_x$ are capable of initiating host cell mediated homologous recombination of $(ES)_x$ at a target site $(TS)_x$ of said host cell genome; and
  (ii) for each said target site $(TS)_x$, a nuclease $(N)_x$ capable of cleaving at $(TS)_x$, whereupon said cleaving results in homologous recombination of $(ES)_x$ at $(TS)_x$;
 and
 (b) recovering a host cell wherein each selected exogenous nucleic acid $(ES)_x$ has integrated at each selected target sequence $(TS)_x$,
 wherein x is any integer from 1 to n wherein n is at least 2.

FIG. 2 provides an exemplary embodiment of simultaneous genomic integration of a plurality of exogenous nucleic acids using a plurality of site-specific nucleases. In this example, three polynucleotides are introduced to a host cell, wherein each polynucleotide comprises an exogenous nucleic acid $(ES)_x$ comprising a nucleic acid of interest $(D)_x$, wherein x=1, 2 or 3. Each $(D)_x$ is flanked by a first homology region $(HR1)_x$ and a second homology region $(HR2)_x$. $(HR1)_x$ and $(HR2)_x$ share homology with 5' and 3' regions, respectively, of a selected target site $(TS)_x$, of three total unique target sites in the genome. A plurality of site-specific nucleases $(N)_x$ is also introduced to the host cell, wherein each $(N)_x$ is capable of recognizing and cleaving a unique sequence within its corresponding target site, $(TS)_x$. Upon cleavage of a target site $(TS)_x$ by its corresponding site-specific nuclease $(N)_x$, endogenous homologous recombination machinery facilitates integration of the corresponding nucleic acid interest $(D)_x$ at $(TS)_x$.

In particular embodiments, each exogenous nucleic acid $(ES)_x$, optionally comprising a nucleic acid of interest $(D)_x$, is integrated into its respective genomic target site $(TS)_x$ simultaneously, i.e., with a single transformation of the host cell with the plurality of integration polynucleotides and plurality of nucleases. In some embodiments, the methods are useful to simultaneously integrate any plurality of exogenous nucleic acids $(ES)_x$, that is, where x is any integer from 1 to n wherein n is at least 2, in accordance with the variables recited for the above described method. In some embodiments, the method of simultaneous integration provided herein is useful to simultaneously integrate up to 10 exogenous nucleic acids $(ES)_x$ into 10 selected target sites $(TS)_x$, that is, where x is any integer from 1 to n wherein n=2, 3, 4, 5, 6, 7, 8, 9, or 10. In some embodiments, the method of simultaneous integration provided herein is useful to simultaneously integrate up to 20 exogenous nucleic acids $(ES)_x$ into 20 selected target sites $(TS)_x$, that is, where x is any integer from 1 to n wherein n=2, 3, 4, 5, 6, 7, 8, 9, 10, 11, 12, 13, 14, 15, 16, 17, 18, 19 or 20. In some embodiments, n=2. In some embodiments, n=3. In some embodiments, n=4. In some embodiments, n=5. In some embodiments, n=6. In some embodiments, n=7. In some embodiments, n=8. In some embodiments, n=9. In some embodiments, n=10. In some embodiments, n=11. In some embodiments, n=12. In some embodiments, n=13. In some embodiments, n=14. In some embodiments, n=15. In some embodiments, n=16. In some embodiments, n=17. In some embodiments, n=18. In some embodiments, n=19. In some embodiments, n=20. In some embodiments, the method of simultaneous integration provided herein is useful to simultaneously integrate more than 20 exogenous nucleic acids.

As with integration of a single exogenous nucleic acid at a single target site, the simultaneous multiple integration of a plurality of exogenous nucleic acids occurs at a substantially higher frequency as compared to not contacting the target sites with a nuclease capable of inducing a double-stranded break. In some embodiments, during the simultaneous integration of a plurality of exogenous nucleic acids at multiple loci, i.e., in the presence of multiple nucleases, the frequency of integration at any single loci is substantially higher compared to the frequency of integration at the same locus during a single integration event, i.e., in the presence of a single nuclease. Such an advantage is demonstrated in Example 6 (Section 7.5.2) below. Without being bound by theory, it is believed that the presence and activity of multiple nucleases, creating double-strand breaks (DSBs) at a plurality of target sites, enriches for transformants that successfully repair the DSBs by integrating donor DNA(s) at the cut site, and/or selects against transformants unable to repair the DSBs. Since DSBs are toxic to cells, it is believed that an increased number of nucleases leads to more DSBs, and correspondingly, an enrichment for cells able to repair the DSBs through HR-mediated integration of donor DNA(s).

In some embodiments, this increased frequency of integration obviates the requirement for co-integration of one or more selectable markers for the identification of the plurality of recombination events. In some embodiments, markerless recovery of a transformed cell comprising a plurality of successfully integrated exogenous nucleic acid occurs within a frequency of about one every 1000, 900, 800, 700, 600, 500, 400, 300, 200 or 100 contacted host cells, or clonal populations thereof, screened. In particular embodiments, markerless recovery occurs within a frequency of about one every 90, 80, 70, 60, 50, 40, 30, 20, or 10 contacted host cells, or clonal populations thereof, screened. In more particular embodiments, markerless recovery occurs within a frequency of about one every 9, 8, 7, 6, 5, 4, 3, or 2 contacted host cells, or clonal populations thereof, screened. In more particular embodiments, the host cell is a yeast cell, and the increased frequency of integration derives from yeast's increased capacity for homologous recombination relative to other host cell types.

6.2.1. Methods for Metabolic Pathway Engineering

The methods and compositions described herein provide particular advantages for constructing recombinant organisms comprising optimized biosynthetic pathways, for example, towards the conversion of biomass into biofuels, pharmaceuticals or biomaterials. Functional non-native biological pathways have been successfully constructed in microbial hosts for the production of precursors to the antimalarial drug artemisinin (see, e.g., Martin et al., *Nat Biotechnol* 21:796-802 (2003); fatty acid derives fuels and chemicals (e.g., fatty esters, fatty alcohols and waxes; see, e.g., Steen et al., *Nature* 463:559-562 (2010); methyl halide-derived fuels and chemicals (see, e.g., Bayer et al., *J Am Chem Soc* 131:6508-6515 (2009); polyketide synthases that make cholesterol lowering drugs (see, e.g., Ma et al., *Science* 326:589-592 (2009); and polyketides (see, e.g., Kodumal, *Proc Natl Acad Sci USA* 101:15573-15578 (2004).

Traditionally, metabolic engineering, and in particular, the construction of biosynthetic pathways, has proceeded in a one-at-a-time serial fashion whereby pathway components have been introduced, i.e., integrated into the host cell genome at a single loci at a time. The methods of integration provided herein can be utilized to reduce the time typically required to engineer a host cell, for example, a microbial cell, to comprise one or more heterologous nucleotide sequences encoding enzymes of a new metabolic pathway, i.e., a metabolic pathway that produces a metabolite that is not endogenously produced by the host cell. In other particular embodiments, the methods of integration provided herein can be used to efficiently engineer a host cell to comprise one or more heterologous nucleotide sequences encoding enzymes of a metabolic pathway that is endogenous to the host cell, i.e., a metabolic pathway that produces a metabolite that is endogenously produced by the host cell. In one example, a design strategy may seek to replace three native genes of a host cell with a complementary exogenous pathway. Modifying these three endogenous loci using the current state of the art requires three separate transformations. By contrast, the methods of simultaneous multiple integration provided herein enables all three integrations to be performed in a single transformation, thus reducing the rounds of engineering needed by three-fold. Moreover, the methods enable the porting of DNA assemblies, comprising optimized pathway components integrated at multiple sites in one host cell chassis, to analogous sites in a second host cell chassis. By reducing the number of rounds needed to engineer a desired genotype, the pace of construction of metabolic pathways is substantially increased.

6.2.1.1 Isoprenoid Pathway Engineering

In some embodiments, the methods provided herein can be utilized to simultaneously introduce or replace one or more components of a biosynthetic pathway to modify the product profile of an engineered host cell. In some embodiments, the biosynthetic pathway is the isoprenoid pathway.

Terpenes are a large class of hydrocarbons that are produced in many organisms. When terpenes are chemically modified (e.g., via oxidation or rearrangement of the carbon skeleton) the resulting compounds are generally referred to as terpenoids, which are also known as isoprenoids. Isoprenoids play many important biological roles, for example, as quinones in electron transport chains, as components of membranes, in subcellular targeting and regulation via protein prenylation, as photosynthetic pigments including carotenoids, chlorophyll, as hormones and cofactors, and as plant defense compounds with various monoterpenes, sesquiterpenes, and diterpenes. They are industrially useful as antibiotics, hormones, anticancer drugs, insecticides, and chemicals.

Terpenes are derived by linking units of isoprene ($C_5H_8$), and are classified by the number of isoprene units present. Hemiterpenes consist of a single isoprene unit. Isoprene itself is considered the only hemiterpene. Monoterpenes are made of two isoprene units, and have the molecular formula $C_{10}H_{16}$. Examples of monoterpenes are geraniol, limonene, and terpineol. Sesquiterpenes are composed of three isoprene units, and have the molecular formula $C_{15}H_{24}$. Examples of sesquiterpenes are farnesenes and farnesol. Diterpenes are made of four isoprene units, and have the molecular formula $C_{20}H_{32}$. Examples of diterpenes are cafestol, kahweol, cembrene, and taxadiene. Sesterterpenes are made of five isoprene units, and have the molecular formula $C_{25}H_{40}$. An example of a sesterterpenes is geranylfarnesol. Triterpenes consist of six isoprene units, and have the molecular formula $C_{30}H_{48}$. Tetraterpenes contain eight isoprene units, and have the molecular formula $C_{40}H_{64}$. Biologically important tetraterpenes include the acyclic lycopene, the monocyclic gamma-carotene, and the bicyclic alpha- and beta-carotenes. Polyterpenes consist of long chains of many isoprene units. Natural rubber consists of polyisoprene in which the double bonds are cis.

Terpenes are biosynthesized through condensations of isopentenyl pyrophosphate (isopentenyl diphosphate or IPP) and its isomer dimethylallyl pyrophosphate (dimethylallyl diphosphate or DMAPP). Two pathways are known to generate IPP and DMAPP, namely the mevalonate-dependent (MEV) pathway of eukaryotes (FIG. 3), and the mevalonate-independent or deoxyxylulose-5-phosphate (DXP) pathway of prokaryotes. Plants use both the MEV pathway and the DXP pathway. IPP and DMAPP in turn are condensed to polyprenyl diphosphates (e.g., geranyl disphosphate or GPP, farnesyl diphosphate or FPP, and geranylgeranyl diphosphate or GGPP) through the action of prenyl disphosphate synthases (e.g., GPP synthase, FPP synthase, and GGPP synthase, respectively). The polyprenyl diphosphate intermediates are converted to more complex isoprenoid structures by terpene synthases.

Terpene synthases are organized into large gene families that form multiple products. Examples of terpene synthases include monoterpene synthases, which convert GPP into monoterpenes; diterpene synthases, which convert GGPP into diterpenes; and sesquiterpene synthases, which convert FPP into sesquiterpenes. An example of a sesquiterpene synthase is farnesene synthase, which converts FPP to farnesene. Terpene synthases are important in the regulation of pathway flux to an isoprenoid because they operate at metabolic branch points and dictate the type of isoprenoid produced by the cell. Moreover, the terpene synthases hold the key to high yield production of such terpenes. As such, one strategy to improve pathway flux in hosts engineered for heterologous isoprenoid production is to introduce multiple copies of nucleic acids encoding terpene synthases. For example, in engineered microbes comprising the MEV pathway where the production of sesquiterpenes such as farnesene is desired, a sesquiterpene synthase, e.g., a farnesene synthase is utilized as the terminal enzyme of the pathway, and multiple copies of farnesene synthase genes may be introduced into the host cell towards the generation of a strain optimized for farnesene production.

Because the biosynthesis of any isoprenoid relies on the same pathway components upstream of the prenyl disphosphate synthase and terpene synthase, these pathway components, once engineered into a host "platform" strain, can be utilized towards the production of any sesquiterpene, and the identity of the sesquiterpene can be dictated by the particular sesquiterpene synthase introduced into the host cell. Moreover, where production of terpenes having different isoprene units is desired, for example a monoterpene instead of a sesquiterpene, both the prenyl diphosphate synthase and the terpene synthase can be replaced to produce the different terpene while still utilizing the upstream components of the pathway.

Accordingly, the methods and compositions provided herein can be utilized to efficiently modify a host cell comprising an isoprenoid producing pathway, e.g., the MEV pathway to produce a desired isoprenoid. In some embodiments, the host cell comprises the MEV pathway, and the methods of simultaneous multiple integration provided herein can be utilized to simultaneously introduce multiple copies of a prenyl diphosphate synthase and/or a terpene synthase to define the terpene product profile of the host cell. In some embodiments, the prenyl diphosphate synthase is GPP synthase and the terpene synthase is a monoterpene synthase. In some embodiments, the prenyl diphosphate synthase is FPP synthase and the terpene synthase is a sesquiterpene synthase. In some embodiments, the prenyl diphosphate synthase is GGPP synthase and the terpene synthase is a diterpene synthase. In other embodiments, the host cell comprises the MEV pathway and a prenyl disphosphate synthase and/or a terpene synthase for the production of a first type of terpene, for example, farnesene, and the methods of simultaneous multiple integration provided herein can be utilized to simultaneously replace one or more copies of the prenyl diphosphate synthase and/or a terpene synthase to produce a second type of terpene, for example, amorphadiene. These embodiments are exemplified in Examples 3 and 4 below. The methods provided herein can be similarly utilized towards the construction and/or modification of any biosynthetic pathway which utilizes multiple copies of pathway components, and are particularly useful for engineering host cells whose product profile can be readily modified with the addition or exchange of multiple copies of a single pathway component.

6.2.1.2 Methods of Generating Combinatorial Integration Libraries

Once biosynthetic pathways are constructed, the expression levels of all the components need to be orchestrated to optimize metabolic flux and achieve high product titers. Common approaches for optimizing flux include varying the identity of the pathway component gene, the codon optimization of the gene, the use of solubility tags, the use of truncations or known mutations, and the expression context of the gene (i.e. promoter and terminator choice). To sample this variability in the course of building a strain using traditional methods requires generating and archiving an impractically large number of strains. For example, if a strain engineer plans to integrate constructs at three loci, and has devised 10 variants for each locus, 1,000 strains would need to be generated to fully sample the combinatorial diversity. Since pathway genes work in concert, and not all metabolite intermediates can easily be screened for, it is often impossible to evaluate the individual contribution of the pathway genes after each integration cycle. Thus, strain engineers routinely make choices that severely limit the design space that they sample when constructing a novel metabolic pathway.

To better identify the optimal pathway design, the methods of genomic modification provided herein can be utilized to generate strains comprising combinatorial libraries of rationally designed integration constructs. The methods rely on the introduction of one or more nucleases and one or more donor DNA assemblies into the cell to facilitate multiple simultaneous integration of donor DNA at specified locations in the genome. However, to generate a diversity of engineered strains, the methods comprise co-transforming a library of donor DNAs, i.e., a mixture of integration constructs for each targeted locus, such that combinatorial integration libraries of host strains can be generated (FIG. 4). The high frequency of multiple integrations achieved means that the resultant strains can reasonably be screened directly for product without extensive genomic quality control, and the identity of top strains can be determined after screening, for example, by sequencing. This method removes the burden of individual strain generation, quality control and archiving, and allows the engineer to generate diverse integration combinations in a single tube, and sort out the best performing strains by screening, e.g., for the terminal product of the pathway.

Thus, in some embodiments, the methods for integrating a plurality of exogenous nucleic acids into a host cell genome provided herein comprise:

(d) contacting a host cell with:
(i) a plurality of libraries, wherein each library (L)x comprises a plurality of exogenous nucleic acids, wherein a selected exogenous nucleic acid comprises, in a 5' to 3' orientation, a first homology region $(HR1)_x$, any nucleic acid of interest selected from the group $(D)_x$, and a second homology region $(HR2)_x$, wherein $(HR1)_x$ and $(HR2)_x$ are capable of initiating host cell mediated homologous recombination of said selected exogenous nucleic acid at a target site $(TS)_x$ of said host cell genome; and
(ii) for each said target site $(TS)_x$, a nuclease $(N)_x$ capable of cleaving at $(TS)_x$, whereupon said cleaving results in homologous recombination of said selected exogenous nucleic acid at $(TS)_x$; and (e) recovering a host cell wherein an exogenous nucleic acid from each library $(L)_x$ has integrated at each selected target sequence $(TS)_x$, wherein x is any integer from 1 to n wherein n is at least 2.

A schematic representation of this method is provided in FIG. 4.

Also provided herein is a host cell comprising:
(a) a plurality of libraries, wherein each library (L)x comprises a plurality of exogenous nucleic acids, wherein a selected exogenous nucleic acid comprises, in a 5' to 3' orientation, a first homology region $(HR1)_x$, any nucleic acid of interest selected from the group $(D)_x$, and a second homology region $(HR2)_x$, wherein $(HR1)_x$ and $(HR2)_x$ are capable of initiating host cell mediated homologous recombination of said selected exogenous nucleic acid at a target site $(TS)_x$ of said host cell genome; and
(b) for each said target site $(TS)_x$, a nuclease $(N)_x$ capable of cleaving at $(TS)_x$, whereupon said cleaving results in homologous recombination of said selected exogenous nucleic acid at $(TS)_x$, wherein x is any integer from 1 to n wherein n is at least 2.

In some embodiments, each library $(L)_x$ comprises exogenous nucleic acids encoding enzymes of a common biosynthetic pathway. In some embodiments, the group $(D)_x$ comprises at least $10^1$, $10^2$, $10^3$, $10^4$, $10^5$, $10^6$, or more than $10^6$ unique nucleic acids of interest. In some embodiments, each library $(L)_x$ comprises a plurality of exogenous nucleic acids encoding variants of an enzyme of a biosynthetic pathway. As used herein, the term "variant" refers to an enzyme of a biosynthetic pathway that compared to a selected enzyme has a different nucleotide or amino acid sequence. For example, in some embodiments, a library $(L)_x$ comprises sesquiterpene synthase variants, and compared to the wild-type version of the selected sesquiterpene synthase, the sesquiterpene synthase variant may comprise nucleotide additions, deletions, and/or substitutions that may or may not result in changes to the corresponding amino acid sequence. In other embodiments, the enzyme variant comprises amino acid additions, deletions and/or substitutions relative to a reference enzyme, e.g., the wild-type version.

In some embodiments, the host cell comprises one or more heterologous nucleotide sequences encoding one or more enzymes of a biosynthetic pathway prior to said contacting. In some embodiments, the one or more heterologous nucleotide sequences encoding one or more enzymes of a biosynthetic pathway are genomically integrated.

6.3 Integration Polynucleotides

Advantageously, an integration polynucleotide, i.e., donor DNA, facilitates integration of one or more exogenous nucleic acid constructs into a selected target site of a host cell genome. In preferred embodiments, an integration polynucleotide comprises an exogenous nucleic acid $(ES)_x$ comprising a first homology region $(HR1)_x$ and a second homology region $(HR2)_x$, and optionally a nucleic acid of interest positioned between $(HR1)_x$ and $(HR2)_x$. In some embodiments, the integration polynucleotide is a linear DNA molecule. In other embodiments, the integration polynucleotide is a circular DNA molecule.

The integration polynucleotide can be generated by any technique apparent to one skilled in the art. In certain embodiments, the integration polynucleotide is generated using polymerase chain reaction (PCR) and molecular cloning techniques well known in the art. See, e.g., *PCR Technology: Principles and Applications for DNA Amplification*, ed. HA Erlich, Stockton Press, New York, N.Y. (1989); Sambrook et al., 2001, *Molecular Cloning—A Laboratory Manual*, 3rd edition, Cold Spring Harbor Laboratory, Cold Spring Harbor, N.Y.; *PCR Technology: Principles and Applications for DNA Amplification*, ed. HA Erlich, Stockton Press, New York, N.Y. (1989); U.S. Pat. No. 8,110,360.

6.3.1. Genomic Integration Sequences

In preferred embodiments, an integration polynucleotide comprises an exogenous nucleic acid $(ES)_x$ comprising a first homology region $(HR1)_x$ and a second homology region (HR2)$_x$, wherein (HR1)$_x$ and (HR2)$_x$ are capable of initiating host cell mediated homologous recombination at a selected target site (TS)$_x$ within the host cell genome. To integrate an exogenous nucleic acid into the genome by homologous recombination, the integration polynucleotide preferably comprises (HR1)$_x$ at one terminus and (HR2)$_x$ at the other terminus. In some embodiments, (HR1)$_x$ is homologous to a 5' region of the selected genomic target site (TS)$_x$, and (HR2)$_x$, is homologous to a 3' region of the selected target site (TS)$_x$. In some embodiments, (HR1)$_x$ is about 70%, 75%, 80%, 85%, 90%, 95% or 100% homologous to a 5' region of the selected genomic target site (TS)$_x$. In some embodiments, (HR2)$_x$, is about 70%, 75%, 80%, 85%, 90%, 95% or 100% homologous to a 3' region of the selected target site (TS)$_x$.

In certain embodiments, (HR1)$_x$ is positioned 5' to a nucleic acid of interest (D)$_x$. In some embodiments, (HR1)$_x$ is positioned immediately adjacent to the 5' end of (D)$_x$. In some embodiments, (HR1)$_x$ is positioned upstream to the 5' of (D)$_x$. In certain embodiments, (HR2)$_x$ is positioned 3' to a nucleic acid of interest (D)$_x$. In some embodiments, (HR2)$_x$ is positioned immediately adjacent to the 3' end of (D)$_x$. In some embodiments, (HR2)$_x$ is positioned downstream to the 3' of (D)$_x$.

Properties that may affect the integration of an integration polynucleotide at a particular genomic locus include but are not limited to: the lengths of the genomic integration sequences, the overall length of the excisable nucleic acid construct, and the nucleotide sequence or location of the genomic integration locus. For instance, effective heteroduplex formation between one strand of a genomic integration sequence and one strand of a particular locus in a host cell genome may depend on the length of the genomic integration sequence. An effective range for the length of a genomic integration sequence is 50 to 5,000 nucleotides. For a discussion of effective lengths of homology between genomic integration sequences and genomic loci. See, Hasty et al., *Mol Cell Biol* 11:5586-91 (1991).

In some embodiments, (HR1)$_x$ and (HR2)$_x$ can comprise any nucleotide sequence of sufficient length and sequence identity that allows for genomic integration of the exogenous nucleic acid (ES)$_x$ at any yeast genomic locus. In certain embodiments, each of (HR1)$_x$ and (HR2)$_x$ independently consists of about 50 to 5,000 nucleotides. In certain embodiments, each of (HR1)$_x$ and (HR2)$_x$ independently consists of about 100 to 2,500 nucleotides. In certain embodiments, each of (HR1)$_x$ and (HR2)$_x$ independently consists of about 100 to 1,000 nucleotides. In certain embodiments, each of (HR1)$_x$ and (HR2)$_x$ independently consists of about 250 to 750 nucleotides. In certain embodiments, each of (HR1)$_x$ and (HR2)$_x$ independently consists of about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900 or 5,000 nucleotides. In some embodiments, each of (HR1)$_x$ and (HR2)$_x$ independently consists of about 500 nucleotides.

6.3.2. Nucleic Acids of Interest

In some embodiments, the integration polynucleotide further comprises a nucleic acid of interest (D)$_x$. The nucleic acid of interest can be any DNA segment deemed useful by one of skill in the art. For example, the DNA segment may comprise a gene of interest that can be "knocked in" to a host genome. In other embodiments, the DNA segment functions as a "knockout" construct that is capable of specifically disrupting a target gene upon integration of the construct into the target site of the host cell genome, thereby rendering the disrupted gene non-functional. Useful examples of a nucleic acid of interest (D)$_x$ include but are not limited to: a protein-coding sequence, reporter gene, fluorescent marker coding sequence, promoter, enhancer, terminator, transcriptional activator, transcriptional repressor, transcriptional activator binding site, transcriptional repressor binding site, intron, exon, poly-A tail, multiple cloning site, nuclear localization signal, mRNA stabilization signal, integration loci, epitope tag coding sequence, degradation signal, or any other naturally occurring or synthetic DNA molecule. In some embodiments, (D)$_x$ can be of natural origin. Alternatively, (D)$_x$ can be completely of synthetic origin, produced in vitro. Furthermore, (D)$_x$ can comprise any combination of isolated naturally occurring DNA molecules, or any combination of an isolated naturally occurring DNA molecule and a synthetic DNA molecule. For example, (D)$_x$ may comprise a heterologous promoter operably linked to a protein coding sequence, a protein coding sequence linked to a poly-A tail, a protein coding sequence linked in-frame with a epitope tag coding sequence, and the like. The nucleic acid of interest (D)$_x$ may be obtained by standard procedures known in the art from cloned DNA (e.g., a DNA "library"), by chemical synthesis, by cDNA cloning, or by the cloning of genomic DNA, or fragments thereof, purified from the desired cell, or by PCR amplification and cloning. See, for example, Sambrook et al., *Molecular Cloning, A Laboratory Manual*, 3d. ed., Cold Spring Harbor Laboratory Press, Cold Spring Harbor, N.Y. (2001); Glover, D. M. (ed.), *DNA Cloning: A Practical Approach*, 2d. ed., MRL Press, Ltd., Oxford, U.K. (1995).

In particular embodiments, the nucleic acid of interest (D)$_x$ does not comprise nucleic acid encoding a selectable marker. In these embodiments, the high efficiency of integration provided by the methods described herein allows for the screening and identification of integration events without the requirement for growth of transformed cells on selection media. However, in other embodiments where growth on selective media is nonetheless desired, the nucleic acid of interest (D)$_x$ can comprise a selectable marker that may be used to select for the integration of the exogenous nucleic acid into a host genome.

A wide variety of selectable markers are known in the art (see, for example, Kaufman, *Meth. Enzymol.*, 185:487 (1990); Kaufman, *Meth. Enzymol.*, 185:537 (1990); Srivastava and Schlessinger, *Gene*, 103:53 (1991); Romanos et al., in *DNA Cloning 2: Expression Systems*, 2nd Edition, pages 123-167 (IRL Press 1995); Markie, *Methods Mol. Biol.*, 54:359 (1996); Pfeifer et al., *Gene*, 188:183 (1997); Tucker and Burke, *Gene*, 199:25 (1997); Hashida-Okado et al., FEBS Letters, 425:117 (1998)). In some embodiments, the selectable marker is a drug resistant marker. A drug resistant marker enables cells to detoxify an exogenous drug that would otherwise kill the cell. Illustrative examples of drug resistant markers include but are not limited to those which confer resistance to antibiotics such as ampicillin, tetracycline, kanamycin, bleomycin, streptomycin, hygromycin, neomycin, Zeocin™, and the like. In other embodiments, the selectable marker is an auxotrophic marker. An auxotrophic marker allows cells to synthesize an essential component (usually an amino acid) while grown in media that lacks that essential component. Selectable auxotrophic gene sequences include, for example, hisD, which allows growth in histidine free media in the presence of histidinol. Other selectable markers include a bleomycin-resistance gene, a metallothionein gene, a hygromycin B-phosphotransferase gene, the AURI gene, an adenosine deaminase gene, an aminoglycoside phosphotransferase gene, a dihydrofolate reductase gene, a thymidine kinase gene, a xanthine-guanine phosphoribosyltransferase gene, and the like. In other embodiments, the selectable marker is a marker other than one which rescues an auxotophic mutation. For example, the host cell strain can comprise mutations other than auxotrophic mutations, for example, mutations that are not lethal to the host and that also do not cause adverse effects on the intended use of the strain, e.g., industrial fermentation, so long as the mutations can be identified by a known selection method.

Host cell transformants comprising a chromosomally integrated polynucleotide can also be identified by selecting host cell transformants exhibiting other traits encoded by individual DNA segments or by combinations of DNA segments, e.g., expression of peptides that emit light, or by molecular analysis of individual host cell colonies, e.g., by restriction enzyme mapping, PCR amplification, or sequence analysis of isolated assembled polynucleotides or chromosomal integration sites.

6.4 Nucleases

In some embodiments of the methods described herein, a host cell genome is contacted with one or more nucleases capable of cleaving, i.e., causing a double-stranded break at a designated region within a selected target site. In some embodiments, a double-strand break inducing agent is any agent that recognizes and/or binds to a specific polynucleotide recognition sequence to produce a break at or near the recognition sequence. Examples of double-strand break inducing agents include, but are not limited to, endonucleases, site-specific recombinases, transposases, topoisomerases, and zinc finger nucleases, and include modified derivatives, variants, and fragments thereof.

In some embodiments, each of the one or more nucleases is capable of causing a double-strand break at a designated region within a selected target site $(TS)_x$. In some embodiments, the nuclease is capable of causing a double-strand break at a region positioned between the 5' and 3' regions of $(TS)_x$ with which $(HR1)_x$ and $(HR2)_x$ share homology, respectively. In other embodiments, the nuclease is capable of causing a double-strand break at a region positioned upstream or downstream of the 5' and 3' regions of $(TS)_x$.

A recognition sequence is any polynucleotide sequence that is specifically recognized and/or bound by a double-strand break inducing agent. The length of the recognition site sequence can vary, and includes, for example, sequences that are at least 10, 12, 14, 16, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more nucleotides in length.

In some embodiments, the recognition sequence is palindromic, that is, the sequence on one strand reads the same in the opposite direction on the complementary strand. In some embodiments, the nick/cleavage site is within the recognition sequence. In other embodiments, the nick/cleavage site is outside of the recognition sequence. In some embodiments, cleavage produces blunt end termini. In other embodiments, cleavage produces single-stranded overhangs, i.e., "sticky ends," which can be either 5' overhangs, or 3' overhangs.

In some embodiments, the recognition sequence within the selected target site can be endogenous or exogenous to the host cell genome. When the recognition site is an endogenous sequence, it may be a recognition sequence recognized by a naturally-occurring, or native double-strand break inducing agent. Alternatively, an endogenous recognition site could be recognized and/or bound by a modified or engineered double-strand break inducing agent designed or selected to specifically recognize the endogenous recognition sequence to produce a double-strand break. In some embodiments, the modified double-strand break inducing agent is derived from a native, naturally-occurring double-strand break inducing agent. In other embodiments, the modified double-strand break inducing agent is artificially created or synthesized. Methods for selecting such modified or engineered double-strand break inducing agents are known in the art. For example, amino acid sequence variants of the protein(s) can be prepared by mutations in the DNA. Methods for mutagenesis and nucleotide sequence alterations include, for example, Kunkel, (1985) *Proc Natl Acad Sci USA* 82:488-92; Kunkel, et al., (1987) *Meth Enzymol* 154:367-82; U.S. Pat. No. 4,873,192; Walker and Gaastra, eds. (1983) *Techniques in Molecular Biology* (MacMillan Publishing Company, New York) and the references cited therein. Guidance regarding amino acid substitutions not likely to affect biological activity of the protein is found, for example, in the model of Dayhoff, et al., (1978) *Atlas of Protein Sequence and Structure* (Natl Biomed Res Found, Washington, D.C.). Conservative substitutions, such as exchanging one amino acid with another having similar properties, may be preferable. Conservative deletions, insertions, and amino acid substitutions are not expected to produce radical changes in the characteristics of the protein, and the effect of any substitution, deletion, insertion, or combination thereof can be evaluated by routine screening assays. Assays for double strand break inducing activity are known and generally measure the overall activity and specificity of the agent on DNA substrates containing recognition sites.

In some embodiments of the methods provided herein, one or more of the nucleases is an endonuclease. Endonucleases are enzymes that cleave the phosphodiester bond within a polynucleotide chain, and include restriction endonucleases that cleave DNA as specific sites without damaging the bases. Restriction endonucleases include Type I, Type II, Type III, and Type IV endonucleases, which further include subtypes. Restriction endonucleases are further described and classified, for example in the REBASE database (webpage at rebase.neb.com; Roberts, et al., (2003) *Nucleic Acids Res* 31:418-20), Roberts, et al., (2003) *Nucleic Acids Res* 31:1805-12, and Belfort, et al., (2002) in *Mobile DNA II, pp.* 761-783, Eds. Craigie, et al., ASM Press, Washington, D.C.

As used herein, endonucleases also include homing endonucleases, which like restriction endonucleases, bind and cut at a specific recognition sequence. However the recognition sites for homing endonucleases are typically longer, for example, about 18 bp or more. Homing endonucleases, also known as meganucleases, have been classified into the following families based on conserved sequence motifs: an LAGLIDADG (SEQ ID NO: 50) homing endonuclease, an HNH homing endonuclease, a His-Cys box homing endonuclease, a GIY-YIG (SEQ ID NO: 51) homing endonuclease, and a cyanobacterial homing endonuclease. See, e.g., Stoddard, *Quarterly Review of Biophysics* 38(1): 49-95 (2006). These families differ greatly in their conserved nuclease active-site core motifs and catalytic mechanisms, biological and genomic distributions, and wider relationship to non-homing nuclease systems. See, for example, Guhan and Muniyappa (2003) *Crit Rev Biochem Mol Biol* 38:199-248; Lucas, et al., (2001) *Nucleic Acids Res* 29:960-9; Jurica and Stoddard, (1999) *Cell Mol Life Sci* 55:1304-26; Stoddard, (2006) *Q Rev Biophys* 38:49-95; and Moure, et al., (2002) *Nat Struct Biol* 9:764. Examples of useful specific homing endonucleases from these families include, but are not limited to: I-CreI (see, Rochaix et al., *Nucleic Acids Res.* 13: 975-984 (1985), I-MsoI (see, Lucas et al., *Nucleic Acids Res.* 29: 960-969 (2001), I-SceI (see, Foury et al., *FEBS Lett.* 440: 325-331 (1998), I-SceIV (see, Moran et al., *Nucleic Acids Res.* 20: 4069-4076 (1992), H-DreI (see, Chevalier et al., *Mol. Cell* 10: 895-905 (2002), I-HmuI (see, Goodrich-Blair et al., *Cell* 63: 417-424 (1990); Goodrich-Blair et al., *Cell* 84: 211-221 (1996), I-PpoI (see, Muscarella et al., *Mol. Cell. Biol.* 10: 3386-3396 (1990), 1-DirI (see, Johansen et al., *Cell* 76: 725-734 (1994); Johansen, *Nucleic Acids Res.* 21: 4405 (1993), I-NjaI (see, Elde et al., *Eur. J. Biochem.* 259: 281-288 (1999); De Jonckheere et al., *J. Eukaryot. Microbiol.* 41: 457-463 (1994), I-NanI (see, Elde et al., *S. Eur. J. Biochem.* 259: 281-288 (1999); De Jonckheere et al., *J. Eukaryot. Microbiol.* 41: 457-463 (1994)), I-NitI (see, De Jonckheere et al., *J. Eukaryot. Microbiol.* 41: 457-463 (1994); Elde et al., *Eur. J. Biochem.* 259: 281-288 (1999), I-TevI (see, Chu et al., *Cell* 45: 157-166 (1986), I-TevII (see, Tomaschewski et al., *Nucleic Acids Res.* 15: 3632-3633 (1987), I-TevIII (see, Eddy et al., *Genes Dev.* 5: 1032-1041 (1991), F-TevI (see, Fujisawa et al., *Nucleic Acids Res.* 13: 7473-7481 (1985), F-TevII (see, Kadyrov et al., *Dokl. Biochem.* 339: 145-147 (1994); Kaliman, *Nucleic Acids Res.* 18: 4277 (1990), F-CphI (see, Zeng et al., *Curr. Biol.* 19: 218-222 (2009), PI-MgaI (see, Saves et al., *Nucleic Acids Res.* 29:4310-4318 (2001), I-CsmI (see, Colleaux et al., *Mol. Gen. Genet.* 223:288-296 (1990), I-CeuI (see, Turmel et al., *J. Mol. Biol.* 218: 293-311 (1991) and PI-SceI (see, Hirata et al., *J. Biol. Chem.* 265: 6726-6733 (1990).

In some embodiments of the methods described herein, a naturally occurring variant, and/or engineered derivative of a homing endonuclease is used. Methods for modifying the kinetics, cofactor interactions, expression, optimal conditions, and/or recognition site specificity, and screening for activity are known. See, for example, Epinat, et al., (2003) *Nucleic Acids Res* 31:2952-62; Chevalier, et al., (2002) *Mol Cell* 10:895-905; Gimble, et al., (2003) *Mol Biol* 334:993-1008; Seligman, et al., (2002) *Nucleic Acids Res* 30:3870-9; Sussman, et al., (2004) *J Mol Biol* 342:31-41; Rosen, et al., (2006) *Nucleic Acids Res* 34:4791-800; Chames, et al., (2005) *Nucleic Acids Res* 33:e178; Smith, et al., (2006) *Nucleic Acids Res* 34:e149; Gruen, et al., (2002) *Nucleic Acids Res* 30:e29; Chen and Zhao, (2005) *Nucleic Acids Res* 33:e154; WO2005105989; WO2003078619; WO2006097854; WO2006097853; WO2006097784; and WO2004031346. Useful homing endonucleases also include those described in WO04/067736; WO04/067753; WO06/097784; WO06/097853; WO06/097854; WO07/034,262; WO07/049,095; WO07/049,156; WO07/057,781; WO07/060,495; WO08/152,524; WO09/001,159; WO09/095,742; WO09/095,793; WO10/001,189; WO10/015,899; and WO10/046,786.

Any homing endonuclease can be used as a double-strand break inducing agent including, but not limited to: H-DreI, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, Pi-PspI, F-SceI, F-SceII, F-SuvI, F-CphI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MgaI, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, or PI-TliII, or any variant or derivative thereof.

In some embodiments, the endonuclease binds a native or endogenous recognition sequence. In other embodiments, the endonuclease is a modified endonuclease that binds a non-native or exogenous recognition sequence and does not bind a native or endogenous recognition sequence.

In some embodiments of the methods provided herein, one or more of the nucleases is a TAL-effector DNA binding domain-nuclease fusion protein (TALEN). TAL effectors of plant pathogenic bacteria in the genus *Xanthomonas* play important roles in disease, or trigger defense, by binding host DNA and activating effector-specific host genes. see, e.g., Gu et al. (2005) *Nature* 435:1122-5; Yang et al., (2006) *Proc. Natl. Acad. Sci. USA* 103:10503-8; Kay et al., (2007) *Science* 318:648-51; Sugio et al., (2007) *Proc. Natl. Acad. Sci. USA* 104:10720-5; Romer et al., (2007) *Science* 318: 645-8; Boch et al., (2009) *Science* 326(5959):1509-12; and Moscou and Bogdanove, (2009) 326(5959):1501. A TAL effector comprises a DNA binding domain that interacts with DNA in a sequence-specific manner through one or more tandem repeat domains. The repeated sequence typically comprises 34 amino acids, and the repeats are typically 91-100% homologous with each other. Polymorphism of the repeats is usually located at positions 12 and 13, and there appears to be a one-to-one correspondence between the identity of repeat variable-diresidues at positions 12 and 13 with the identity of the contiguous nucleotides in the TAL-effector's target sequence.

The TAL-effector DNA binding domain may be engineered to bind to a desired target sequence, and fused to a nuclease domain, e.g., from a type II restriction endonuclease, typically a nonspecific cleavage domain from a type II restriction endonuclease such as FoId (see e.g., Kim et al. (1996) *Proc. Natl. Acad. Sci. USA* 93:1156-1160). Other useful endonucleases may include, for example, HhaI, HindIII, Nod, BbvCI, EcoRI, BglI, and AlwI. Thus, in preferred embodiments, the TALEN comprises a TAL effector domain comprising a plurality of TAL effector repeat sequences that, in combination, bind to a specific nucleotide sequence in the target DNA sequence, such that the TALEN cleaves the target DNA within or adjacent to the specific nucleotide sequence. TALENS useful for the methods provided herein include those described in WO10/079,430 and U.S. Patent Application Publication No. 2011/0145940.

In some embodiments, the TAL effector domain that binds to a specific nucleotide sequence within the target DNA can comprise 10 or more DNA binding repeats, and preferably 15 or more DNA binding repeats. In some embodiments, each DNA binding repeat comprises a repeat variable-diresidue (RVD) that determines recognition of a base pair in the target DNA sequence, wherein each DNA binding repeat is responsible for recognizing one base pair in the target DNA sequence, and wherein the RVD comprises one or more of: HD for recognizing C; NG for recognizing T; NI for recognizing A; NN for recognizing G or A; NS for recognizing A or C or G or T; N* for recognizing C or T, where * represents a gap in the second position of the RVD; HG for recognizing T; H* for recognizing T, where * represents a gap in the second position of the RVD; IG for recognizing T; NK for recognizing G; HA for recognizing C; ND for recognizing C; HI for recognizing C; HN for recognizing G; NA for recognizing G; SN for recognizing G or A; and YG for recognizing T.

In some embodiments of the methods provided herein, one or more of the nucleases is a site-specific recombinase. A site-specific recombinase, also referred to as a recombinase, is a polypeptide that catalyzes conservative site-specific recombination between its compatible recombination sites, and includes native polypeptides as well as derivatives, variants and/or fragments that retain activity, and native polynucleotides, derivatives, variants, and/or fragments that encode a recombinase that retains activity. For reviews of site-specific recombinases and their recognition sites, see, Sauer (1994) *Curr Op Biotechnol* 5:521-7; and Sadowski, (1993) *FASEB* 7:760-7. In some embodiments, the recombinase is a serine recombinase or a tyrosine recombinase. In some embodiments, the recombinase is from the Integrase or Resolvase families. In some embodiments, the recombinase is an integrase selected from the group consisting of FLP, Cre, lambda integrase, and R. For other members of the Integrase family, see for example, Esposito, et al., (1997) *Nucleic Acids Res* 25:3605-14 and Abremski, et al., (1992) *Protein Eng* 5:87-91. Methods for modifying the kinetics, cofactor interaction and requirements, expression, optimal conditions, and/or recognition site specificity, and screening for activity of recombinases and variants are known, see for example Miller, et al., (1980) *Cell* 20:721-9; Lange-Gustafson and Nash, (1984) *J Biol Chem* 259:12724-32; Christ, et al., (1998) *J Mol Biol* 288:825-36; Lorbach, et al., (2000) *J Mol Biol* 296:1175-81; Vergunst, et al., (2000) *Science* 290:979-82; Dorgai, et al., (1995) *J Mol Biol* 252:178-88; Dorgai, et al., (1998) *J Mol Biol* 277:1059-70; Yagu, et al., (1995) *J Mol Biol* 252:163-7; Sclimente, et al., (2001) *Nucleic Acids Res* 29:5044-51; Santoro and Schultze, (2002) *Proc Natl Acad Sci USA* 99:4185-90; Buchholz and Stewart, (2001) *Nat Biotechnol* 19:1047-52; Voziyanov, et al., (2002) *Nucleic Acids Res* 30:1656-63; Voziyanov, et al., (2003) *J Mol Biol* 326:65-76; Klippel, et al., (1988) *EMBO J* 7:3983-9; Arnold, et al., (1999) *EMBO J* 18:1407-14; WO03/08045; WO99/25840; and WO99/25841. The recognition sites range from about 30 nucleotide minimal sites to a few hundred nucleotides. Any recognition site for a recombinase can be used, including naturally occurring sites, and variants. Variant recognition sites are known, see for example Hoess, et al., (1986) *Nucleic Acids Res* 14:2287-300; Albert, et al., (1995) *Plant J* 7:649-59; Thomson, et al., (2003) *Genesis* 36:162-7; Huang, et al., (1991) *Nucleic Acids Res* 19:443-8; Siebler and Bode, (1997) *Biochemistry* 36:1740-7; Schlake and Bode, (1994) *Biochemistry* 33:12746-51; Thygarajan, et al., (2001) *Mol Cell Biol* 21:3926-34; Umlauf and Cox, (1988) *EMBO J* 7:1845-52; Lee and Saito, (1998) *Gene* 216:55-65; WO01/23545; WO99/25821; WO99/25851; WO01/11058; WO01/07572 and U.S. Pat. No. 5,888,732.

In some embodiments of the methods provided herein, one or more of the nucleases is a transposase. Transposases are polypeptides that mediate transposition of a transposon from one location in the genome to another. Transposases typically induce double strand breaks to excise the transposon, recognize subterminal repeats, and bring together the ends of the excised transposon, in some systems other proteins are also required to bring together the ends during transposition. Examples of transposons and transposases include, but are not limited to, the Ac/Ds, Dt/rdt, Mu-Ml/Mn, and Spm(En)/dSpm elements from maize, the Tam elements from snapdragon, the Mu transposon from bacteriophage, bacterial transposons (Tn) and insertion sequences (IS), Ty elements of yeast (retrotransposon), Tal elements from *Arabidopsis* (retrotransposon), the P element transposon from *Drosophila* (Gloor, et al., (1991) *Science* 253:1110-1117), the Copia, Mariner and Minos elements from *Drosophila*, the Hermes elements from the housefly, the PiggyBack elements from Trichplusia ni, Tc1 elements from *C. elegans*, and IAP elements from mice (retrotransposon).

In some embodiments of the methods provided herein, one or more of the nucleases is a zinc-finger nuclease (ZFN). ZFNs are engineered double-strand break inducing agents comprised of a zinc finger DNA binding domain and a double strand break inducing agent domain. Engineered ZFNs consist of two zinc finger arrays (ZFAs), each of which is fused to a single subunit of a non-specific endonuclease, such as the nuclease domain from the FokI enzyme, which becomes active upon dimerization. Typically, a single ZFA consists of 3 or 4 zinc finger domains, each of which is designed to recognize a specific nucleotide triplet (GGC, GAT, etc.). Thus, ZFNs composed of two "3-finger" ZFAs are capable of recognizing an 18 base pair target site; an 18 base pair recognition sequence is generally unique, even within large genomes such as those of humans and plants. By directing the co-localization and dimerization of two Fold nuclease monomers, ZFNs generate a functional site-specific endonuclease that creates a double-stranded break (DSB) in DNA at the targeted locus.

Useful zinc-finger nucleases include those that are known and those that are engineered to have specificity for one or more target sites (TS) described herein. Zinc finger domains are amenable for designing polypeptides which specifically bind a selected polynucleotide recognition sequence, for example, within the target site of the host cell genome. ZFNs consist of an engineered DNA-binding zinc finger domain linked to a non-specific endonuclease domain, for example nuclease domain from a Type Hs endonuclease such as HO or FokI. Alternatively, engineered zinc finger DNA binding domains can be fused to other double-strand break inducing agents or derivatives thereof that retain DNA nicking/cleaving activity. For example, this type of fusion can be used to direct the double-strand break inducing agent to a different target site, to alter the location of the nick or cleavage site, to direct the inducing agent to a shorter target site, or to direct the inducing agent to a longer target site. In some examples a zinc finger DNA binding domain is fused to a site-specific recombinase, transposase, or a derivative thereof that retains DNA nicking and/or cleaving activity. Additional functionalities can be fused to the zinc-finger binding domain, including transcriptional activator domains, transcription repressor domains, and methylases. In some embodiments, dimerization of nuclease domain is required for cleavage activity.

Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind a 18 nucleotide recognition sequence. Useful designer zinc finger modules include those that recognize various GNN and ANN triplets (Dreier, et al., (2001) *J Biol Chem* 276:29466-78; Dreier, et al., (2000) *J Mol Biol* 303:489-502; Liu, et al., (2002) *J Biol Chem* 277:3850-6), as well as those that recognize various CNN or TNN triplets (Dreier, et al., (2005) *J Biol Chem* 280:35588-97; Jamieson, et al., (2003) *Nature Rev Drug Discov* 2:361-

8). See also, Durai, et al., (2005) *Nucleic Acids Res* 33:5978-90; Segal, (2002) *Methods* 26:76-83; Porteus and Carroll, (2005) *Nat Biotechnol* 23:967-73; Pabo, et al., (2001) *Ann Rev Biochem* 70:313-40; Wolfe, et al., (2000) *Ann Rev Biophys Biomol Struct* 29:183-212; Segal and Barbas, (2001) *Curr Opin Biotechnol* 12:632-7; Segal, et al., (2003) *Biochemistry* 42:2137-48; Beerli and Barbas, (2002) *Nat Biotechnol* 20:135-41; Carroll, et al., (2006) *Nature Protocols* 1:1329; Ordiz, et al., (2002) *Proc Natl Acad Sci USA* 99:13290-5; Guan, et al., (2002) *Proc Natl Acad Sci USA* 99:13296-301; WO2002099084; WO00/42219; WO02/42459; WO2003062455; US20030059767; US Patent Application Publication Number 2003/0108880; U.S. Pat. Nos. 6,140,466, 6,511,808 and 6,453,242. Useful zinc-finger nucleases also include those described in WO03/080809; WO05/014791; WO05/084190; WO08/021,207; WO09/042,186; WO09/054,985; and WO10/065,123.

6.5 Genomic Target Sites

In the methods provided herein, a nuclease is introduced to the host cell that is capable of causing a double-strand break near or within a genomic target site, which greatly increases the frequency of homologous recombination at or near the cleavage site. In preferred embodiments, the recognition sequence for the nuclease is present in the host cell genome only at the target site, thereby minimizing any off-target genomic binding and cleavage by the nuclease.

In some embodiments, the genomic target site is endogenous to the host cell, such as a native locus. In some embodiments, the native genomic target site is selected according to the type of nuclease to be utilized in the methods of integration provided herein. If the nuclease to be utilized is a zinc finger nuclease, optimal target sites may be selected using a number of publicly available online resources. See, e.g., Reyon et al., *BMC Genomics* 12:83 (2011), which is hereby incorporated by reference in its entirety. For example, Oligomerized Pool Engineering (OPEN) is a highly robust and publicly available protocol for engineering zinc finger arrays with high specificity and in vivo functionality, and has been successfully used to generate ZFNs that function efficiently in plants, zebrafish, and human somatic and pluripotent stem cells. OPEN is a selection-based method in which a pre-constructed randomized pool of candidate ZFAs is screened to identify those with high affinity and specificity for a desired target sequence. ZFNGenome is a GBrowse-based tool for identifying and visualizing potential target sites for OPEN-generated ZFNs. ZFNGenome provides a compendium of potential ZFN target sites in sequenced and annotated genomes of model organisms. ZFNGenome currently includes a total of more than 11.6 million potential ZFN target sites, mapped within the fully sequenced genomes of seven model organisms; *S. cerevisiae, C. reinhardtii, A. thaliana, D. melanogaster, D. rerio, C. elegans,* and *H. sapiens*. Additional model organisms, including three plant species; *Glycine max* (soybean), *Oryza sativa* (rice), *Zea mays* (maize), and three animal species *Tribolium castaneum* (red flour beetle), *Mus musculus* (mouse), *Rattus norvegicus* (brown rat) will be added in the near future. ZFNGenome provides information about each potential ZFN target site, including its chromosomal location and position relative to transcription initiation site(s). Users can query ZFNGenome using several different criteria (e.g., gene ID, transcript ID, target site sequence).

If the nuclease to be utilized is a TAL-effector nuclease, in some embodiments, optimal target sites may be selected in accordance with the methods described by Sanjana et al., *Nature Protocols,* 7:171-192 (2012), which is hereby incorporated by reference in its entirety. In brief, TALENs function as dimers, and a pair of TALENs, referred to as the left and right TALENs, target sequences on opposite strands of DNA. TALENs are engineered as a fusion of the TALE DNA-binding domain and a monomeric FokI catalytic domain. To facilitate FokI dimerization, the left and right TALEN target sites are chosen with a spacing of approximately 14-20 bases. Therefore, for a pair of TALENs, each targeting 20-bp sequences, an optimal target site should have the form 5'-TN$^{19}$N$^{14-20}$N$^{19}$A-3', the left TALEN targets 5'-TN$^{19}$-3' and the right TALEN targets the antisense strand of 5'-N$^{19}$A-3' (N=A, G, T or C).

In other embodiments of the methods provided herein, the genomic target site is exogenous to the host cell. For example, one or more genomic target sites can be engineered into the host cell genome using traditional methods, e.g., gene targeting, prior to performing the methods of integration described herein. In some embodiments, multiple copies of the same target sequence are engineered into the host cell genome at different loci, thereby facilitating simultaneous multiple integration events with the use of only a single nuclease that specifically recognizes the target sequence. In other embodiments, a plurality of different target sequences is engineered into the host cell genome at different loci. In some embodiments, the engineered target site comprises a target sequence that is not otherwise represented in the native genome of the host cell. For example, homing endonucleases target large recognition sites (12-40 bp) that are usually embedded in introns or inteins, and as such, their recognition sites are extremely rare, with none or only a few of these sites present in a mammalian-sized genome. Thus, in some embodiments, the exogenous genomic target site is a recognition sequence for a homing endonuclease. In some embodiments, the homing nuclease is selected from the group consisting of: H-DreI, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, Pi-PspI, F-SceI, F-SceII, F-SuvI, F-CphI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp68031, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MgaI, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, or PI-TliII, or any variant or derivative thereof. In particular embodiments, the exogenous genomic target site is the recognition sequence for I-SceI, VDE (PI-SceI), F-CphI, PI-MgaI or PI-MtuII, each of which are provided below.

TABLE 1

Recognition and cleavage sites for select homing endonucleases.

| Nuclease | Recognition sequence |
|---|---|
| I-SceI | TAGGGATAACAGGGTAAT (SEQ ID NO: 52) |
| VDE (PI-SceI) | TATGTCGGGTGCGGAGAAAGAGGTAATGAAA (SEQ ID NO: 53) |
| F-CphI | GATGCACGAGCGCAACGCTCACAA (SEQ ID NO: 54) |

TABLE 1-continued

Recognition and cleavage sites for select homing endonucleases.

| Nuclease | Recognition sequence |
|---|---|
| PI-MgaI | GCGTAGCTGCCCAGTATGAGTCAG (SEQ ID NO: 55) |
| PI-MtuII | ACGTGCACTACGTAGAGGGTCGCACCGCACCGATCTACAA (SEQ ID NO: 56) |

6.6 Delivery

In some embodiments, the one or more nucleases useful for the methods described herein are provided, e.g., delivered into the host cell as a purified protein. In other embodiments, the one or more nucleases are provided via polynucleotide(s) comprising a nucleic acid encoding the nuclease. In other embodiments, the one or more nucleases are introduced into the host cell as purified RNA which can be directly translated in the host cell nucleus.

In certain embodiments, an integration polynucletide, a polynucleotide encoding a nuclease, or a purified nuclease protein as described above, or any combination thereof, may be introduced into a host cell using any conventional technique to introduce exogenous protein and/or nucleic acids into a cell known in the art. Such methods include, but are not limited to, direct uptake of the molecule by a cell from solution, or facilitated uptake through lipofection using, e.g., liposomes or immunoliposomes; particle-mediated transfection; etc. See, e.g., U.S. Pat. No. 5,272,065; Goeddel et al., eds, 1990, *Methods in Enzymology*, vol. 185, Academic Press, Inc., CA; Krieger, 1990, *Gene Transfer and Expression—A Laboratory Manual*, Stockton Press, NY; Sambrook et al., 1989, *Molecular Cloning—A Laboratory Manual*, Cold Spring Harbor Laboratory, NY; and Ausubel et al., eds., Current Edition, *Current Protocols in Molecular Biology*, Greene Publishing Associates and Wiley Interscience, NY. Particular methods for transforming cells are well known in the art. See Hinnen et al., *Proc. Natl. Acad. Sci. USA* 75:1292-3 (1978); Cregg et al., *Mol. Cell. Biol.* 5:3376-3385 (1985). Exemplary techniques include but are not limited to, spheroplasting, electroporation, PEG 1000 mediated transformation, and lithium acetate or lithium chloride mediated transformation.

In some embodiments, biolistics are utilized to introduce an integration polynucletide, a polynucleotide encoding a nuclease, a purified nuclease protein, or any combination thereof into the host cell, in particular, host cells that are otherwise difficult to transform/transfect using conventional techniques, such as plants. Biolistics work by binding the transformation reaction to microscopic gold particles, and then propelling the particles using compressed gas at the target cells.

In some embodiments, the polynucleotide comprising nucleic acid encoding the nuclease is an expression vector that allows for the expression of a nuclease within a host cell. Suitable expression vectors include but are not limited to those known for use in expressing genes in *Escherichia coli*, yeast, or mammalian cells. Examples of *Escherichia coli* expression vectors include but are not limited to pSCM525, pDIC73, pSCM351, and pSCM353. Examples of yeast expression vectors include but are not limited to pPEX7 and pPEX408. Other examples of suitable expression vectors include the yeast-*Escherichia coli* pRS series of shuttle vectors comprising CEN.ARS sequences and yeast selectable markers; and 2µ plasmids. In some embodiments, a polynucleotide encoding a nuclease can be modified to substitute codons having a higher frequency of usage in the host cell, as compared to the naturally occurring polynucleotide sequence. For example the polynucleotide encoding the nuclease can be modified to substitute codons having a higher frequency of usage in *S. cerevisiae*, as compared to the naturally occurring polynucleotide sequence.

In some embodiments where the nuclease functions as a heterodimer requiring the separate expression of each monomer, as is the case for zinc finger nucleases and TAL-effector nucleases, each monomer of the heterodimer may be expressed from the same expression plasmid, or from different plasmids. In embodiments where multiple nucleases are introduced to the cell to effect double-strand breaks at different target sites, the nucleases may be encoded on a single plasmid or on separate plasmids.

In certain embodiments, the nuclease expression vector further comprises a selectable marker that allows for selection of host cells comprising the expression vector. Such selection can be helpful to retain the vector in the host cell for a period of time necessary for expression of sufficient amounts of nuclease to occur, for example, for a period of 12, 24, 36, 48, 60, 72, 84, 96, or more than 96 hours, after which the host cells may be grown under conditions under which the expression vector is no longer retained. In certain embodiments, the selectable marker is selected from the group consisting of: URA3, hygromycin B phosphotransferase, aminoglycoside phosphotransferase, zeocin resistance, and phosphinothricin N-acetyltransferase. In some embodiments, the nuclease expression vector vector may comprise a counter-selectable marker that allows for selection of host cells that do not contain the expression vector subsequent to integration of the one or more donor nucleic acid molecules. The nuclease expression vector used may also be a transient vector that has no selection marker, or is one that is not selected for. In particular embodiments, the progeny of a host cell comprising a transient nuclease expression vector loses the vector over time.

In certain embodiments, the expression vector further comprises a transcription termination sequence and a promoter operatively linked to the nucleotide sequence encoding the nuclease. In some embodiments, the promoter is a constitutive promoter. In some embodiments, the promoter is an inducible promoter. Illustrative examples of promoters suitable for use in yeast cells include, but are not limited to the promoter of the TEF1 gene of *K. lactis*, the promoter of the PGK1 gene of *Saccharomyces cerevisiae*, the promoter of the TDH3 gene of *Saccharomyces cerevisiae*, repressible promoters, e.g., the promoter of the CTR3 gene of *Saccharomyces cerevisiae*, and inducible promoters, e.g., galactose inducible promoters of *Saccharomyces cerevisiae* (e.g., promoters of the GAL1 GAL7, and GAL10 genes).

In some embodiments, an additional nucleotide sequence comprising a nuclear localization sequence (NLS) is linked to the 5' of the nucleotide sequence encoding the nuclease. The NLS can facilitate nuclear localization of larger nucleases (>25 kD). In some embodiments, the nuclear localization sequence is an SV40 nuclear localization sequence. In some embodiments, the nuclear localization sequence is a yeast nuclear localization sequence.

A nuclease expression vector can be made by any technique apparent to one skilled in the art. In certain embodiments, the vector is made using polymerase chain reaction (PCR) and molecular cloning techniques well known in the art. See, e.g., *PCR Technology: Principles and Applications*

*for DNA Amplification*, ed. HA Erlich, Stockton Press, New York, N.Y. (1989); Sambrook et al., 2001, *Molecular Cloning—A Laboratory Manual*, 3$^{rd}$ edition, Cold Spring Harbor Laboratory, Cold Spring Harbor, N.Y.

6.7 Host Cells

In another aspect, provided herein is a modified host cell generated by any of the methods of genomically integrating one or more exogenous nucleic acids described herein. Suitable host cells include any cell in which integration of a nucleic acid or "donor DNA" of interest into a chromosomal or episomal locus is desired. In some embodiments, the cell is a cell of an organism having the ability to perform homologous recombination. Although several of the illustrative embodiments are demonstrated in yeast (*S. cerevisiae*), it is believed that the methods of genomic modification provided herein can be practiced on all biological organisms having a functional recombination system, even where the recombination system is not as proficient as in yeast. Other cells or cell types that have a functional homologous recombination systems include bacteria such as *Bacillus subtilis* and *E. coli* (which is RecE RecT recombination proficient; Muyrers et al., *EMBO rep.* 1: 239-243, 2000); protozoa (e.g., *Plasmodium*, *Toxoplasma*); other yeast (e.g., *Schizosaccharomyces pombe*); filamentous fungi (e.g., *Ashbya gossypii*); plants, for instance the moss *Physcomitrella patens* (Schaefer and Zryd, *Plant J.* 11: 1195-1206, 1997); and animal cells, such as mammalian cells and chicken DT40 cells (Dieken et al., *Nat. Genet.* 12:174-182, 1996).

In some embodiments, the host cell is a prokaryotic cell. In some embodiments, the host cell is a eukaryotic cell. In some embodiments, the cell is a fungal cell (for instance, a yeast cell), a bacteria cell, a plant cell, or an animal cell (for instance, a chicken cell). In some embodiments, the host cell is a mammalian cell. In some embodiments, the host cell is a Chinese hamster ovary (CHO) cell, a COS-7 cell, a mouse fibroblast cell, a mouse embryonic carcinoma cell, or a mouse embryonic stem cell. In some embodiments, the host cell is an insect cell. In some embodiments, the host cell is a S2 cell, a Schneider cell, a S12 cell, a 5B1-4 cell, a Tn5 cell, or a Sf9 cell. In some embodiments, the host cell is a unicellular eukaryotic organism cell.

In particular embodiments, the host cell is a yeast cell. Useful yeast host cells include yeast cells that have been deposited with microorganism depositories (e.g. IFO, ATCC, etc.) and belong to the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endoinycopsella, Eremascus, Eremothecium, Erythrobasidium, Fellomyces, Filobasidium, Galactomyces, Geotrichum, Guilliennondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniotnyces, Waltomyces, Wickerhamia, Wickerhamiella, Williopsis, Yamadazyma, Yarrowia, Zygoascus, Zygosaccharomyces, Zygowilliopsis,* and *Zygozyma,* among others.

In some embodiments, the yeast host cell is a *Saccharomyces cerevisiae* cell, a *Pichia pastoris* cell, a *Schizosaccharomyces pombe* cell, a *Dekkera bruxellensis* cell, a *Kluyveromyces lactis* cell, a *Arxula adeninivorans* cell, or a *Hansenula polymorpha* (now known as *Pichia angusta*) cell. In a particular embodiment, the yeast host cell is a *Saccharomyces cerevisiae* cell. In some embodiments, the yeast host cell is a *Saccharomyces fragilis* cell or a *Kluyveromyces lactis* (previously called *Saccharomyces lactis*) cell. In some embodiments, the yeast host cell is a cell belonging to the genus *Candida*, such as *Candida lipolytica, Candida guilliemondii, Candida krusei, Candida pseudotropicalis*, or *Candida utilis*. In another particular embodiment, the yeast host cell is a *Kluveromyces marxianus* cell.

In particular embodiments, the yeast host cell is a *Saccharomyces cerevisiae* cell selected from the group consisting of a Baker's yeast cell, a CBS 7959 cell, a CBS 7960 cell, a CBS 7961 cell, a CBS 7962 cell, a CBS 7963 cell, a CBS 7964 cell, a IZ-1904 cell, a TA cell, a BG-1 cell, a CR-1 cell, a SA-1 cell, a M-26 cell, a Y-904 cell, a PE-2 cell, a PE-5 cell, a VR-1 cell, a BR-1 cell, a BR-2 cell, a ME-2 cell, a VR-2 cell, a MA-3 cell, a MA-4 cell, a CAT-1 cell, a CB-1 cell, a NR-1 cell, a BT-1 cell, and a AL-1 cell. In some embodiments, the host cell is a *Saccharomyces cerevisiae* cell selected from the group consisting of a PE-2 cell, a CAT-1 cell, a VR-1 cell, a BG-1 cell, a CR-1 cell, and a SA-1 cell. In a particular embodiment, the *Saccharomyces cerevisiae* host cell is a PE-2 cell. In another particular embodiment, the *Saccharomyces cerevisiae* host cell is a CAT-1 cell. In another particular embodiment, the *Saccharomyces cerevisiae* host cell is a BG-1 cell.

In some embodiments, the yeast host cell is a cell that is suitable for industrial fermentation, e.g., bioethanol fermentation. In particular embodiments, the cell is conditioned to subsist under high solvent concentration, high temperature, expanded substrate utilization, nutrient limitation, osmotic stress due, acidity, sulfite and bacterial contamination, or combinations thereof, which are recognized stress conditions of the industrial fermentation environment.

6.8 Kits

In another aspect, provided herein is a kit useful for performing the methods for genomically integrating one or more exogenous nucleic acids described herein. In some embodiments, the kit comprises:

(a) a plurality of exogenous nucleic acids, wherein each exogenous nucleic acid $(ES)_x$ comprises:

(i) a first homology region $(HR1)_x$ and a second homology region $(HR2)_x$, wherein $(HR1)_x$ and $(HR2)_x$ are capable of initiating host cell mediated homologous recombination of $(ES)_x$ at a selected target site $(TS)_x$ of a host cell genome; and (ii) a nucleic acid of interest $(D)_x$ positioned 3' of $(HR1)_x$ and 5' of $(HR2)_x$;

(b) a plurality of nucleases, wherein each nuclease $(N)_x$ capable of cleaving at $(TS)_x$, whereupon said cleaving results in homologous recombination of $(ES)_x$ at $(TS)_x$;

wherein x is any integer from 1 to n wherein n is at least 2.

In some embodiments, $(D)_x$ is selected from the group consisting of a selectable marker, a promoter, a nucleic acid sequence encoding an epitope tag, a gene of interest, a reporter gene, and a nucleic acid sequence encoding a termination codon. In some embodiments, the kit further comprises a plurality of primer pairs $(P)_x$, wherein each primer pair is capable of identifying integration of $(ES)_x$ at $(TS)_x$ by PCR. In some embodiments, $(ES)_x$ is linear. In some embodiments, $(ES)_x$ is circular.

In a particular embodiment, the kit enables site-specific integration of an exogenous nucleic acid at a unique target site within any of the approximately 6000 genetic loci of the yeast genome. In these embodiments, n=≥6000, wherein each $(TS)_x$ is unique to a single locus of the yeast cell genome.

In some embodiments, the kit further comprises instructions for use that describe methods for integrating one or more exogenous nucleic acids into any genetic locus of a host yeast cell.

7. EXAMPLES

7.1 Example 1

Simultaneous Multiple Integration of a Plurality of Exogenous Nucleic Acids

The methods and compositions described herein are implemented to create a modified yeast cell comprising two exogenous nucleic acids integrated at two loci of the yeast cell genome in a single transformation step, wherein recovery of the modified yeast cell does not require the use of selectable marker(s).

A host strain is provided comprising: (a) a previously introduced recognition site for the F-CphI endonuclease positioned within the NDT80 locus; and (b): a previously introduced recognition site for the I-SceI endonuclease positioned within the HO locus. The host cell is simultaneously transformed with: (1) an expression plasmid encoding F-CphI; (2) an expression plasmid encoding I-SceI; (3) a linear DNA comprising an expression cassette encoding green fluorescent protein (GFP), flanked by two stretches of >500 bp sequence corresponding to the 5' and 3' regions of the NDT80 locus; and (4) a linear DNA comprising an expression cassette encoding lacZ, flanked by two stretches of >500 bp sequence corresponding to the 5' and 3' regions of the HO locus. As an alternative to inclusion of the expression plasmids encoding F-CphI and 1-SceI, respectively, purified F-CphI and I-SceI protein are included in the transformation reaction. A non-double strand break control is performed by transforming host cells with the linear integration constructs (3) and (4) only, in the absence of F-CphI and I-SceI expression plasmid or purified protein.

Experimental and control transformants are plated on selection-free media, and colonies from each plate are visualized for expression of GFP and lacZ, respectively. Colony PCR is independently performed with a primer pair which anneals upstream and downstream of the junction between the integrated integration construct (3) or (4), respectively, and their respective target sequences, to confirm fidelity and frequency of integration.

7.2 Example 2

Simultaneous Multiple Integration of a Plurality of Exogenous Nucleic Acids

This Example provides results which demonstrate simultaneous integration of three exogenous nucleic acids at three different loci of a *S. cerevisiae* host following the induction of targeted double-stranded breaks in the host cell genome. In brief, an exogenous "target" nucleic acid sequence encoding a truncated, non-functional copy of Emerald Green Fluorescent Protein (emgfpΔ) was integrated into the HO, YGR250c and NDT80 loci, respectively, of host yeast cells. Recombinant cells were transformed with linear "donor" DNA encoding an intact, functional copy of Emerald Green Fluorescent Protein (EmGFP) and either: (1) empty vector; or (2) an expression vector, pZFN.gfp, encoding a zinc-finger nuclease (ZFN.gfp) that specifically recognizes and cleaves a sequence within the emgfpΔ coding sequence. Transformed colonies were screened by colony PCR (cPCR) for the replacement of one, two or three genomically integrated copies of the target emgfpΔ coding sequence with the donor EmGFP coding sequence.

7.2.1. Construction and Integration of Target DNA

To generate exogenous genomic target sites for nuclease-mediated double-strand breaks, target DNAs encoding emgfpΔ were constructed using RYSE-mediated assembly, as described in U.S. Pat. No. 8,110,360, the contents of which are hereby incorporated by reference in their entirety. Nucleotides 450 to 462 of the wild-type EmGFP coding sequence (SEQ ID NO:1) were replaced with the following sequence: 5'-CGTCTAAATCATG-3' (SEQ ID NO:2), resulting in the introduction of: (1) a premature stop codon at position 152 of EmGFP (emgfpΔ); and (2) the recognition/cleavage sequence for ZFN.gfp.

For the targeted integration of the emgfpΔ coding sequence into each of the HO, YGR250c and NDT80 loci, the emgfpΔ coding sequence was flanked with ~200-500 bp of upstream and downstream homologous sequences for each loci (SEQ ID NOS:3-8). A unique selectable marker was also incorporated into each construct, positioned 5' to the emgfpΔ coding sequence, for selection of colonies having successful integration events. The HO integration construct included KanR, the YGR250c integration construct included URA3, and the NDT80 integration construct included NatR. Each integration construct was transformed sequentially into a naïve CEN.PK2 haploid yeast strain (strain A), and the strain was confirmed to have three integrated copies of the emgfpΔ coding sequence.

7.2.2. Construction of ZFN Yeast Expression Plasmid

Zinc finger nucleases consist of two functional domains: a DNA-binding domain comprised of a chain of zinc finger proteins and a DNA-cleaving domain comprised of the nuclease domain of FokI. The endonuclease domain of FokI functions as an obligate heterodimer in order to cleave DNA, and thus, a pair of ZFNs is required to bind and cut its target sequence. The target sequence of ZFN.gfp (CompoZr® Zinc Finger Nuclease, Sigma-Aldrich, St. Louis, Mo.) is: 5'-ACAACTACAACAGCCACAACgtctatATCATGGC-CGACAAGCA-3' (SEQ ID NO: 9), with the recognition sequence indicated in uppercase and the cleavage sequence indicated in lowercase.

A high-copy ZFN.gfp yeast expression plasmid, pZFN.gfp, was constructed as follows. The genes ZFN.gfp.1 and ZFN.gfp.2, each encoding one member of the ZFN.gfp obligate heterodimer, were PCR-amplified from a mammalian expression plasmid and fused to the divergent $P_{GAL1,10}$ promoter and ADH1 and CYC1 terminators, respectively. Individual PCR products of $P_{GAL10}$>ZFN.gfp.1-$T_{ADH1}$ and $P_{GAL1}$>ZFN.gfp.2-$T_{CYC1}$, along with a linearized vector backbone comprising a LEU2 selectable marker, were co-transformed into a naïve yeast strain for in vivo assembly via homologous recombination of overlapping ends. The PCR products recombined at the pGAL1,10 promoter sequence and assembled into the vector backbone via homologous sequences added by the terminal primers. Transformants were selected on minimal media lacking leucine, isolated, and grown in liquid media. The plasmids from multiple clones were extracted from yeast using the Zymoprep Yeast Plasmid Miniprep I kit (Zymo Research). The eluent from the extraction protocol was then transformed into E. coli XL-1 blue chemically competent cells. Plasmids were propagated overnight in E. coli and miniprepped (Qiagen, Valencia, Calif.). Correct clones were identified by restriction mapping.

7.2.3. Transformation with Donor DNA and Induction of Double-Strand Breaks

A standard lithium acetate/SSDNA/PEG protocol (Gietz and Woods, Methods Enzymol. 350:87-96 (2002)) was used to co-transform strain A with linear "donor" DNA encoding EmGFP and either: (1) empty vector; or (2) the pZFN.gfp expression vector. The EmGFP coding sequence differs from the emgfpΔ coding sequence at positions within the recognition/cleavage site for ZFN.gfp, namely positions 450 (C→G), 456 (A→T), 461 (T→C) and 462 (G→C). Thus, ZFN.gfp is expected to recognize and cleave within the emgfpΔ sequence but not within the EmGFP sequence.

One microgram of the appropriate plasmid DNA was co-transformed with 70 ul of linear EmGFP DNA (~300 ng/ul). All transformations were recovered overnight in YP+2% galactose to induce ZFN expression. Various dilutions were plated onto minimal media agar plates lacking leucine to select for colonies transformed with plasmid DNA. Plates were incubated for 3 days at 30° C.

7.2.4. Confirmation of Multiple Simultaneous Integration

Colony PCR was performed to determine the frequency of replacement of the emgfpΔ coding sequence with the EmGFP coding sequence at each target locus. DNA was prepped from 96 colonies from each transformation and probed with primer pairs specific for EmGFP and HO, EmGFP and NDT80, and EmGFP and YGR250c, respectively, such that successful integration of the EmGFP coding sequence at each locus was expected to produce an amplicon of a predicted size, while non-integration was expected to produce no amplicon.

TABLE 2

| Primer sequences for cPCR verification of multiple integration of the EmGFPcoding sequence | | | |
|---|---|---|---|
| Primer Name | Description | Sequence | SEQ ID NO |
| KMH749-Fixed GFP-fwd | Forward primer specific to Em.GFP | CAACTACAACAGCCACAAGGTCTATATCACC | SEQ ID NO: 10 |
| CR813 | Reverse primer for HO locus | CTCTAACGCTGTTGGTAGATTG | SEQ ID NO: 11 |
| KMH773-NDT80-Ar | Reverse primer for NDT80 locus | ACCATGTGATAATACACTACTAATGTGACTACTAGTTGA | SEQ ID NO: 12 |
| KMH679-YGR250c 3' rev | Reverse primer for YGR250c locus | TCAGACGCGTTCGGAGGAGAGTGCATTCAC | SEQ ID NO: 13 |

As indicated in FIG. 5, of the 96 colonies transformed with linear EmGFP donor DNA (SEQ ID NO:1) and empty vector control, no amplicons were produced during PCR, indicating that there were no successful integration events, i.e., replacements at any of the three loci comprising the target emgfpΔ coding sequence in the absence of a double-strand break. By contrast, of the 96 colonies transformed with linear EmGFP DNA and pZFN.gfp, 2 colonies had one locus replaced, 4 colonies had two loci replaced, and 23 colonies had all three loci replaced with the EmGFP coding sequence (FIG. 6). Colony PCR results were corroborated by visualizing the fluorescence of transformed colonies on plates (data not shown). None of the colonies transformed with EmGFP DNA and empty vector appeared green, indicating that none of the target emgfpΔ coding sequences were replaced with functional EmGFP coding sequences. By contrast, ~20% of colonies transformed with EmGFP DNA and pZFN.gfp appeared green, roughly correlating with the frequency of integration events observed by cPCR.

These results demonstrate that induction of multiple targeted double-strand breaks in the genome of a host cell can facilitate simultaneous multiple targeted integration of exogenous donor nucleic acids.

7.3 Example 3

Simultaneous Multiple Integration of Terpene Synthase Genes to Facilitate Conversion of a Farnesene Producing Strain to an Amorphadiene Producing Strain This Example provides results which demonstrate simultaneous integration of three sesquiterpene synthase genes at three different engineered loci of a *S. cerevisiae* host engineered for high mevalonate pathway flux. As a result, a parental strain producing farnesene and comprising a plasmid-based copy of the farnesene synthase gene was converted into an amorphadiene producing strain comprising multiple genomically integrated copies of amorphadiene synthase. In brief, URA3, NatR and KanR marker cassettes flanked by F-CphI sites were integrated at the Ga180, HXT3 and Matα locus, respectively, of the host strain. The host was then co-transformed with a plasmid encoding the F-CphI endonuclease as well as three linear "donor" DNA constructs containing distinct codon optimizations of the amorphadiene synthase (ADS) gene expressed from the Gal1 promoter and terminated by the CYC1 terminator (ADS cassette), each flanked by homology regions for their respective target locus. Transformed colonies were screened by colony PCR (cPCR) for the replacement of one, two or three genomically integrated target marker loci with the ADS cassettes. A triply-integrated strain was identified and further engineered by integrating a fourth ADS cassette, and the resulting strain was cultured under conditions allowing for loss of the plasmid encoding farnesene synthase, such that its product profile was fully converted from farnesene to amorphadiene.

7.3.1. Construction of a Parental Farnesene Producing Strain

A farnesene-producing yeast strain, Y3639, useful for the multiple simultaneous integration of exogenous donor DNAs encoding amorphadiene synthase, was prepared as follows.

Strains Y93 (MAT A) and Y94 (MAT alpha) were generated by replacing the promoter of the ERG9 gene of yeast strains Y002 and Y003 (CEN.PK2 background MAT A or MAT alpha, respectively; ura3-52; trp1-289; leu2-3,112; his3Δ1; MAL2-8C; SUC2; van Dijken et al. (2000) *Enzyme Microb. Technol.* 26:706-714), respectively, with the promoter of the MET3 gene of *Saccharomyces cerevisiae*. To this end, exponentially growing Y002 and Y003 cells were transformed with integration construct i8 (SEQ ID NO: 14), which comprised the kanamycin resistance marker (KanMX) flanked by the promoter and terminator of the Tef1 gene of *Kluyveromyces lactis*, the ERG9 coding sequence, a truncated segment of the ERG9 promoter (trunc. PERG9), and the MET3 promoter (PMET3), flanked by ERG9 upstream and downstream sequences. Host cell transformants were selected on medium comprising 0.5 µg/mL Geneticin (Invitrogen Corp., Carlsbad, Calif.), and selected clones were confirmed by diagnostic PCR, yielding strains Y93 and Y94.

Strains Y176 (MAT A) and Y177 (MAT alpha) were generated by replacing the coding sequence of the ADE1 gene in strains Y93 and Y94, respectively, with the coding sequence of the LEU2 gene of *Candida glabrata* (CgLEU2). To this end, the 3.5 kb CgLEU2 genomic locus was PCR amplified from *Candida glabrata* genomic DNA (ATCC, Manassas, Va.) using primers 61-67-CPK066-G (SEQ ID NO: 15) and 61-67-CPK067-G (SEQ ID NO: 16), and transforming the PCR product into exponentially growing Y93 and Y94 cells. Host cell transformants were selected on CSM-L, and selected clones were confirmed by diagnostic PCR, yielding strains Y176 and Y177.

Strain Y188 was generated by introducing into strain Y176 an additional copy of the coding sequences of the ERG13, ERG10, and ERG12 genes of *Saccharomyces cerevisiae*, and a truncated coding sequence of the HMG1 gene of *Saccharomyces cerevisiae*, each under regulatory control of a galactose inducible promoter of the GAL1 or GAL10 gene of *Saccharomyces cerevisiae*. To this end, exponentially growing Y176 cells were transformed with 2 µg of expression plasmids pAM491 and pAM495 digested with PmeI restriction endonuclease (New England Biolabs, Beverly, Mass.). Host cell transformants were selected on CSM lacking uracil and histidine (CSM-U-H), and selected clones were confirmed by diagnostic PCR, yielding strain Y188.

Strain Y189 was generated by introducing into strain Y177 an additional copy of the coding sequences of the ERG20, ERG8, and ERG19 genes of *Saccharomyces cerevisiae*, and a truncated coding sequence of the HMG1 gene of *Saccharomyces cerevisiae*, each under regulatory control of a galactose inducible promoter of the GAL1 or GAL10 gene of *Saccharomyces cerevisiae*. To this end, exponentially growing Y188 cells were transformed with 2 µg of expression plasmids pAM489 and pAM497 digested with PmeI restriction endonuclease. Host cell transformants were selected on CSM lacking tryptophan and histidine (CSM-T-H), and selected clones were confirmed by diagnostic PCR, yielding strain Y189.

Strain Y238 was generated by mating strains Y188 and Y189, and by introducing an additional copy of the coding sequence of the IDI1 gene of *Saccharomyces cerevisiae* and a truncated coding sequence of the HMG1 gene of *Saccharomyces cerevisiae*, each under regulatory control of a galactose inducible promoter of the GAL1 or GAL10 gene of *Saccharomyces cerevisiae*. To this end, approximately $1 \times 10^7$ cells of strains Y188 and Y189 were mixed on a YPD medium plate for 6 hours at room temperature, diploid cells were selected on CSM-H-U-T, and exponentially growing diploids were transformed with 2 µg of expression plasmid pAM493 digested with PmeI restriction endonuclease. Host cell transformants were selected on CSM lacking adenine (CSM-A), and selected clones were confirmed by diagnostic PCR, yielding strain Y238.

Strains Y210 (MAT A) and Y211 (MAT alpha) were generated by sporulating strain Y238. The diploid cells were sporulated in 2% potassium acetate and 0.02% raffinose liquid medium, and approximately 200 genetic tetrads were isolated using a Singer Instruments MSM300 series micromanipulator (Singer Instrument Co, LTD. Somerset, UK). Spores were selected on CSM-A-H-U-T, and selected clones were confirmed by diagnostic PCR, yielding strains Y210 (MAT A) and Y211 (MAT alpha).

Strain Y221 was generated by transforming exponentially growing Y211 cells with vector pAM178. Host cell transformants were selected on CSM-L.

Strain Y290 was generated by deleting the coding sequence of the GAL80 gene of strain Y221. To this end, exponentially growing Y221 cells were transformed with integration construct i32 (SEQ ID NO: 17), which comprised the hygromycin B resistance marker (hph) flanked by the promoter and terminator of the Tef1 gene of *Kluyveromyces lactis* flanked by GAL80 upstream and downstream sequences. Host cell transformants were selected on medium comprising hygromycin B, and selected clones were confirmed by diagnostic PCR, yielding strain Y290.

Strain Y318 was generated by removing the pAM178 vector from strain Y290 by serial propagation in leucine-rich media, and testing individual colonies for their inability to grow on CSM-L, yielding strain Y318.

Strain Y409 was generated by introducing a heterologous nucleotide sequence encoding a β-farnesene synthase into strain Y318. To this end, exponentially growing Y318 cells were transformed with expression plasmid pAM404. Host cell transformants were selected on CSM-L, yielding strain Y409.

Strain Y419 was generated by rendering the GAL promoters of strain Y409 constitutively active. To this end, exponentially growing Y409 cells were transformed with integration construct i33 (SEQ ID NO: 18), which comprised the nourseothricin resistance marker of *Streptomyces noursei* (NatR) flanked by the promoter and terminator of the Tef1 gene of *Kluyveromyces lactis*, and the coding sequence of the GAL4 gene of *Saccharomyces cerevisiae* under regulatory control of an "operative constitutive" version of its native promoter (PGAL4oc; Griggs & Johnston (1991) *PNAS* 88(19):8597-8601) and the GAL4 terminator (TGAL4), flanked by upstream and downstream sequences of the modified ERG9 promoter and coding sequences. Host cell transformants were selected on medium comprising nourseothricin, and selected clones were confirmed by diagnostic PCR, yielding strain Y419.

Strain Y677 was generated by introducing at the modified GAL80 locus of strain Y419 an additional copy of the coding region of the ERG12 gene of *Saccharomyces cerevisiae* under regulatory control of the promoter of the GAL1 gene of *Saccharomyces cerevisiae*. To this end, exponentially growing Y677 cells were transformed with integration construct i37 (SEQ ID NO: 19), which comprised the kanamycin resistance marker of *Streptomyces noursei* (KanR) flanked by the promoter and terminator of the Tef1 gene of *Kluyveromyces lactis*, and the coding and terminator sequences of the ERG12 gene of *Saccharomyces cerevisiae* flanked by the GAL1 promoter (PGAL1) and the ERG12 terminator (TERG12). Host cell transformants were selected on medium comprising kanamycin, and selected clones were confirmed by diagnostic PCR, yielding strain Y677.

Strain Y1551 was generated from strain Y677 by chemical mutagenesis. Mutated strains were screened for increased production of β-farnesene, yielding strain Y1551.

Strain Y1778 was generated from strain Y1551 by chemical mutagenesis. Mutated strains were screened for increased production of β-farnesene, yielding strain Y1778.

Strain Y1816 was generated by replacing the HXT3 coding sequence of strain Y1778 with two copies of an acetoacetyl-CoA thiolase coding sequence, one being derived from *Saccharomyces cerevisiae* and the other from *C. butylicum*, and one copy of the coding sequence of the HMGS gene of *B. juncea*. To this end, exponentially growing Y1778 cells were transformed with integration construct i301 (SEQ ID NO: 20), which comprised the hygromycin B resistance marker (hyg) flanked by the promoter and terminator of the Tef1 gene of *Kluyveromyces lactis*, the coding sequence of the ERG10 gene of *Saccharomyces cerevisiae* flanked by a truncated TDH3 promoter (tPTDH3) and the AHP1 terminator (TAHP1), the coding sequence of the acetoacetyl-CoA thiolase gene of *C. butylicum* (thiolase) flanked by the YPD1 promoter (PYPD1) and CCW12 terminator (TCCW12), and the coding sequence of the HMGS gene of *B. juncea* (HMGS) preceded by the TUB2 promoter (PTUB2), flanked by upstream and downstream sequences of the HXT3 gene of *Saccharomyces cerevisiae*. Host cell transformants were selected on medium comprising hygromycin B, and selected clones were confirmed by diagnostic PCR, yielding strain Y1816.

Strain Y2055 was generated from strain Y1778 by chemical mutagenesis. Mutant strains were screened for increased production of β-farnesene, yielding strain Y2055.

Strain Y2295 was generated from strain Y2055 by chemical mutagenesis. Mutant strains were screened for increased production of β-farnesene, yielding strain Y2295.

Strain Y3111 was generated by switching the mating type of strain Y2295 from MAT A to MAT alpha. To this end, exponentially growing Y2295 cells were transformed with integration construct i476 (SEQ ID NO: 21), which comprised the MAT alpha mating locus and the hygromycin B resistance marker (hygA). Host cell transformants were selected on medium comprising hygromycin B, and selected clones were confirmed by diagnostic PCR, yielding strain Y3111.

Strain Y2168 was generated from strain Y1816 by chemical mutagenesis. Mutant strains were screened for increased production of β-farnesene, yielding strain Y2168.

Strain Y2446 was generated from strain Y2168 by chemical mutagenesis. Mutant strains were screened for increased production of β-farnesene, yielding strain Y2446.

Strain Y3118 was generated by inserting into the native URA3 locus of strain Y2446 the coding sequence, promoter, and terminator of the GAL80 gene of *Saccharomyces cerevisiae*. To this end, exponentially growing Y2446 cells were transformed with integration construct i477 (SEQ ID NO: 22), which comprised the promoter, terminator, and coding sequence of the GAL80 gene of *Saccharomyces cerevisiae* (GAL80) flanked by overlapping URA3 sequences (which enable loop-out excision of the GAL80 gene by homologous recombination and restoration of the original URA3 sequence). Host cell transformants were selected on medium comprising 5-FOA, yielding strain Y3118.

Strain Y3215 was generated by mating strains Y3111 and Y3118. Approximately $1 \times 10^7$ cells of strains Y3111 and Y3118 were mixed on a YPD medium plate for 6 hours at room temperature to allow for mating, followed by plating on YPD agar plate to isolate single colonies. Diploids were identified by screening by colony PCR for the presence of both the hphA-marked MAT alpha locus and the wild-type MAT A locus.

Strain Y3000 was generated by sporulating strain Y3215 and looping out the GAL80 coding sequence. The diploid cells were sporulated in 2% potassium acetate and 0.02% raffinose liquid medium. Random spores were isolated, plated on YPD agar, grown for 3 days, and then replica-plated to CSM-U to permit growth only of cells lacking GAL80 (i.e., having a functional URA3 gene). Spores were then tested for β-farnesene production, the best producer was identified, and the presence of integration construct i301 was confirmed by diagnostic PCR, yielding strain Y3000.

Strain Y3284 was generated by removing the URA3 marker from strain Y3000. To this end, exponentially growing Y3000 cells were transformed with integration construct i94 (SEQ ID NO: 23), which comprised the hisG coding sequence of *Salmonella*, and the coding sequence of the ERG13 gene and a truncated coding sequence of the HMG1 gene of *Saccharomyces cerevisiae* under control of a galactose inducible promoter of the GAL1 or GAL10 gene of *Saccharomyces cerevisiae*, flanked by upstream and downstream sequences of the URA3 gene of *Saccharomyces cerevisiae*. Host cell transformants were selected on medium comprising 5-FOA, and selected clones were confirmed by diagnostic PCR, yielding strain Y3284.

Strain Y3385 was generated by replacing the NDT80 coding sequence of strain Y3284 with an additional copy of the coding sequence of an acetyl-CoA synthetase gene of *Saccharomyces cerevisiae* and the coding sequence of the PDC gene of *Z. mobilis*. To this end, exponentially growing Y3385 cells were transformed with integration construct i467 (SEQ ID NO: 24), which comprised the URA3 marker, the coding sequence of the ACS2 gene of *Saccharomyces cerevisiae* (ACS2) flanked by the HXT3 promoter (PHXT3) and PGK1 terminator (TPGK1), and the coding sequence of the PDC gene of *Z. mobilis* (zmPDC) flanked by the GAL7 promoter (PGAL7) and the TDH3 terminator (TTDH3), flanked by upstream and downstream NDT80 sequences. Host cell transformants were selected on CSM-U, and selected clones were confirmed by diagnostic PCR, yielding strain Y3385.

Strain Y3547 was generated from strain Y3385 by chemical mutagenesis. Mutated strains were screened for increased production of β-farnesene, yielding strain Y3547.

Strain Y3639 was generated from strain Y3547 by chemical mutagenesis. Mutated strains were screened for increased production of β-farnesene, yielding strain Y3639.

7.3.2. Construction and Integration of Target DNA

Exogenous genomic target sites for FcphI endonuclease-mediated double-strand breaks were integrated into three different loci of strain Y3639. Three target site cassettes were constructed using PCR assembly of overlapping fragments, each comprising the recognition sequence for the FcphI endonuclease and the coding sequence for: (1) URA3 (flanked by homology regions for the modified Ga180 locus) (SEQ ID NO: 25); (2) NatR (flanked by homology regions for the modified HXT3 locus) (SEQ ID NO: 26); and (3) KanR (flanked by homology regions for the modified Matα locus) (SEQ ID NO: 27), respectively. Each target site cassette was serially transformed into Y3639, and the strain was confirmed by colony PCR to have three integrated copies of the F-CphI-flanked marker cassettes at the correct loci ("strain B").

7.3.3. Construction of F-CphI Yeast Expression Plasmid

The F-CphI yeast expression plasmid pAM1799, comprising a HygR selectable marker, has been described previously in U.S. Pat. No. 7,919,605, which is hereby incorporated by reference in its entirety.

7.3.4. Transformation with Donor DNA and Induction of Double-Strand Breaks

The standard lithium acetate/SSDNA/PEG protocol (Gietz and Woods, *Methods Enzymol.* 2002; 350:87-96) was modified to include a 30 minute, 30 degree incubation of the cells prior to the 42 degree heat shock. This method was used to co-transform strain B with pAM1799, encoding FcphI endonuclease, and three linear "donor" DNAs, each comprising a codon optimized coding sequence for amorphadiene synthase (ADS) of *Artemisia annua*, flanked by homology regions to the modified Ga180 (SEQ ID NO: 28), HXT3 (SEQ ID NO: 29) and Matα loci (SEQ ID NO: 30), respectively, of strain B.

One microgram of pAM1799 was co-transformed with ~100 ng of each of the ADS donor DNAs. All transformations were recovered overnight in YP+2% galactose to induce F-CphI expression. Various dilutions were plated onto YPD agar plates containing hygromycin to select for colonies transformed with plasmid DNA. Plates were incubated for 3 days at 30° C.

7.3.5. Confirmation of Multiple Simultaneous Integration

Colony PCR (cPCR) was performed to determine the frequency of replacement of the F-CphI-flanked marker cassette coding sequences with the ADS cassette coding sequence. DNA was prepped from 20 colonies probed with primer pairs specific for ADS and the Ga180 locus, ADS and the HXT3 locus, and ADS and the Matα locus, respectively, such that successful integration of the ADS cassette coding sequence at each locus was expected to produce an amplicon of a predicted size, while non-integration was expected to produce no amplicon. PCR reactions to produce amplicons from the 5' and 3' ends of each locus were attempted in multiplex. In some cases, only the 5' or the 3' amplicon was successfully detected, but proper integration of the ADS cassette was confirmed at these loci by sequencing larger PCR fragments.

TABLE 3

Primer sequences for cPCR verification of multiple integration of the ADS cassette coding sequence

| Primer Name | Description | Sequence | SEQ ID NO |
|---|---|---|---|
| CUT24 | Gal80 locus US FOR | GTTTCTTTTGGATTGCGCTTGCC | SEQ ID NO: 31 |
| ART12 | ADS codon v2 5' REV | TACTGACAACCACATGTTAC | SEQ ID NO: 32 |
| ART45 | ADS ORF 5' REV | TACTGCTTCGGTAGTAGTTTCACC CTTCA | SEQ ID NO: 33 |
| ART210 | Gal80 locus DS REV | GGGAAGTCCAATTCAATAGT | SEQ ID NO: 34 |
| HJ207 | HXT3 locus US FOR | CATCTTCTCGAGATAACACCTGG AG | SEQ ID NO: 35 |
| KB349 | CYC1T FOR | ACGCGTGTACGCATGTAAC | SEQ ID NO: 36 |
| HJ602 | HXT3 locus DS REV | CAATTGGGGTTCTGGCAGTC | SEQ ID NO: 37 |
| CUT76 | Matα locus US FOR | GAAGCCTGCTTTCAAAATTAAGA ACAAAGC | SEQ ID NO: 38 |
| HJ632 | Matα locus DS REV | GAATTTACCTGTTCTTAGCTTGTA CCAGAG | SEQ ID NO: 39 |

Of the 20 colonies screened by cPCR, 14 had ADS integrated at the Gal80 locus, 17 had ADS integrated at the HXT3 locus, and four had ADS integrated at the Matα locus. The low rate of integration at the Matα locus can be explained by self-closure at this locus mediated by a direct repeat sequence flanking the F-CphI sites. In total, 6 clones had ADS integrated at a single site, 10 clones had ADS integrated at two sites, and three clones had ADS integrated at all three loci ("strains C"). The triply integrated strains were further confirmed by sequencing longer PCR products encompassing both flanks.

1.1.5 Completion of the Integrated ADS Strain and Sesquiterpene Assay

The triply integrated ADS strains were further engineered by integrating a final copy of ADS marked with a URA cassette (SEQ ID NO: 40) at the His3 locus using a standard protocol, and a resulting strain was confirmed for this fourth copy ("strain D"). Finally, strain D cells were passaged in non-selective media to lose the Leu+ marked high copy farnesene synthase plasmid (pAM404) ("strain E").

Several isolates of strain E were assayed for sesquiterpene production alongside strain D and the original parent strain B. In brief, isolates of strains B, D and E were incubated in separate wells of a 96-well plate containing 360 μL of Bird Seed Medium (BSM) with 2% sucrose per well (preculture). After 3 days of incubation at 33.5° C. with 999 rpm agitation, 14.4 μL of each well was inoculated into a well of a new 96-well plate containing 360 μL of fresh BSM with 4% sucrose (production culture). After another 2 days of incubation at 33.5° C. with 999 rpm agitation, samples were taken and analyzed for sesquiterpene production by gas chromatography (GC) analysis. Samples were extracted with methanol-heptane (1:1 v/v), and the mixtures were centrifuged to remove cellular material. An aliquot of the methanol-heptane extract was diluted into heptane, and then injected onto a methyl silicone stationary phase using a pulsed split injection. Farnesene and amorphadiene were separated by boiling point using GC with flame ionization detection (FID). Trans-β-caryophyllene was used as a retention time marker to monitor successful injection and elution during the specified GC oven profile.

As shown in FIG. 7, total sesquiterpene production remained nearly identical (3-3.5 g/L) for all strains, but the product profile was successfully converted from Farnesene (strain B) to mixed product (strain D) to amorphadiene (strain E).

These results demonstrate that induction of multiple targeted double-strand breaks in the genome of a host cell can facilitate simultaneous multiple integrations of a functional gene cassette, in this case facilitating conversion of a farnesene-producing strain into an amorphadiene-producing strain in a single transformation.

7.4 Example 4

Simultaneous Replacement of Multiple Integrated Copies of Farnesene Synthase with Amorphadiene Synthase This Example provides results which demonstrate the simultaneous replacement of four genomically integrated terpene synthase genes, facilitated by designer nuclease-induced double-strand breaks within the synthase coding regions. In brief, an existing farnesene production strain, derived from strain Y3639 (described in Example 3) but comprising four integrated rather than extrachromasomal copies of the farnesene synthase (FS) gene, was co-transformed with a plasmid encoding a designer TAL-effector nuclease (TALEN) and four linear donor DNAs encoding new terpene synthase genes. The designer TALEN is capable of binding to and cleaving a sequence unique to the integrated farnesene synthase genes. Transformed colonies were screened by colony PCR (cPCR) and strains with one, two or three or four genomically integrated target marker loci were identified.

7.4.1. Construction and Integration of Target DNA

Four donor cassettes, each comprising a terpene synthase coding sequence flanked by homology regions (~500 bp) to its respective target loci, were assembled by overlap PCR. Three of the donor DNAs comprised ADS coding sequences and no selectable marker (SEQ ID NOs: 41-43), while the final donor DNA was a cassette comprising a novel codon optimization of the farnesene synthase (FS) fused to a URA3 marker cassette (SEQ ID NO: 44). None of the donor DNAs contained the target site recognized by the FS-specific TALEN (5'-TAGTGGAGGAATTAAAAGAGGAAGT-TAAGAAGGAATTGATAACTATCAA-3' (SEQ ID NO:45)).

For the replacement of the four integrated FS cassettes in the strain (Strain F), the hyg+ marked TALEN plasmid was co-transformed into the host strain along with ~500 ng of each linear donor DNA using the protocol described in Example 3. Various dilutions were plated onto CSM-URA+ Hyg plates and incubated at 30 degrees for 3 day.

7.4.2. Confirmation of Multiple Simultaneous Integration

After selection for the TALEN plasmid and integration of the URA3 marked codon-FS cassette on CSM-URA+Hyg plates, colony PCR was performed to determine the frequency of replacement of the integrated FS cassettes with the unmarked ADS cassettes at three loci. DNA was prepped from 20 colonies and probed with primer pairs specific for integration of the ADS cassette at the NDT80, DIT1 and ERG10 loci, such that successful integration of the ADS cassette coding sequence at each locus was expected to produce an amplicon of a predicted size, while non-integration was expected to produce no amplicon.

TABLE 4

Primer sequences for cPCR verification of replacement of multiple farnesene synthase cassettes with amorphadiene synthase cassettes.

| Primer Name | Description | Sequence | SEQ ID NO |
|---|---|---|---|
| HJ272 | NDT80 5' FOR | ATAACAATATTATAAAAGCGCTTAA | SEQ ID NO: 46 |
| ART45 | ADS ORF 5' REV | TACTGCTTCGGTAGTAGTTTCACCCTTCA | SEQ ID NO: 47 |
| HJ643 | DIT1 5' FOR | AAAATCCTTATATTATTGGCCC | SEQ ID NO: 48 |
| HJ799 | ERG10 5' FOR | GTAGCCTAAAACAAGCGCC | SEQ ID NO: 49 |

Three out of 48 clones examined had integrated a single ADS cassette in addition to the URA3-marked FS, one clone had integrated two ADS cassettes, and one clone had integrated all three ADS cassettes. Multiple integration results were further confirmed by sequencing longer PCR products encompassing both flanks.

These results demonstrate that expression of a site-specific designer nuclease in a host cell comprising a biosynthetic pathway can facilitate the simultaneous replacement of multiple integrated copies of a pathway gene with new pathway genes in a single transformation step.

7.5 Example 5

Simultaneous Multiple Integration of Markerless DNA Constructs into Two Loci Cut with Distinct Designer Nucleases This Example provides results which demonstrate the simultaneous integration of two markerless DNA constructs at two native target sites, each site being cut with a distinct designer nuclease. In brief, an ADE⁻ host strain was co-transformed with: (1) a linear DNA fragment comprising a GFP cassette (flanked by upstream and downstream regions homologous to the SFC1 locus); (2) a linear DNA fragment comprising an ADE2 cassette (flanked with upstream and downstream regions homologous to the YJR030c locus); and (3) plasmid(s) encoding designer nucleases that target sequences in the native SFC1 and YJR030c open reading frames, respectively. After selection for the plasmid(s), transformed colonies were screened visually for GFP fluorescence and for white color, indicating complementation of the ADE⁻ phenotype. Colony PCR (cPCR) was also performed to confirm replacement of both loci. Interestingly, a significant improvement in the rate of integration at both target loci was observed when the designer endonucleases were used in combination compared to the rate of integration when only a single designer nuclease was used.

7.5.1. Construction of donor DNA cassettes

Two donor DNAs were generated using PCR assembly of overlapping fragments: (1) a linear DNA fragment comprising a GFP cassette flanked by ~500 bp of upstream and downstream regions homologous to the SFC1 locus (SEQ ID NO: 58); and (2) a linear DNA fragment comprising an ADE2 cassette flanked by ~500 bp of upstream and downstream regions homologous to the YJR030c locus (SEQ ID NO: 59).

7.5.2. Construction of Heterodimeric ZFN Expression Plasmids

A plasmid encoding the YJR030c-specific zinc finger nuclease (ZFN) was constructed in two ways. In the first version, the two ORFs of a heterodimeric ZFN under expression of a divergent Gal1-10 promoter and terminated by the Adh1 and CYC1 terminators were cloned into a Kan marked CEN-ARS vector by a three part gap repair in yeast (pCUT006). A second version was also constructed wherein both ORFs of the heterodimeric ZFN were expressed from the Gal10 promoter as a single ORF with the monomers separated by a DNA sequence encoding a cleavable peptide linker. This second plasmid was constructed by a three-part ligation using linkers produced by type IIS restriction enzyme digest of PCR fragments into a Kan marked CEN-ARS vector backbone (pCUT016). A plasmid encoding the SFC1-specific ZFN was also constructed as a single ORF using the same linker strategy, marker and backbone (pCUT015). The marker was then changed to URA by means of a gap repair reaction in yeast (pCUT058). To construct a single plasmid for expression of both the YJR030c and SFC1-specific nucleases, the single ORFs from pCUT16 and pCUT15 were subcloned into a new CEN-ARS Kan+ vector backbone, and expressed from the Gal1-10 divergent promoter with Cyc1 and Adh1 terminators (pCUT032).

7.5.1. Transformation with Donor DNA and Induction of Double-Strand Breaks

One microgram of each designer nuclease plasmid DNA, or the plasmid containing both designer endonucleases on a single plasmid, was co-transformed with ~1 microgram of each of the donor DNAs. All transformations were recovered overnight in YP+2% galactose to induce nuclease expression. Various dilutions were plated onto URA dropout+Kan agar plates (for the dual plasmids) or YPD+Kan to select for colonies transformed with plasmid DNA. Plates were incubated for 3-4 days at 30° C.

7.5.2. Confirmation of Multiple Simultaneous Integration

Marker-less integration at the SFC1 locus was scored by observation of GFP fluorescence under UV light using appropriate filters. Marker-less integration of ADE2 was scored by observation of a white colony color, indicating complementation of the ADE2 deletion phenotype (pink colonies) in the host strain. In a typical experiment, 50-150 colonies were assayed. The visual scoring strategy was confirmed in a subset of colonies by colony PCR using primers 5' of the integration construct and an internal reverse primer. Integration at each locus was expected to produce an amplicon of a predicted size, while non-integration was expected to produce no amplicon. The cPCR results confirmed the accuracy of the visual scoring method.

As indicated in FIG. 8, in cells co-transformed with linear donor DNAs for the SFC1 and YJR030c loci, and the YJR030c endonuclease plasmid (pCUT006) and SFC1 endonuclease plasmid (pCUT058), 80% of colonies selected on URA dropout+Kan agar plates were GFP positive. Of these colonies, 91% were positive for ADE2 integration. In total, 72.8% of colonies had integrated the donor DNA at both loci.

In cells co-transformed with linear donor DNA for the SFC1 locus and the designer nuclease plasmid targeting SFC1 (pCUT015), 50% of the cells were positive for GFP. When cells were co-transformed with linear donor DNA for the YJR030c locus and the designer nuclease plasmid targeting the YJR030c locus (pCUT016), only 5% of the cells were positive for ADE2 integration. When the host cells were co-transformed with linear DNAs for the SFC1 and YJR030c loci, and the SFC1/YJR030c designer nuclease plasmid (pCUT032), 76% of the cells were GFP positive, and 63% were ADE2 positive. This result is notable in that it demonstrates an unexpectedly significant improvement in integration efficiency when multiple sites are targeted by designer endonucleases.

These results demonstrate that induction of multiple targeted double-strand breaks at native loci in the genome of a host cell can facilitate simultaneous, multiple, marker-less integrations of functional gene cassettes.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

TABLE 4

Primer sequences for successful cPCR verification of multiple integration of the ADS cassette coding sequence

| Primer Name | Description | Sequence | SEQ ID NO |
|---|---|---|---|
| CUT351 | SFC1 5' cPCR | GCGAATGAGCCATGAATTATTAACCGC | SEQ ID NO: 63 |
| CUT350 | YJR030c 5' cPCR | AGATGAAACGAATTACTAGCATTTTATCCGTTC | SEQ ID NO: 64 |
| CUT371 | ADE2 cassette REV | TAACTACCATTACTCAGTGTACTTGATTGTTTTGTCCGATTTTCTTG | SEQ ID NO: 65 |
| HJ788 | GFP cassette REV | GCCGGGTGACAGAGAAATATTG | SEQ ID NO: 66 |

What is claimed is:

1. A host cell comprising:
   (a) a plurality of (n) exogenous donor nucleic acids to be integrated into the host cell genome, wherein:
   n is at least 2, x is an integer from 1 to n, and for each integer x, each exogenous donor nucleic acid $(ES)_x$ comprises a first homology region $(HR1)_x$ and a second homology region $(HR2)_x$, wherein $(HR1)_x$ and $(HR2)_x$ are capable of initiating host cell mediated homologous recombination of $(ES)_x$ at a target site $(TS)_x$ selected from a plurality of (n) target sites of said host cell genome; and
   (b) for each said target site $(TS)_x$, a nuclease $(N)_x$ capable of cleaving at $(TS)_x$, whereupon said cleaving results in homologous recombination of $(ES)_x$ at (TS),
   wherein the host cell comprises one or more heterologous nucleotide sequences encoding one or more enzymes of a biosynthetic pathway.

2. The host cell of claim 1, wherein $(HR1)_x$ is homologous to a 5' region of $(TS)_x$, and $(HR2)_x$ is homologous to a 3' region of $(TS)_x$.

3. The host cell of claim 2, wherein $(N)_x$ is capable of cleaving at a region positioned between said 5' and 3' regions of $(TS)_x$.

4. The host cell of claim 1, wherein a single nuclease is capable of cleaving each $(TS)_x$.

5. The host cell of claim 1, wherein n=3, 4, 5, 6, 7, 8, 9 or 10.

6. The host cell of claim 1, wherein $(N)_x$ is capable of cleaving an endogenous genomic sequence within $(TS)_x$.

7. The host cell of claim 1, wherein $(N)_x$ is capable of cleaving an exogenous sequence within $(TS)_x$, wherein x is 1 or any integer from 1 to n.

8. The host cell of claim 7, wherein the exogenous sequence is a recognition sequence for a homing endonuclease.

9. The host cell of claim 8, wherein the homing endonuclease is F-cphI.

10. The host cell of claim 7, wherein $(ES)_x$ further comprises a nucleic acid of interest $(D)_x$ positioned 3' of $(HR1)_x$ and 5' of $(HR2)_x$.

11. The host cell of claim 10, wherein $(D)_x$ is selected from the group consisting of a protein-coding sequence, reporter gene, fluorescent marker coding sequence, promoter, enhancer, terminator, transcriptional activator, transcriptional repressor, transcriptional activator binding site, transcriptional repressor binding site, intron, exon, poly-A tail, multiple cloning site, nuclear localization signal, mRNA stabilization signal, integration loci, epitope tag coding sequence, and degradation signal.

12. The host cell of claim 1, wherein $(ES)_x$ is linear.

13. The host cell of claim 1, wherein the one or more heterologous nucleotide sequences encoding one or more enzymes of a biosynthetic pathway are genomically integrated.

14. The host cell of claim 1, wherein each said exogenous nucleic acid $(ES)_x$ comprises a nucleic acid of interest $(D)_x$ positioned 3' of $(HR1)_x$ and 5' of $(HR2)_x$, encoding an enzyme of a biosynthetic pathway.

15. The host cell of claim 1, wherein $(N)_x$ is provided as an expression vector comprising a nucleic acid sequence encoding $(N)_x$.

16. The host cell of claim 1, wherein $(N)_x$ is transformed into the host cell as a purified protein.

17. The host cell of claim 1, wherein $(N)_x$ is transformed into the host cell as a purified RNA.

18. The host cell of claim 1, wherein $(N)_x$ is selected from the group consisting of an endonuclease, a zinc finger nuclease, a TAL-effector DNA binding domain-nuclease fusion protein (TALEN), a transposase, and a site-specific recombinase.

19. The host cell of claim 18, wherein the zinc finger nuclease is a fusion protein comprising the cleavage domain of a TypeIIS restriction endonuclease fused to an engineered zinc finger binding domain.

20. The host cell of claim 19, wherein the TypeIIS restriction endonuclease is selected from the group consisting of HO endonuclease and Fok I endonuclease.

21. The host cell of claim 19, wherein the zinc finger binding domain comprises 3, 5 or 6 zinc fingers.

22. The host cell of claim 18, wherein the endonuclease is a homing endonuclease selected from the group consisting of: an LAGLIDADG homing endonuclease, an HNH homing endonuclease, a His-Cys box homing endonuclease, a GIY-YIG homing endonuclease, and a cyanobacterial homing endonuclease.

23. The host cell of claim 18, wherein the endonuclease is selected from the group consisting of: H-DreI, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, Pi-PspI, F-SceI, F-SceII, F-SuvI, F-CphI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp68031, I-SthPhiJP, I-SthPhiST3P, I-SthPhiSTe3bP, I-TdeIP, I-TevI, I-TevII, I-TevIII, i-UarAP, i-UarHGPAIP, I-UarHGPA13P, I-VinIP, I-ZbiIP, PI-MgaI, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, and PI-TliII.

24. The host cell of claim 18, wherein the endonuclease is modified to specifically bind an endogenous host cell genomic sequence, wherein the modified endonuclease no longer binds to its wild type endonuclease recognition sequence.

25. The host cell of claim 24, wherein the modified endonuclease is derived from a homing endonuclease selected from the group consisting of: an LAGLIDADG homing endonuclease, an HNH homing endonuclease, a His-Cys box homing endonuclease, a GIY-YIG homing endonuclease, and a cyanobacterial homing endonuclease.

26. The host cell of claim 24, wherein the modified endonuclease is derived from an endonuclease selected from the group consisting of: H-DreI, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, Pi-PspI, F-SceI, F-SceII, F-SuvI, F-CphI, F-TeeI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I—HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp68031, I-SthPhiJP, I-SthPhiST3P, I-SthPhiSTe3bP, I-TdeIP, I-TevI, I-TevII, I-TevIII, i-UarAP, i-UarHGPAIP, I-UarHGPA13P, I-VinIP, I-ZbiIP, PI-MgaI, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, and PI-TliII.

27. The host cell of claim 1, wherein the host cell is selected from the group consisting of a fungal cell, a bacterial cell, a plant cell, and an animal cell.

28. The host cell of claim 1, wherein the host cell is a yeast cell.

29. The yeast cell of claim 28, wherein the yeast cell is a *Saccharomyces cerevisiae* cell.

30. A host cell comprising:
  (a) a plurality of (n) libraries, wherein n is at least 2, x is any integer from 1 to n, and for each integer x, each library $(L)_x$ comprises a plurality of exogenous donor nucleic acids to be integrated into the host cell genome, wherein a selected exogenous donor nucleic acid comprises, in a 5' to 3' orientation, a first homology region $(HR1)_x$, any nucleic acid of interest selected from a group $(D)_x$, and a second homology region $(HR2)_x$, wherein $(HR1)_x$ and $(HR2)_x$ are capable of initiating host cell mediated homologous recombination of said selected exogenous nucleic acid at a target site $(TS)_x$ of said host cell genome; and
  (b) for each said target site $(TS)_x$, a nuclease $(N)_x$ capable of cleaving at $(TS)_x$, whereupon said cleaving results in homologous recombination of said selected exogenous nucleic acid at $(TS)_x$.

31. The host cell of claim 30, wherein $(D)_x$ is selected from the group consisting of a protein-coding sequence, reporter gene, fluorescent marker coding sequence, promoter, enhancer, terminator, transcriptional activator, transcriptional repressor, transcriptional activator binding site, transcriptional repressor binding site, intron, exon, poly-A tail, multiple cloning site, nuclear localization signal, mRNA stabilization signal, integration loci, epitope tag coding sequence, and degradation signal.

32. The host cell of claim 30 or 31, wherein the host cell comprises at least $10^1$, $10^2$, $10^3$, $10^4$, $10^5$, $10^6$, or more than $10^6$ unique nucleic acids of interest $(D)_x$ in each library $(L)_x$.

33. The host cell of claim 30, wherein each exogenous nucleic acid $(ES)_x$ does not comprise nucleic acid encoding a selectable marker.

34. The host cell of claim 30, wherein $(HR1)_x$ is homologous to a 5' region of $(TS)_x$, and $(HR2)_x$ is homologous to a 3' region of $(TS)_x$.

35. The host cell of claim 34, wherein $(N)_x$ is capable of cleaving at a region positioned between said 5' and 3' regions of $(TS)_x$.

36. The host cell of claim 30, wherein a single nuclease is capable of cleaving each $(TS)_x$.

37. The host cell of claim 30, wherein $(N)_x$ is capable of cleaving an endogenous genomic sequence within $(TS)_x$.

38. The host cell of claim 30, wherein $(N)_x$ is capable of cleaving an exogenous sequence within $(TS)_x$, wherein x is 1 or any integer from 1 to n.

39. The host cell of claim 38, wherein the exogenous sequence is a recognition sequence for a homing endonuclease.

40. The host cell of claim 30, wherein $(N)_x$ is selected from the group consisting of an endonuclease, a zinc finger nuclease, a TAL-effector DNA binding domain-nuclease fusion protein (TALEN), a transposase, and a site-specific recombinase.

41. The host cell of claim 40, wherein the endonuclease is modified to specifically bind an endogenous host cell genomic sequence, wherein the modified endonuclease no longer binds to its wild type endonuclease recognition sequence.

42. The host cell of claim 30, wherein the host cell is selected from the group consisting of a fungal cell, a bacterial cell, a plant cell, and an animal cell.

43. The host cell of claim 30, wherein the host cell is a yeast cell.

44. The yeast cell of claim 43, wherein the yeast cell is a *Saccharomyces cerevisiae* cell.

* * * * *